(12) United States Patent
McKerrall et al.

(10) Patent No.: US 10,947,251 B2
(45) Date of Patent: Mar. 16, 2021

(54) THERAPEUTIC COMPOUNDS AND METHODS OF USE THEREOF

(71) Applicant: GENENTECH, INC., South San Francisco, CA (US)

(72) Inventors: Steven McKerrall, South San Francisco, CA (US); Brian Salvatore Safina, South San Francisco, CA (US); Aleksandr Kolesnikov, South San Francisco, CA (US); Birong Zhang, South San Francisco, CA (US); Wenfeng Liu, Shanghai (CN); Kwong Wah Lai, Shanghai (CN)

(73) Assignee: GENENTECH, INC., South San Fancisco, CA (US)

( * ) Notice: Subject to any disclaimer, the term of this patent is extended or adjusted under 35 U.S.C. 154(b) by 0 days.

(21) Appl. No.: 16/370,756

(22) Filed: Mar. 29, 2019

(65) Prior Publication Data

US 2019/0300544 A1 Oct. 3, 2019

(30) Foreign Application Priority Data

Mar. 30, 2018 (WO) ................ PCT/CN2018/081250

(51) Int. Cl.
*C07D 498/04* (2006.01)
*C07D 471/04* (2006.01)
*A61P 11/00* (2006.01)
*A61P 9/00* (2006.01)
*A61P 25/24* (2006.01)
*A61P 25/00* (2006.01)
*A61P 29/00* (2006.01)

(52) U.S. Cl.
CPC .............. *C07D 498/04* (2013.01); *A61P 9/00* (2018.01); *A61P 11/00* (2018.01); *A61P 25/00* (2018.01); *A61P 25/24* (2018.01); *A61P 29/00* (2018.01); *C07D 471/04* (2013.01)

(58) Field of Classification Search
CPC ........................... C07D 498/04; C07D 471/04
See application file for complete search history.

(56) References Cited

U.S. PATENT DOCUMENTS

| | | | |
|---|---|---|---|
| 3,705,185 A | 12/1972 | Moore et al. | |
| 4,225,609 A | 9/1980 | Cragoe et al. | |
| 5,171,748 A | 12/1992 | Roberts et al. | |
| 5,573,653 A | 11/1996 | Bandlish | |
| 5,580,982 A | 12/1996 | O'Malley et al. | |
| 5,753,653 A | 5/1998 | Bender et al. | |
| 6,096,771 A | 8/2000 | Kojima et al. | |
| 7,262,304 B2 | 8/2007 | Ueno et al. | |
| 7,291,638 B2 | 11/2007 | Lee et al. | |
| 7,858,639 B2 | 12/2010 | Sun et al. | |
| 8,153,814 B2 | 4/2012 | Beaudoin et al. | |
| 8,193,194 B2 | 6/2012 | Martinborough et al. | |
| 8,642,660 B2 | 2/2014 | Goldfarb | |
| 8,889,741 B2 | 11/2014 | Shinozuka et al. | |
| 8,933,236 B2 | 1/2015 | Chowdhury et al. | |
| 8,952,169 B2 | 2/2015 | Andrez et al. | |
| 9,102,621 B2 | 8/2015 | Brown et al. | |
| 9,481,677 B2 | 11/2016 | Liu et al. | |
| 9,493,429 B2 | 11/2016 | Chen et al. | |
| 9,546,164 B2 | 1/2017 | Andrez et al. | |
| 9,550,775 B2 | 1/2017 | Bichler et al. | |
| 9,630,929 B2 | 4/2017 | Sun et al. | |
| 9,694,002 B2 | 7/2017 | Andrez et al. | |
| 9,771,376 B2 | 9/2017 | Chowdhury et al. | |
| 9,810,473 B2 | 11/2017 | Lauchnor | |
| 2006/0069093 A1 | 3/2006 | Scarborough et al. | |
| 2007/0088015 A1 | 4/2007 | Silva et al. | |
| 2008/0161303 A1 | 7/2008 | Zhang et al. | |
| 2008/0312286 A1 | 12/2008 | Pinkerton et al. | |
| 2009/0012103 A1 | 1/2009 | Abelman et al. | |

(Continued)

FOREIGN PATENT DOCUMENTS

| | | |
|---|---|---|
| CN | 101466665 A | 6/2009 |
| CN | 101643458 A | 2/2010 |

(Continued)

OTHER PUBLICATIONS

Diss , et al., "Identification and characterization of the promoter region of the NaV1.7 voltage-gated sodium channel gene (SCN9A)", Mol. Cell. Neurosci. 37, 537-547 (2008).
Dong , et al., "Small interfering RNA-mediated selective knockdown of Na(V)1.8 tetrodotoxin-resistant sodium channel reverses mechanical allodynia in neuropathic rats", Neuroscience 146, 812-821 (2007).
Emery, E , et al., "Nav1.7 and other voltage-gated sodium channels as drug targets for pain relief", Expert Opinion of Therapeutic Targets 20(8), 975-983 (2016).

(Continued)

*Primary Examiner* — Noble E Jarrell
(74) *Attorney, Agent, or Firm* — Viksnins Harris Padys Malen LLP

(57) ABSTRACT

The invention provides a compound of formula (I):

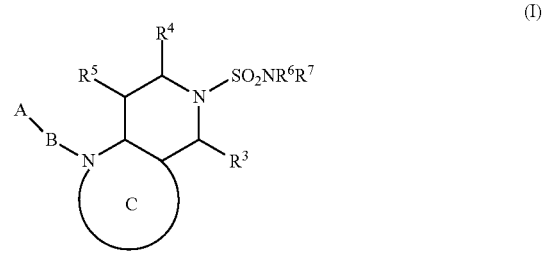

or a pharmaceutically acceptable salt thereof; wherein, A, B, ring C, $R^3$, $R^4$, $R^5$, $R^6$, and $R^7$ have the meaning as described herein, and compositions containing such compounds and methods for using such compounds and compositions.

20 Claims, No Drawings

(56) References Cited

U.S. PATENT DOCUMENTS

| | | |
|---|---|---|
| 2010/0179137 A1 | 7/2010 | Kamikubo et al. |
| 2010/0197655 A1 | 8/2010 | Beaudoin et al. |
| 2010/0286110 A1 | 11/2010 | Fyfe et al. |
| 2011/0092703 A1 | 4/2011 | Sakuma et al. |
| 2012/0004714 A1 | 1/2012 | Kleve et al. |
| 2012/0010182 A1 | 1/2012 | Brown et al. |
| 2012/0010183 A1 | 1/2012 | Bell et al. |
| 2012/0010207 A1 | 1/2012 | Bell et al. |
| 2012/0196869 A1 | 8/2012 | Hadida Ruah et al. |
| 2013/0317000 A1 | 11/2013 | Chowdhury et al. |
| 2013/0324525 A1 | 12/2013 | Abelman et al. |
| 2013/0338111 A1 | 12/2013 | Beaudoin et al. |
| 2014/0213616 A1 | 7/2014 | Hadida-Ruah et al. |
| 2014/0296266 A1 | 10/2014 | Hu et al. |
| 2015/0224071 A1 | 8/2015 | Chowdhury et al. |
| 2015/0252038 A1 | 9/2015 | Andrez et al. |
| 2015/0291514 A1 | 10/2015 | Brown et al. |
| 2015/0322002 A1 | 11/2015 | Dehnhardt et al. |
| 2016/0340309 A1 | 11/2016 | Chowdhury et al. |
| 2017/0002017 A1 | 1/2017 | Andrez et al. |
| 2017/0190662 A1 | 7/2017 | Andrez et al. |
| 2018/0105504 A1 | 4/2018 | Sutherlin et al. |
| 2018/0230079 A1 | 8/2018 | Hemeon et al. |

FOREIGN PATENT DOCUMENTS

| | | |
|---|---|---|
| EP | 0179619 B1 | 9/1990 |
| EP | 0516392 A2 | 12/1992 |
| EP | 2184278 A1 | 5/2010 |
| EP | 2813491 A1 | 12/2014 |
| EP | 2974730 A1 | 1/2016 |
| EP | 2870138 B1 | 8/2018 |
| WO | 1990008128 A1 | 7/1990 |
| WO | 2000039077 A2 | 7/2000 |
| WO | 2003059882 A1 | 7/2003 |
| WO | 2004014913 A2 | 2/2004 |
| WO | 2004052869 A1 | 6/2004 |
| WO | 2004092145 A1 | 10/2004 |
| WO | 2005013914 A2 | 2/2005 |
| WO | 2005032488 A2 | 4/2005 |
| WO | 2006015158 A1 | 2/2006 |
| WO | 2006020830 A2 | 2/2006 |
| WO | 2006020830 A3 | 2/2006 |
| WO | 2006039212 A2 | 4/2006 |
| WO | 2006121097 A1 | 11/2006 |
| WO | 2006122800 A1 | 11/2006 |
| WO | 2007030582 A3 | 3/2007 |
| WO | 2007045572 A1 | 4/2007 |
| WO | 2007062078 A2 | 5/2007 |
| WO | 2007067994 A1 | 6/2007 |
| WO | 2007120647 A2 | 10/2007 |
| WO | 2008094602 A2 | 8/2008 |
| WO | 2008097991 A1 | 8/2008 |
| WO | 2008118758 A1 | 10/2008 |
| WO | 2009010784 A1 | 1/2009 |
| WO | 2009012242 A3 | 1/2009 |
| WO | 2009157399 A1 | 12/2009 |
| WO | 2010022055 A2 | 2/2010 |
| WO | 2010079443 A1 | 7/2010 |
| WO | 2011014462 A1 | 2/2011 |
| WO | 2011016234 A1 | 2/2011 |
| WO | 2011037192 A1 | 2/2011 |
| WO | 2011059042 A1 | 5/2011 |
| WO | 2011063001 A1 | 5/2011 |
| WO | 2011088201 A1 | 7/2011 |
| WO | 2011100433 A1 | 8/2011 |
| WO | 2011153588 A1 | 12/2011 |
| WO | 2012004664 A2 | 1/2012 |
| WO | 2012004706 A2 | 1/2012 |
| WO | 2012004706 A3 | 1/2012 |
| WO | 2012004714 A2 | 1/2012 |
| WO | 2012004743 A1 | 1/2012 |
| WO | 2012007836 A1 | 1/2012 |
| WO | 2012007861 A1 | 1/2012 |
| WO | 2012007868 A2 | 1/2012 |
| WO | 2012007869 A2 | 1/2012 |
| WO | 2012007877 A2 | 1/2012 |
| WO | 2012007883 A1 | 1/2012 |
| WO | 2012035023 A1 | 3/2012 |
| WO | 2012039657 A1 | 3/2012 |
| WO | 2012085650 A1 | 6/2012 |
| WO | 2012095781 A1 | 7/2012 |
| WO | 2012135113 A2 | 10/2012 |
| WO | 2013025883 A1 | 2/2013 |
| WO | 2013056232 A2 | 4/2013 |
| WO | 2013063459 A1 | 5/2013 |
| WO | 2013064983 A1 | 5/2013 |
| WO | 2013064984 A1 | 5/2013 |
| WO | 2013072758 A1 | 5/2013 |
| WO | 2013086229 A1 | 6/2013 |
| WO | 2013088315 A1 | 6/2013 |
| WO | 2013102826 A1 | 7/2013 |
| WO | 2013118805 A1 | 8/2013 |
| WO | 2013118854 A1 | 8/2013 |
| WO | 2013122897 A1 | 8/2013 |
| WO | 2013134518 A1 | 9/2013 |
| WO | 2013146969 A1 | 10/2013 |
| WO | 2013177224 A1 | 11/2013 |
| WO | 2014008458 A2 | 1/2014 |
| WO | 2014014050 A1 | 1/2014 |
| WO | 2014066490 A1 | 5/2014 |
| WO | 2014066491 A1 | 5/2014 |
| WO | 2014096941 A1 | 6/2014 |
| WO | 2014144545 A2 | 9/2014 |
| WO | 2014151472 A1 | 9/2014 |
| WO | 2014153037 A1 | 9/2014 |
| WO | 2015051043 A1 | 4/2015 |
| WO | 2015077905 A1 | 6/2015 |
| WO | 2015078374 A1 | 6/2015 |
| WO | 2016007534 A1 | 1/2016 |
| WO | 2016021742 A1 | 2/2016 |
| WO | 2016141035 A1 | 9/2016 |
| WO | 2017106226 A1 | 6/2017 |
| WO | 2017106409 A1 | 6/2017 |
| WO | 2017165204 A1 | 9/2017 |
| WO | 2018017896 A1 | 1/2018 |
| WO | 2018072602 A1 | 4/2018 |

OTHER PUBLICATIONS

England, et al., "Isoform-selective voltage-gated Na(+) channel modulators as next-generation analgesics", Future Med Chem 2 (5), 775-790 (2010).

Estacion, et al., "A sodium channel gene SCN9A polymorphism that increases nociceptor excitability", Ann Neurol 66 (6), 862-866 (2009).

Federal Register, vol. 76(27), 7162-7175, Slide 1, 64-67 (2011).

File Caplus, Registry No. 1333872-40-4, entered STN: Sep. 29, 2011.

Fishman, et al., "Intravenous lidocaine for treatment-resistant pruritus", American J. of Medicine 102, 584-585 (1997).

Fraser, et al., "Voltage-gated sodium channel expression and potentiation of human breast cancer metastasis", Clin. Cancer Res. 11(15), 5381-5389 (2005).

Freshney, et al., "Culture of Animal Cells, A Manual of Basic Technique", Alan R. Liss, Inc., New York, 7 pages (1983).

Goldberg, et al., "Loss-of-function mutations in the Nav1.7 gene underlie congenital indifference to pain in multiple human populations", Clin. Genet. 71, 311-319 (2007).

Goldin, et al., "Nomenclature of Voltage-Gated Sodium Channels", Neuron vol. 28, 365-368 (2000).

Gould, et al., "Development of inflammatory hypersensitivity and augmentation of sodium channels in rat dorsal root ganglia", Brain Res. 824 (2), 296-299 (1999).

Hains, et al., "Upregulation of sodium channel Nav1.3 and functional involvement in neuronal hyperexcitability associated with central neuropathic pain after spinal cord injury", J. Neurosci. 23 (26), 8881-8892 (2003).

Hayes, et al., "Na(V)1.7 Paint Control: A Novel Target", Neurosurgery 73, N16 (2013).

(56) References Cited

OTHER PUBLICATIONS

Ikoma, et al., "Neuronal sensitization for histamine-induced itch in lesional skin of patients with atopic dermatitis", Arch. Dermatol. 139, 1445-1458 (2003).
Ikoma, et al., "The neurobiology of itch", Nature Reviews Neuroscience 7, 535-547 (2006).
Ikuma, et al., "Preparation of 3-substituted proline derivatives as FXIa inhibitors", CA159:371450 (2013).
Kis-Toth, et al., "Voltage-gated sodium channel NaV1.7 maintains the membrane potential and regulates the 45 activation and chemokine-induced migration of a monocyte-derived dendritic cell subset", J. Immunology 187, 1273-1280 (2011).
Klugbauer, et al., "Structure and functional expression of a new member of the tetrodotoxin-sensitive voltage-activated sodium channel family from human neuroendocrine cells", EMBO J. 14 (6), 1084-1090 (1995).
Kuo, et al., "Application of CoMFA and CoMSIA 3D-QSAR and Docking Studies in Optimization of Mercaptobenzenesulfonamides as HIV-1 Integrase Inhibitors", Journal of Medicinal Chemistry. American Chemical Society. US. vol. 47. No. 2, 385-399 (2003).
Kutt, et al., "A Comprehensive Self-Consistent Spectrophotometric Acidity Scale of Neutral Bronsted Acids in Acetonitrile", J. Org. Chem. 71, 2829-2838 (2006).
Lai, et al., "Inhibition of neuropathic pain by decreased expression of the tetrodotoxin-resistant sodium channel, NaV1.8", Pain 95 (1-2), 143-152 (2002).
Lai, et al., "The role of voltage-gated sodium channels in neuropathic pain", Current Opinion in Neurobiology 13, 291-297 (2003).
Lamoureux, G., et al., "Use of the adamantane structure in medicinal chemistry", Curr Med Chem 17(26), 2967-2978 (2010).
Lee, J, et al., "A monoclonal antibody that targets a NaV1.7 channel voltage sensor for pain and itch relief", Cell 157(6), 1393-1404 (2014).
Leeman, et al., "Preparation of 4-benzimidazolylmethoxy-3-halophenylmethoxybenzoates and analogs as tRNA synthetase inhibitors", CA 133:35021 (2000).
Li, et al., "Recent advances in the structure-activity relationship study of small-molecule sodium channel blockers with analgesic effects", Acta Pharmaceutica Sinica, vol. 44, (2), 101-108 (2009). [English Translation.].
Liu, et al., "Mutations in cardiac sodium channels: clinical implications", Am. J. Pharmacogenomics 3(3), 173-179 (2003).
Mao, et al., "Systemic lidocaine for neuropathic pain relief", Pain 87, 7-17 (2000).
Massah, et al., "Synthesis. in vitro antibacterial and carbonic anyydrase II inhibitory activities of N-acylsulfonamides 2 using silica sulfuric acid as an efficient catalyst under both solvent-free and heterogeneous conditions", Bioorganic & Medicinal Chemistry 16, 5465-5472 (2008).
Meisler, et al., "Sodium channel gene family: epilepsy mutations, gene interactions and modifier effects", The Journal of Physiology 588.11, 1841-1848 (2010).
Morinville, et al., "Distribution of the voltage-gated sodium channel NaV1.7 in the rat: expression in the autonomic and endocrine systems", J. Comparative Neurology 504, 680-689 (2007).
Oaklander, et al., "Intractable post-herpetic itch and cutaneous deafferentation after facial singles", Pain 96,9-12 (2002).
Patani, George A., et al., "Bioisosterism: A Rational Approach in Drug Design", Chem Rev 96, 3147-3176 (1996).
Patent Cooperation Treaty, International Searching Authority, Search Report and Written Opinion for PCT/US2019/025028, 11 pages, dated Aug. 27, 2019.
Priest, et al., "Contribution of the tetrodotoxin-resistant voltage-gated sodium channel NaV1.9 to sensory transmission and nociceptive behavior", Proc Nail Acad Sci 102 (26) 9382-9387 (2005).
Priest, "Future potential and status of selective sodium channel blockers for the treatment of pain", Current Opinion in Drug Discovery and Development, 12(5), 682-692 (2009).
Prodrug, Dictionary 1-2, Internet (2002).

Pubchem, Compound Summary for CID 14280666, N-(1,2-benzoxazol-3-yl) methanesulfonamide, https://pubchem.ncbi.nim.nih.gov/summary/summary.cgi?cid=14280666, 3 pages (2007).
Raymond, et al., "Expression of alternatively spliced sodium channel alpha-subunit genes. Unique splicing patterns are observed in dorsal root ganglia", J. Biol. Chern. 279(44), 46234-46241 (2004).
Reimann, et al., "Pain perception is altered by a nucleotide polymorphism in SCN9A", Proc. Nail. Acad. Sci. 107, 5148-5153 (2010).
Roberts, et al., "Molybdenum-Mediated Carbonylaiton of Aryl Halides with Nucleophiles Using Microwave Irradiation", Organic Letters, vol. 12 (19), 4280-4283 (2010).
Roberts, et al., "Novel Aryl and Heteroaryl Acyl Sulfamide Synthesis via Microwave-Assisted Palladium-Catalyzed Carbonylation", Organic Letters, vol. 12 (6), 1264-1267 (2010).
Ruan, et al., "Sodium channel mutations and arrhythmias", Nature Reviews Cardiology, 6, 337-348 (2009).
Rugiero, et al., "Selective Expression of a Persistent Tetrodotoxin-Resistant Na+ Current and NaV1.9 Subunit in Myenteric Sensory Neurons", J. Neurosci 23 (7), 2715-2725 (2003).
Sakuma, et al., "Preparation of piperazine", CA150:260220 (2009).
Sangameswaran, et al., "A novel tetrodotoxin-sensitive, voltage-gated sodium channel expressed in rat and human dorsal root ganglia", J. Bioi. Chern. 272 (23), 14805-14809 (1997).
Sato, et al., "The voltage-sensitive sodium channel is a bell-shaped molecule with several cavities", Nature 409, 1047-1051 (2001).
Schmelz, et al., "Itch and pain", Neuroscience and Biobehaviorial Reviews, 34, 171-176 (2010).
Amaya, et al., "The voltage-gated sodium channel Na(v)1.9 is an effector of peripheral inftammatory pain hypersensitivity", J. Neurosci 26 (50), 12852-12860 (2006).
Arcangeli, et al., "Targeting Ion Channels in Cancer: A Novel Frontier in AntineoplasticTherapy", Current Medicinal Chemistry 16, 66-93 (2009).
Bach, et al., "A novel series of piperazinyl-pyridine ureas as antagonists of the purinergic P2712 receptor", Bioorganic & Medicinal Chemistry Letters 21, 2877-2881 (2011).
Banks, et al., "The Reaction of N-Aikylhydroxamic Acids with Sulphinyl Chlorides", J. Chern. Soc. Perkin Trans. II, 1211-1216 (1986).
Bean, et al., "Lidocaine Block of Cardiac Sodium Channels", J. Gen. Physiol. 81, 613-642 (1983).
Binder, et al., "Disease Mechanisms in Neuropathic Itch", Nature Clinical Practice Neurology 4(6), 329-337 (2008).
Black, et al., "Changes in the expression of tetrodotoxin-sensitive sodium channels within dorsal root ganglia neurons in inflammatory pain", Pain 108 (3), 237-247 (2004).
Blair, et al., "Roles of tetrodotoxin (TIX)-sensitive Na+ current, TIX-resistant Na+ current, and Ca2+ current in the action potentials of nociceptive sensory neurons", J. Neurosci 22, 10277-10290 (2002).
Borhade, S, et al., "Preclinical Characterization of Acyl Sulfonimidamides: Potential Carboxylic Acid Bioisosteres with Tunable Properties", ChemMedChem 10, 455-460 (2015).
Brackenbury, et al., "Activity-dependent regulation of voltage-gated Na+ channel expression in Mat-LyLu rat prostate cancer cell line", J. Physiol 573.2, 343-356 (2006).
Braga, et al., "Making crystals from crystals: a green route to crystal engineering and polymorphism", Chern Commun J Roy Soc Chern, 3635-3645 (2005).
Caldwell, et al., "Sodium channel Na(v)1.6 is localized at nodes of ranvier, dendrites, and synapses", Proc. Nail. Acad. Sci. 97(10), 5616-5620 (2000).
CAS Registry, Nos. 1027529-26-5, 1027209-51-3 and 1026292-79-4, 1 page (2015).
Catron, et al., "Preparation of 4-[4-[2-phenylcclohexen-1-en-1-yl)methyl]piperazin-1-ui]-N-(phenylsulfonyl) 13 benzamides and 4-[4-[(2-phenylcyclohexen-1-en-1-yl)methyl]piperazin-1-71]-N-(3-pyridylsulfonlyl) benzamides", 'CAPLUS 2012:637301, 156:638098, 2 pages (2012).

(56) References Cited

OTHER PUBLICATIONS

Catterall, "From ionic currents to molecular mechanisms: the structure and function of voltage-gated sodium channels", Neuron 26 (1), 13-25 (2000).
Catterall, "Molecular mechanisms of gating and drug block of sodium channels", Novartis Foundation Symposium 241, 206-225 (2002).
Catterall, "Structural biology: A 3D view of sodium channels", Nature, vol. 409, 988-990 (2001).
Cestele, et al., "Molecular mechanisms of neurotoxin action on voltage-gated sodium channels", Biochimie vol. 82 (9-1 0), 883-892 (2000).
Chan, et al., "Rh(II)-Catalyzed Intermolecular Oxidative Sulfamidalion of Aldehydes: A Mild Efficient Synthesis of N-Sulfonylcarboxamides", J. Am. Chern. Soc., 129, 14106-14107 (2007).
Chemical Abstract Service, STN Registry Database No. 891026-77-0 [entered STN: Jul. 9, 2006].
Chemical Abstract Service, STN Registry Database No. 892698-09-8 [entered STN: Jul. 14, 2006].
Chemical Abstracts_4, XP002744146, Database accession No. 1294599-14-6 Abstract, (May 15, 2011).
Chemical Abstracts_1, XP002744143, Database accession No. 1321299-48-2 Abstract (Aug. 22, 2011).
Chemical Abstracts_10, XP002744152, Database accession No. 1288553-28-5 Abstract (May 1, 2011).
Chemical Abstracts_11, XP002744153, Database accession No. 1278399-39-5 Abstract (Apr. 11, 2011).
Chemical Abstracts_12, XP002744154, Database accession No. 1297052-59-5 Abstract (May 19, 2011).
Chemical Abstracts_13, XP002744155, Database accession No. 1277490-84-2 Abstract (Apr. 10, 2011).
Chemical Abstracts_2, XP002744144, Database accession No. 1320435-32-2 Abstract (Aug. 22, 2011).
Chemical Abstracts_3, XP002744145, Database accession No. 1319619-74-3 Abstract (Aug. 18, 2011).
Chemical Abstracts_5, XP002744147, Database accession No. 1051238-85-7 Abstract (Sep. 21, 2008).
Chemical Abstracts_6, XP002744148, Database accession No. 1051172-94-1 Abstract (Sep. 21, 2008).
Chemical Abstracts_7, XP002744149, Database accession No. 1301192-24-4 (May 26, 2011).
Chemical Abstracts_8, XP002744150, Database accession No. 1299653-84-3 Abstract (May 24, 2011).
Chemical Abstracts_9, XP002744151, Database accession No. 299214-10-0 (May 24, 2011).
Chen, Y, "N-Monoacylation of Sulfonimidamides", Synthesis, 48, 1019-1028 (2016).
Chioni, et al., "A novel adhesion molecule in human breast cancer cell lines: Voltage-gated Na+ channel β1 subunit", Int'l J. Biochem. Cell Biol. 41, 1216-1227 (2009).
Chung, et al., "Sodium channels and neuropathic pain", Novartis Foundation Symposium 261, 19-31 (2004).
Clare, et al., "Voltage-gated sodium channels as therapeutic targets", Drug Discovery Today 5(11), 506-520 (2000).
Cox, et al., "An SCN9A channelopathy causes congenital inability to experience pain", Nature 444, 894-898 (2006).
Daeniker, et al., "234. Uber bicyclische Sulfonamide", Helvetica Chimica ACTA, vol. 45 (6), 1972-1981 (1962). [English Translation.].
Database Reaxys, XP002692384, Accession No. XRN: 6729065, 6731122, 1 page, (D. Bertoia et al., ""Base 24 promoted ring-opening reactions of 2-p-lolyl-5,6-dihydro-1, 4,3-oxathizaine 4,4-dioxides, Gazella Chimica Ilaliana, vol. 118 (6), 435-440 (1988).
Deng, Jinxia, et al., "Dynamic 1-15 Receptor-Based Pharmacophore Model Development and Its Application in Designing Novel HIV-1 Integrase Inhibitors", Journal of Medicinal Chemistry. vol. 48. No. 5, 1496-1505 (2005), Supporting Information, S1-S14. XP055285519. DOI: 10.1021jjm049410e (2005).
Dermer, G, "Another Anniversary for the War on Cancer", Bio/Technology 12, 320 (1994).
Devor, et al., "Na+ ChannelImmunolocalization in Peripheral Mammalian Axons and Changes following Nerve Injury and Neuroma Formation", J. Neurosci. 13 (5), 1976-1992 (1993).
Dib-Hajj, et al., "Genetics and Molecular Pathophysiology of NaV1.7-related Pain Syndromes", Advances in Genetics 63,85-110 (2008).
Dib-Hajj, et al., "NaN, a novel voltage-gated Na channel, is expressed preferentially in peripheral sensory neurons and down-regulated after axotomy", Proc. Natl. Acad. Sci. 95 (15), 8963-8968 (1998).
Dib-Hajj, et al., "The Na(V)1.7 sodium channel: from molecule to man", Nature Reviews Neuroscience 14, 49-62 (2013).
Dickore, "Synthese and reaktionen von 1.3.4-oxathiazolin-3-dioxyden", Justus Liebigs Annalen Der Chemie, vol. 671, 135-146, XP055053742, Compounds IVa, IVb, IVd, V, VI (1964). [English Translation.].
Diss, et al., "A potential novel marker for human prostate cancer: voltage-gated sodium channel expression in vivo", Prostate Cancer and Prostatic Diseases 8, 266-273 (2005).
Diss, et al., "Expression profiles of voltage-gated sodium channel a-subunit genes in rat and human prostate cancer cell lines", The Prostate 48, 165-178 (2001).
Seddon, "Pseudopolymorph: A Polemic", Crystal Growth and Design vol. 4(6), 1087 (2004).
Silos-Santiago, "Drugs in Clinical Development for Neuropathic Pain", presented at First World Conference Abdominal and Pelvic Pain, Amsterdam, pp. 1-23 (Jun. 6, 2013).
Smith, et al., "Sodium channel protein expression enhances the invasiveness of rat and human prostate cancer cells", FEBS Letters, 423, 19-24 (1998).
Tamaoka, "Paramyotonia congenita and skeletal sodium channelopathy", Intern. Med. 42 (9), 769-770 (2003).
Tanelian, et al., "Neuropathic pain can be relieved by drugs that are use-dependent sodium channel blockers: lidocaine, carbamazepine and mexiletine", Anesthesiology, 74(5), 949-951 (1991).
Termin, et al., "Recent Advances in Voltage-Gated Sodium Channel Blockers: Therapeutic Potential as Drug Targets in the CNS", Annual Reports in Medicinal Chemistry 43, 43-60 (2008).
Toledo-Aral, et al., "Identification of PN1, a predominant voltage-dependent sodium channel expressed principally in peripheral neurons", Proc. Nail. Acad. Sci. 94 (4), 1527-1532 (1997).
Vetter, I, et al., "Nav1.7 as a pain target—From gene to pharmacology", Pharmacology & Therapeutics 172, 73-100 (2017).
Villamil, et al., "Efficacy of lidocaine in the treatment of pruritus in patients with chronic chlolestatic liver disease", Am. J. Med, 118, 1160-1163 (2005).
Vippagunta, et al., "Crystal Solids", Adv Drug Del Rev vol. 48, 3-26 (2001).
Wakchaure, P, et al., "Synthesis of Vinyl- and Aryl-Acyl Sulfonimifamides Through Pd-Catalyzed Carbonylation Using Mo(CO)6 as ex situ CO Source", Eur. J. Org. Chem, 213-219 (2015).
Wallace, et al., "Efficacy of oral mexileline for neuropathic pain with allodynia: a double-blind, placebo-controlled, crossover study", Reg. Anesth. Pain Med. 25 (5), 459-467 (2000).
Wolff, "Burger's Medicinal Chemistry and Drug Discovery", Fifth Edition, vol. 1: Principles and Practice, 975-977 (1995).
Wood, et al., "Voltage-gated sodium channels and pain pathways", J. Neurobiol. 61(1), 55-71 (2004).
Xiao, et al., "C-fiber spontaneous discharge evoked by chronic inftammation is suppressed by a long-term infusion of lidocaine yielding nanogram per milliliter plasma levels", Pain, 137,218-228 (2008).
Yang, et al., "Mutations in SCN9A, encoding a sodium channel alpha subunit, in patients with primary erythermalgia", J. Med. Genet. 41 (3), 171-174 (2004).
Yu, et al., "Reduced sodium current in GABAergic interneurons in a mouse model of severe myoclonic epilepsy in infancy", Nat. Neurosci 9, 1142-1149 (2006).
Yu, et al., "Sodium Channel β4. a New Disulfide-Linked Auxiliary Subunit with Similarity to β2", J. Neurosci. 23(20), 7577-7585 (2003).

(56) References Cited

OTHER PUBLICATIONS

Yu, et al., "The VGL-chanome: a protein superfamily specialized for electrical signaling and ionic homeostasis", Sci. STKE 253, re15, 17 pages (2004).
Zhao, et al., "Voltage-gated sodium channel expression in rat and human epidermal keratinocytes: evidence for a role pain", Pain, 139, 90-105 (2008).
Zuliani, et al., "Sodium channel blockers for neuropathic pain", Expert Opinion Ther Patents 20(6), 755-779 (2010).

THERAPEUTIC COMPOUNDS AND METHODS OF USE THEREOF

CROSS-REFERENCE TO RELATED APPLICATION

This application claims priority to International Application Number PCT/CN2018/081250 filed Mar. 30, 2018. The entire content of the application referenced above is hereby incorporated by reference herein.

The present invention relates to organic compounds useful for therapy in a mammal, and in particular to inhibitors of sodium channel (e.g., NaV1.7) that are useful for treating sodium channel-mediated diseases or conditions, such as pain, as well as other diseases and conditions associated with the modulation of sodium channels.

Voltage-gated sodium channels are transmembrane proteins that initiate action potentials in nerve, muscle and other electrically excitable cells, and are a necessary component of normal sensation, emotions, thoughts and movements (Catterall, W. A., Nature (2001), Vol. 409, pp. 988-990). These channels consist of a highly processed alpha subunit that is associated with auxiliary beta subunits. The pore-forming alpha subunit is sufficient for channel function, but the kinetics and voltage dependence of channel gating are in part modified by the beta subunits (Goldin et al., Neuron (2000), Vol. 28, pp. 365-368). Electrophysiological recording, biochemical purification, and molecular cloning have identified ten different sodium channel alpha subunits and four beta subunits (Yu, F. H., et al., Sci. STKE (2004), 253; and Yu, F. H., et al., Neurosci. (2003), 20:7577-85).

The sodium channel family of proteins has been extensively studied and shown to be involved in a number of vital body functions. Research in this area has identified variants of the alpha subunits that result in major changes in channel function and activities, which can ultimately lead to major pathophysiological conditions. The members of this family of proteins are denoted NaV1.1 to NaV1.9.

NaV1.7 is a tetrodotoxin-sensitive voltage-gated sodium channel encoded by the gene SCN9A. Human NaV1.7 was first cloned from neuroendocrine cells (Klugbauer, N., et al., 1995 EMBO J., 14 (6): 1084-90.) and rat NaV1.7 was cloned from a pheochromocytoma PC12 cell line (Toledo-Aral, J. J., et al., Proc. Natl. Acad. Sci. USA (1997), 94:1527-1532) and from rat dorsal root ganglia (Sangameswaran, L., et al., (1997), J. Biol. Chem., 272 (23): 14805-9). NaV1.7 is expressed primarily in the peripheral nervous system, especially nociceptors and olfactory neurons and sympathetic neurons. The inhibition, or blocking, of NaV1.7 has been shown to result in analgesic activity. Knockout of NaV1.7 expression in a subset of sensory neurons that are predominantly nociceptive results in resistance to inflammatory pain (Nassar, et al., op. cit.). Likewise, loss of function mutations in humans results in congenital indifference to pain (CIP), in which the individuals are resistant to both inflammatory and neuropathic pain (Cox, J. J., et al., Nature (2006); 444:894-898; Goldberg, Y. P., et al., Clin. Genet. (2007); 71:311-319). Conversely, gain of function mutations in NaV1.7 have been established in two human heritable pain conditions, primary erythromelalgia and familial rectal pain, (Yang, Y., et al., J. Med. Genet. (2004), 41(3): 171-4). In addition, a single nucleotide polymorphism (R1150W) that has very subtle effects on the time- and voltage-dependence of channel gating has large effects on pain perception (Estacion, M., et al., 2009. Ann Neurol 66: 862-6; Reimann, F., et al., Proc Natl Acad Sci USA (2010), 107: 5148-53). About 10% of the patients with a variety of pain conditions have the allele conferring greater sensitivity to pain and thus might be more likely to respond to block of NaV1.7. Because NaV1.7 is expressed in both sensory and sympathetic neurons, one might expect that enhanced pain perception would be accompanied by cardiovascular abnormalities such as hypertension, but no correlation has been reported. Thus, both the CIP mutations and SNP analysis suggest that human pain responses are more sensitive to changes in NaV1.7 currents than are perturbations of autonomic function.

Sodium channel blockers have been shown to be useful in the treatment of pain, (see, e.g., Wood, J. N., et al., J. Neurobiol. (2004), 61(1), 55-71. Genetic and functional studies have provided evidence to support that activity of NaV1.7 as a major contributor to pain signalling in mammals. (See Hajj, et al. Nature Reviews Neuroscience; 2013, vol 14, 49-62; and Lee, et al. Cell; 2014, vol 157; 1-12). Presently, there are a limited number of effective sodium channel blockers for the treatment of pain with a minimum of adverse side effects which are currently in the clinic. Thus there remains a need for selective voltage-gated sodium channel modulators (e.g., modulators of NaV1.7) that can provide a greater therapeutic index for treatment.

SUMMARY

In one aspect the present invention provides novel compounds having sodium channel blocking activity that are useful for the treatment of pain.

In a first embodiment (Embodiment 1; abbreviated as "E1") the invention provides a compound of the invention, which is a compound of formula (I):

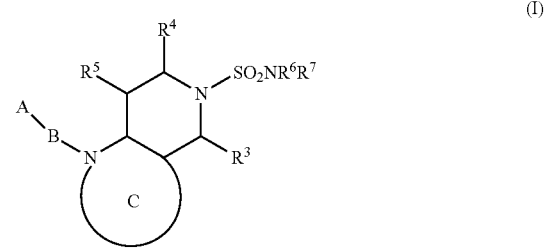

or a pharmaceutically acceptable salt thereof, wherein,

A is a 6-12 membered aryl ring that is optionally substituted with one or more groups $R^A$ independently selected from the group consisting of F, Cl, Br, I, —CN, —C(=O)OR$^{A1}$, —SO$_2$R$^{A1}$, —OR$^{A1}$, —(X$^{RA}$)-(3-15 membered carbocyclyl), —(X$^{RA}$)-(6-12 membered aryl), —(X$^{RA}$)-(5-12 membered heteroaryl), and —R$^{A2}$, wherein said 3-15 membered carbocyclyl, 6-12 membered aryl, and 5-12 membered heteroaryl of $R^A$ is optionally substituted with from 1 to 5 substitutents $R^a$ independently selected from the group consisting of F, Cl, Br, I, C$_{1-4}$ alkyl, halo(C$_{1-4}$alkyl), amino, (C$_{1-4}$ alkyl)amino, di(C$_{1-4}$alkyl)amino, halo(C$_{1-4}$alkoxy), and —C(O)N(R)$_2$; R$^{A1}$ is selected from the group consisting of hydrogen, C$_{1-8}$ alkyl, C$_{2-8}$ alkenyl, halo(C$_{1-8}$alkyl), C$_{3-8}$ cycloalkyl, phenyl and benzyl; R$^{A2}$ is selected from the group consisting of C$_{1-8}$ alkyl that is optionally substituted with one or more substituents independently selected from oxo (=O), fluoro, hydroxy, amino, (C$_{1-4}$ alkyl)amino and di(C$_{1-4}$alkyl)amino; X$^{RA}$ is selected from the group consisting of absent, —C(=O)—, and C$_{1-4}$ alkylene; wherein any C$_{1-4}$ alkylene, of X$^{RA}$ is optionally substituted with 1 to 3 substituents independently selected from the group consisting of C$_{1-4}$ alkyl, halo(C$_{1-4}$alkyl), and phenyl that is optionally substituted with 1 to 5 substitutents independently selected from, F, Cl, Br, I, —NH$_2$, —OH, —CN, —NO$_2$, C$_{1-4}$ alkyl, halo(C$_{1-4}$alkyl), C$_{1-4}$ alkoxy, halo(C$_{1-4}$alkoxy), (C$_{1-4}$ alkyl)amino and di(C$_{1-4}$alkyl)amino;

B is a 5-12 membered heteroaryl or a 6-12 membered aryl ring, wherein ring B is optionally substituted with one or more groups R$^B$ independently selected from the group consisting of F, Cl, Br, I, —CN, —C(=O)OR$^{B1}$, —SO$_2$R$^{B1}$, —OR$^{B1}$, —(X$^{RB}$)-(3-15 membered carbocyclyl), —(X$^{RB}$)-(6-12 membered aryl), —(X$^{RB}$)-(5-12 membered heteroaryl), and —R$^{B2}$, wherein said 3-15 membered carbocyclyl, 6-12 membered aryl, and 5-12 membered heteroaryl of R$^B$ is optionally substituted with from 1 to 5 substituents R$^b$ independently selected from the group consisting of F, Cl, Br, I, C$_{1-4}$ alkyl, halo(C$_{1-4}$alkyl), amino, (C$_{1-4}$ alkyl)amino, di(C$_{1-4}$alkyl)amino, halo(C$_{1-4}$alkoxy), and —C(O)N(R)$_2$; RBI is selected from the group consisting of hydrogen, C$_{1-8}$ alkyl, C$_{2-8}$ alkenyl, halo(C$_{1-8}$alkyl), C$_{3-8}$ cycloalkyl, phenyl and benzyl; R$^{B2}$ is selected from the group consisting of C$_{1-8}$ alkyl that is optionally substituted with one or more substituents independently selected from oxo (=O), fluoro, hydroxy, amino, (C$_{1-4}$ alkyl)amino and di(C$_{1-4}$alkyl)amino; X$^{RB}$ is selected from the group consisting of absent, —C(=O)—, and C$_{1-4}$ alkylene; wherein any C$_{1-4}$ alkylene, of X$^{RB}$ is optionally substituted with 1 to 3 substituents independently selected from the group consisting of C$_{1-4}$ alkyl, halo(C$_{1-4}$alkyl), and phenyl that is optionally substituted with 1 to 5 substitutents independently selected from, F, Cl, Br, I, —NH$_2$, —OH, —CN, —NO$_2$, C$_{1-4}$ alkyl, halo(C$_{1-4}$alkyl), C$_{1-4}$ alkoxy, halo(C$_{1-4}$alkoxy), (C$_{1-4}$ alkyl) amino and di(C$_{1-4}$ alkyl)amino;

ring C is a 5-, 6-, or 7-membered heterocyclyl, which 5-, 6-, or 7-membered heterocyclyl is optionally substituted with one or more groups R$^c$ independently selected from the group consisting of C$_{1-4}$alkyl, halo, oxo (=O), thioxo (=S), and halo(C$_{1-4}$ alkyl);

R$^3$, R$^4$, and R$^5$ are each independently selected from the group consisting of H, F, C$_{1-4}$ alkyl, C$_{3-8}$ cycloalkyl, halo (C$_{1-8}$alkyl) and C$_{1-8}$ alkoxy; and R$^6$ is selected from the group consisting of H, C$_{1-8}$ alkyl, C$_{3-8}$ cycloalkyl, aryl, and aryl(C$_{1-4}$ alkyl); and R$^7$ is selected from the group consisting of C$_{1-8}$ alkyl, 3-15 membered heterocyclyl, 5-12 membered heteroaryl, —C(O)N(R$^d$)$_2$ and —C(=NCN)N(R$^d$)$_2$; or R$^6$ and R$^7$, together with the nitrogen to which they are attached, form a 3-15 membered heterocyclyl or 5-12 membered heteroaryl; wherein any C$_{1-8}$alkyl, C$_{3-8}$cycloalkyl, aryl, aralkyl, 3-15 membered heterocyclyl, and 5-12 membered heteroaryl is optionally substituted with one or more groups R$^e$ that are independently selected from the group consisting of F, Cl, Br, I, —NH$_2$, —OH, —CN, —NO$_2$, C$_{1-4}$ alkyl, halo(C$_{1-4}$alkyl), C$_{1-4}$ alkoxy, halo(C$_{1-4}$alkoxy), (C$_{1-4}$ alkyl)amino and di(C$_{1-4}$alkyl)amino; each R$^d$ is independently selected from the group consisting of hydrogen, C$_{1-8}$ alkyl, C$_{3-8}$ cycloalkyl, phenyl and benzyl.

In a second embodiment (Embodiment 2; abbreviated as "E2") the invention provides for a compound of formula I which is a compound of formula Ia:

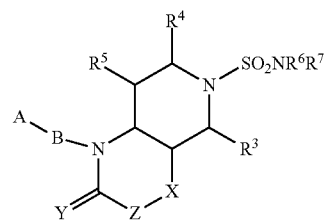

(Ia)

wherein, X is CH$_2$, O, S, SO, or SO$_2$; Y is H$_2$ or O; and Z is CH$_2$ or O; provided that when Z is O, X is CH$_2$.

In another embodiment (Embodiment 3; abbreviated as "E3") the invention provides for a compound of formula I which is a compound of formula Ib:

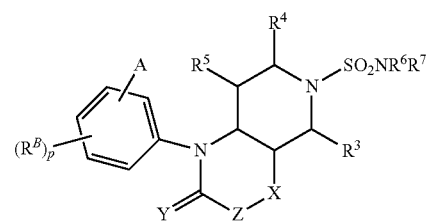

(Ib)

wherein, X is CH$_2$, O, S, SO, or SO$_2$; Y is H$_2$, or O; Z is CH$_2$ or O; provided that when Z is O, X is CH$_2$; and p is 1, 2, 3, or 4, or a pharmaceutically acceptable salt thereof.

In another embodiment (Embodiment 4; abbreviated as "E4") the invention provides for a compound of formula I which is a compound of formula Ic:

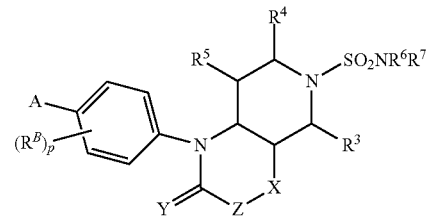

(Ic)

wherein, X is CH$_2$, O, S, SO, or SO$_2$; Y is H$_2$, or O; Z is CH$_2$ or O; provided that when Z is O, X is CH$_2$; and p is 1, 2, 3, or 4, or a pharmaceutically acceptable salt thereof.

In another embodiment (Embodiment 5; abbreviated as "E5") the invention provides for a compound of formula I which is a compound of formula Id:

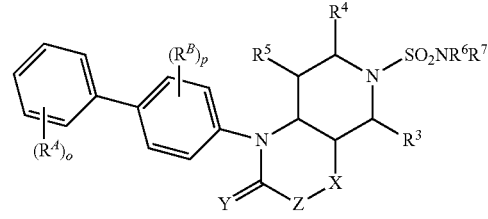

(Id)

wherein, X is CH$_2$, O, S, SO, or SO$_2$; Y is H$_2$, or O; Z is CH$_2$ or O; provided that when Z is O, X is CH$_2$; p is 1, 2, 3, or 4; and o is 1, 2, 3, 4, or 5; or a pharmaceutically acceptable salt thereof.

In another embodiment (Embodiment 6; abbreviated as "E6") the invention provides for a compound of formula I which is a compound of formula Ie:

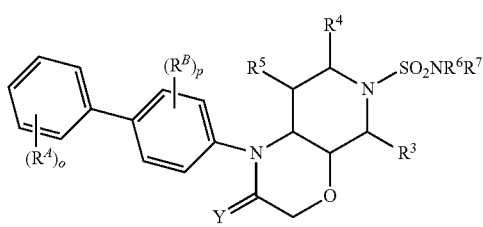

wherein, Y is H$_2$, or O; p is 1, 2, 3, or 4; and o is 1, 2, 3, 4, or 5; or a pharmaceutically acceptable salt thereof.

In another embodiment (Embodiment 7; abbreviated as "E7") the invention provides for a compound of formula I which is a compound of formula If:

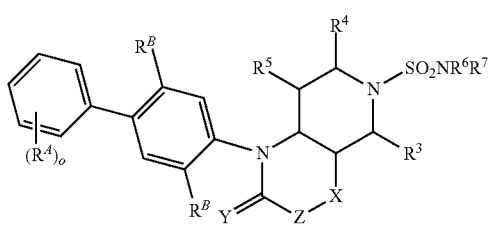

wherein, X is CH$_2$, O, S, SO, or SO$_2$; Y is H$_2$, or O; Z is CH$_2$ or O; provided that when Z is O, X is CH$_2$; and o is 1, 2, 3, 4, or 5; or a pharmaceutically acceptable salt thereof.

In another embodiment (Embodiment 8; abbreviated as "E8") the invention provides for a compound of formula I which is a compound of formula Ig:

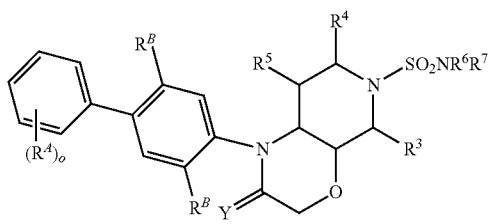

wherein, Y is H$_2$, or O; and o is 1, 2, 3, 4, or 5; or a pharmaceutically acceptable salt thereof.

Further embodiments of the compounds of the invention are described below.

E9. A compound of E2, E3, E4, E5, or E7, or a pharmaceutically acceptable salt thereof, wherein X is O, S, SO, or SO$_2$; Y is H$_2$; and Z is CH$_2$.

E10. A compound of E2, E3, E4, E5, or E7, or a pharmaceutically acceptable salt thereof, wherein X is O, S, SO, or SO$_2$; Y is O; and Z is CH$_2$.

E11. A compound of E6 or E8, or a pharmaceutically acceptable salt thereof, wherein Y is H$_2$.

E12. A compound of E6 or E8, or a pharmaceutically acceptable salt thereof, wherein Y is O.

E13. A compound of E1, E2, E3, E4, E5, E6, E7, E8, E9, E10, E11, or E12, or a pharmaceutically acceptable salt thereof, wherein R$^3$ is H.

E14. A compound of E1, E2, E3, E4, E5, E6, E7, E8, E9, E10, E11, or E12, or a pharmaceutically acceptable salt thereof, wherein R$^4$ is H.

E15. A compound of E1, E2, E3, E4, E5, E6, E7, E8, E9, E10, E11, or E12, or a pharmaceutically acceptable salt thereof, wherein R$^5$ is H.

E16. A compound of E1, E2, E3, E4, E5, E6, E7, E8, E9, E10, E11, or E12, or a pharmaceutically acceptable salt thereof, wherein R$^3$, R$^4$, and R$^5$ are each independently selected from the group consisting of H, F, and C$_{1-4}$ alkyl.

E17. A compound of E1, E2, E3, E4, E5, E6, E7, E8, E9, E10, E11, or E12, or a pharmaceutically acceptable salt thereof, wherein R$^3$, R$^4$, and R$^5$ are each H.

E18. A compound of E1, E2, E3, E4, E5, E6, E7, E8, E9, E10, E11, E12, E13, E14, E15, E16 or E17, or a pharmaceutically acceptable salt thereof, wherein —NR$^6$R$^7$ is:

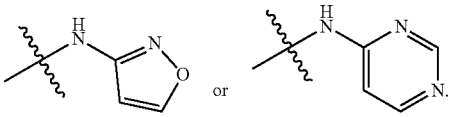 [SMILES: *Nc1ccon1 ; *Nc1ccncn1]

E19. A compound of E1, E2, E3, E4, E5, E6, E7, E8, E9, E10, E11, E12, E13, E14, E15, E16 or E17, or a pharmaceutically acceptable salt thereof, wherein —NR$^6$R$^7$ is:

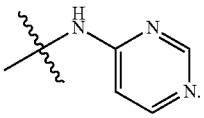

E20. A compound of E1, E2, E3, E4, E5, E6, E7, E8, E9, E10, E11, E12, E13, E14, E15, E16 or E17, or a pharmaceutically acceptable salt thereof, wherein R$^6$ is H and R$^7$ is 5-6 membered heteroaryl.

E21. A compound of E1, E2, E3, E4, E5, E6, E7, E8, E9, E10, E11, E12, E13, E14, E15, E16, E17, E18, E19, or E20, or a pharmaceutically acceptable salt thereof, wherein each R$^A$ is independently selected from the group consisting of, F, Cl, Br, I, —OR$^{41}$, and —R$^{42}$, wherein R$^{41}$ is selected from the group consisting of C$_{1-8}$ alkyl and halo(C$_{1-8}$alkyl), and wherein R$^{42}$ is C$_{1-8}$ alkyl that is optionally substituted with one or more substituents independently selected from the group consisting of fluoro and chloro.

E22. A compound of E1, E2, E3, E4, E5, E6, E7, E8, E9, E10, E11, E12, E13, E14, E15, E16, E17, E18, E19, E20, or E21, or a pharmaceutically acceptable salt thereof, wherein each R$^B$ is independently selected from the group consisting of, F, Cl, Br, I, —CN, and —OR$^{41}$, wherein R$^{41}$ is selected from the group consisting of C$_{1-8}$ alkyl and halo(C$_{1-8}$alkyl).

E23. A compound of E1, E2, E3, E4, E5, E6, E7, E8, E9, E10, E11, E12, E13, E14, E15, E16, E17, E18, E19, E20, E21 or E22, or a pharmaceutically acceptable salt thereof, wherein each R$^A$ is independently selected from the group consisting of, F, Cl, trifluoromethoxy, CF$_2$, and CF$_3$.

E24. A compound of E1, E2, E3, E4, E5, E6, E7, E8, E9, E10, E11, E12, E13, E14, E15, E16, E17, E18, E19, E20, E21, E22, or E23, or a pharmaceutically acceptable salt thereof, wherein each $R^B$ is independently selected from the group consisting of, F, —CN, and methoxy.

In another aspect the present invention provides for a pharmaceutical composition comprising a compound as described herein or a pharmaceutically acceptable salt thereof, and a pharmaceutically acceptable excipient.

In another aspect the present invention provides for a method of treating a disease or condition in a mammal selected from the group consisting of pain, depression, cardiovascular diseases, respiratory diseases, and psychiatric diseases, and combinations thereof, wherein the method comprises administering to the mammal in need thereof a therapeutically effective amount of a compound as described herein, or a pharmaceutically acceptable salt thereof. In another aspect of the present invention said disease or condition is selected from the group consisting of neuropathic pain, inflammatory pain, visceral pain, cancer pain, chemotherapy pain, trauma pain, surgical pain, post-surgical pain, childbirth pain, labor pain, neurogenic bladder, ulcerative colitis, chronic pain, persistent pain, peripherally mediated pain, centrally mediated pain, chronic headache, migraine headache, sinus headache, tension headache, phantom limb pain, dental pain, peripheral nerve injury or a combination thereof. In another aspect of the present invention said disease or condition is selected from the group consisting of pain associated with HIV, HIV treatment induced neuropathy, trigeminal neuralgia, post-herpetic neuralgia, eudynia, heat sensitivity, tosarcoidosis, irritable bowel syndrome, Crohns disease, pain associated with multiple sclerosis (MS), amyotrophic lateral sclerosis (ALS), diabetic neuropathy, peripheral neuropathy, arthritis, rheumatoid arthritis, osteoarthritis, atherosclerosis, paroxysmal dystonia, myasthenia syndromes, myotonia, malignant hyperthermia, cystic fibrosis, pseudoaldosteronism, rhabdomyolysis, hypothyroidism, bipolar depression, anxiety, schizophrenia, sodium channel toxin related illnesses, familial erythromelalgia, primary erythromelalgia, familial rectal pain, cancer, epilepsy, partial and general tonic seizures, restless leg syndrome, arrhythmias, fibromyalgia, neuroprotection under ischaemic conditions cause by stroke or neural trauma, tach-arrhythmias, atrial fibrillation and ventricular fibrillation.

In another aspect the present invention provides for a method of treating pain in a mammal by the inhibition of ion flux through a voltage-dependent sodium channel in the mammal, wherein the method comprises administering to the mammal in need thereof a therapeutically effective amount of a compound as described herein, or a pharmaceutically acceptable salt thereof.

In another aspect the present invention provides for a method of decreasing ion flux through a voltage-dependent sodium channel in a cell in a mammal, wherein the method comprises contacting the cell with a compound as described herein, or a pharmaceutically acceptable salt thereof.

In another aspect the present invention provides for a method of treating pruritus in a mammal, wherein the method comprises administering to the mammal in need thereof a therapeutically effective amount of a compound of the invention, or a pharmaceutically acceptable salt thereof.

In another aspect the present invention provides for a method of treating cancer in a mammal, wherein the method comprises administering to the mammal in need thereof a therapeutically effective amount a compound as described herein, or a pharmaceutically acceptable salt thereof.

In another aspect the present invention provides for a method of treating, but not preventing, pain in a mammal, wherein the method comprises administering to the mammal in need thereof a therapeutically effective amount of a compound as described herein, or a pharmaceutically acceptable salt thereof. In another aspect of the present invention the pain is selected from the group consisting of neuropathic pain, inflammatory pain, visceral pain, cancer pain, chemotherapy pain, trauma pain, surgical pain, post-surgical pain, childbirth pain, labor pain, neurogenic bladder, ulcerative colitis, chronic pain, persistent pain, peripherally mediated pain, centrally mediated pain, chronic headache, migraine headache, sinus headache, tension headache, phantom limb pain, dental pain, peripheral nerve injury or a combination thereof. In another aspect the present invention the pain is associated with a disease or condition selected from the group consisting of HIV, HIV treatment induced neuropathy, trigeminal neuralgia, post-herpetic neuralgia, eudynia, heat sensitivity, tosarcoidosis, irritable bowel syndrome, Crohns disease, pain associated with multiple sclerosis (MS), amyotrophic lateral sclerosis (ALS), diabetic neuropathy, peripheral neuropathy, arthritis, rheumatoid arthritis, osteoarthritis, atherosclerosis, paroxysmal dystonia, myasthenia syndromes, myotonia, malignant hyperthermia, cystic fibrosis, pseudoaldosteronism, rhabdomyolysis, hypothyroidism, bipolar depression, anxiety, schizophrenia, sodium channel toxin related illnesses, familial erythromelalgia, primary erythromelalgia, familial rectal pain, cancer, epilepsy, partial and general tonic seizures, restless leg syndrome, arrhythmias, fibromyalgia, neuroprotection under ischaemic conditions cause by stroke or neural trauma, tach-arrhythmias, atrial fibrillation and ventricular fibrillation.

In another aspect the present invention provides for a method for the treatment or prophylaxis of pain, depression, cardiovascular disease, respiratory disease, or psychiatric disease, or a combinations thereof, in an animal which method comprises administering an effective amount of a compound of as described herein, or a pharmaceutically acceptable salt thereof.

In another aspect the present invention provides for a compound as described herein, or a pharmaceutically acceptable salt thereof for the use as a medicament for the treatment of diseases and disorders selected from the group consisting of pain, depression, cardiovascular diseases, respiratory diseases, and psychiatric diseases, or a combination thereof.

In another aspect the present invention provides for the use of a compound as described herein, or a pharmaceutically acceptable salt thereof for the manufacture of a medicament for the treatment of diseases and disorders selected from the group consisting of pain, depression, cardiovascular diseases, respiratory diseases, and psychiatric diseases, or a combination thereof.

In another aspect the present invention provides for the invention as described herein.

DETAILED DESCRIPTION

Definitions

As used herein, the term "alkyl", by itself or as part of another substituent, means, unless otherwise stated, a straight or branched chain hydrocarbon radical, having the number of carbon atoms designated (i.e., $C_{1-8}$ means one to eight carbons). Examples of alkyl groups include methyl, ethyl, n-propyl, iso-propyl, n-butyl, t-butyl, iso-butyl, sec-butyl, n-pentyl, n-hexyl, n-heptyl, n-octyl, and the like.

The terms "alkoxy," "alkylamino" and "alkylthio", are used in their conventional sense, and refer to those alkyl groups attached to the remainder of the molecule via an oxygen atom ("oxy"), an amino group ("amino") or thio group. Additionally, for dialkylamino groups, the alkyl portions can be the same or different.

The terms "halo" by itself or as part of another substituent, mean, unless otherwise stated, a fluorine, chlorine, bromine, or iodine atom.

The term "halo($C_{1-x}$alkyl)" refers to an alkyl that has 1-x carbon atoms and that is substituted with one or more (e.g. 1, 2, 3, 4, 5, or 6) halo groups. For example the term includes an alkyl group having 1-6 carbon atoms that is substituted with one or more halo groups. Non-limiting examples of the term halo($C_1$-$C_6$alkyl) include fluoromethyl, difluoromethyl, trifluoromethyl, chloromethyl, and 2,2,2-trifluoroethyl.

The term "halo($C_{1-x}$alkoxy)" refers to an alkoxy group that has 1-x carbon atoms and that is substituted with one or more (e.g. 1, 2, 3, 4, 5, or 6) halo groups. For example the term includes an alkoxy group having 1-6 carbon atoms that is substituted with one or more halo groups. Non-limiting examples of the term halo($C_1$-$C_6$alkyl) include fluoromethoxy, difluoromethoxy, trifluoromethoxy, chloromethoxy, and 2,2,2-trifluoroethoxy.

The term "aryl" as used herein refers to a single all carbon aromatic ring or a multiple condensed all carbon ring system wherein at least one of the rings is aromatic. For example, in certain embodiments, an aryl group has 6 to 12 carbon atoms. Aryl includes a phenyl radical. Aryl also includes multiple condensed ring systems (e.g., ring systems comprising 2, 3 or 4 rings) having about 9 to 12 carbon atoms in which at least one ring is aromatic and wherein the other rings may be aromatic or not aromatic (i.e., carbocycle). Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. Non-limiting examples of aryl groups include, but are not limited to, phenyl, indenyl, naphthyl, 1, 2, 3, 4-tetrahydronaphthyl, and the like.

The term "carbocycle" or "carbocyclyl" refers to a single saturated (i.e., cycloalkyl) or a single partially unsaturated (e.g., cycloalkenyl, cycloalkadienyl, etc.) all carbon ring having 3 to 7 carbon atoms (i.e., ($C_3$-$C_7$)carbocycle). The term "carbocycle" or "carbocyclyl" also includes multiple condensed, saturated and partially unsaturated all carbon ring systems (e.g., ring systems comprising 2, 3 or 4 carbocyclic rings). Accordingly, carbocycle includes multicyclic carbocyles such as a bicyclic carbocycles (e.g., bicyclic carbocycles having about 6 to 15 or 6 to 12 carbon atoms such as bicyclo[3.1.0]hexane and bicyclo[2.1.1]hexane), and polycyclic carbocycles (e.g tricyclic and tetracyclic carbocycles with up to about 15 carbon atoms). The rings of the multiple condensed ring system can be connected to each other via fused, spiro and bridged bonds when allowed by valency requirements. For example, multicyclic carbocyles can be connected to each other via a single carbon atom to form a spiro connection (e.g., spiropentane, spiro[4,5]decane, etc), via two adjacent carbon atoms to form a fused connection (e.g., carbocycles such as decahydronaphthalene, norsabinane, norcarane) or via two non-adjacent carbon atoms to form a bridged connection (e.g., norbornane, bicyclo[2.2.2]octane, etc). The "carbocycle" or "carbocyclyl" can also be optionally substituted with one or more (e.g., 1, 2 or 3) oxo groups. In one embodiment the term carbocycle includes a $C_{3-15}$ carbocycle. In one embodiment the term carbocycle includes a $C_{3-12}$ carbocycle. In one embodiment the term carbocycle includes a $C_{3-8}$ carbocycle. In one embodiment the term carbocycle includes a $C_{3-6}$ carbocycle. In one embodiment the term carbocycle includes a $C_{3-5}$ carbocycle. Non-limiting examples of carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, bicyclo[2.2.1]heptane, pinane, adamantane, norborene, spirocyclic $C_{5-12}$ alkane, and 1-cyclohex-3-enyl. In one embodiment the term "cycloalkyl" refers to a single saturated all carbon ring having 3 to 8 carbon atoms. Non-limiting examples of carbocycles include cyclopropyl, cyclobutyl, cyclopentyl, and cyclohexyl.

The term "heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from heteroaryls (to form for example a naphthyridinyl such as 1,8-naphthyridinyl), heterocycles, (to form for example a 1, 2, 3, 4-tetrahydronaphthyridinyl such as 1,2,3,4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system) has about 1-20 carbon atoms and about 1-6 heteroatoms within the heteroaryl ring. A heteroaryl (a single aromatic ring or multiple condensed ring system) can also have about 5 to 12 or about 5 to 10 members within the heteroaryl ring. Multiple condensed ring systems may be optionally substituted with one or more (e.g., 1, 2, 3 or 4) oxo groups on the carbocycle or heterocycle portions of the condensed ring. The rings of a multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heteroaryl) can be at any position of the multiple condensed ring system including a heteroaryl, heterocycle, aryl or carbocycle portion of the multiple condensed ring system. It is also to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen).

Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl, thianaphthenyl, pyrrolo[2,3-b]pyridinyl, quinazolinyl-4(3H)-one, triazolyl, 4,5,6,7-tetrahydro-1H-indazole and 3b,4,4a,5-tetrahydro-1H-cyclopropa[3,4]cyclopenta[1,2-c]pyrazole. In one embodiment the term "heteroaryl" refers to a single aromatic ring containing at least one heteroatom. For example, the term includes 5-membered and 6-membered monocyclic aromatic rings that include one or more heteroatoms. Non-limiting examples of heteroaryl include but are not limited to pyridyl, furyl, thiazole, pyrimidine, oxazole, and thiadiazole.

The term "heterocyclyl" or "heterocycle" as used herein refers to a single saturated or partially unsaturated ring that has at least one atom other than carbon in the ring, wherein the atom is selected from the group consisting of oxygen, nitrogen and sulfur; the term also includes multiple condensed ring systems that have at least one such saturated or partially unsaturated ring, which multiple condensed ring systems are further described below. Thus, the term includes single saturated or partially unsaturated rings (e.g., 3, 4, 5, 6 or 7-membered rings) from about 1 to 6 carbon atoms and from about 1 to 3 heteroatoms selected from the group consisting of oxygen, nitrogen and sulfur in the ring. The ring may be substituted with one or more (e.g., 1, 2 or 3) oxo groups and the sulfur and nitrogen atoms may also be present in their oxidized forms. Exemplary heterocycles include but are not limited to azetidinyl, tetrahydrofuranyl and piperidinyl. The term "heterocycle" also includes multiple condensed ring systems (e.g., ring systems comprising 2, 3 or 4 rings) wherein a single heterocycle ring (as defined above) can be condensed with one or more groups selected from heterocycles (to form for example a 1,8-decahydronapthyridinyl), carbocycles (to form for example a decahydroquinolyl) and aryls to form the multiple condensed ring system. Thus, a heterocycle (a single saturated or single partially unsaturated ring or multiple condensed ring system) has about 2-20 carbon atoms and 1-6 heteroatoms within the heterocycle ring. Such multiple condensed ring systems may be optionally substituted with one or more (e.g., 1, 2, 3 or 4) oxo groups on the carbocycle or heterocycle portions of the multiple condensed ring. The rings of the multiple condensed ring system can be connected to each other via fused, spiro and bridged bonds when allowed by valency requirements. It is to be understood that the individual rings of the multiple condensed ring system may be connected in any order relative to one another. Accordingly, a heterocycle (a single saturated or single partially unsaturated ring or multiple condensed ring system) has about 3-20 atoms including about 1-6 heteroatoms within the heterocycle ring system. It is also to be understood that the point of attachment of a multiple condensed ring system (as defined above for a heterocycle) can be at any position of the multiple condensed ring system including a heterocycle, aryl and carbocycle portion of the ring. It is also to be understood that the point of attachment for a heterocycle or heterocycle multiple condensed ring system can be at any suitable atom of the heterocycle or heterocycle multiple condensed ring system including a carbon atom and a heteroatom (e.g., a nitrogen). In one embodiment the term heterocycle includes a $C_{2-20}$ heterocycle. In one embodiment the term heterocycle includes a $C_{2-7}$ heterocycle. In one embodiment the term heterocycle includes a $C_{2-5}$ heterocycle. In one embodiment the term heterocycle includes a $C_{2-4}$ heterocycle. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl, 1,4-benzodioxanyl, spiro[cyclopropane-1,1'-isoindolinyl]-3'-one, isoindolinyl-1-one, 2-oxa-6-azaspiro[3.3]heptanyl, imidazolidin-2-one N-methylpiperidine, imidazolidine, pyrazolidine, butyrolactam, valerolactam, imidazolidinone, hydantoin, dioxolane, phthalimide, 1,4-dioxane, thiomorpholine, thiomorpholine-S-oxide, thiomorpholine-S,S-oxide, pyran, 3-pyrroline, thiopyran, pyrone, tetrhydrothiophene, quinuclidine, tropane, 2-azaspiro[3.3]heptane, (1R,5S)-3-azabicyclo[3.2.1]octane, (1s,4s)-2-azabicyclo[2.2.2]octane, (1R,4R)-2-oxa-5-azabicyclo[2.2.2]octane and pyrrolidin-2-one. In one embodiment the term "heterocycle" refers to a monocyclic, saturated or partially unsaturated, 3-8 membered ring having at least one heteroatom. For example, the term includes a monocyclic, saturated or partially unsaturated, 4, 5, 6, or 7 membered ring having at least one heteroatom. Non-limiting examples of heterocycle include aziridine, azetidine, pyrrolidine, piperidine, piperidine, piperazine, oxirane, morpholine, and thiomorpholine. The term "9- or 10-membered heterobicycle" as used herein refers to a partially unsaturated or aromatic fused bicyclic ring system having at least one heteroatom. For example, the term 9- or 10-membered heterobicycle includes a bicyclic ring system having a benzo ring fused to a 5-membered or 6-membered saturated, partially unsaturated, or aromatic ring that contains one or more heteroatoms.

As used herein, the term "heteroatom" is meant to include oxygen (O), nitrogen (N), sulfur (S) and silicon (Si). The nitrogen and sulfur can be in an oxidized form when feasible.

As used herein, the term "chiral" refers to molecules which have the property of non-superimposability of the mirror image partner, while the term "achiral" refers to molecules which are superimposable on their mirror image partner.

As used herein, the term "stereoisomers" refers to compounds which have identical chemical constitution, but differ with regard to the arrangement of the atoms or groups in space.

As used herein a wavy line " ⌇ " that intersects a bond in a chemical structure indicates the point of attachment of the bond that the wavy bond intersects in the chemical structure to the remainder of a molecule.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers can separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95% the absolute stereoisomer depicted. In another embodiment, the compound may be at least 97% the absolute stereoisomer depicted. In another embodiment, the compound may be at least 98% the absolute stereoisomer depicted. In another embodiment, the compound may be at least 99% the absolute stereoisomer depicted.

As used herein, the term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

As used herein, the term "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

As used herein, the term "protecting group" refers to a substituent that is commonly employed to block or protect a particular functional group on a compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl) ethyl, 2-(trimethylsilyl)ethoxymethyl, 2-(p-toluenesulfonyl) ethyl, 2-(p-nitrophenylsulfenyl)ethyl, 2-(diphenylphosphino)-ethyl, nitroethyl and the like. For a general description of protecting groups and their use, see P. G. M. Wuts and T. W. Greene, Greene's Protective Groups in Organic Synthesis 4$^{th}$ edition, Wiley-Interscience, New York, 2006.

As used herein, the term "mammal" includes, but is not limited to, humans, mice, rats, guinea pigs, monkeys, dogs, cats, horses, cows, pigs, and sheep.

As used herein, Y is "$H_2$" means that Y is two hydrogens, forming $CH_2$ when taken together with the carbon to which Y is attached.

As used herein, the term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. As used herein the term "prodrug" refers to those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs of the invention include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of a compound of the invention can be derivatized as an amide or alkyl ester. As another example, compounds of this invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115.

Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as $(C_{1-6})$alkanoyloxymethyl, 1-(($C_{1-6}$)alkanoyloxy)ethyl, 1-methyl-1-(($C_{1-6}$)alkanoyloxy)ethyl, $(C_{1-6})$alkoxycarbonyloxymethyl, N—$(C_{1-6})$alkoxycarbonylaminomethyl, succinoyl, $(C_{1-6})$alkanoyl, alpha-amino$(C_{1-4})$alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_{1-6})alkyl)_2$ or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Additionally, the present invention provides for metabolites of compounds of the invention. As used herein, a "metabolite" refers to a product produced through metabolism in the body of a specified compound or salt thereof. Such products can result for example from the oxidation, reduction, hydrolysis, amidation, deamidation, esterification, deesterification, enzymatic cleavage, and the like, of the administered compound.

Metabolite products typically are identified by preparing a radiolabelled (e.g., 14C or $^3$H) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Pharmaceutical Compositions and Administration

In addition to one or more of the compounds provided above (or stereoisomers, geometric isomers, tautomers, solvates, metabolites, isotopes, pharmaceutically acceptable salts, or prodrugs thereof), the invention also provides for compositions and medicaments comprising a compound of the invention and at least one pharmaceutically acceptable carrier, diluent or excipient. The compositions of the invention can be used to selectively inhibit NaV1.7 in patients (e.g, humans).

The term "composition," as used herein, is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

In one embodiment, the invention provides for pharmaceutical compositions (or medicaments) comprising a compound as described herein, and its stereoisomers, geometric isomers, tautomers, solvates, metabolites, isotopes, pharmaceutically acceptable salts, or prodrugs thereof) and a pharmaceutically acceptable carrier, diluent or excipient. In another embodiment, the invention provides for preparing compositions (or medicaments) comprising compounds of the invention. In another embodiment, the invention provides for administering a compound of the invention or a and compositions comprising a compound of the invention to a patient (e.g., a human patient) in need thereof.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The effective amount of the compound to be administered will be governed by such considerations, and is the minimum amount necessary to inhibit NaV1.7 activity as required to prevent or treat the undesired disease or disorder, such as for example, pain. For example, such amount may be below the amount that is toxic to normal cells, or the mammal as a whole.

In one example, the therapeutically effective amount of the compound of the invention administered parenterally per dose will be in the range of about 0.01-100 mg/kg, alternatively about e.g., 0.1 to 20 mg/kg of patient body weight per day, with the typical initial range of compound used being 0.3 to 15 mg/kg/day. The daily does is, in certain embodiments, given as a single daily dose or in divided doses two to six times a day, or in sustained release form. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, intracerebral, intraocular, intralesional or subcutaneous administration.

The compositions comprising compounds as described herein or an embodiment thereof are normally formulated in accordance with standard pharmaceutical practice as a pharmaceutical composition. A typical formulation is prepared by mixing a compound of the present invention and a diluent, carrier or excipient. Suitable diluents, carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which a compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). A active pharmaceutical ingredient of the invention (e.g., compound of f of the invention) can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy: Remington the Science and Practice of Pharmacy (2005) $21^{St}$ Edition, Lippincott Williams & Wilkins, Philidelphia, Pa.

Sustained-release preparations of a compound can be prepared. Suitable examples of sustained-release preparations include semipermeable matrices of solid hydrophobic polymers containing a compound as described herein, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate (Sidman et al., Biopolymers 22:547, 1983), non-degradable ethylene-vinyl acetate (Langer et al., J. Biomed. Mater. Res. 15:167, 1981), degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid (EP 133,988A). Sustained release compositions also include liposomally entrapped compounds, which can be prepared by methods known per se (Epstein et al., Proc. Natl. Acad. Sci. U.S.A. 82:3688, 1985; Hwang et al., Proc. Natl. Acad. Sci. U.S.A. 77:4030, 1980; U.S. Pat. Nos. 4,485,045 and 4,544,545; and EP 102,324A). Ordinarily, the liposomes are of the small (about 200-800 Angstroms) unilamelar type in which the lipid content is greater than about 30 mol % cholesterol, the selected proportion being adjusted for the optimal therapy.

The formulations include those suitable for the administration routes detailed herein. The formulations can conveniently be presented in unit dosage form and can be prepared by any of the methods well known in the art of pharmacy. Techniques and formulations generally are found in Remington: The Science and Practice of Pharmacy: Remington the Science and Practice of Pharmacy (2005) $21^{st}$ Edition, Lippincott Williams & Wilkins, Philidelphia, Pa. Such methods include the step of bringing into association the active ingredient with the carrier which constitutes one or more accessory ingredients.

In general the formulations are prepared by uniformly and intimately bringing into association the active ingredient with liquid carriers, diluents or excipients or finely divided solid carriers, diluents or excipients, or both, and then, if necessary, shaping the product. A typical formulation is prepared by mixing a compound of the present invention and a carrier, diluent or excipient. The formulations can be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. A compound of the present invention is typically formulated into pharmaceutical dosage forms to provide an easily controllable dosage of the drug and to enable patient compliance with the prescribed regimen.

In one example, compounds as described herein may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of the invention is formulated in an acetate buffer, at pH 5. In another embodiment, a compound of the invention is sterile. The compound may be stored, for example, as a solid or amorphous composition, as a lyophilized formulation or as an aqueous solution.

Formulations of a compound as described herein suitable for oral administration can be prepared as discrete units such as pills, capsules, cachets or tablets each containing a predetermined amount of a compound of the invention.

Compressed tablets can be prepared by compressing in a suitable machine the active ingredient in a free-flowing form such as a powder or granules, optionally mixed with a binder, lubricant, inert diluent, preservative, surface active or dispersing agent. Molded tablets can be made by molding in a suitable machine a mixture of the powdered active ingredient moistened with an inert liquid diluent. The tablets can optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs can be prepared for oral use. Formulations of a compound o as described herein intended for oral use can be prepared according to any method known to the art for the manufacture of pharmaceutical compositions and such compositions can contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients can be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets can be uncoated or can be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax can be employed.

An example of a suitable oral administration form is a tablet containing about 1 mg, 5 mg, 10 mg, 25 mg, 30 mg, 50 mg, 80 mg, 100 mg, 150 mg, 250 mg, 300 mg and 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredient can be employed with either a paraffinic or a water-miscible ointment base. Alternatively, the active ingredients can be formulated in a cream with an oil-in-water cream base. If desired, the aqueous phase of the cream base can include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations can desirably include a compound which enhances absorption or penetration of the active ingredient through the skin or other affected areas. Examples of such dermal penetration enhancers include dimethyl sulfoxide and related analogs.

The oily phase of the emulsions of this invention can be constituted from known ingredients in a known manner. While the phase can comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

In one aspect of topical applications, it is desired to administer an effective amount of a pharmaceutical composition according to the invention to target area, e.g., skin surfaces, mucous membranes, and the like, which are adjacent to peripheral neurons which are to be treated. This amount will generally range from about 0.0001 mg to about 1 g of a compound of the invention per application, depending upon the area to be treated, whether the use is diagnostic, prophylactic or therapeutic, the severity of the symptoms, and the nature of the topical vehicle employed. A preferred topical preparation is an ointment, wherein about 0.001 to about 50 mg of active ingredient is used per cc of ointment base. The pharmaceutical composition can be formulated as transdermal compositions or transdermal delivery devices ("patches"). Such compositions include, for example, a backing, active compound reservoir, a control membrane, liner and contact adhesive. Such transdermal patches may be used to provide continuous pulsatile, or on demand delivery of the compounds of the present invention as desired.

Aqueous suspensions of a compound o as described herein contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose or saccharin.

Formulations of a compound as described herein can be in the form of a sterile injectable preparation, such as a sterile injectable aqueous or oleaginous suspension. This suspension can be formulated according to the known art using those suitable dispersing or wetting agents and suspending agents which have been mentioned above. The sterile injectable preparation can also be a sterile injectable solution or suspension in a non-toxic parenterally acceptable diluent or solvent, such as a solution in 1,3-butanediol or prepared as a lyophilized powder. Among the acceptable vehicles and solvents that can be employed are water, Ringer's solution and isotonic sodium chloride solution. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

The amount of active ingredient that can be combined with the carrier material to produce a single dosage form will vary depending upon the host treated and the particular mode of administration. For example, a time-release formulation intended for oral administration to humans can contain approximately 1 to 1000 mg of active material compounded with an appropriate and convenient amount of carrier material which can vary from about 5 to about 95% of the total compositions (weight:weight). The pharmaceutical composition can be prepared to provide easily measurable amounts for administration. For example, an aqueous solution intended for intravenous infusion can contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which can contain anti-oxidants, buffers, bacteriostats and solutes which render the formulation isotonic with the blood of the intended recipient; and aqueous and non-aqueous sterile suspensions which can include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration can be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration can be prepared according to conventional methods and can be delivered with other therapeutic agents such as compounds heretofore used in the treatment of disorders as described below.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

When the binding target is located in the brain, certain embodiments of the invention provide for a compound as described herein to traverse the blood-brain barrier. Certain neurodegenerative diseases are associated with an increase in permeability of the blood-brain barrier, such that a compound of of the invention can be readily introduced to the brain. When the blood-brain barrier remains intact, several art-known approaches exist for transporting molecules across it, including, but not limited to, physical methods, lipid-based methods, and receptor and channel-based methods.

Physical methods of transporting a compound o as described herein across the blood-brain barrier include, but are not limited to, circumventing the blood-brain barrier entirely, or by creating openings in the blood-brain barrier. Circumvention methods include, but are not limited to, direct injection into the brain (see, e.g., Papanastassiou et al., Gene Therapy 9:398-406, 2002), interstitial infusion/convection-enhanced delivery (see, e.g., Bobo et al., Proc. Natl. Acad. Sci. U.S.A. 91:2076-2080, 1994), and implanting a delivery device in the brain (see, e.g., Gill et al., Nature Med. 9:589-595, 2003; and Gliadel Wafers™, Guildford Pharmaceutical). Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Volumes 1 and 2, Plenum Press, N.Y., 1989)), and permeabilization by, e.g., bradykinin or permeabilizer A-7 (see, e.g., U.S. Pat. Nos. 5,112,596, 5,268,164, 5,506,206, and 5,686,416).

Lipid-based methods of transporting a compound o as described herein across the blood-brain barrier include, but are not limited to, encapsulating the a compound o as described herein in liposomes that are coupled to antibody binding fragments that bind to receptors on the vascular endothelium of the blood-brain barrier (see, e.g., U.S. Patent Application Publication No. 2002/0025313), and coating a compound as described herein in low-density lipoprotein particles (see, e.g., U.S. Patent Application Publication No. 2004/0204354) or apolipoprotein E (see, e.g., U.S. Patent Application Publication No. 2004/0131692).

Receptor and channel-based methods of transporting a compound o as described herein across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating a compound o as described herein with a transferrin and modulating activity of the one or more transferrin receptors (see, e.g., U.S. Patent Application Publication No. 2003/0129186), and cationizing the antibodies (see, e.g., U.S. Pat. No. 5,004,697).

For intracerebral use, in certain embodiments, the compounds can be administered continuously by infusion into the fluid reservoirs of the CNS, although bolus injection may be acceptable. The inhibitors can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the inhibitors can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer's disease patients and animal models for Parkinson's disease, as described by Harbaugh, J. Neural Transm. Suppl. 24:271, 1987; and DeYebenes et al., Mov. Disord. 2: 143, 1987.

A compound as described herein used in the invention are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. A compound as described herein need not be, but is optionally formulated with one or more agent currently used to prevent or treat the disorder in question. The effective amount of such other agents depends on the amount of a compound of the invention present in the formulation, the type of disorder or treatment, and other factors discussed above.

These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of a compound as described herein (when used alone or in combination with other agents) will depend on the type of disease to be treated, the properties of the compound, the severity and course of the disease, whether the compound is administered for preventive or therapeutic purposes, previous therapy, the patient's clinical history and response to the compound, and the discretion of the attending physician. The compound is suitably administered to the patient at one time or over a series of treatments. Depending on the type and severity of the disease, about 1 μg/kg to 15 mg/kg (e.g., 0.1 mg/kg-10 mg/kg) of compound can be an initial candidate dosage for administration to the patient, whether, for example, by one or more separate administrations, or by continuous infusion. One typical daily dosage might range from about 1 μg kg to 100 mg/kg or more, depending on the factors mentioned above. For repeated administrations over several days or longer, depending on the condition, the treatment would generally be sustained until a desired suppression of disease symptoms occurs. One exemplary dosage of a compound of the invention would be in the range from about 0.05 mg/kg to about 10 mg/kg. Thus, one or more doses of about 0.5 mg/kg, 2.0 mg/kg, 4.0 mg/kg, or 10 mg/kg (or any combination thereof) may be administered to the patient. Such doses may be administered intermittently, e.g., every week or every three weeks (e.g., such that the patient receives from about two to about twenty, or, e.g., about six doses of the antibody). An initial higher loading dose, followed by one or more lower doses may be administered. An exemplary dosing regimen comprises administering an initial loading dose of about 4 mg/kg, followed by a weekly maintenance dose of about 2 mg kg of the compound. However, other dosage regimens may be useful. The progress of this therapy is easily monitored by conventional techniques and assays.

Other typical daily dosages might range from, for example, about 1 g/kg to up to 100 mg/kg or more (e.g., about 1 μg kg to 1 mg/kg, about 1 μg/kg to about 5 mg/kg, about 1 mg kg to 10 mg/kg, about 5 mg/kg to about 200 mg/kg, about 50 mg/kg to about 150 mg/mg, about 100 mg/kg to about 500 mg/kg, about 100 mg/kg to about 400 mg/kg, and about 200 mg/kg to about 400 mg/kg), depending on the factors mentioned above. Typically, the clinician will administer a compound until a dosage is reached that results in improvement in or, optimally, elimination of, one or more symptoms of the treated disease or condition. The progress of this therapy is easily monitored by conventional assays. One or more agent provided herein may be administered together or at different times (e.g., one agent is administered prior to the administration of a second agent). One or more agent may be administered to a subject using different techniques (e.g., one agent may be administered orally, while a second agent is administered via intramuscular injection or intranasally). One or more agent may be administered such that the one or more agent has a pharmacologic effect in a subject at the same time. Alternatively, one or more agent may be administered, such that the pharmacological activity of the first administered agent is expired prior the administration of one or more secondarily administered agents (e.g., 1, 2, 3, or 4 secondarily administered agents).

Indications and Methods of Treatment

The compounds of the invention modulate, preferably inhibit, ion flux through a voltage-dependent sodium channel in a mammal, (e.g, a human). Any such modulation, whether it be partial or complete inhibition or prevention of ion flux, is sometimes referred to herein as "blocking" and corresponding compounds as "blockers" or "inhibitors". In general, the compounds of the invention modulate the activity of a sodium channel downwards by inhibiting the voltage-dependent activity of the sodium channel, and/or reduce or prevent sodium ion flux across a cell membrane by preventing sodium channel activity such as ion flux.

Accordingly, the compounds of the invention are sodium channel blockers and are therefore useful for treating diseases and conditions in mammals, for example humans, and other organisms, including all those diseases and conditions which are the result of aberrant voltage-dependent sodium channel biological activity or which may be ameliorated by modulation of voltage-dependent sodium channel biological activity. In particular, the compounds of the invention, i.e., the compounds of formula (I) and embodiments and (or stereoisomers, geometric isomers, tautomers, solvates, metabolites, isotopes, pharmaceutically acceptable salts, or prodrugs thereof), are useful for treating diseases and conditions in mammals, for example humans, which are the result of aberrant voltage-dependent NaV1.7 biological activity or which may be ameliorated by the modulation, preferably the inhibition, of NaV1.7 biological activity. In certain aspects, the compounds of the invention selectively inhibit NaV1.7 over NaV1.5.

As defined herein, a sodium channel-mediated disease or condition refers to a disease or condition in a mammal, preferably a human, which is ameliorated upon modulation of the sodium channel and includes, but is not limited to, pain, central nervous conditions such as epilepsy, anxiety, depression and bipolar disease; cardiovascular conditions such as arrhythmias, atrial fibrillation and ventricular fibrillation; neuromuscular conditions such as restless leg syndrome and muscle paralysis or tetanus; neuroprotection against stroke, neural trauma and multiple sclerosis; and channelopathies such as erythromyalgia and familial rectal pain syndrome.

In one aspect, the present invention relates to compounds, pharmaceutical compositions and methods of using the compounds and pharmaceutical compositions for the treatment of sodium channel-mediated diseases in mammals, preferably humans and preferably diseases and conditions related to pain, central nervous conditions such as epilepsy, anxiety, depression and bipolar disease; cardiovascular conditions such as arrhythmias, atrial fibrillation and ventricular fibrillation; neuromuscular conditions such as restless leg syndrome and muscle paralysis or tetanus; neuroprotection against stroke, neural trauma and multiple sclerosis; and channelopathies such as erythromyalgia and familial rectal pain syndrome, by administering to a mammal, for example a human, in need of such treatment an effective amount of a sodium channel blocker modulating, especially inhibiting, agent.

A sodium channel-mediated disease or condition also includes pain associated with HIV, HIV treatment induced neuropathy, trigeminal neuralgia, glossopharyngeal neuralgia, neuropathy secondary to metastatic infiltration, adiposis dolorosa, thalamic lesions, hypertension, autoimmune disease, asthma, drug addiction (e.g., opiate, benzodiazepine, amphetamine, cocaine, alcohol, butane inhalation), Alzheimer, dementia, age-related memory impairment, Korsakoff syndrome, restenosis, urinary dysfunction, incontinence, Parkinson's disease, cerebrovascular ischemia, neurosis, gastrointestinal disease, sickle cell anemia, transplant rejection, heart failure, myocardial infarction, reperfusion injury, intermittant claudication, angina, convulsion, respiratory disorders, cerebral or myocardial ischemias, long-QT syndrome, Catecholeminergic polymorphic ventricular tachycardia, ophthalmic diseases, spasticity, spastic paraplegia, myopathies, myasthenia gravis, paramyotonia congentia, hyperkalemic periodic paralysis, hypokalemic periodic paralysis, alopecia, anxiety disorders, psychotic disorders, mania, paranoia, seasonal affective disorder, panic disorder, obsessive compulsive disorder (OCD), phobias, autism, Aspergers Syndrome, Retts syndrome, disintegrative disorder, attention deficit disorder, aggressivity, impulse control disorders, thrombosis, pre clampsia, congestive cardiac failure, cardiac arrest, Freidrich's ataxia, Spinocerebellear ataxia, myelopathy, radiculopathy, systemic lupus erythamatosis, granulomatous disease, olivo-ponto-cerebellar atrophy, spinocerebellar ataxia, episodic ataxia, myokymia, progressive pallidal atrophy, progressive supranuclear palsy and spasticity, traumatic brain injury, cerebral oedema, hydrocephalus injury, spinal cord injury, anorexia nervosa, bulimia, Prader-Willi syndrome, obesity, optic neuritis, cataract, retinal haemorrhage, ischaemic retinopathy, retinitis pigmentosa, acute and chronic glaucoma, macular degeneration, retinal artery occlusion, Chorea, Huntington's chorea, cerebral edema, proctitis, post-herpetic neuralgia, eudynia, heat sensitivity, sarcoidosis, irritable bowel syndrome, Tourette syndrome, Lesch-Nyhan Syndrome, Brugado syndrome, Liddle syndrome, Crohns disease, multiple sclerosis and the pain associated with multiple sclerosis (MS), amyotrophic lateral sclerosis (ALS), disseminated sclerosis, diabetic neuropathy, peripheral neuropathy, charcot marie tooth syndrome, arthritic, rheumatoid arthritis, osteoarthritis, chondrocalcinosis, atherosclerosis, paroxysmal dystonia, myasthenia syndromes, myotonia, myotonic dystrophy, muscular dystrophy, malignant hyperthermia, cystic fibrosis, pseudoaldosteronism, rhabdomyolysis, mental handicap, hypothyroidism, bipolar depression, anxiety, schizophrenia, sodium channel toxin related illnesses, familial erythromelalgia, primary erythromelalgia, rectal pain, cancer, epilepsy, partial and general tonic seizures, febrile seizures, absence seizures (petit mal), myoclonic seizures, atonic seizures, clonic seizures, Lennox Gastaut, West Syndome (infantile spasms), multiresistant seizures, seizure prophylaxis (anti-epileptogenic), familial Mediterranean fever syndrome, gout, restless leg syndrome, arrhythmias, fibromyalgia, neuroprotection under ischaemic conditions caused by stroke or neural trauma, tachy-arrhythmias, atrial fibrillation and ventricular fibrillation and as a general or local anaesthetic.

As used herein, the term "pain" refers to all categories of pain and is recognized to include, but is not limited to, neuropathic pain, inflammatory pain, nociceptive pain, idiopathic pain, neuralgic pain, orofacial pain, burn pain, burning mouth syndrome, somatic pain, visceral pain, myofacial pain, dental pain, cancer pain, chemotherapy pain, trauma pain, surgical pain, post-surgical pain, childbirth pain, labor pain, chronic regional pain syndrome (CRPS), reflex sympathetic dystrophy, brachial plexus avulsion, neurogenic bladder, acute pain (e.g., musculoskeletal and post-operative pain), chronic pain, persistent pain, peripherally mediated pain, centrally mediated pain, chronic headache, migraine headache, familial hemiplegic migraine, conditions associated with cephalic pain, sinus headache, tension headache, phantom limb pain, peripheral nerve injury, pain following stroke, thalamic lesions, radiculopathy, HIV pain, post-herpetic pain, non-cardiac chest pain, irritable bowel syndrome and pain associated with bowel disorders and dyspepsia, and combinations thereof.

Furthermore, sodium channel blockers have clinical uses in addition to pain. The present invention therefore also relates to compounds, pharmaceutical compositions and methods of using the compounds and pharmaceutical compositions for the treatment of diseases or conditions such as cancer and pruritus (itch).

Pruritus, commonly known as itch, is a common dermatological condition. While the exact causes of pruritus are complex and incompletely understood, there has long been evidence that itch involves sensory neurons, especially C fibers, similar to those that mediate pain (Schmelz, M., et al., J. Neurosci. (1997), 17: 8003-8). In particular, it is believed that sodium influx through voltage-gated sodium channels is essential for the propagation of itch sensation from the skin. Transmission of the itch impulses results in the unpleasant sensation that elicits the desire or reflex to scratch.

Multiple causes and electrical pathways for eliciting itch are known. In humans, pruritus can be elicited by histamine or PAR-2 agonists such as mucunain that activate distinct populations of C fibers (Namer, B., et al., J. Neurophysiol. (2008), 100: 2062-9). A variety of neurotrophic peptides are known to mediate itch in animal models (Wang, H., and Yosipovitch, G., International Journal of Dermatology (2010), 49: 1-11). Itch can also be elicited by opioids, evidence of distinct pharmacology from that of pain responses.

There exists a complex interaction between itch and pain responses that arises in part from the overlapping sensory input from the skin (Ikoma, A., et al., Arch. Dermatol. (2003), 139: 1475-8) and also from the diverse etiology of both pain and pruritus. Pain responses can exacerbate itching by enhancing central sensitization or lead to inhibition of painful scratching. Particularly severe forms of chronic itch occur when pain responses are absent, as in the case of post-herpetic itch (Oaklander, A. L., et al., Pain (2002), 96: 9-12).

The compounds of the invention can also be useful for treating pruritus. The rationale for treating itch with inhibitors of voltage-gated sodium channels, especially NaV1.7, is as follows: The propagation of electrical activity in the C fibers that sense pruritinergic stimulants requires sodium entry through voltage-gated sodium channels.

NaV1.7 is expressed in the C fibers and kerotinocytes in human skin (Zhao, P., et al., Pain (2008), 139: 90-105).

A gain of function mutation of NaV1.7 (L858F) that causes erythromelalgia also causes chronic itch (Li, Y., et al., Clinical and Experimental Dermatology (2009), 34: e313-e4).

Chronic itch can be alleviated with treatment by sodium channel blockers, such as the local anesthetic lidocaine (Oaklander, A. L., et al., Pain (2002), 96: 9-12; Villamil, A. G., et al., The American Journal of Medicine (2005), 118: 1160-3). In these reports, lidocaine was effective when administered either intravenously or topically (a Lidoderm patch). Lidocaine can have multiple activities at the plasma concentrations achieved when administered systemically, but when administered topically, the plasma concentrations are only about 1 µM (Center for Drug Evaluation and Research NDA 20-612). At these concentrations, lidocaine is selective for sodium channel block and inhibits spontaneous electrical activity in C fibers and pain responses in animal models (Xiao, W. H., and Bennett, G. J. Pain (2008), 137: 218-28). The types of itch or skin irritation, include, but are not limited to:

psoriatic pruritus, itch due to hemodyalisis, aguagenic pruritus, and itching caused by skin disorders (e.g., contact dermatitis), systemic disorders, neuropathy, psychogenic factors or a mixture thereof;

itch caused by allergic reactions, insect bites, hypersensitivity (e.g., dry skin, acne, eczema, psoriasis), inflammatory conditions or injury;

itch associated with vulvar vestibulitis; and skin irritation or inflammatory effect from administration of another therapeutic such as, for example, antibiotics, antivirals and antihistamines.

The compounds of the invention are also useful in treating certain cancers, such as hormone sensitive cancers, such as prostate cancer (adenocarcinoma), breast cancer, ovarian cancer, testicular cancer and thyroid neoplasia, in a mammal, preferably a human. The voltage gated sodium channels have been demonstrated to be expressed in prostate and breast cancer cells. Up-regulation of neonatal NaV1.5 occurs as an integral part of the metastatic process in human breast cancer and could serve both as a novel marker of the metastatic phenotype and a therapeutic target (Clin. Cancer Res. (2005), August 1; 11(15): 5381-9). Functional expression of voltage-gated sodium channel alpha-subunits, specifically NaV1.7, is associated with strong metastatic potential in prostate cancer (CaP) in vitro. Voltage-gated sodium channel alpha-subunits immunostaining, using antibodies specific to the sodium channel alpha subunit was evident in prostatic tissues and markedly stronger in CaP vs non-CaP patients (Prostate Cancer Prostatic Dis., 2005; 8(3):266-73). See also Diss, J. K. J., et al., Mol. Cell. Neurosci. (2008), 37:537-547 and Kis-Toth, K., et al., The Journal of Immunology (2011), 187:1273-1280.

In consideration of the above, in one embodiment, the present invention provides a method for treating a mammal for, or protecting a mammal from developing, a sodium channel-mediated disease, especially pain, comprising administering to the mammal, especially a human, in need thereof, a therapeutically effective amount of a compound of the invention or a pharmaceutical composition comprising a therapeutically effective amount of a compound of the invention wherein the compound modulates the activity of one or more voltage-dependent sodium channels.

In another embodiment of the invention is a method of treating a disease or a condition in a mammal, preferably a human, wherein the disease or condition is selected from the group consisting of pain, depression, cardiovascular diseases, respiratory diseases, and psychiatric diseases, and combinations thereof, and wherein the method comprises administering to the mammal in need thereof a therapeutically effective amount of an embodiment of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

One embodiment of this embodiment is wherein the disease or condition is selected from the group consisting of acute pain, chronic pain, neuropathic pain, inflammatory pain, visceral pain, cancer pain, chemotherapy pain, trauma pain, surgical pain, post surgical pain, childbirth pain, labor pain, neurogenic bladder, ulcerative colitis, persistent pain, peripherally mediated pain, centrally mediated pain, chronic headache, migraine headache, sinus headache, tension headache, phantom limb pain, peripheral nerve injury, and combinations thereof.

Another embodiment of this embodiment is wherein the disease or condition is selected from the group consisting of pain associated with HIV, HIV treatment induced neuropathy, trigeminal neuralgia, post herpetic neuralgia, eudynia, heat sensitivity, tosarcoidosis, irritable bowel syndrome, Crohns disease, pain associated with multiple sclerosis (MS), amyotrophic lateral sclerosis (ALS), diabetic neuropathy, peripheral neuropathy, arthritic, rheumatoid arthritis, osteoarthritis, atherosclerosis, paroxysmal dystonia, myasthenia syndromes, myotonia, malignant hyperthermia, cystic fibrosis, pseudoaldosteronism, rhabdomyolysis, hypothyroidism, bipolar depression, anxiety, schizophrenia, sodium channel toxin related illnesses, familial erythromelalgia, primary erythromelalgia, familial rectal pain, cancer, epilepsy, partial and general tonic seizures, restless leg syndrome, arrhythmias, fibromyalgia, neuroprotection under ischaemic conditions caused by stroke or neural trauma, tachy arrhythmias, atrial fibrillation and ventricular fibrillation.

Another embodiment of the invention is a method of treating, but not preventing, pain in a mammal, wherein the method comprises administering to the mammal in need thereof a therapeutically effective amount of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

One embodiment of this embodiment is a method wherein the pain is selected from the group consisting of neuropathic pain, inflammatory pain, visceral pain, cancer pain, chemotherapy pain, trauma pain, surgical pain, post surgical pain, childbirth pain, labor pain, dental pain, chronic pain, persistent pain, peripherally mediated pain, centrally mediated pain, chronic headache, migraine headache, sinus headache, tension headache, phantom limb pain, peripheral nerve injury, trigeminal neuralgia, post herpetic neuralgia, eudynia, familial erythromelalgia, primary erythromelalgia, familial rectal pain or fibromyalgia, and combinations thereof.

Another embodiment of this embodiment is a method wherein the pain is associated with a disease or condition selected from HIV, HIV treatment induced neuropathy, heat sensitivity, tosarcoidosis, irritable bowel syndrome, Crohns disease, multiple sclerosis, amyotrophic lateral sclerosis, diabetic neuropathy, peripheral neuropathy, rheumatoid arthritis, osteoarthritis, atherosclerosis, paroxysmal dystonia, myasthenia syndromes, myotonia, malignant hyperthermia, cystic fibrosis, pseudoaldosteronism, rhabdomyolysis, hypothyroidism, bipolar depression, anxiety, schizophrenia, sodium channel toxin related illnesses, neurogenic bladder, ulcerative colitis, cancer, epilepsy, partial and general tonic seizures, restless leg syndrome, arrhythmias, ischaemic conditions caused by stroke or neural trauma, tachy arrhythmias, atrial fibrillation and ventricular fibrillation.

Another embodiment of the invention is the method of treating pain in a mammal, preferably a human, by the inhibition of ion flux through a voltage dependent sodium channel in the mammal, wherein the method comprises administering to the mammal in need thereof a therapeutically effective amount of an embodiment of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

Another embodiment of the invention is the method of treating pruritus in a mammal, preferably a human, wherein the method comprises administering to the mammal in need thereof a therapeutically effective amount of an embodiment of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

Another embodiment of the invention is the method of treating cancer in a mammal, preferably a human, wherein the method comprises administering to the mammal in need thereof a therapeutically effective amount of an embodiment of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

Another embodiment of the invention is the method of decreasing ion flux through a voltage dependent sodium channel in a cell in a mammal, wherein the method comprises contacting the cell with an embodiment of a compound of the invention, as set forth above, as a stereoisomer, enantiomer or tautomer thereof or mixtures thereof, or a pharmaceutically acceptable salt, solvate or prodrug thereof.

Another embodiment of the invention is the method of selectively inhibiting a first voltage-gated sodium channel over a second voltage-gated sodium channel in a mammal, wherein the method comprises administering to the mammal an inhibitory amount of a compound of formula (I), or an embodiment of a compound of formula (I).

Another embodiment of the invention is the method of selectively inhibiting NaV1.7 in a mammal or a mammalian cell as compared to NaV1.5, wherein the method comprises administering to the mammal in need thereof an inhibitory amount of a compound of formula (I) or an embodiment of an embodiment thereof.

For each of the above embodiments described related to treating diseases and conditions in a mammal, the present invention also contemplates relatedly a compound as described herein for the use as a medicament in the treatment of such diseases and conditions.

For each of the above embodiments described related to treating diseases and conditions in a mammal, the present invention also contemplates relatedly the use of a compound o as described herein for the manufacture of a medicament for the treatment of such diseases and conditions.

Another embodiment of the invention is a method of using a compound as described herein as a standard or control in in vitro or in vivo assays in determining the efficacy of test compounds in modulating voltage-dependent sodium channels.

In another embodiment of the invention, the compounds as described herein are isotopically-labeled by having one or more atoms therein replaced by an atom having a different atomic mass or mass number. Such isotopically-labeled (i.e., radiolabelled) compounds are considered to be within the scope of this invention. Examples of isotopes that can be incorporated into the compounds include isotopes of hydrogen, carbon, nitrogen, oxygen, phosphorous, sulfur, fluorine, chlorine, and iodine, such as, but not limited to, $^2H$, $^3H$, $^{11}C$, $^{13}C$, $^{14}C$, $^{13}N$, $^5N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These isotopically-labeled compounds would be useful to help determine or measure the effectiveness of the compounds, by characterizing, for example, the site or mode of action on the sodium channels, or binding affinity to pharmacologically important site of action on the sodium channels, particularly NaV1.7. Certain isotopically-labeled compounds, for example, those incorporating a radioactive isotope, are useful in drug and/or substrate tissue distribution studies. The radioactive isotopes tritium, i.e. $^3H$, and carbon-14, i.e., $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds can generally be prepared by conventional techniques known to those skilled in the art or by processes analogous to those described in the Examples as set out below using an appropriate isotopically-labeled reagent in place of the non-labeled reagent previously employed.

Testing Compounds

The assessment of the compounds of the invention in mediating, especially inhibiting, the sodium channel ion flux can be determined using the assays described hereinbelow. Alternatively, the assessment of the compounds in treating conditions and diseases in humans may be established in industry standard animal models for demonstrating the efficacy of compounds in treating pain. Animal models of human neuropathic pain conditions have been developed that result in reproducible sensory deficits (allodynia, hyperalgesia, and spontaneous pain) over a sustained period of time that can be evaluated by sensory testing. By establishing the degree of mechanical, chemical, and temperature induced allodynia and hyperalgesia present, several physiopathological conditions observed in humans can be modeled allowing the evaluation of pharmacotherapies.

In rat models of peripheral nerve injury, ectopic activity in the injured nerve corresponds to the behavioural signs of pain. In these models, intravenous application of the sodium channel blocker and local anesthetic lidocaine can suppress the ectopic activity and reverse the tactile allodynia at concentrations that do not affect general behaviour and motor function (Mao, J. and Chen, L. L, Pain (2000), 87:7-17). Allometric scaling of the doses effective in these rat models, translates into doses similar to those shown to be efficacious in humans (Tanelian, D. L. and Brose, W. G., Anesthesiology (1991), 74(5):949-951). Furthermore, Lidoderm®, lidocaine applied in the form of a dermal patch, is currently an FDA approved treatment for post-herpetic neuralgia (Devers, A. and Glaler, B. S., Clin. J. Pain (2000), 16(3):205-8).

The present invention readily affords many different means for identification of sodium channel modulating agents that are useful as therapeutic agents. Identification of modulators of sodium channel can be assessed using a variety of in vitro and in vivo assays, e.g., measuring current, measuring membrane potential, measuring ion flux, (e.g., sodium or guanidinium), measuring sodium concentration, measuring second messengers and transcription levels, and using e.g., voltage-sensitive dyes, radioactive tracers, and patch-clamp electrophysiology.

One such protocol involves the screening of chemical agents for ability to modulate the activity of a sodium channel thereby identifying it as a modulating agent.

A typical assay described in Bean et al., J. General Physiology (1983), 83:613-642, and Leuwer, M., et al., Br. J. Pharmacol (2004), 141(1):47-54, uses patch-clamp techniques to study the behaviour of channels. Such techniques are known to those skilled in the art, and may be developed, using current technologies, into low or medium throughput assays for evaluating compounds for their ability to modulate sodium channel behaviour.

Throughput of test compounds is an important consideration in the choice of screening assay to be used. In some strategies, where hundreds of thousands of compounds are to be tested, it is not desirable to use low throughput means. In other cases, however, low throughput is satisfactory to identify important differences between a limited number of compounds. Often it will be necessary to combine assay types to identify specific sodium channel modulating compounds.

Electrophysiological assays using patch clamp techniques is accepted as a gold standard for detailed characterization of sodium channel compound interactions, and as described in Bean et al., op. cit. and Leuwer, M., et al., op. cit. There is a manual low-throughput screening (LTS) method which can compare 2-10 compounds per day; a recently developed system for automated medium-throughput screening (MTS)

at 20-50 patches (i.e. compounds) per day; and a technology from Molecular Devices Corporation (Sunnyvale, Calif.) which permits automated high-throughput screening (HTS) at 1000-3000 patches (i.e. compounds) per day.

One automated patch-clamp system utilizes planar electrode technology to accelerate the rate of drug discovery. Planar electrodes are capable of achieving high-resistance, cells-attached seals followed by stable, low-noise whole-cell recordings that are comparable to conventional recordings. A suitable instrument is the PatchXpress 7000A (Axon Instruments Inc, Union City, Calif.). A variety of cell lines and culture techniques, which include adherent cells as well as cells growing spontaneously in suspension are ranked for seal success rate and stability. Immortalized cells (e.g. HEK and CHO) stably expressing high levels of the relevant sodium ion channel can be adapted into high-density suspension cultures.

Other assays can be selected which allow the investigator to identify compounds which block specific states of the channel, such as the open state, closed state or the resting state, or which block transition from open to closed, closed to resting or resting to open. Those skilled in the art are generally familiar with such assays.

Binding assays are also available. Designs include traditional radioactive filter based binding assays or the confocal based fluorescent system available from Evotec OAI group of companies (Hamburg, Germany), both of which are HTS.

Radioactive flux assays can also be used. In this assay, channels are stimulated to open with veratridine or aconitine and held in a stabilized open state with a toxin, and channel blockers are identified by their ability to prevent ion influx. The assay can use radioactive 22[Na] and 14[C] guanidinium ions as tracers. FlashPlate & Cytostar-T plates in living cells avoids separation steps and are suitable for HTS. Scintillation plate technology has also advanced this method to HTS suitability. Because of the functional aspects of the assay, the information content is reasonably good.

Yet another format measures the redistribution of membrane potential using the FLIPR system membrane potential kit (HTS) available from Molecular Dynamics (a division of Amersham Biosciences, Piscataway, N.J.). This method is limited to slow membrane potential changes. Some problems may result from the fluorescent background of compounds. Test compounds may also directly influence the fluidity of the cell membrane and lead to an increase in intracellular dye concentrations. Still, because of the functional aspects of the assay, the information content is reasonably good.

Sodium dyes can be used to measure the rate or amount of sodium ion influx through a channel. This type of assay provides a very high information content regarding potential channel blockers. The assay is functional and would measure Na+ influx directly. CoroNa Red, SBFI and/or sodium green (Molecular Probes, Inc. Eugene Oreg.) can be used to measure Na influx; all are Na responsive dyes. They can be used in combination with the FLIPR instrument. The use of these dyes in a screen has not been previously described in the literature. Calcium dyes may also have potential in this format.

In another assay, FRET based voltage sensors are used to measure the ability of a test compound to directly block Na influx. Commercially available HTS systems include the VIPR™ II FRET system (Life Technologies, or Aurora Biosciences Corporation, San Diego, Calif., a division of Vertex Pharmaceuticals, Inc.) which may be used in conjunction with FRET dyes, also available from Aurora Biosciences. This assay measures sub-second responses to voltage changes. There is no requirement for a modifier of channel function. The assay measures depolarization and hyperpolarizations, and provides ratiometric outputs for quantification. A somewhat less expensive MTS version of this assay employs the FLEXstation™ (Molecular Devices Corporation) in conjunction with FRET dyes from Aurora Biosciences. Other methods of testing the compounds disclosed herein are also readily known and available to those skilled in the art.

Modulating agents so identified are then tested in a variety of in vivo models so as to determine if they alleviate pain, especially chronic pain or other conditions such as cancer and pruritus (itch) with minimal adverse events. The assays described below in the Biological Assays Section are useful in assessing the biological activity of the instant compounds.

Typically, the efficacy of a compound of the invention is expressed by its IC50 value ("Inhibitory Concentration—50%"), which is the measure of the amount of compound required to achieve 50% inhibition of the activity of the target sodium channel over a specific time period. For example, representative compounds of the present invention have demonstrated IC50's ranging from less than 100 nanomolar to less than 10 micromolar in the patch voltage clamp NaV1.7 electrophysiology assay described herein.

In another aspect of the invention, the compounds of the invention can be used in in vitro or in vivo studies as exemplary agents for comparative purposes to find other compounds also useful in treatment of, or protection from, the various diseases disclosed herein.

Another aspect of the invention relates to inhibiting NaV1.1, NaV1.2, NaV1.3, NaV1.4, NaV1.5, NaV1.6, NaV1.7, NaV1.8, or NaV1.9 activity, preferably NaV1.7 activity, in a biological sample or a mammal, preferably a human, which method comprises administering to the mammal, preferably a human, or contacting said biological sample with a compound as described herein or a pharmaceutical composition comprising a compound as described herein. The term "biological sample", as used herein, includes, without limitation, cell cultures or extracts thereof; biopsied material obtained from a mammal or extracts thereof, and blood, saliva, urine, feces, semen, tears, or other body fluids or extracts thereof.

Inhibition of NaV1.1, NaV1.2, NaV1.3, NaV1.4, NaV1.5, NaV1.6, NaV1.7, NaV1.8, or NaV1.9 activity in a biological sample is useful for a variety of purposes that are known to one of skill in the art. Examples of such purposes include, but are not limited to, the study of sodium ion channels in biological and pathological phenomena; and the comparative evaluation of new sodium ion channel inhibitors.

The compounds of the invention (or stereoisomers, geometric isomers, tautomers, solvates, metabolites, isotopes, pharmaceutically acceptable salts, or prodrugs thereof) and/or the pharmaceutical compositions described herein which comprise a pharmaceutically acceptable excipient and one or more compounds of the invention, can be used in the preparation of a medicament for the treatment of sodium channel-mediated disease or condition in a mammal.

Combination Therapy

The compounds of the invention may be usefully combined with one or more other compounds of the invention or one or more other therapeutic agent or as any combination thereof, in the treatment of sodium channel-mediated diseases and conditions. For example, a compound of the invention may be administered simultaneously, sequentially or separately in combination with other therapeutic agents, including, but not limited to:

opiates analgesics, e.g., morphine, heroin, cocaine, oxymorphine, levorphanol, levallorphan, oxycodone, codeine, dihydrocodeine, propoxyphene, nalmefene, fentanyl, hydrocodone, hydromorphone, meripidine, methadone, nalorphine, naloxone, naltrexone, buprenorphine, butorphanol, nalbuphine and pentazocine;

non-opiate analgesics, e.g., acetomeniphen, salicylates (e.g., aspirin);

nonsteroidal antiinflammatory drugs (NSAIDs), e.g., ibuprofen, naproxen, fenoprofen, ketoprofen, celecoxib, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac;

anticonvulsants, e.g., carbamazepine, oxcarbazepine, lamotrigine, valproate, topiramate, gabapentin and pregabalin;

antidepressants such as tricyclic antidepressants, e.g., amitriptyline, clomipramine, desipramine, imipramine and nortriptyline;

COX-2 selective inhibitors, e.g., celecoxib, rofecoxib, parecoxib, valdecoxib, deracoxib, etoricoxib, and lumiracoxib;

alpha-adrenergics, e.g., doxazosin, tamsulosin, clonidine, guanfacine, dexmetatomidine, modafinil, and 4-amino-6,7-dimethoxy-2-(5-methane sulfonamido-1,2,3,4-tetrahydroisoquinol-2-yl)-5-(2-pyridyl) quinazoline;

barbiturate sedatives, e.g., amobarbital, aprobarbital, butabarbital, butabital, mephobarbital, metharbital, methohexital, pentobarbital, phenobartital, secobarbital, talbutal, theamylal and thiopental; tachykinin (NK) antagonist, particularly an NK-3, NK-2 or NK-1 antagonist, e.g., (aR, 9R)-7-[3,5-bis(trifluoromethyl)benzyl)]-8,9,10,11-tetrahydro-9-methyl-5-(4-methylphenyl)-7H-[1,4]diazocino[2,1-g][1,7]-naphthyridine-6-13-dione (TAK-637), 5-[[2R,3S)-2-[(1R)-1-[3,5-bis(trifluoromethylphenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy5-(trifluoromethoxy)phenyl]-methylamino]-2-phenylpiperidine (2S,3S);

coal-tar analgesics, in particular paracetamol;

serotonin reuptake inhibitors, e.g., paroxetine, sertraline, norfluoxetine (fluoxetine desmethyl metabolite), metabolite demethylsertraline, '3 fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine, trazodone and fluoxetine;

noradrenaline (norepinephrine) reuptake inhibitors, e.g., maprotiline, lofepramine, mirtazepine, oxaprotiline, fezolamine, tomoxetine, mianserin, buprorion, buproprion metabolite hydroxybuproprion, nomifensine and viloxazine (Vivalan®)), especially a selective noradrenaline reuptake inhibitor such as reboxetine, in particular (S,S)-reboxetine, and venlafaxine duloxetine neuroleptics sedative/anxiolytics;

dual serotonin-noradrenaline reuptake inhibitors, such as venlafaxine, venlafaxine metabolite O-desmethylvenlafaxine, clomipramine, clomipramine metabolite desmethylclomipramine, duloxetine, milnacipran and imipramine;

acetylcholinesterase inhibitors such as donepezil;

5-HT3 antagonists such as ondansetron;

metabotropic glutamate receptor (mGluR) antagonists;

local anaesthetic such as mexiletine and lidocaine;

corticosteroid such as dexamethasone;

antiarrhythimics, e.g., mexiletine and phenytoin;

muscarinic antagonists, e.g., tolterodine, propiverine, tropsium t chloride, darifenacin, solifenacin, temiverine and ipratropium;

cannabinoids;

vanilloid receptor agonists (e.g., resinferatoxin) or antagonists (e.g., capsazepine);

sedatives, e.g., glutethimide, meprobamate, methaqualone, and dichloralphenazone;

anxiolytics such as benzodiazepines, antidepressants such as mirtazapine, topical agents (e.g., lidocaine, capsacin and resiniferotoxin);

muscle relaxants such as benzodiazepines, baclofen, carisoprodol, chlorzoxazone, cyclobenzaprine, methocarbamol and orphrenadine;

anti-histamines or H1 antagonists;

NMDA receptor antagonists;

5-HT receptor agonists/antagonists;

PDEV inhibitors;

Tramadol®;

cholinergic (nicotinc) analgesics;

alpha-2-delta ligands;

prostaglandin E2 subtype antagonists;

leukotriene B4 antagonists;

5-lipoxygenase inhibitors; and

5-HT3 antagonists.

Sodium channel-mediated diseases and conditions that may be treated and/or prevented using such combinations include but not limited to, pain, central and peripherally mediated, acute, chronic, neuropathic as well as other diseases with associated pain and other central nervous disorders such as epilepsy, anxiety, depression and bipolar disease; or cardiovascular disorders such as arrhythmias, atrial fibrillation and ventricular fibrillation; neuromuscular disorders such as restless leg syndrome and muscle paralysis or tetanus; neuroprotection against stroke, neural trauma and multiple sclerosis; and channelopathies such as erythromyalgia and familial rectal pain syndrome.

As used herein "combination" refers to any mixture or permutation of one or more compounds of the invention and one or more other compounds of the invention or one or more additional therapeutic agent. Unless the context makes clear otherwise, "combination" may include simultaneous or sequentially delivery of a compound of the invention with one or more therapeutic agents. Unless the context makes clear otherwise, "combination" may include dosage forms of a compound of the invention with another therapeutic agent. Unless the context makes clear otherwise, "combination" may include routes of administration of a compound of the invention with another therapeutic agent. Unless the context makes clear otherwise, "combination" may include formulations of a compound of the invention with another therapeutic agent. Dosage forms, routes of administration and pharmaceutical compositions include, but are not limited to, those described herein.

The invention will be more fully understood by reference to the following examples. They should not, however, be construed as limiting the scope of the invention.

EXAMPLES

These examples serve to provide guidance to a skilled artisan to prepare and use the compounds, compositions and methods of the invention. While a particular embodiment of the present invention are described, the skilled artisan will appreciate that various changes and modifications can be made without departing from the spirit and scope of the inventions.

The chemical reactions in the examples described can be readily adapted to prepare a number of other compounds of the invention, and alternative methods for preparing the compounds of this invention are deemed to be within the scope of this invention. For example, the synthesis of non-exemplified compounds according to the invention can be successfully performed by modifications apparent to those skilled in the art, for example, by appropriately protecting interfering groups by utilizing other suitable reagents known in the art other than those described, and/or by making routine modifications of reaction conditions.

In the examples below, unless otherwise indicated all temperatures are set forth in degrees Celsius. Commercially available reagents were purchased from suppliers such as Aldrich Chemical Company, Lancaster, TCI or Maybridge and were used without further purification unless otherwise indicated. The reactions set forth below were done under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. $^1$H NMR spectra were obtained in deuterated CDCl$_3$, d$_6$-DMSO, CH$_3$OD or d$_6$-acetone solvent solutions (reported in ppm) using or trimethylsilane (TMS) or residual non-deuterated solvent peaks as the reference standard. When peak multiplicities are reported, the following abbreviates are used: s (singlet), d (doublet), t (triplet), q (quartet), m (multiplet), br (broad), dd (doublet of doublets), dt (doublet of triplets). Coupling constants, when given, are reported in Hz (Hertz).

All abbreviations used to describe reagents, reaction conditions or equipment are intended to be consistent with the definitions set forth in the "List of standard abbreviates and acronyms". The chemical names of discrete compounds of the invention were obtained using the structure naming feature of ChemDraw naming program.

Abbreviations
MeCN Acetonitrile
EtOAc Ethyl acetate
DCE Dichloroethane
DCM Dichloromethane
DIPEA Diisopropylethylamine
DEA Diethylamine
DMAP 4-dimethylaminopyridine
DMF N,N-Dimethylformamide
DMSO Dimethyl sulfoxide
FA Formic acid
IPA Isopropyl alcohol
TFA Trifluoroacetic acid
EDCI 1-Ethyl-3-(3-dimethylaminopropyl)carbodiimide hydrochloride
HCl Hydrochloric acid
HPLC High Pressure Liquid Chromatography
LCMS Liquid Chromatography Mass Spectrometry
MeOH Methanol
NMP N-methyl-2-pyrrolidone
RPHPLC Reverse phase high pressure liquid chromatography
RT Retention time
SFC Supercritical Fluid Chromatography
THF Tetrahydrofuran
TEA Triethylamine Example 1 & Example 2

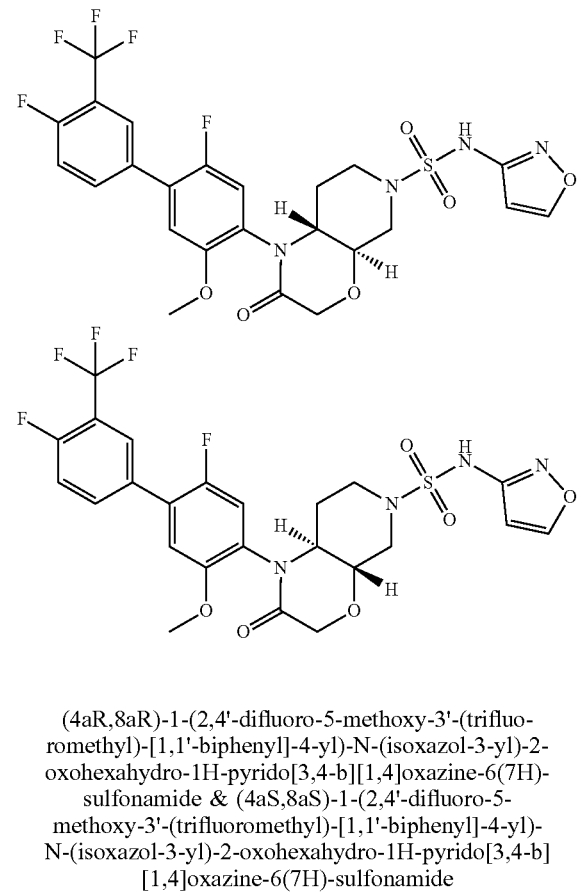

(4aR,8aR)-1-(2,4'-difluoro-5-methoxy-3'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide & (4aS,8aS)-1-(2,4'-difluoro-5-methoxy-3'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide

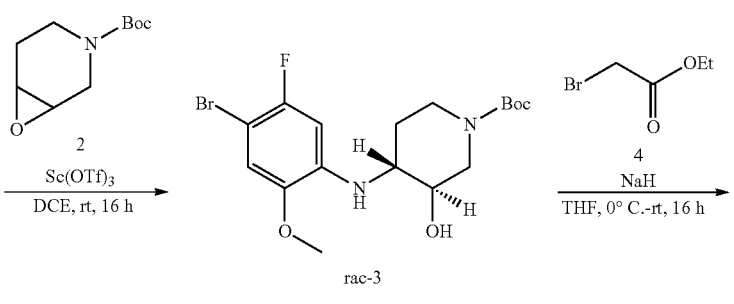

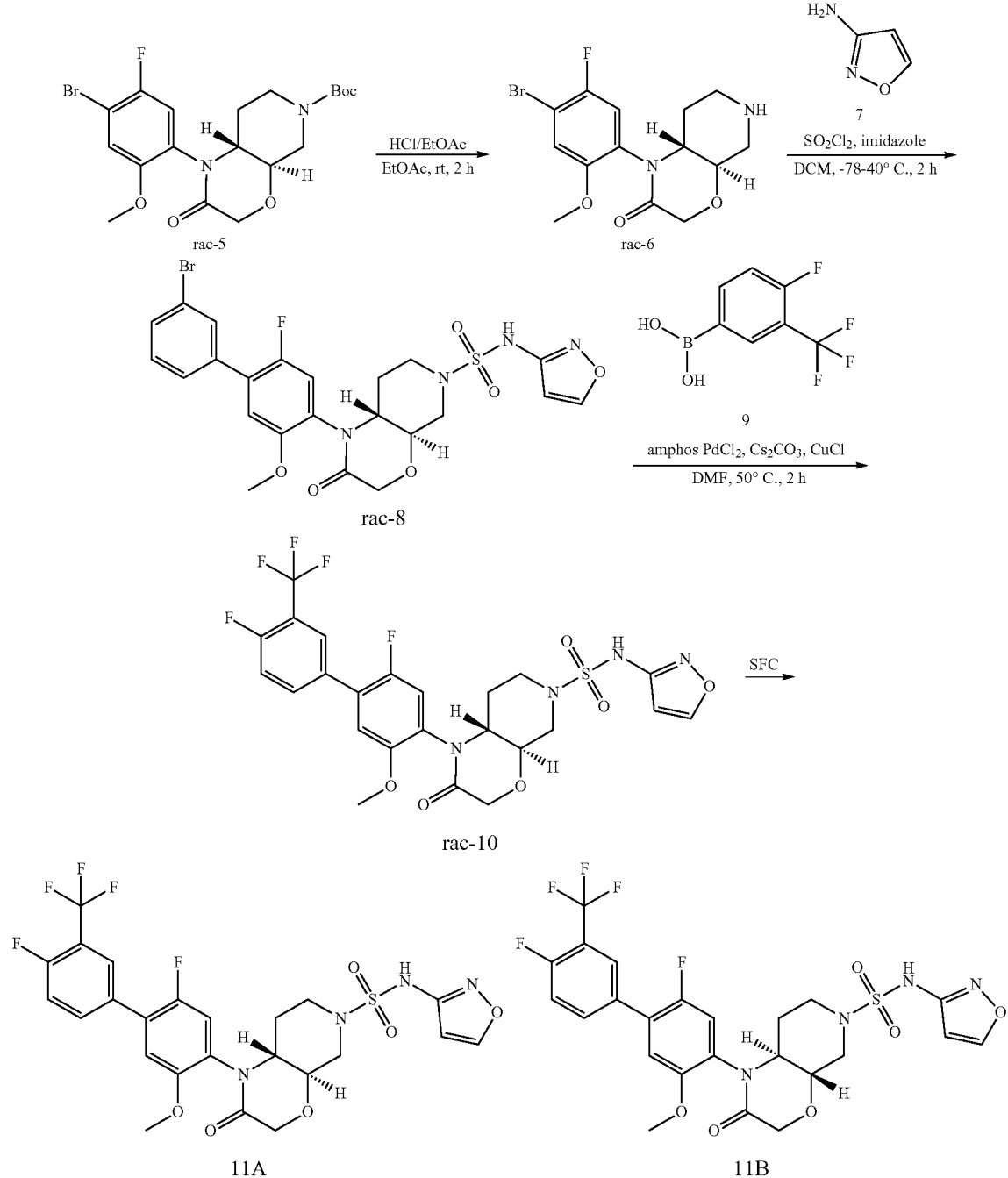

Step 1:

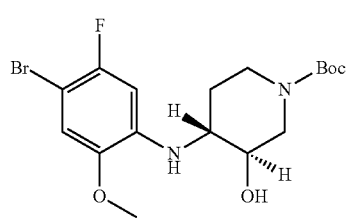 [SMILES: COc1cc(Br)c(F)cc1N[C@@H]1CCN(C(=O)OC(C)(C)C)C[C@H]1O]

Rac-trans-tert-butyl 4-((4-bromo-5-fluoro-2-methoxyphenyl)amino)-3-hydroxypiperidine-1-carboxylate To a solution of 4-bromo-5-fluoro-2-methoxyaniline (1.33 g, 6.02 mmol), tert-butyl 7-oxa-3-azabicyclo[4.1.0]heptane-3-carboxylate (1.0 g, 5.02 mmol) in 1,2-dichloroethane (30 mL) was added Sc(OTf)$_3$ (371 mg, 0.75 mmol). The mixture was stirred at room temperature for 16 h. The mixture was concentrated in vacuo and the crude residue was purified by silica gel chromatography (solvent gradient: 0-25% EtOAc in petroleum ether) to give the title compound (1.1 g, 52%) as yellow oil. $^1$H NMR (400 MHz, CDCl$_3$) δ

6.82 (d, J=6.4 Hz, 1H), 6.54 (d, J=10.4 Hz, 1H), 4.28-4.24 (m, 1H), 4.06-4.00 (m, 1H), 3.82 (s, 3H), 3.54-3.46 (m, 1H), 3.24-3.19 (m, 1H), 2.75-2.88 (m, 2H), 2.09-2.05 (m, 1H), 1.45 (s, 9H), 1.38-1.31 (m, 1H).

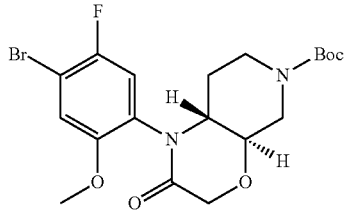 [SMILES: COc1cc(Br)c(F)cc1N1C(=O)CO[C@@H]2CN(C(=O)OC(C)(C)C)CC[C@H]21]

Rac-trans-tert-butyl 1-(4-bromo-5-fluoro-2-methoxyphenyl)-2-oxohexahydro-1H-pyrido[3,4-b][1,4]oxazine-6(7H)-carboxylate To a solution of rac-trans-tert-butyl 4-((4-bromo-5-fluoro-2-methoxyphenyl)amino)-3-hydroxypiperidine-1-carboxylate (1.1 g, 2.62 mmol) in THF (12 mL) was added NaH (260 mg, 6.56 mmol) at 0° C. under a nitrogen atmosphere. After stirring at 0° C. for 0.5 h, ethyl 2-bromoacetate (0.46 mL, 4.2 mmol) was added dropwise. The mixture was warmed to room temperature and stirred for an additional 16 h. The reaction was quenched with sat. aq. NH$_4$Cl. The mixture was concentrated in vacuo and the residue was purified by silica gel chromatography (solvent gradient: 0-20% EtOAc in petroleum ether) to give the title compound (1.0 g, 83%) as a white solid. $^1$H NMR (400 MHz, CDCl$_3$) δ 7.14-7.11 (m, 1H), 6.97-6.92 (m, 1H), 4.52-4.39 (m, 3H), 4.20-4.10 (m, 1H), 3.84-3.80 (m, 3H), 3.78-3.71 (m, 1H), 3.58-3.51 (m, 1H), 2.73-2.55 (m, 2H), 1.46 (s, 9H), 1.40-1.28 (m, 2H) Step 3:

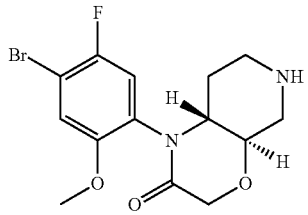 [SMILES: COc1cc(Br)c(F)cc1N1C(=O)CO[C@@H]2CNCC[C@H]21]

Rac-trans-1-(4-bromo-5-fluoro-2-methoxyphenyl)hexahydro-1H-pyrido[3,4-b][1,4]oxazin-2(3H)-one To a stirred solution of rac-(trans)-tert-butyl 1-(4-bromo-5-fluoro-2-methoxyphenyl)-2-oxohexahydro-1H-pyrido[3,4-b][1,4]oxazine-6(7H)-carboxylate (260 mg, 0.57 mmol) in EtOAc (5 mL) was added 4 M HCl (0.71 mL, 2.83 mmol) in EtOAc. The mixture was stirred at room temperature for 2 h. The reaction was quenched with sat. aq. NaHCO$_3$ (10 mL) and extracted with EtOAc (10 mL×2). The combined organic layers were dried over anhydrous Na$_2$SO$_4$, filtered and concentrated in vacuo to give the title compound (210 mg, crude) as yellow oil that required no further purification. $^1$H NMR (400 MHz, DMSO-d$_6$) δ 7.49-7.40 (m, 1H), 7.27-7.24 (m, 1H), 4.32-4.21 (m, 2H), 3.85-3.73 (m, 3H), 3.57-3.46 (m, 2H), 3.11-3.01 (m, 1H), 2.85-2.72 (m, 1H), 2.42-2.22 (m, 2H), 1.33-1.15 (m, 2H).

Step 4:

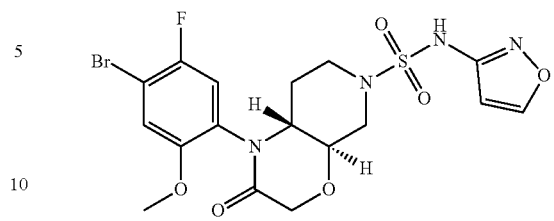

Rac-trans-1-(3'-bromo-2-fluoro-5-methoxy-[1,1'-biphenyl]-4-yl)-N-(isoxazol-3-yl)-2-oxohexahydro-1H-pyrido[3,4-b][1,4]oxazine-6(7H)-sulfonamide To a solution of imidazole (1.99 g, 29.23 mmol) and 3-aminoisoxazole (787 mg, 9.35 mmol) in DCM (4 mL) was added SO$_2$Cl$_2$ (0.77 mL, 9.35 mmol) at −78° C. Then the mixture was warmed to room temperature and stirred for 0.5 h. A solution of rac-trans-1-(4-bromo-5-fluoro-2-methoxyphenyl)hexahydro-1H-pyrido[3,4-b][1,4]oxazin-2(3H)-one (210 mg, 0.58 mmol) in DCM (4 mL) was added dropwise. The reaction mixture was heated to 40° C. for 1 h. The reaction mixture was quenched with water (20 mL) and extracted with DCM (20 mL). The organic layer was washed with brine (5 mL), dried over anhydrous Na$_2$SO$_4$, filtered and concentrated in vacuo. The crude residue was purified by silica gel chromatography (solvent gradient: 0-5% methanol in DCM) to give the title compound (260 mg, 88%) as yellow solid. $^1$H NMR (400 MHz, CDCl$_3$) δ 8.23 (s, 1H), 8.08-8.06 (m, 1H), 7.14-7.10 (m, 1H), 6.95-6.90 (m, 1H), 6.42-6.38 (m, 1H), 4.49-4.33 (m, 2H), 3.84-3.79 (m, 3H), 3.76-3.59 (m, 4H), 2.82-2.67 (m, 2H), 1.54-1.35 (m, 2H).

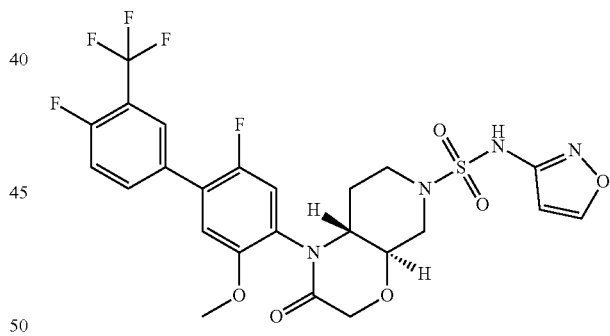

Rac-trans-1-(2,4'-difluoro-5-methoxy-3'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide To a solution of rac-trans-1-(3'-bromo-2-fluoro-5-methoxy-[1,1'-biphenyl]-4-yl)-N-(isoxazol-3-yl)-2-oxohexahydro-1H-pyrido[3,4-b][1,4]oxazine-6(7H)-sulfonamide (300 mg, 0.42 mmol), bis(di-tert-butyl(4-dimethylaminophenyl)phosphine)dichloropalladium(II) (59 mg, 0.08 mmol), Cs$_2$CO$_3$ (258 mg, 0.79 mmol) and CuCl (123 mg, 1.25 mmol) in DMF (5 mL) was added (4-fluoro-3-(trifluoromethyl)phenyl)boronic acid (259 mg, 1.25 mmol). The reaction mixture was heated to 50° C. for 2 h under a nitrogen atmosphere. After cooling to room temperature, the reaction mixture was quenched with water (50 mL), extracted with EtOAc (50 mL). The organic layer was washed with brine (20 mL), dried over anhydrous $Na_2SO_4$, filtered and concentrated in vacuo. The residue was purified by reverse phase chromatography (acetonitrile 65-95/ 0.225% formic acid in water) to give the title compound (90 mg, 37%) as yellow oil. LCMS (ESI) m/z: 589.0 [M+H]+.

Step 6:

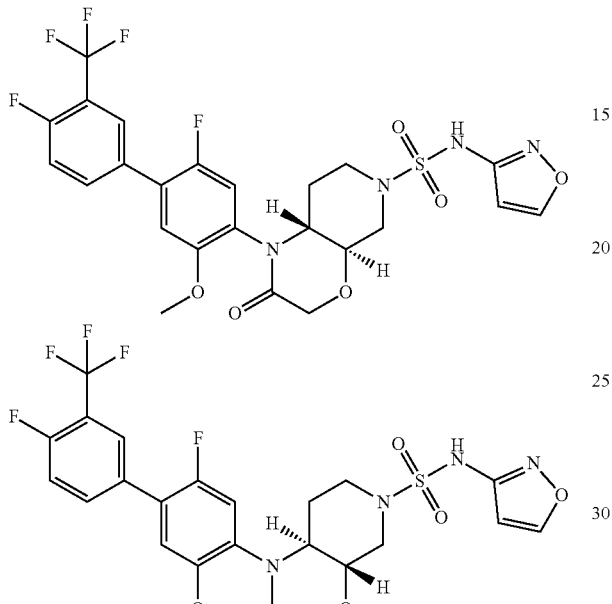

(4aR,8aR)-1-(2,4'-difluoro-5-methoxy-3'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide & (4aS,8aS)-1-(2,4'-difluoro-5-methoxy-3'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide Rac-trans-1-(2,4'-difluoro-5-methoxy-3'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide was separated by using chiral SFC (Phenomenex C2 (250 mm*30 mm, 10 um), Supercritical $CO_2$/EtOH+0.1% $NH_4OH$=60/40; 50 mL/min) to give (4aR,8aR)-1-(2,4'-difluoro-5-methoxy-3'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide (11 mg, first peak) as white powder and (4aS,8aS)-1-(2,4'-difluoro-5-methoxy-3'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide (11 mg, second peak) as a white solid. Absolute configuration was arbitrarily assigned to each enantiomer. Example 1: LCMS (ESI) m/z: 589.1 [M+H]+. 1H NMR (400 MHz, DMSO-$d_6$) δ 8.73-8.66 (m, 1H), 8.04-7.94 (m, 2H), 7.71-7.63 (m, 1H), 7.42-7.19 (m, 2H), 6.37 (s, 1H), 4.41-4.27 (m, 2H), 3.88-3.78 (m, 4H), 3.76-3.53 (m, 3H), 2.83-2.69 (m, 2H), 1.42-1.35 (m, 1H), 1.41-1.23 (m, 2H). Example 2: LCMS (ESI) m/z: 589.1 [M+H]+. 1H NMR (400 MHz, DMSO-$d_6$) δ 8.74-8.65 (m, 1H), 8.03-7.92 (m, 2H), 7.71-7.63 (m, 1H), 7.43-7.18 (m, 2H), 6.37 (s, 1H), 4.41-4.27 (m, 2H), 3.89-3.78 (m, 4H), 3.76-3.53 (m, 3H), 2.83-2.68 (m, 2H), 1.42-1.19 (m, 2H)

Example 3 & Example 4

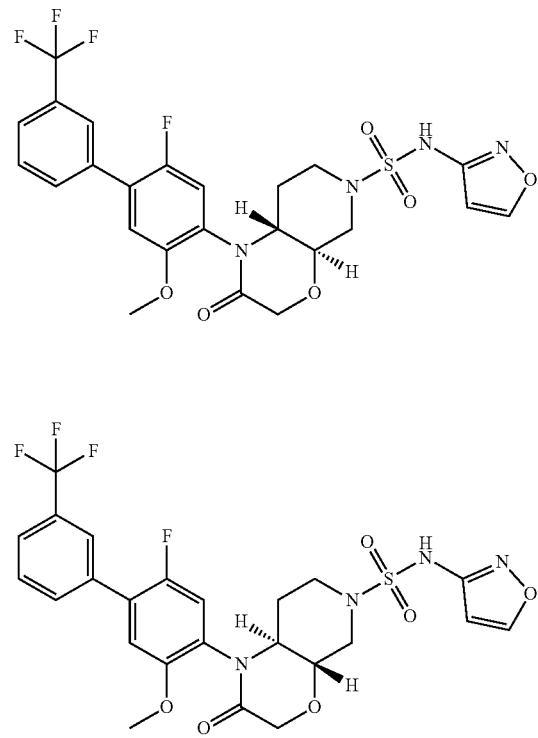

(4aR,8aR)-1-(2-fluoro-5-methoxy-3'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide & (4aS,8aS)-1-(2-fluoro-5-methoxy-3'-(trifluoromethyl)-[1,1'-biphenyl]-4-yl)-N-(isoxazol-3-yl)-2-oxohexahydro-1H-pyrido[3,4-bi][1,4]oxazine-6(7H)-sulfonamide

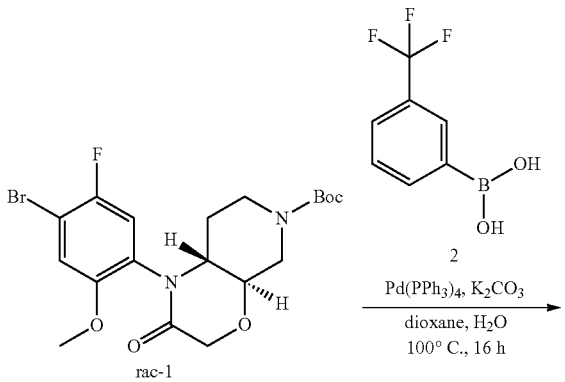

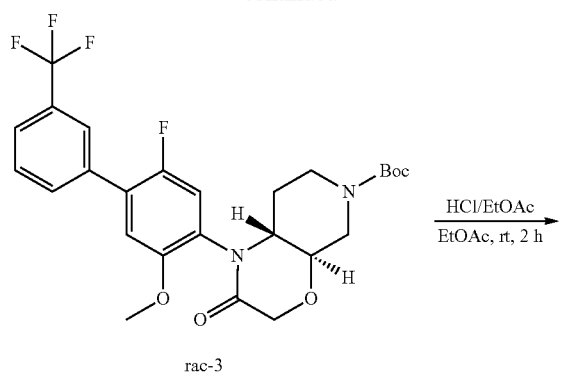

rac-3

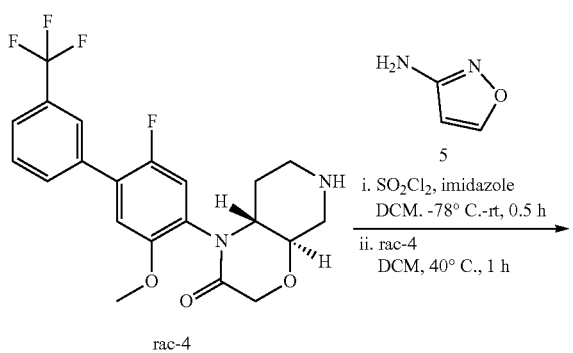

rac-4

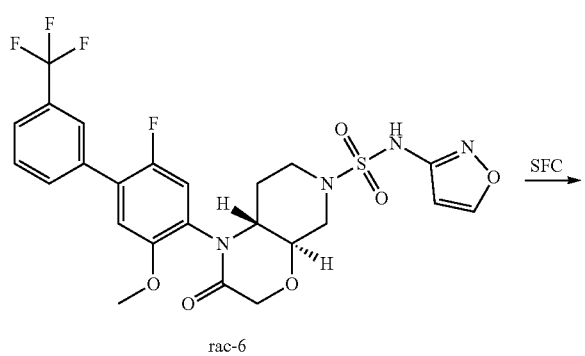

rac-6

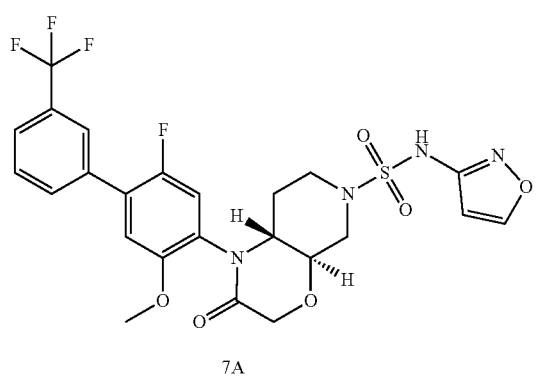

7A

HCl/EtOAc
EtOAc, rt, 2 h →

H₂N—isoxazole
5
i. SO₂Cl₂, imidazole
  DCM, −78° C.-rt, 0.5 h
ii. rac-4
  DCM, 40° C., 1 h →

SFC →

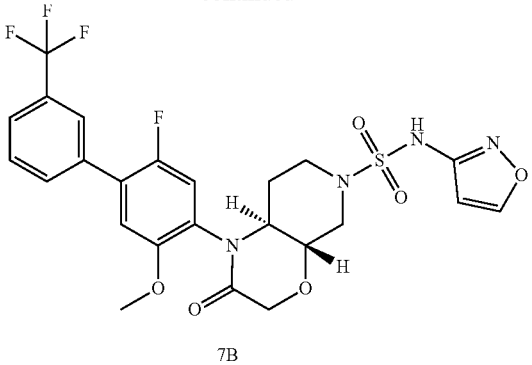 [SMILES: COc1cc(-c2cccc(C(F)(F)F)c2)c(F)cc1N1C(=O)CO[C@H]2CN(S(=O)(=O)Nc3ccon3)CC[C@@H]21]

7B

Step 1:

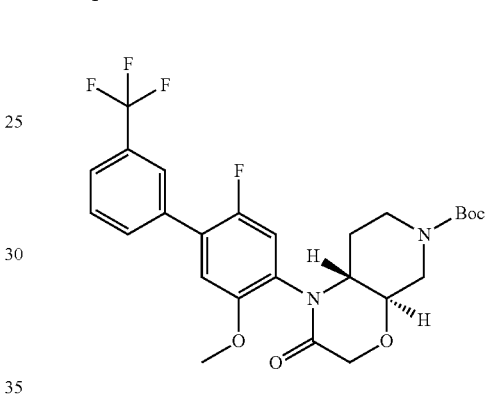

Rac-trans-tert-butyl 1-(2-fluoro-5-methoxy-3'-(trifluoromethyl)-[1,1'-biphenyl]-4-yl)-2-oxohexahydro-1H-pyrido[3,4-b][1,4]oxazine-6(7H)-carboxylate To a solution of 3-(trifluoromethyl)phenylboronic acid (11.83 g, 62.27 mmol), rac-trans-tert-butyl 1-(4-bromo-5-fluoro-2-methoxyphenyl)-2-oxohexahydro-1H-pyrido[3,4-b][1,4]oxazine-6(7H)-carboxylate (26.0 g, 56.61 mmol) and K₂CO₃ (23.47 g, 169.82 mmol) in water (50 mL) and 1,4-dioxane (260 mL) was added tetrakis(triphenylphosphine)palladium (6.54 g, 5.66 mmol). The reaction mixture was heated to 100° C. for 16 h under a nitrogen atmosphere. After cooling to room temperature, the reaction mixture was diluted with water (50 mL) and extracted with EtOAc (150 mL×3). The combined organic layers were washed with water (160 mL), brine (140 mL), dried over anhydrous Na₂SO₄, filtered and concentrated in vacuo. The crude residue was purified by silica gel chromatography (solvent gradient: 0-35% ethyl acetate in petroleum ether) to give the title compound (29 g, 98%) as yellow oil. ¹H NMR (400 MHz, CDCl₃) δ 7.77 (s, 1H), 7.75-7.64 (m, 2H), 7.62-7.56 (m, 1H), 7.05-6.94 (m, 2H), 4.59-4.30 (m, 3H), 4.26-4.00 (m, 1H), 3.92-3.85 (m, 3H), 3.84-3.78 (m, 1H), 3.67-3.52 (m, 1H), 2.85-2.54 (m, 2H), 1.68-1.57 (m, 1H), 1.48 (s, 9H), 1.40-1.30 (m, 1H).

Step 2:

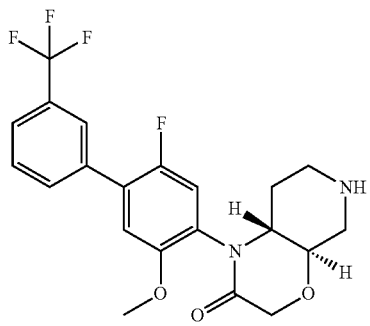 [SMILES: COc1cc(-c2cccc(C(F)(F)F)c2)c(F)cc1N1C(=O)CO[C@@H]2CNCC[C@H]21]

Rac-trans-1-(2-fluoro-5-methoxy-3'-(trifluoromethyl)-[1,1'-biphenyl]-4-yl)hexahydro-1H-pyrido[3,4-b][1,4]oxazin-2(3H)-one To a solution of Rac-trans-tert-butyl 1-(2-fluoro-5-methoxy-3'-(trifluoromethyl)-[1,1'-biphenyl]-4-yl)-2-oxohexahydro-1H-pyrido[3,4-b][1,4]oxazine-6(7H)-carboxylate (29.0 g, 55.29 mmol) in EtOAc (260 mL) was added 4M HCl (276 mL, 1105.8 mmol) in EtOAc. The reaction mixture was stirred at room temperature for 2 h. The reaction mixture was concentrated in vacuo to give the title compound (23 g, 98%) as a yellow solid that required no further purification. $^1$H NMR (400 MHz, CDCl$_3$) δ 8.25-8.20 (m, 1H), 7.78-7.75 (m, 1H), 7.70-7.62 (m, 2H), 7.60-7.50 (m, 1H), 6.99-6.94 (m, 2H), 4.55-4.41 (m, 2H), 3.91-3.85 (m, 3H), 3.83-3.54 (m, 2H), 3.39-3.31 (m, 1H), 3.09-2.98 (m, 1H), 2.71-2.51 (m, 2H), 1.62-1.24 (m, 2H).

Step 3:

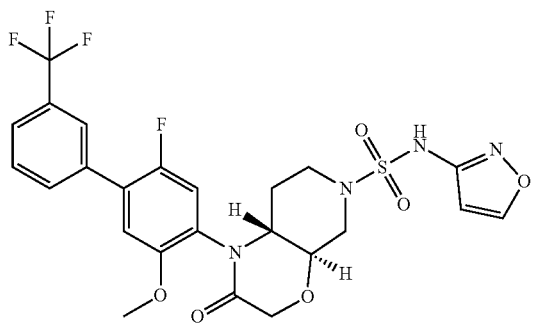 [SMILES: COc1cc(-c2cccc(C(F)(F)F)c2)c(F)cc1N1C(=O)CO[C@@H]2CN(S(=O)(=O)Nc3ccon3)CC[C@H]21]

Rac-trans-1-(2-fluoro-5-methoxy-3'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide To a solution of imidazole (18.45 g, 270.98 mmol) and 3-aminoisoxazole (7.29 g, 86.71 mmol) in DCM (500 mL) was added SO$_2$Cl$_2$ (11.70 g, 86.71 mmol) at −78° C. The reaction mixture was stirred at room temperature for 30 min. Then rac-trans-1-(2-fluoro-5-methoxy-3'-(trifluoromethyl)-[1,1'-biphenyl]-4-yl)hexahydro-1H-pyrido[3,4-b][1,4]oxazin-2(3H)-one (23.0 g, 54.2 mmol) in DCM (500 mL) was added dropwise. The reaction mixture was heated to 40° C. for 1 h. The reaction mixture was diluted with water (50 mL) and extracted with EtOAc (200 mL). The organic layer was washed with water (50 mL), sat. aq. citric acid (50 mL), brine (40 mL), dried over anhydrous Na$_2$SO$_4$, filtered and concentrated in vacuo. The residue was purified by silica gel chromatography (solvent gradient: 0-25% EtOAc (10% MeOH) in petroleum ether) to give the title compound (22 g, crude). The crude product (28 g) were recrystallized from propan-2-ol (90 mL) to give the title compound (18.7 g, 60%) as yellow solid. LCMS (ESI) m/z: 571.1 [M+H]$^+$.

Step 4:

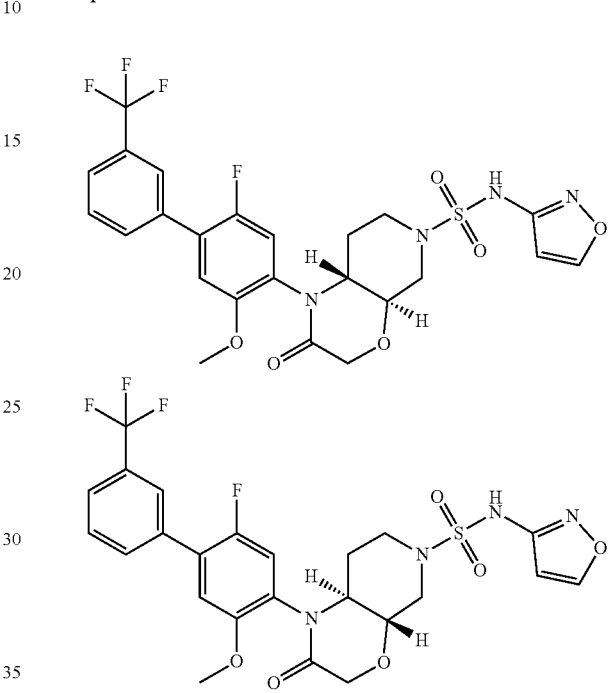

(4aR,8aR)-1-(2-fluoro-5-methoxy-3'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide & (4aS,8aS)-1-(2-fluoro-5-methoxy-3'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide Rac-trans-1-(2-fluoro-5-methoxy-3'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide (18.7 g) was separated by using chiral SFC (Chiralpak AD (250 mm*50 mm, 10 um)), Supercritical CO$_2$/EtOH+0.1% NH$_4$OH=60/40; 200 mL/min) to give (4aR,8aR)-1-(2-fluoro-5-methoxy-3'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide (5.92 g, 31.7%, second peak) as a white solid and (4aS,8aS)-1-(2-fluoro-5-methoxy-3'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide (7.93 g, 42%, first peak) as a white solid. Absolute configuration was arbitrarily assigned to each enantiomer. Example 3: LCMS (ESI) m/z: 571.2 [M+H]$^+$. $^1$H NMR (400 MHz, DMSO-d$_6$) δ 11.20 (s, 1H), 8.81-8.76 (m, 1H), 7.95-7.90 (m, 2H), 7.84-7.72 (m, 2H), 7.42-7.19 (m, 2H), 6.41-6.38 (m, 1H), 4.41-4.27 (m, 2H), 3.90-3.79 (m, 4H), 3.73-3.56 (m, 3H), 2.88-2.65 (m, 2H), 1.53-1.18 (m, 2H). Example 4: LCMS (ESI) m/z: 571.2 [M+H]$^+$. $^1$H NMR (400 MHz, DMSO-d$_6$) δ 11.20 (s, 1H), 8.81-8.76 (m, 1H), 7.95-7.90 (m, 2H), 7.84-7.72 (m, 2H), 7.42-7.19 (m, 2H), 6.41-6.38 (m, 1H), 4.41-4.27 (m, 2H), 3.90-3.79 (m, 4H), 3.73-3.56 (m, 3H), 2.88-2.65 (m, 2H), 1.53-1.18 (m, 2H).

Example 5 & Example 6

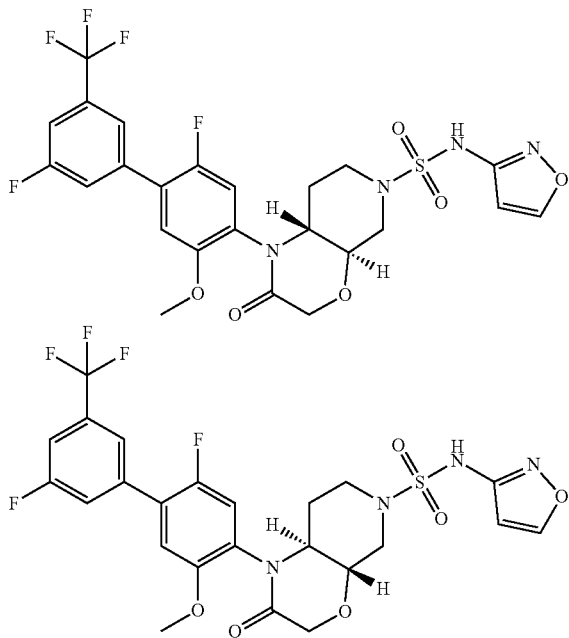

(4aR,8aR)-1-(2,3'-difluoro-5-methoxy-5'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide & (4aS,8aS)-1-(2,3'-difluoro-5-methoxy-5'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide Step 1:

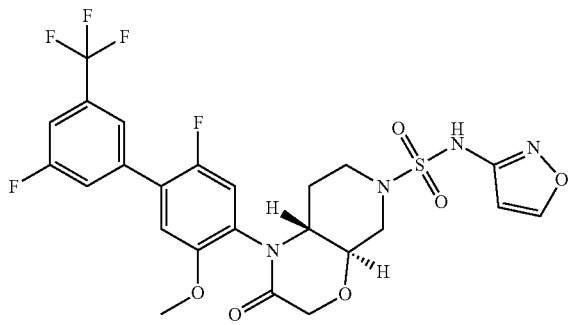 [SMILES: COc1cc(-c2cc(F)cc(C(F)(F)F)c2)c(F)cc1N1C(=O)CO[C@@H]2CN(S(=O)(=O)Nc3ccon3)CC[C@H]21]

Rac-trans-1-(2,3'-difluoro-5-methoxy-5'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide Following the procedure described in Example 1, step 5 and making non-critical variations as required to replace (4-fluoro-3-(trifluoromethyl)phenyl)boronic acid with (3-fluoro-5-(trifluoromethyl)phenyl)boronic acid, Rac-trans-1-(2,3'-difluoro-5-methoxy-5'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide (150 mg, 43% yield) was obtained as yellow oil.

Step 2:

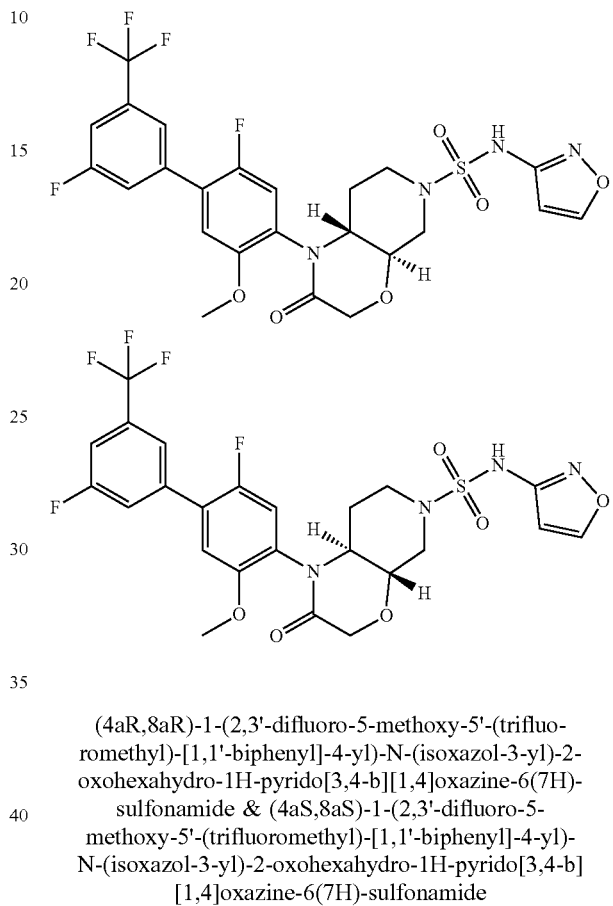

(4aR,8aR)-1-(2,3'-difluoro-5-methoxy-5'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide & (4aS,8aS)-1-(2,3'-difluoro-5-methoxy-5'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide Rac-trans-(4aR,8aR)-1-(2,3'-difluoro-5-methoxy-5'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide (150 mg) was separated by using chiral SFC (chiralpak IC (250 mm*30 mm, 5 um), Supercritical $CO_2$/ EtOH+0.1% $NH_4OH$=55/45; 60 mL/min) to give (4aR, 8aR)-1-(2,3'-difluoro-5-methoxy-5'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide (15 mg, first peak) as a white solid and (4aS,8aS)-1-(2,3'-difluoro-5-methoxy-5'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide (16 mg, second peak) as a white solid. Absolute configuration was arbitrarily assigned to each enantiomer. Example 5: LCMS (ESI) m/z: 589.1 [M+H]$^+$. $^1$H NMR (400 MHz, DMSO-$d_6$) δ 11.18 (s, 1H), 8.78-8.73 (m, 1H), 7.86 (d, J=8.8 Hz, 1H), 7.83-7.75 (m, 2H), 7.45-7.20 (m, 2H), 6.41-6.37 (m, 1H), 4.45-4.26 (m, 2H), 3.90-3.72 (m, 5H), 3.71-3.58 (m, 2H), 2.87-2.69 (m, 2H), 1.53-1.20 (m, 2H). Example 6: LCMS (ESI) m/z: 589.1 [M+H]$^+$. $^1$H NMR (400 MHz, DMSO-$d_6$) δ 11.18 (s, 1H), 8.80-8.71 (m, 1H), 7.87 (d, J=8.8 Hz, 1H), 7.83-7.76 (m, 2H), 7.45-7.21 (m, 2H), 6.41-6.37 (m, 1H), 4.42-4.28 (m, 2H), 3.91-3.71 (m, 5H), 3.70-3.56 (m, 2H), 2.86-2.69 (m, 2H), 1.51-1.20 (m, 2H).

Example 7 & Example 8

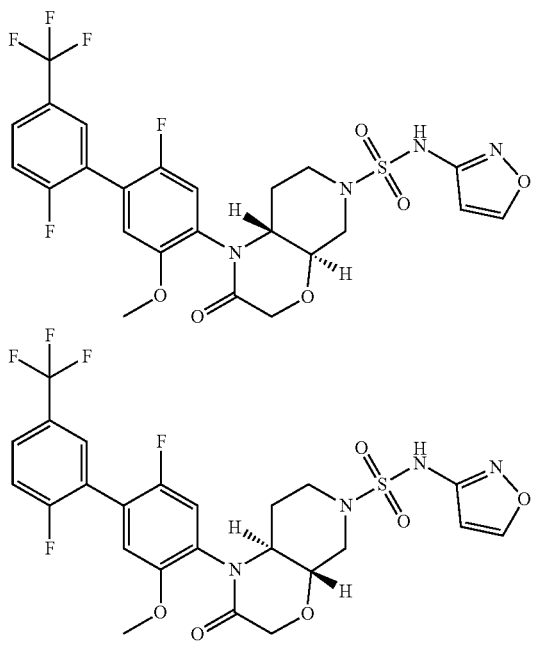

(4aR,8aR)-1-(2,2'-difluoro-5-methoxy-5'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide & (4aS,8aS)-1-(2,2'-difluoro-5-methoxy-5'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide Step 1:

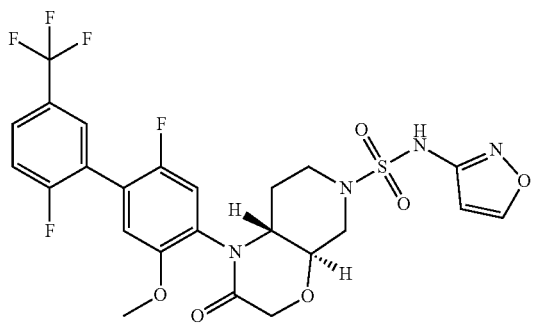 [SMILES: COc1cc(-c2cc(C(F)(F)F)ccc2F)c(F)cc1N1C(=O)CO[C@@H]2CN(S(=O)(=O)Nc3ccon3)CC[C@H]21]

Rac-trans-1-(2,2'-difluoro-5-methoxy-5'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide Following the procedure described in Example 1, step 5 and making non-critical variations as required to replace (4-fluoro-3-(trifluoromethyl)phenyl)boronic acid with (2-fluoro-5-(trifluoromethyl)phenyl)boronic acid, Rac-trans-1-(2,2'-difluoro-5-methoxy-5'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide (120 mg, 29%) as yellow oil.

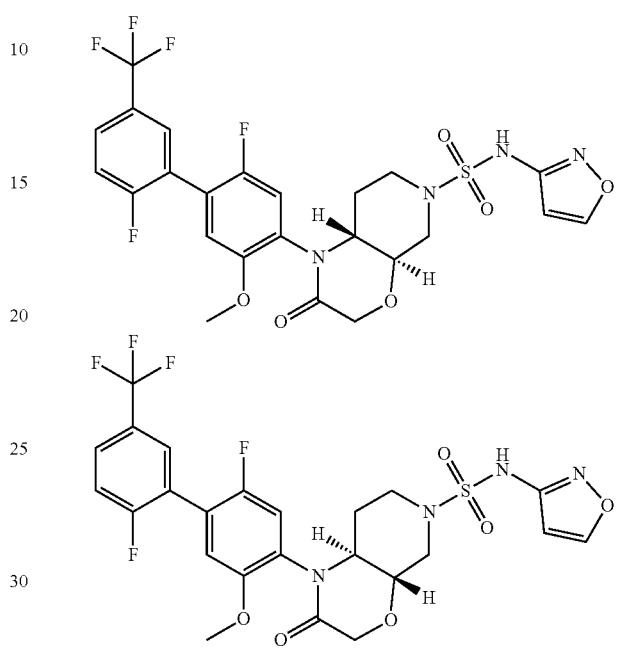

(4aR,8aR)-1-(2,2'-difluoro-5-methoxy-5'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide & (4aS,8aS)-1-(2,2'-difluoro-5-methoxy-5'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide Rac-trans-1-(2,2'-difluoro-5-methoxy-5'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide (120 mg) was separated by using chiral SFC (chiralpak IC (250 mm*30 mm, 5 um), Supercritical $CO_2$/EtOH+0.1% $NH_4OH$=60/40; 50 mL/min) to give (4aR,8aR)-1-(2,2'-difluoro-5-methoxy-5'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide (32 mg, first peak) as a white solid and (4aS,8aS)-1-(2,2'-difluoro-5-methoxy-5'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide (30 mg, second peak) as a white solid. Absolute configuration was arbitrarily assigned to each enantiomer. Example 7: LCMS (ESI) m/z: 589.1 [M+H]$^+$. $^1$H NMR (400 MHz, DMSO-$d_6$) δ 11.15 (s, 1H), 8.70-8.61 (m, 1H), 7.96-7.88 (m, 2H), 7.62-7.57 (m, 1H), 7.39-7.18 (m, 2H), 6.33 (s, 1H), 4.37-4.30 (m, 2H), 3.82-3.74 (m, 4H), 3.70-3.48 (m, 3H), 2.79-2.60 (m, 2H), 1.47-1.32 (m, 2H). Example 8: LCMS (ESI) m/z: 589.1 [M+H]$^+$. $^1$H NMR (400 MHz, DMSO-$d_6$) δ 11.15 (s, 1H), 8.76-8.69 (m, 1H), 7.96-7.88 (m, 2H), 7.62-7.57 (m, 1H), 7.39-7.18 (m, 2H), 6.37-6.34 (m, 1H), 4.38-4.28 (m, 2H), 3.82-3.74 (m, 4H), 3.72-3.50 (m, 3H), 2.82-2.69 (m, 2H), 1.49-1.34 (m, 2H).

Example 9 & Example 10

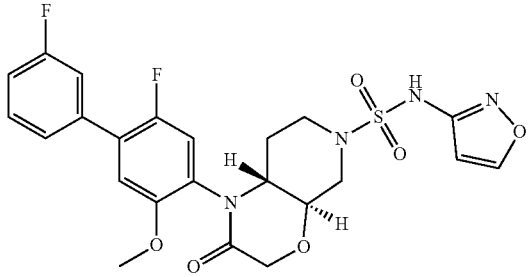

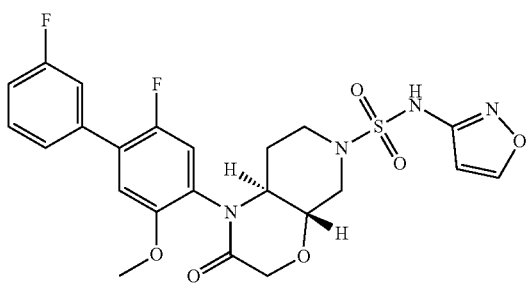

(4aR,8aR)-1-(2,3'-difluoro-5-methoxy-[1,1'-biphenyl]-4-yl)-N-(isoxazol-3-yl)-2-oxohexahydro-1H-pyrido[3,4-b][1,4]oxazine-6(7H)-sulfonamide & (4aS,8aS)-1-(2,3'-difluoro-5-methoxy-[1,1'-biphenyl]-4-yl)-N-(isoxazol-3-yl)-2-oxohexahydro-1H-pyrido[3,4-b][1,4]oxazine-6(7H)-sulfonamide Step 1:

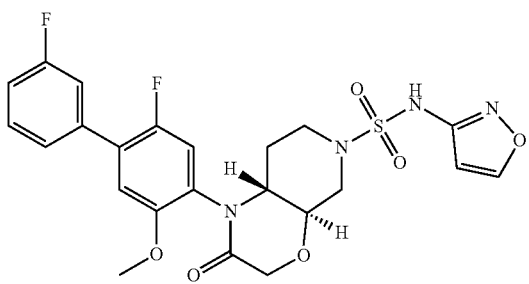

Rac-trans-1-(2,3'-difluoro-5-methoxy-[1'-biphenyl]-4-yl)-N-(isoxazol-3-yl)-2-oxohexahydro-1H-pyrido[3,4-b][1,4]oxazine-6(7H)-sulfonamide Following the procedure described in Example 1, step 5 and making non-critical variations as required to replace (4-fluoro-3-(trifluoromethyl)phenyl)boronic acid with (3-fluorophenyl)boronic acid, Rac-trans-1-(2,3'-difluoro-5-methoxy-[1,1'-biphenyl]-4-yl)-N-(isoxazol-3-yl)-2-oxohexahydro-1H-pyrido[3,4-b][1,4]oxazine-6(7H)-sulfonamide (60 mg, 58%) was obtained as yellow oil. LCMS (ESI) m/z: 521.1 [M+H]$^+$.

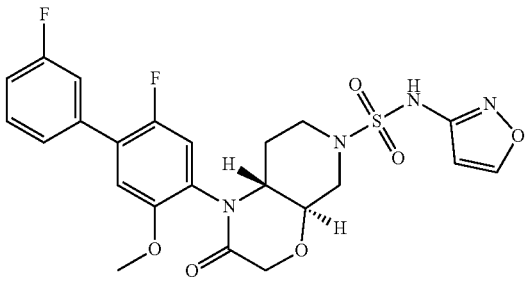 [SMILES: COc1cc(-c2cccc(F)c2)c(F)cc1N1C(=O)CO[C@@H]2CN(S(=O)(=O)Nc3ccon3)CC[C@H]21]

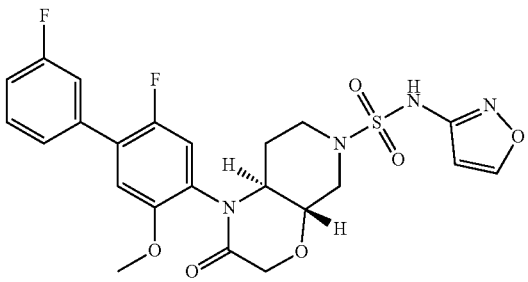

(4aR,8aR)-1-(2,3'-difluoro-5-methoxy-[1,1'-biphenyl]-4-yl)-N-(isoxazol-3-yl)-2-oxohexahydro-1H-pyrido[3,4-b][1,4]oxazine-6(7H)-sulfonamide & (4aS,8aS)-1-(2,3'-difluoro-5-methoxy-[1,1'-biphenyl]-4-yl)-N-(isoxazol-3-yl)-2-oxohexahydro-1H-pyrido[3,4-b][1,4]oxazine-6(7H)-sulfonamide Rac-trans-(4aR,8aR)-1-(2,3'-difluoro-5-methoxy-[1,1'-biphenyl]-4-yl)-N-(isoxazol-3-yl)-2-oxohexahydro-1H-pyrido[3,4-b][1,4]oxazine-6(7H)-sulfonamide (150 mg) was separated by using chiral SFC (Phenomenex C2 (250 mm*30 mm, 5 um), Supercritical $CO_2$/EtOH+0.1% $NH_4OH$=50/50; 80 mL/min) to give (4aR,8aR)-1-(2,3'-difluoro-5-methoxy-[1,1'-biphenyl]-4-yl)-N-(isoxazol-3-yl)-2-oxohexahydro-1H-pyrido[3,4-b][1,4]oxazine-6(7H)-sulfonamide (28 mg, first peak) as a white solid and (4aS,8aS)-1-(2,3'-difluoro-5-methoxy-[1,1'-biphenyl]-4-yl)-N-(isoxazol-3-yl)-2-oxohexahydro-1H-pyrido[3,4-b][1,4]oxazine-6(7H)-sulfonamide (29 mg, second peak) as a white solid. Absolute configuration was arbitrarily assigned to each enantiomer. Example 9: LCMS (ESI) m/z: 521.0 [M+H]$^+$. $^1$H NMR (400 MHz, DMSO-$d_6$) δ 11.18 (s, 1H), 8.81-8.74 (m, 1H), 7.59-7.43 (m, 3H), 7.39-7.15 (m, 3H), 6.41-6.36 (m, 1H), 4.42-4.27 (m, 2H), 3.89-3.78 (m, 4H), 3.75-3.56 (m, 3H), 2.88-2.68 (m, 2H), 1.54-1.17 (m, 2H). Example 10: LCMS (ESI) m/z: 521.0 [M+H]$^+$. $^1$H NMR (400 MHz, DMSO-$d_6$) δ 11.19 (s, 1H), 8.81-8.73 (m, 1H), 7.59-7.42 (m, 3H), 7.39-7.15 (m, 3H), 6.41-6.36 (m, 1H), 4.42-4.26 (m, 2H), 3.90-3.78 (m, 4H), 3.77-3.56 (m, 3H), 2.88-2.70 (m, 2H), 1.53-1.18 (m, 2H).

Example 11 & Example 12

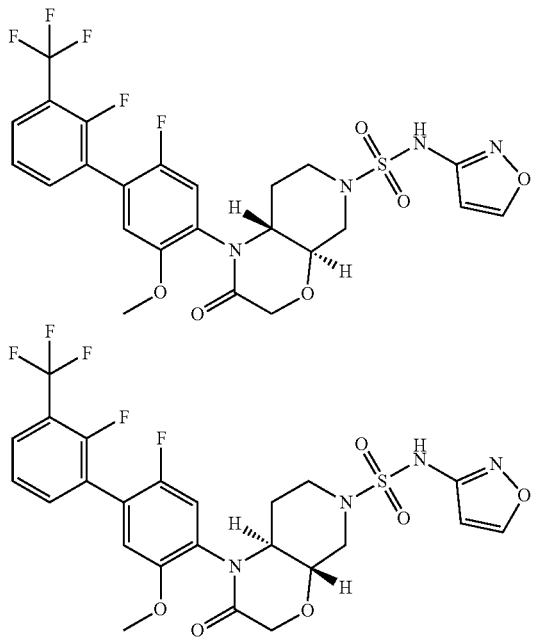

(4aR,8aR)-1-(2,2'-difluoro-5-methoxy-3'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide & (4aS,8aS)-1-(2,2'-difluoro-5-methoxy-3'-(trifluoromethyl)-[1,1'-biphenyl]-4-yl)-N-(isoxazol-3-yl)-2-oxohexahydro-H-pyrido[3,4-b][1,4]oxazine-6(7H)-sulfonamide Step 1:

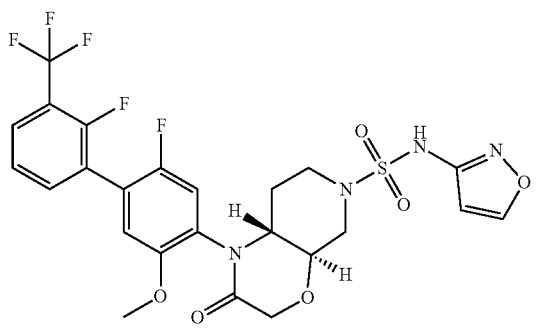 [SMILES: COc1cc(-c2cccc(C(F)(F)F)c2F)c(F)cc1N1C(=O)CO[C@@H]2CN(S(=O)(=O)Nc3ccon3)CC[C@H]21]

Rac-trans-(4aR,8aR)-1-(2,2'-difluoro-5-methoxy-3'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide Following the procedure described in Example 1, step 5 and making non-critical variations as required to replace (4-fluoro-3-(trifluoromethyl)phenyl)boronic acid with (2-fluoro-3-(trifluoromethyl)phenyl)boronic acid, Rac-trans-1-(2,2'-difluoro-5-methoxy-3'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide (40 mg, 9%) was obtained as yellow oil. LCMS (ESI) m/z: 589.1 [M+H]$^+$.

Step 2:

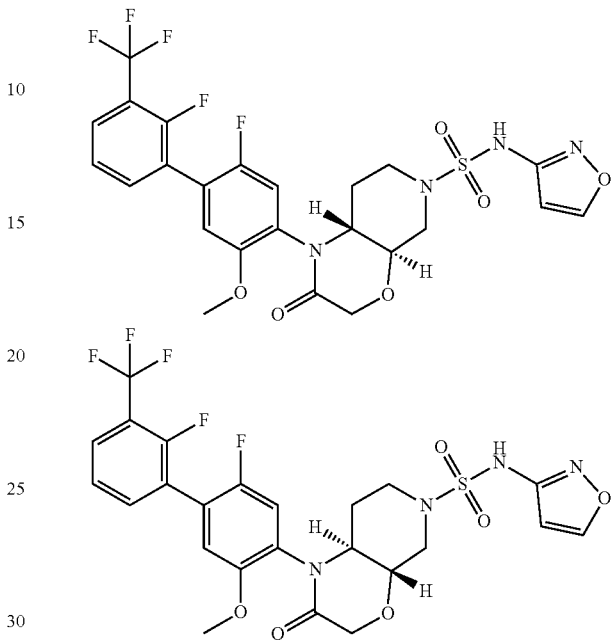

(4aR,8aR)-1-(2,2'-difluoro-5-methoxy-3'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide & (4aS,8aS)-1-(2,2'-difluoro-5-methoxy-3'-(trifluoromethyl)-[1,1'-biphenyl]-4-yl)-N-(isoxazol-3-yl)-2-oxohexahydro-H-pyrido[3,4-b][1,4]oxazine-6(7H)-sulfonamide Rac-trans-1-(2,2'-difluoro-5-methoxy-3'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide (40 mg) was separated by using chiral SFC (Chiralpak C2 (250 mm*30 mm, 5 um), Supercritical $CO_2$/EtOH+0.1% $NH_4OH$=40/60; 55 mL/min) to give (4aR,8aR)-1-(2,2'-difluoro-5-methoxy-3'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide (12 mg, first peak) as white powder and (4aS,8aS)-1-(2,2'-difluoro-5-methoxy-3'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide (12 mg, second peak) as white powder. Absolute configuration was arbitrarily assigned to each enantiomer. Example 11: LCMS (ESI) m/z: 589.2 [M+H]$^+$. $^1$H NMR (400 MHz, DMSO-$d_6$) δ 8.36 (s, 1H), 7.90-7.85 (m, 2H), 7.56-7.51 (m, 1H), 7.23-7.17 (m, 2H), 6.24 (s, 1H), 4.36-4.23 (m, 2H), 3.83-3.74 (m, 3H), 3.73-3.51 (m, 2H), 3.48-3.36 (m, 2H), 2.60-2.50 (m, 2H), 1.45-1.20 (m, 2H). Example 12: LCMS (ESI) m/z: 589.2 [M+H]$^+$. $^1$H NMR (400 MHz, DMSO-$d_6$) δ 8.39 (s, 1H), 7.92-7.83 (m, 2H), 7.55-7.52 (m, 1H), 7.25-7.15 (m, 2H), 6.25 (s, 1H), 4.37-4.22 (m, 2H), 3.80-3.74 (m, 3H), 3.70-3.52 (m, 2H), 3.50-3.40 (m, 2H), 2.60-2.50 (m, 2H), 1.40-1.20 (m, 2H).

Example 13 & Example 14

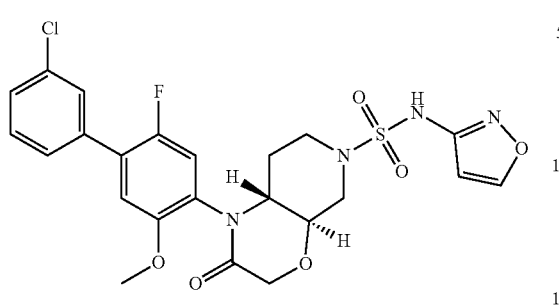

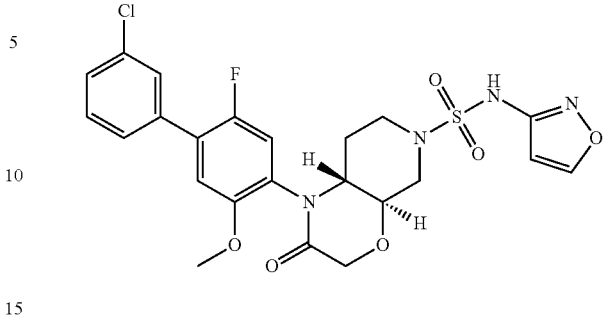

(4aR,8aR)-1-(3'-chloro-2-fluoro-5-methoxy-[1,1'-biphenyl]-4-yl)-N-(isoxazol-3-yl)-2-oxohexahydro-1H-pyrido[3,4-b][1,4]oxazine-6(7H)-sulfonamide &
(4aS,8aS)-1-(3'-chloro-2-fluoro-5-methoxy-[1,1'-biphenyl]-4-yl)-N-(isoxazol-3-yl)-2-oxohexahydro-1H-pyrido[3,4-b][1,4]oxazine-6(7H)-sulfonamide Step 1:

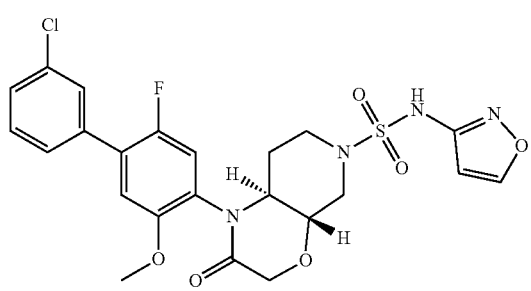

Rac-trans-1-(3'-chloro-2-fluoro-5-methoxy-[1,1'-biphenyl]-4-yl)-N-(isoxazol-3-yl)-2-oxohexahydro-1H-pyrido[3,4-b][1,4]oxazine-6(7H)-sulfonamide Following the procedure described in Example 1, step 5 and making non-critical variations as required to replace (4-fluoro-3-(trifluoromethyl)phenyl)boronic acid with (3-chlorophenyl)boronic acid, Rac-trans-1-(3'-chloro-2-fluoro-5-methoxy-[1,1'-biphenyl]-4-yl)-N-(isoxazol-3-yl)-2-oxohexahydro-1H-pyrido[3,4-b][1,4]oxazine-6(7H)-sulfonamide (50 mg, 23%) was obtained as a white solid. LCMS (ESI) m/z: 537.1 [M+H]+.

Step 2:

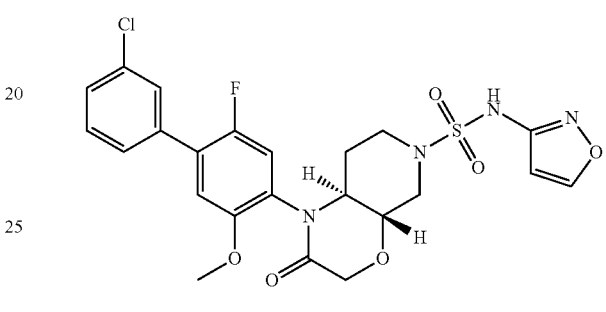

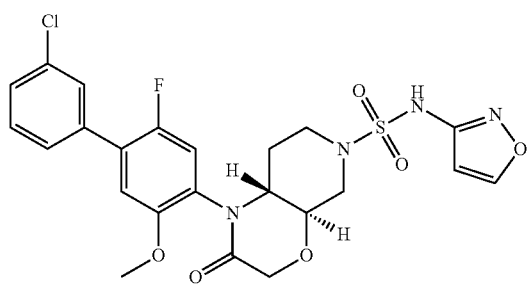

(4aR,8aR)-1-(3'-chloro-2-fluoro-5-methoxy-[1,1'-biphenyl]-4-yl)-N-(isoxazol-3-yl)-2-oxohexahydro-1H-pyrido[3,4-b][1,4]oxazine-6(7H)-sulfonamide &
(4aS,8aS)-1-(3'-chloro-2-fluoro-5-methoxy-[1,1'-biphenyl]-4-yl)-N-(isoxazol-3-yl)-2-oxohexahydro-1H-pyrido[3,4-b][1,4]oxazine-6(7H)-sulfonamide Rac-trans-1-(3'-chloro-2-fluoro-5-methoxy-[1,1'-biphenyl]-4-yl)-N-(isoxazol-3-yl)-2-oxohexahydro-1H-pyrido[3,4-b][1,4]oxazine-6(7H)-sulfonamide (50 mg) was separated by using chiral SFC (Chiralpak C2 IC (250 mm*30 mm, 5 um), Supercritical $CO_2$/EtOH+0.1% $NH_4OH$=40/60; 55 mL/min) to give (4aR,8aR)-1-(3'-chloro-2-fluoro-5-methoxy-[1,1'-biphenyl]-4-yl)-N-(isoxazol-3-yl)-2-oxohexahydro-1H-pyrido[3,4-b][1,4]oxazine-6(7H)-sulfonamide (4 mg, first peak) as a white solid and (4aS,8aS)-1-(3'-chloro-2-fluoro-5-methoxy-[1,1'-biphenyl]-4-yl)-N-(isoxazol-3-yl)-2-oxohexahydro-1H-pyrido[3,4-b][1,4]oxazine-6(7H)-sulfonamide (7 mg, second peak) as a white solid. Absolute configuration was arbitrarily assigned to each enantiomer. Example 13: LCMS (ESI) m/z: 537.0 [M+H]+. $^1$H NMR (400 MHz, DMSO-$d_6$) δ 8.32 (s, 1H), 7.70-7.67 (m, 1H), 7.57-7.51 (m, 2H), 7.24-7.19 (m, 2H), 6.25 (s, 1H), 4.44-4.34 (m, 2H), 3.87-3.80 (m, 3H), 3.77-3.67 (m, 1H), 3.67-3.40 (m, 3H), 2.54-2.50 (m, 2H), 1.45-1.20 (m, 2H). Example 14: LCMS (ESI) m/z: 537.2 [M+H]+. H NMR (400 MHz, DMSO-$d_6$) δ 8.18 (s, 1H), 7.68-7.63 (m, 1H), 7.57-7.52 (m, 2H), 7.48-7.46 (m, 1H), 7.20-7.15 (m, 2H), 6.19-6.17 (m, 1H), 4.36-4.21 (m, 2H), 3.83-3.76 (m, 3H), 3.67-3.56 (m, 2H), 3.53-3.39 (m, 2H), 2.35-2.31 (m, 2H), 1.42-1.20 (m, 2H).

Example 15 & Example 16

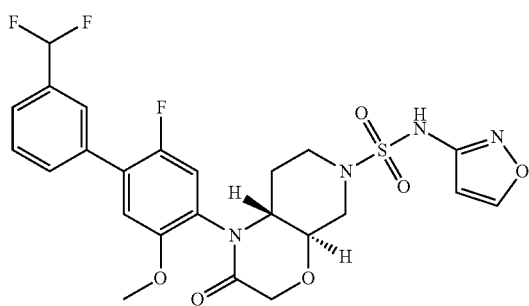

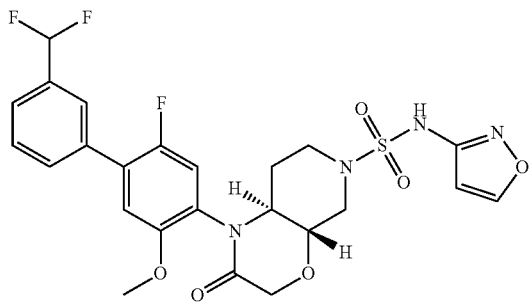

(4aR,8aR)-1-(3'-(difluoromethyl)-2-fluoro-5-methoxy-[1,1'-biphenyl]-4-yl)-N-(isoxazol-3-yl)-2-oxohexahydro-1H-pyrido[3,4-b][1,4]oxazine-6(7H)-sulfonamide & (4aS,8aS)-1-(3'-(difluoromethyl)-2-fluoro-5-methoxy-[1,1'-biphenyl]-4-yl)-N-(isoxazol-3-yl)-2-oxohexahydro-1H-pyrido[3,4-b][1,4]oxazine-6(7H)-sulfonamide Step 1:

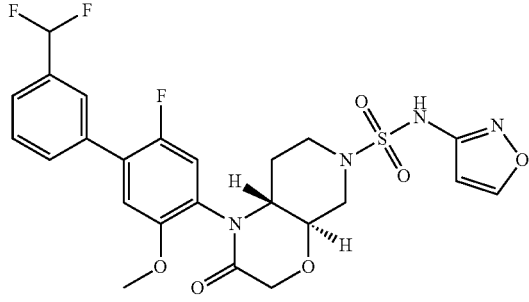 [SMILES: COc1cc(-c2cccc(C(F)F)c2)c(F)cc1N1C(=O)CO[C@@H]2CN(S(=O)(=O)Nc3ccon3)CC[C@H]21]

Following the procedure described in Example 1, step 5 and making non-critical variations as required to replace (4-fluoro-3-(trifluoromethyl)phenyl)boronic acid with (3-(difluoromethyl)-phenyl)boronic acid, rac-trans-1-(3'-(difluoromethyl)-2-fluoro-5-methoxy-[1,1'-biphenyl]-4-yl)-N-(isoxazol-3-yl)-2-oxohexahydro-1H-pyrido[3,4-b][1,4]oxazine-6(7H)-sulfonamide (30 mg, 14%) was obtained as a white solid.

Step 2:

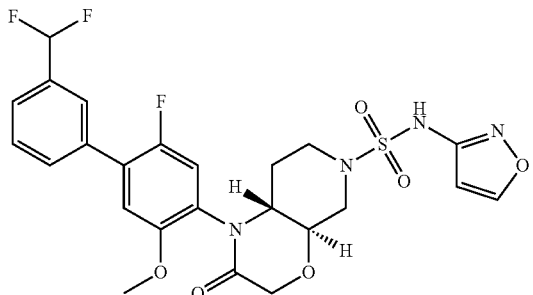

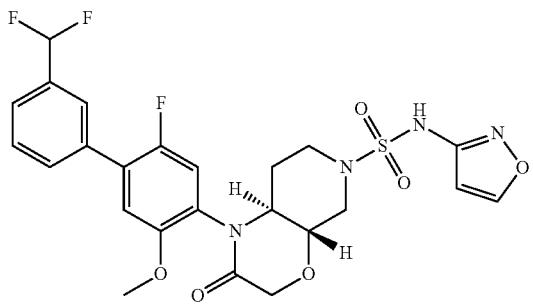

(4aR,8aR)-1-(3'-(difluoromethyl)-2-fluoro-5-methoxy-[1,1'-biphenyl]-4-yl)-N-(isoxazol-3-yl)-2-oxohexahydro-1H-pyrido[3,4-b][1,4]oxazine-6(7H)-sulfonamide & (4aS,8aS)-1-(3'-(difluoromethyl)-2-fluoro-5-methoxy-[1,1'-1,1'-biphenyl]-4-yl)-N-(isoxazol-3-yl)-2-oxohexahydro-1H-pyrido[3,4-b][1,4]oxazine-6(7H)-sulfonamide Rac-trans-1-(3'-(difluoromethyl)-2-fluoro-5-methoxy-[1,1'-biphenyl]-4-yl)-N-(isoxazol-3-yl)-2-oxohexahydro-1H-pyrido[3,4-b][1,4]oxazine-6(7H)-sulfonamide (30 mg) was separated by using chiral SFC (Chiralpak C2 IC (250 mm*30 mm, 5 um), Supercritical $CO_2$/EtOH+0.1% $NH_4OH$=45/55; 50 mL/min) to give (4aR,8aR)-1-(3'-(difluoromethyl)-2-fluoro-5-methoxy-[1,1'-biphenyl]-4-yl)-N-(isoxazol-3-yl)-2-oxohexahydro-1H-pyrido[3,4-b][1,4]oxazine-6(7H)-sulfonamide (6 mg, first peak) as a white solid and (4aS,8aS)-1-(3'-(difluoromethyl)-2-fluoro-5-methoxy-[1,1'-biphenyl]-4-yl)-N-(isoxazol-3-yl)-2-oxohexahydro-1H-pyrido[3,4-b][1,4]oxazine-6(7H)-sulfonamide (8.5 mg, second peak) as a white solid. Absolute configuration was arbitrarily assigned to each enantiomer. Example 15: LCMS (ESI) m/z: 553.2 [M+H]⁺. ¹H NMR (400 MHz, DMSO-$d_6$) δ 8.28 (s, 1H), 7.82-7.76 (m, 2H), 7.69-7.65 (m, 2H), 7.45-7.22 (m, 2H), 7.20-7.00 (m, 1H), 6.24 (s, 1H), 4.39-4.30 (m, 2H), 3.87-3.80 (m, 3H), 3.77-3.67 (m, 1H), 3.63-3.56 (m, 1H), 3.47-3.40 (m, 3H), 1.46-1.33 (m, 2H), 1.32-1.23 (m, 1H). Example 16: LCMS (ESI) m/z: 553.2 [M+H]⁺. ¹H NMR (400 MHz, DMSO-$d_6$) δ 8.30 (s, 1H), 7.82-7.75 (m, 2H), 7.69-7.61 (m, 2H), 7.45-7.22 (m, 2H), 7.20-7.00 (m, 1H), 6.24 (s, 1H), 4.38-4.24 (m, 2H), 3.87-3.80 (s, 3H), 3.72-3.70 (m, 1H), 3.65-3.56 (m, 1H), 3.45-3.42 (m, 1H), 3.29-3.26 (m, 2H), 1.46-1.34 (m, 2H), 1.30-1.23 (s, 1H).

Example 17 & Example 18

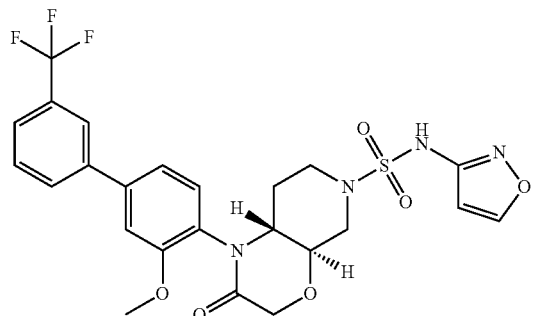

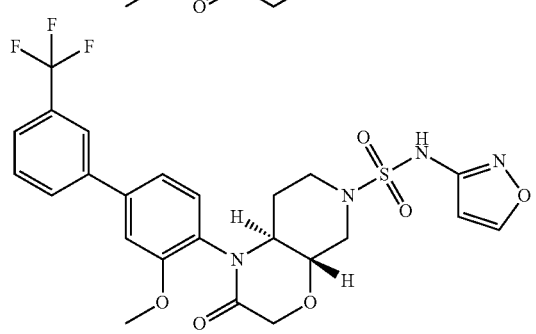

(4aR,8aR)-N-(isoxazol-3-yl)-1-(3-methoxy-3'-(trifluoromethyl)-[1,1'-biphenyl]-4-yl)-2-oxohexahydro-1H-pyrido[3,4-b][1,4]oxazine-6(7H)-sulfonamide & (4aS,8aS)-N-(isoxazol-3-yl)-1-(3-methoxy-3'-(trifluoromethyl)-[1,1'-biphenyl]-4-yl)-2-oxohexahydro-1H-pyrido[3,4-b][1,4]oxazine-6(7H)-sulfonamide

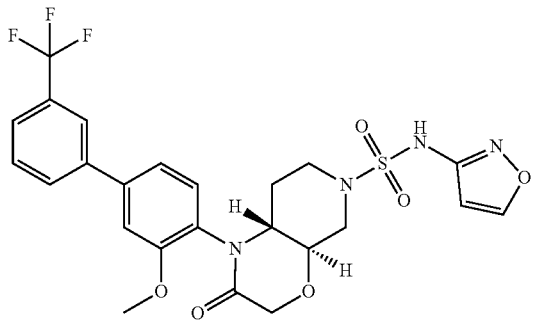

4A

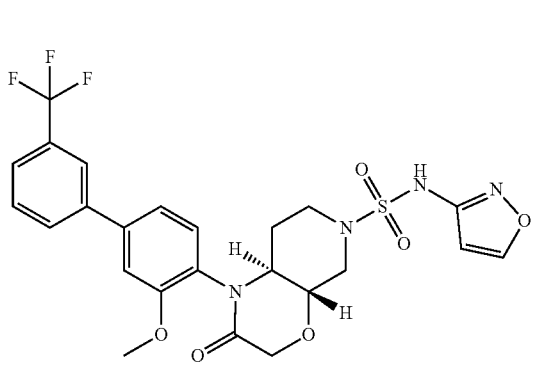

4B

Step 1:

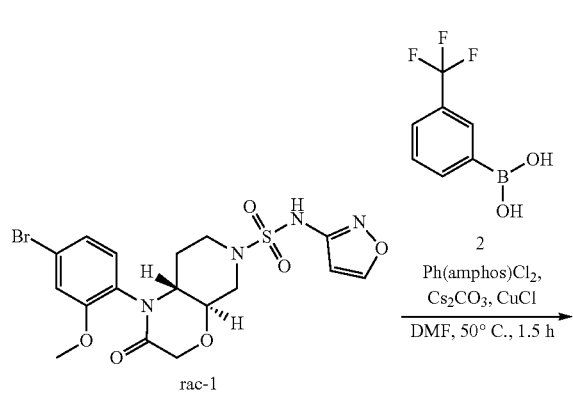

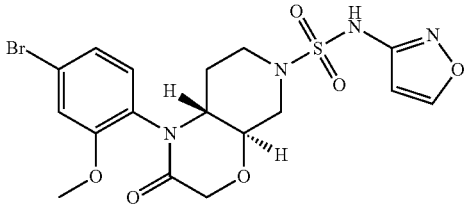 [SMILES: COc1cc(Br)ccc1N1C(=O)CO[C@@H]2CN(S(=O)(=O)Nc3ccon3)CC[C@H]21]

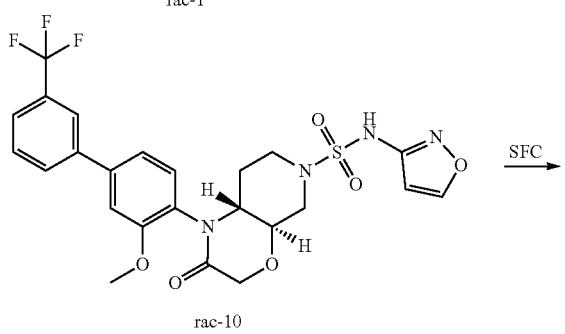

Rac-trans-1-(4-bromo-2-methoxyphenyl)-N-(isoxazol-3-yl)-2-oxohexahydro-1H-pyrido[3,4-b][1,4]oxazine-6(7H)-sulfonamide Following the procedure described in Example 1, step 1-4 and making non-critical variations as required to replace 4-bromo-5-fluoro-2-methoxyaniline with 4-bromo-2-methoxyaniline, Rac-trans-1-(4-bromo-2-methoxyphenyl)-N-(isoxazol-3-yl)-2-oxohexahydro-1H-pyrido[3,4-b][1,4]oxazine-6(7H)-sulfonamide (110 mg, 25%) was obtained as a yellow solid. LCMS (ESI) m/z: 487.0 [M+H]$^+$.

Step 2:

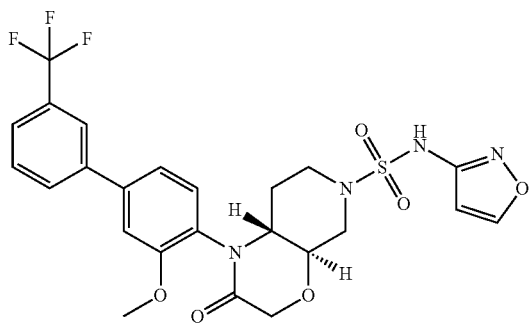 [SMILES: COc1cc(-c2cccc(C(F)(F)F)c2)ccc1N1C(=O)CO[C@@H]2CN(S(=O)(=O)Nc3ccon3)CC[C@H]21]

Rac-trans-N-(isoxazol-3-yl)-1-(3-methoxy-3'-(trifluoromethyl)-[1,1'-biphenyl]-4-yl)-2-oxohexahydro-1H-pyrido[3,4-b][1,4]oxazine-6(7H)-sulfonamide Following the procedure described in Example 1, step 5 and making non-critical variations as required to replace rac-trans-1-(4-bromo-5-fluoro-2-methoxyphenyl)-N-(isoxazol-3-yl)-2-oxohexahydro-1H-pyrido[3,4-b][1,4]oxazine-6(7H)-sulfonamide with rac-trans-1-(4-bromo-2-methoxyphenyl)-N-(isoxazol-3-yl)-2-oxohexahydro-1H-pyrido[3,4-b][1,4]oxazine-6(7H)-sulfonamide, (4-fluoro-3-(trifluoromethyl)phenyl)boronic acid with (3-(trifluoromethyl)phenyl)boronic acid, rac-trans-N-(isoxazol-3-yl)-1-(3-methoxy-3'-(trifluoromethyl)-[1,1'-biphenyl]-4-yl)-2-oxohexahydro-1H-pyrido[3,4-b][1,4]oxazine-6(7H)-sulfonamide (95 mg, 76%) was obtained as a yellow solid. LCMS (ESI) m/z: 553.2 [M+H].

Step 3:

(4aR,8aR)-N-(isoxazol-3-yl)-1-(3-methoxy-3'-(trifluoromethyl)-[1,1'-biphenyl]-4-yl)-2-oxohexahydro-1H-pyrido[3,4-b][1,4]oxazine-6(7H)-sulfonamide & (4aS,8aS)-N-(isoxazol-3-yl)-1-(3-methoxy-3'-(trifluoromethyl)-[1,1'-biphenyl]-4-yl)-2-oxohexahydro-1H-pyrido[3,4-b][1,4]oxazine-6(7H)-sulfonamide Rac-trans-(4aR,8aR)-N-(isoxazol-3-yl)-1-(3-methoxy-3'-(trifluoromethyl)-[1,1'-biphenyl]-4-yl)-2-oxohexahydro-1H-pyrido[3,4-b][1,4]oxazine-6(7H)-sulfonamide (90 mg) was separated by using chiral SFC (Chiralpak IC (250 mm*30 mm, 5 um), Supercritical $CO_2$/EtOH+0.1% $NH_4OH$=50/50; 80 mL/min) to give (4aR,8aR)-N-(isoxazol-3-yl)-1-(3-methoxy-3'-(trifluoromethyl)-[1,1'-biphenyl]-4-yl)-2-oxohexahydro-1H-pyrido[3,4-b][1,4]oxazine-6(7H)-sulfonamide (20 mg, first peak) as a white solid and (4aS,8aS)-N-(isoxazol-3-yl)-1-(3-methoxy-3'-(trifluoromethyl)-[1,1'-biphenyl]-4-yl)-2-oxohexahydro-1H-pyrido[3,4-b][1,4]oxazine-6(7H)-sulfonamide (19 mg, second peak) as a white solid. Absolute configuration was arbitrarily assigned to each enantiomer. Example 17: LCMS (ESI) m/z: 553.1 [M+H]$^+$. $^1$H NMR (400 MHz, $CD_3OD$) δ 8.52 (s, 1H), 7.93-7.91 (m, 2H), 7.69-7.63 (m, 2H), 7.33-7.20 (m, 3H), 6.44 (s, 1H), 4.48-4.38 (m, 2H), 4.03-4.01 (m, 1H), 3.94-3.90 (m, 3H), 3.76-3.72 (m, 3H), 2.89-2.77 (m, 2H), 1.44-1.48 (m, 1H), 1.38-1.24 (m, 1H). Example 18: LCMS (ESI) m/z: 553.1 [M+H]$^+$. $^1$H NMR (400 MHz, $CD_3OD$) δ 8.65 (s, 1H), 7.94-7.86 (m, 2H), 7.72-7.61 (m, 2H), 7.39-7.20 (m, 3H), 6.56 (s, 1H), 4.51-4.32 (m, 2H), 4.05-4.00 (m, 1H), 3.97-3.88 (m, 3H), 3.80-3.65 (m, 3H), 2.95-2.70 (m, 2H), 1.50-1.27 (m, 2H).

Example 19 & Example 20

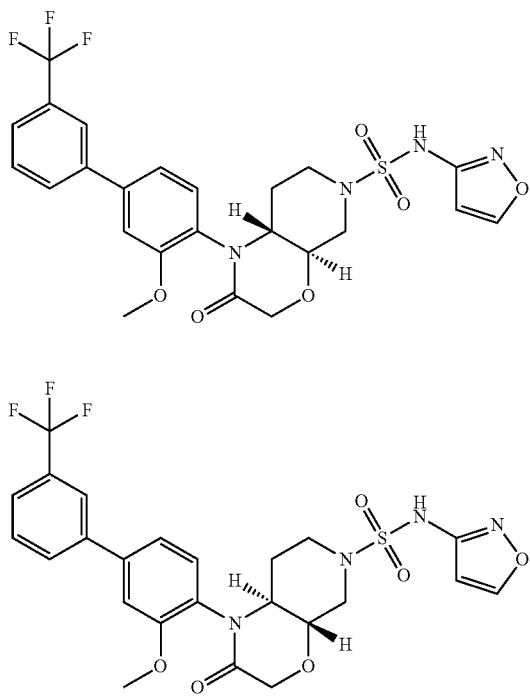

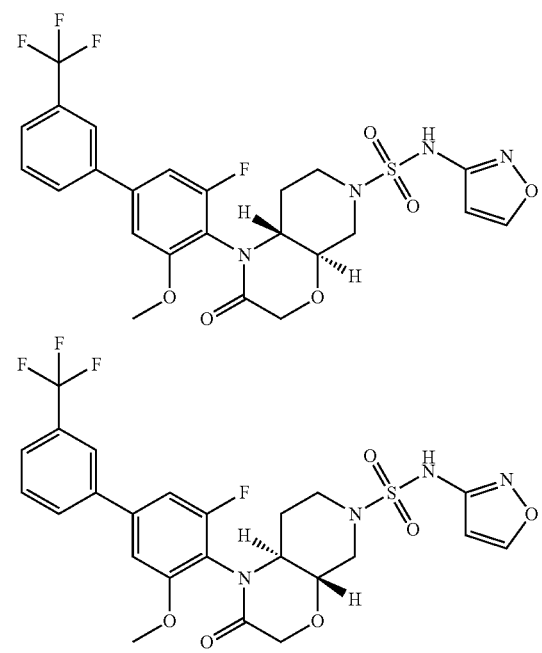 [SMILES: COc1cc(-c2cccc(C(F)(F)F)c2)cc(F)c1N1C(=O)CO[C@@H]2CN(S(=O)(=O)Nc3ccon3)CC[C@H]21 ; COc1cc(-c2cccc(C(F)(F)F)c2)cc(F)c1N1C(=O)CO[C@H]2CN(S(=O)(=O)Nc3ccon3)CC[C@@H]21]

(4aR,8aR)-1-(3-fluoro-5-methoxy-3'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide & (4aS,8aS)-1-(3-fluoro-5-methoxy-3'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamidede

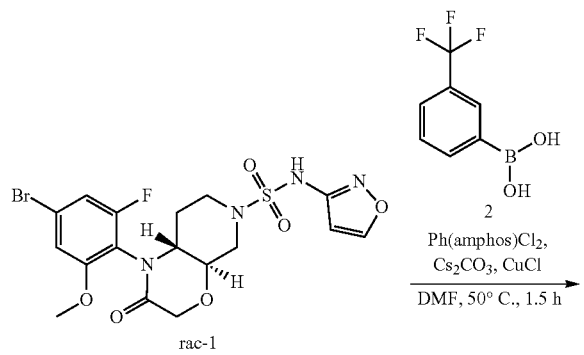

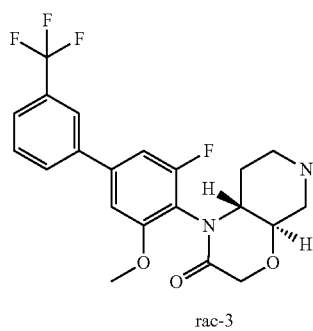

4A

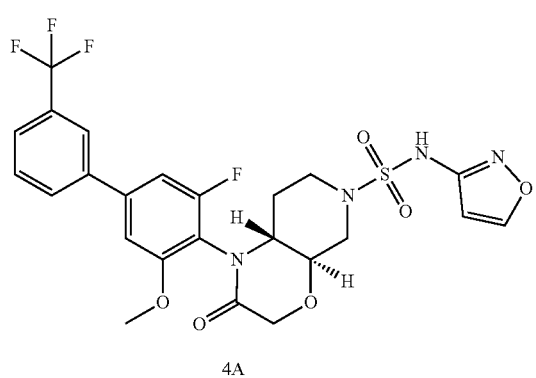

4B

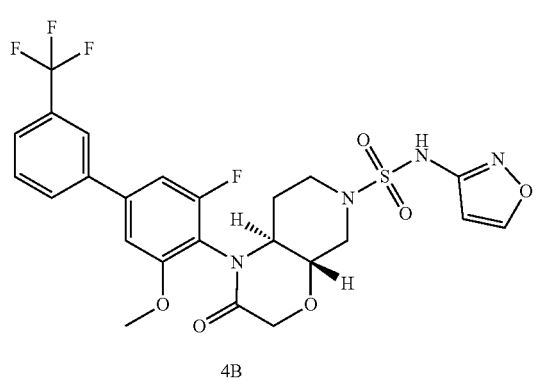

Step 1:

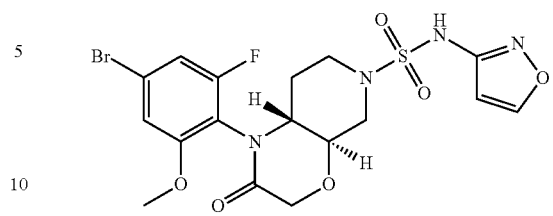

Rac-trans-(4aR,8aR)-1-(4-bromo-2-fluoro-6-methoxyphenyl)-N-(isoxazol-3-yl)-2-oxohexahydro-1H-pyrido[3,4-b][1,4]oxazine-6(7H)-sulfonamide Following the procedure described in Example 1, step 1-4 and making non-critical variations as required to replace 4-bromo-5-fluoro-2-methoxyaniline with 4-bromo-2-fluoro-6-methoxyaniline, Rac-trans-(4aR, 8aR)-1-(4-bromo-2-fluoro-6-methoxyphenyl)-N-(isoxazol-3-yl)-2-oxohexahydro-1H-pyrido[3,4-b][1,4]oxazine-6(7H)-sulfonamide (40 mg, 51%) was obtained as green oil. $^1$H NMR (400 MHz, CDCl$_3$) δ 8.28 (s, 1H), 7.07-6.88 (m, 2H), 6.49-6.44 (m, 1H), 4.51-4.39 (m, 2H), 4.05-4.00 (m, 1H), 3.87-3.83 (m, 3H), 3.82-3.73 (m, 2H), 3.73-3.55 (m, 2H), 3.50-3.45 (m, 1H), 2.85-2.72 (m, 2H), 1.59-1.43 (m, 2H).

Step 2:

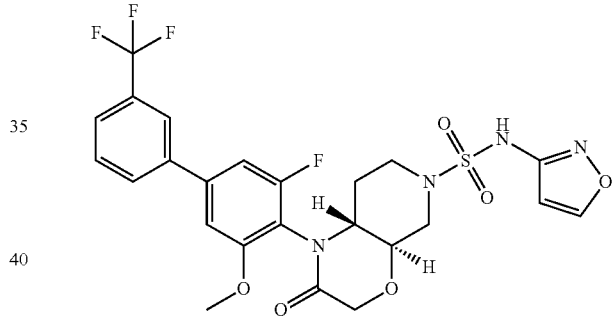

Rac-trans-1-(3-fluoro-5-methoxy-3'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide Following the procedure described in Example 1, step 5 and making non-critical variations as required to replace Rac-trans-1-(4-bromo-5-fluoro-2-methoxyphenyl)-N-(isoxazol-3-yl)-2-oxohexahydro-1H-pyrido[3,4-b][1,4]oxazine-6(7H)-sulfonamide with rac-trans-1-(4-bromo-2-fluoro-6-methoxyphenyl)-N-(isoxazol-3-yl)-2-oxohexahydro-1H-pyrido[3,4-b][1,4]oxazine-6(7H)-sulfonamide, (4-fluoro-3-(trifluoromethyl)phenyl)boronic acid with (3-(trifluoromethyl)phenyl)boronic acid Rac-trans-1-(3-fluoro-5-methoxy-3'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide (110 mg, 29% yield) was obtained as a white solid. LCMS (ESI) m/z: 571.1 [M+H]$^+$. H NMR (400 MHz, CDCl$_3$) δ 8.31 (s, 1H), 7.77 (s, 1H), 7.74-7.65 (m, 2H), 7.62-7.56 (m, 1H), 7.02-6.98 (m, 1H), 6.93-6.90 (m, 1H), 6.48 (s, 1H), 4.57-4.43 (m, 2H), 4.17-4.07 (m, 1H), 3.95-3.90 (m, 3H), 3.85-3.65 (m, 3H), 2.88-2.77 (m, 2H), 2.06-2.04 (m, 1H), 1.29-1.24 (m, 1H).

Step 3:

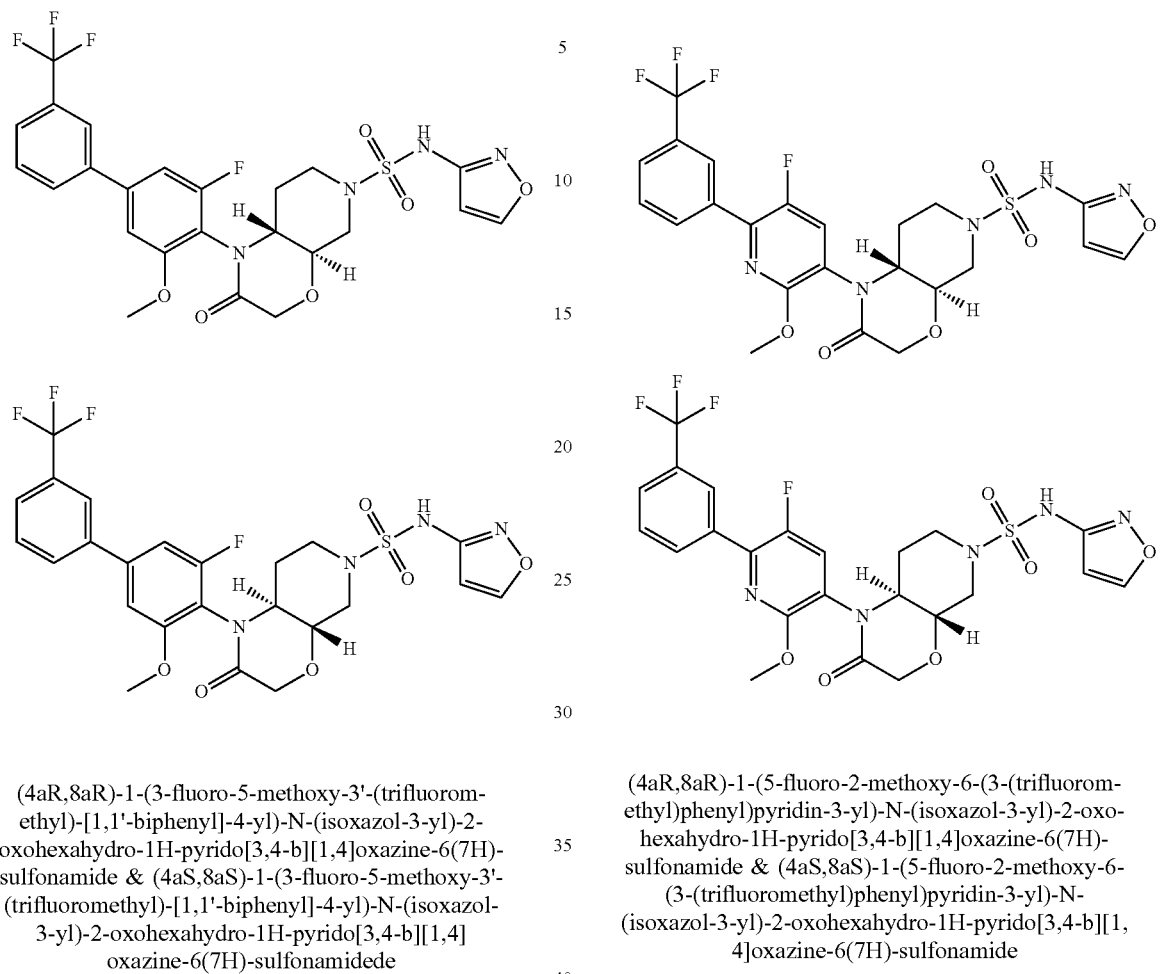

(4aR,8aR)-1-(3-fluoro-5-methoxy-3'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide & (4aS,8aS)-1-(3-fluoro-5-methoxy-3'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamidede Rac-trans-1-(3-fluoro-5-methoxy-3'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide (110 mg) was separated by using chiral SFC (Chiralpak AD (250 mm*30 mm, 5 um), Supercritical $CO_2$/EtOH+0.1% $NH_4OH$=75/25; 60 mL/min) to give (4aR,8aR)-1-(3-fluoro-5-methoxy-3'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide (30 mg, first peak) as a white solid and (4aS,8aS)-1-(3-fluoro-5-methoxy-3'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamidede (25 mg, second peak) as a white solid. Absolute configuration was arbitrarily assigned to each enantiomer. Example 19: LCMS (ESI) m/z: 571.1 [M+H]+. 1H NMR (400 MHz, $CDCl_3$) δ 8.31 (d, J=1.6 Hz, 1H), 7.78 (s, 1H), 7.74-7.65 (m, 2H), 7.62-7.57 (m, 1H), 7.03-6.99 (m, 1H), 6.92 (s, 1H), 6.48 (d, J=1.6 Hz, 1H), 4.56-4.45 (m, 2H), 4.10-4.05 (m, 1H), 3.94 (s, 3H), 3.84-3.74 (m, 3H), 2.89-2.78 (m, 2H), 1.64-1.60 (m, 2H). Example 20: LCMS (ESI) m/z: 571.1 [M+H]+. 1H NMR (400 MHz, $CDCl_3$) δ 8.26-8.20 (m, 1H), 8.12-8.05 (m, 2H), 7.81-7.70 (m, 2H), 7.40-7.25 (m, 2H), 6.22 (s, 1H), 4.44-4.28 (m, 2H), 3.90 (s, 3H), 3.75-3.70 (m, 1H), 3.68-3.60 (m, 1H), 3.45-3.40 (m, 2H), 2.45-2.37 (m, 2H), 1.45-1.31 (m, 2H).

Example 21 & Example 22

(4aR,8aR)-1-(5-fluoro-2-methoxy-6-(3-(trifluoromethyl)phenyl)pyridin-3-yl)-N-(isoxazol-3-yl)-2-oxohexahydro-1H-pyrido[3,4-b][1,4]oxazine-6(7H)-sulfonamide & (4aS,8aS)-1-(5-fluoro-2-methoxy-6-(3-(trifluoromethyl)phenyl)pyridin-3-yl)-N-(isoxazol-3-yl)-2-oxohexahydro-1H-pyrido[3,4-b][1,4]oxazine-6(7H)-sulfonamide

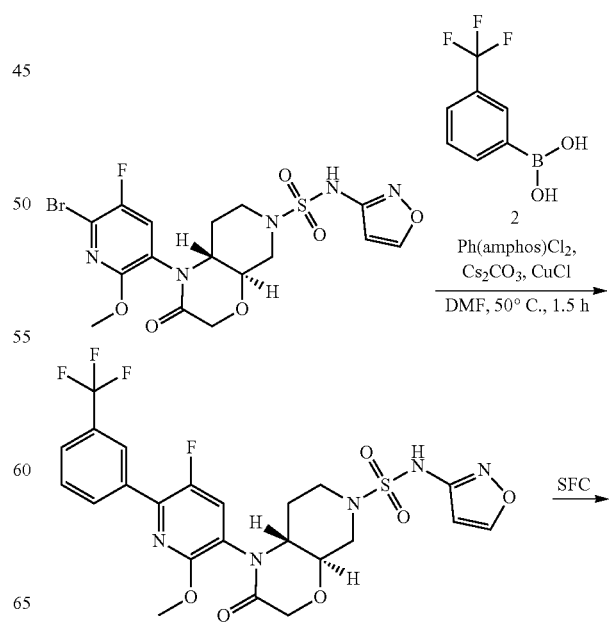

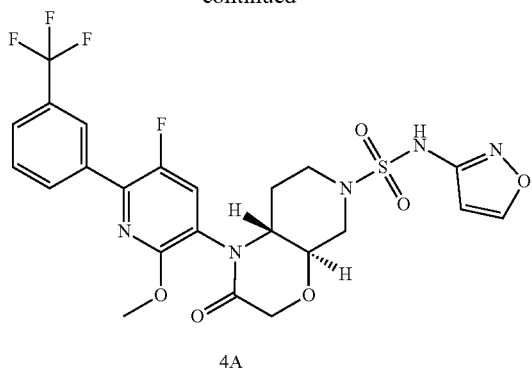

4A

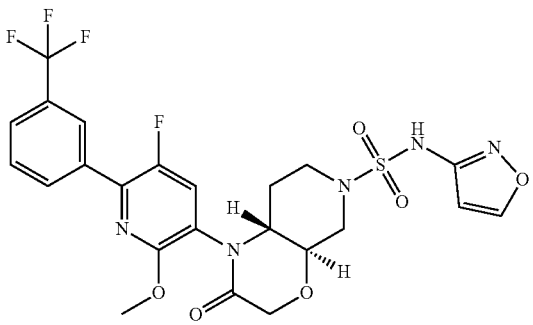 [SMILES: COc1nc(-c2cccc(C(F)(F)F)c2)c(F)cc1N1C(=O)CO[C@@H]2CN(S(=O)(=O)Nc3ccon3)CC[C@H]21]

Rac-trans-1-(5-fluoro-2-methoxy-6-(3-(trifluoromethyl)phenyl)pyridin-3-yl)-N-(isoxazol-3-yl)-2-oxo-hexahydro-1H-pyrido[3,4-b][1,4]oxazine-6(7H)-sulfonamide Following the procedure described in Example 1, step 5 and making non-critical variations as required to replace Rac-trans-1-(4-bromo-5-fluoro-2-methoxyphenyl)-N-(isoxazol-3-yl)-2-oxohexahydro-1H-pyrido[3,4-b][1,4]oxazine-6(7H)-sulfonamide with Rac-trans-1-(6-bromo-5-fluoro-2-methoxypyridin-3-yl)-N-(isoxazol-3-yl)-2-oxohexahydro-1H-pyrido[3,4-b][1,4]oxazine-6(7H)-sulfonamide, (4-fluoro-3-(trifluoromethyl)phenyl)boronic acid with (3-(trifluoromethyl)phenyl)boronic acid, Rac-trans-1-(5-fluoro-2-methoxy-6-(3-(trifluoromethyl)phenyl)pyridin-3-yl)-N-(isoxazol-3-yl)-2-oxohexahydro-1H-pyrido[3,4-b][1,4]oxazine-6(7H)-sulfonamide (150 mg, 55%) as a white solid. LCMS (ESI) m/z: 572.2 [M+H]⁺.

Step 3:

4B

Step 1:

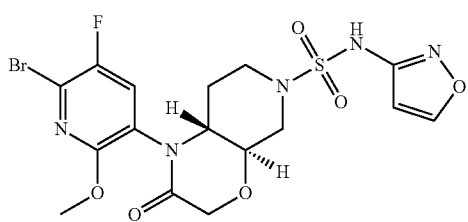

Rac-trans-1-(6-bromo-5-fluoro-2-methoxypyridin-3-yl)-N-(isoxazol-3-yl)-2-oxohexahydro-1H-pyrido[3,4-b][1,4]oxazine-6(7H)-sulfonamide Following the procedure described in Example 1, step 1-4 and making non-critical variations as required to replace 4-bromo-5-fluoro-2-methoxyaniline with 6-bromo-5-fluoro-2-methoxypyridin-3-amine, Rac-trans-1-(6-bromo-5-fluoro-2-methoxypyridin-3-yl)-N-(isoxazol-3-yl)-2-oxohexahydro-1H-pyrido[3,4-b][1,4]oxazine-6(7H)-sulfonamide (290 mg, 45%) was obtained as a yellow solid. LCMS (ESI) m/z: 505.9 [M+H]⁺.

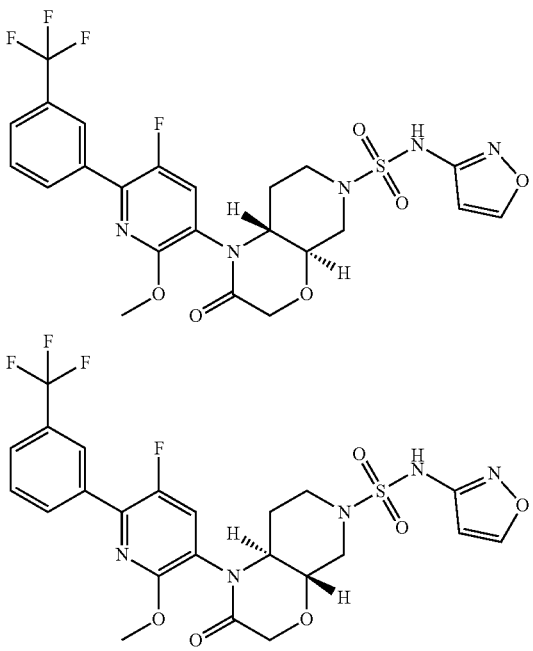

71

(4aR,8aR)-1-(5-fluoro-2-methoxy-6-(3-(trifluoromethyl)phenyl)pyridin-3-yl)-N-(isoxazol-3-yl)-2-oxohexahydro-1H-pyrido[3,4-b][1,4]oxazine-6(7H)-sulfonamide & (4aS,8aS)-1-(5-fluoro-2-methoxy-6-(3-(trifluoromethyl)phenyl)pyridin-3-yl)-N-(isoxazol-3-yl)-2-oxohexahydro-1H-pyrido[3,4-b][1,4]oxazine-6(7H)-sulfonamide Rac-trans-1-(5-fluoro-2-methoxy-6-(3-(trifluoromethyl)phenyl)pyridin-3-yl)-N-(isoxazol-3-yl)-2-oxohexahydro-1H-pyrido[3,4-b][1,4]oxazine-6(7H)-sulfonamide (150 mg) was separated by using chiral SFC (Chiralpak IC (250 mm*30 mm, 5 um), Supercritical $CO_2$/EtOH+0.1% $NH_4OH$=55/45; 60 mL/min) to give (4aR,8aR)-1-(5-fluoro-2-methoxy-6-(3-(trifluoromethyl)phenyl)pyridin-3-yl)-N-(isoxazol-3-yl)-2-oxohexahydro-1H-pyrido[3,4-b][1,4]oxazine-6(7H)-sulfonamide (55 mg, first peak) as a white solid and (4aS,8aS)-1-(5-fluoro-2-methoxy-6-(3-(trifluoromethyl)phenyl)pyridin-3-yl)-N-(isoxazol-3-yl)-2-oxohexahydro-1H-pyrido[3,4-b][1,4]oxazine-6(7H)-sulfonamide (70 mg, second peak) as a white solid. Absolute configuration was arbitrarily assigned to each enantiomer. Example 21: LCMS (ESI) m/z: 572.2 $[M+H]^+$. $^1H$ NMR (400 MHz, DMSO-$d_6$) δ 8.52-8.50 (m, 1H), 8.29 (d, J=7.2 Hz, 1H), 8.25 (s, 1H), 8.09-7.84 (m, 2H), 7.83-7.76 (m, 1H), 6.35-6.26 (m, 1H), 4.45-4.27 (m, 2H), 4.02-3.90 (m, 3H), 3.82-3.61 (m, 3H), 3.54-3.50 (m, 1H), 2.65-2.55 (m, 2H), 1.47-1.40 (m, 1H), 1.34-1.20 (m, 1H). Example 22: LCMS (ESI) m/z: 572.2 $[M+H]^+$. $^1H$ NMR (400 MHz, DMSO-$d_6$) δ 8.47-8.44 (m, 1H), 8.28 (d, J=7.2 Hz, 1H), 8.25 (s, 1H), 8.09-7.84 (m, 2H), 7.83-7.76 (m, 1H), 6.32-6.25 (m, 1H), 4.45-4.27 (m, 2H), 4.00-3.91 (m, 3H), 3.82-3.59 (m, 3H), 3.52-3.49 (m, 1H), 2.63-2.54 (m, 2H), 1.45-1.39 (m, 1H), 1.32-1.17 (m, 1H).

Example 23 & Example 24

72

(4aR,8aR)-1-(5-cyano-2-fluoro-3'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide & (4aS,8aS)-1-(5-cyano-2-fluoro-3'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide

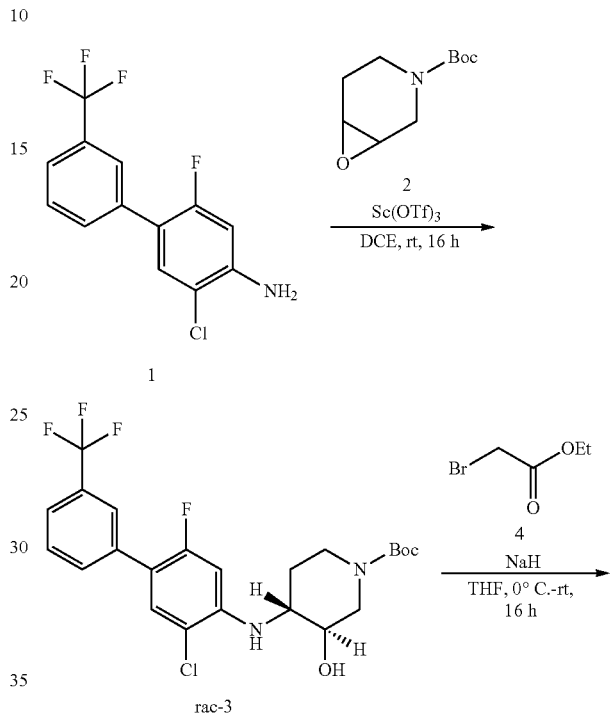

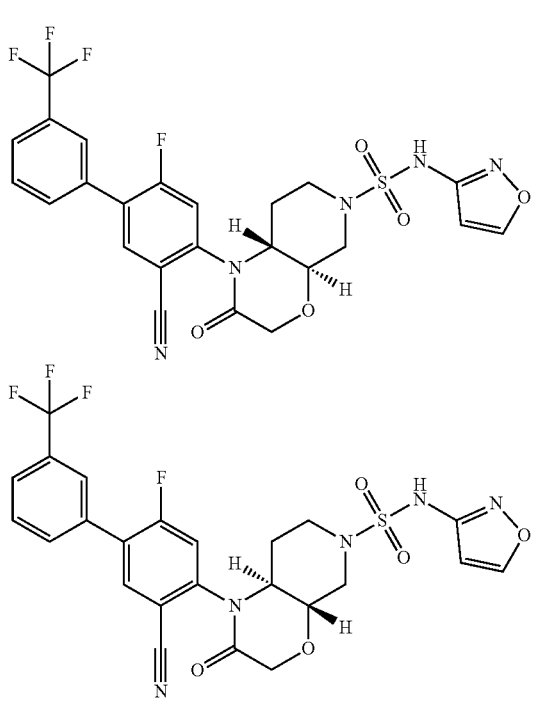

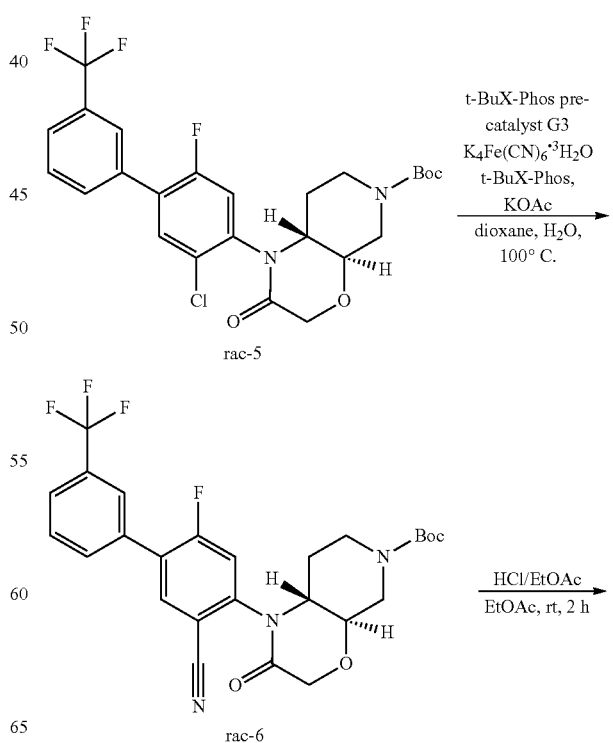

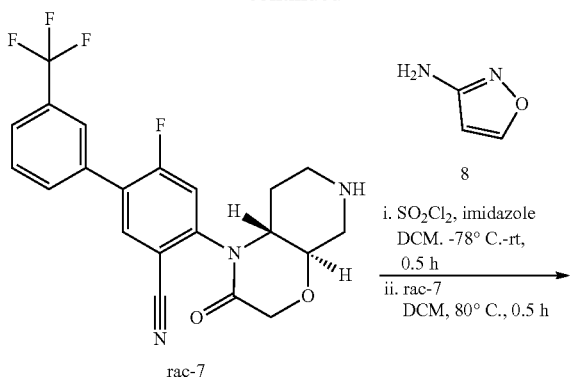

rac-7

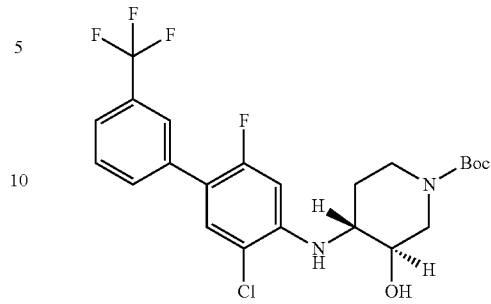

Step 1:

Rac-trans-tert-butyl 4-((5-chloro-2-fluoro-3'-(trifluoromethyl)-[1,1'-biphenyl]-4-yl)amino)-3-hydroxypiperidine-1-carboxylate Following the procedure described in Example 1, step 1 and making non-critical variations as required to replace 4-bromo-5-fluoro-2-methoxyaniline with 5-chloro-2-fluoro-3'-(trifluoromethyl)-[1,1'-biphenyl]-4-amine, rac-trans-tert-butyl 4-((5-chloro-2-fluoro-3'-(trifluoromethyl)-[1,1'-biphenyl]-4-yl)amino)-3-hydroxypiperidine-1-carboxylate (200 mg, 37%) was obtained as yellow oil. $^1$H NMR (400 MHz, CDCl$_3$) δ 7.61 (s, 1H), 7.53 (d, J=7.6 Hz, 1H), 7.46-7.36 (m, 2H), 7.23 (d, J=7.6 Hz, 1H), 6.55 (d, J=13.2 Hz, 1H), 4.39 (s, 1H), 4.18-4.09 (m, 1H), 3.95-3.85 (m, 1H), 3.55-3.43 (m, 1H), 3.31-3.18 (m, 1H), 2.97-2.70 (m, 2H), 2.08-1.97 (m, 1H), 1.37 (s, 9H), 1.36-1.34 (m, 1H).

Step 2:

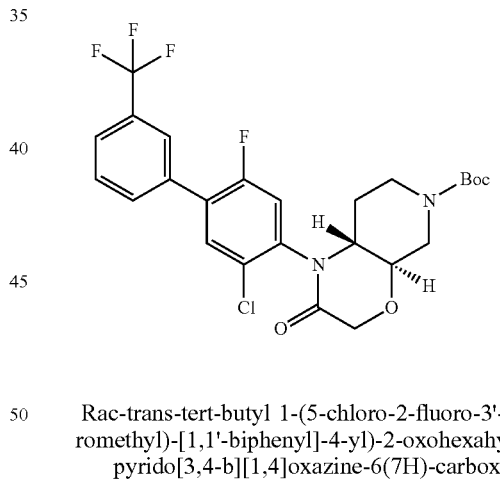

Rac-trans-tert-butyl 1-(5-chloro-2-fluoro-3'-(trifluoromethyl)-[1,1'-biphenyl]-4-yl)-2-oxohexahydro-1H-pyrido[3,4-b][1,4]oxazine-6(7H)-carboxylate Following the procedure described in Example 1, step 2 and making non-critical variations as required to replace rac-trans-tert-butyl 4-((4-bromo-5-fluoro-2-methoxyphenyl)amino)-3-hydroxypiperidine-1-carboxylate with rac-trans-tert-butyl 4-((5-chloro-2-fluoro-3'-(trifluoromethyl)-[1,1'-biphenyl]-4-yl)amino)-3-hydroxypiperidine-1-carboxylate, rac-trans-tert-butyl 1-(5-chloro-2-fluoro-3'-(trifluoromethyl)-[1,1'-biphenyl]-4-yl)-2-oxohexahydro-1H-pyrido[3,4-b][1,4]oxazine-6(7H)-carboxylate (6.1 g, 85%) was obtained as a yellow solid. $^1$H NMR (400 MHz, CDCl$_3$) δ 7.78 (s, 1H), 7.75-7.67 (m, 2H), 7.65-7.56 (m, 2H), 7.18-7.05 (m, 1H), 4.63-4.35 (m, 3H), 4.31-4.17 (m, 1H), 3.95-3.53 (m, 2H), 2.86-2.54 (m, 2H), 1.48 (s, 9H), 1.47-1.45 (m, 2H).

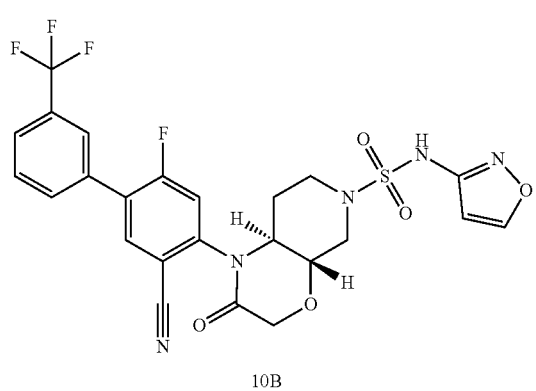

Step 3:

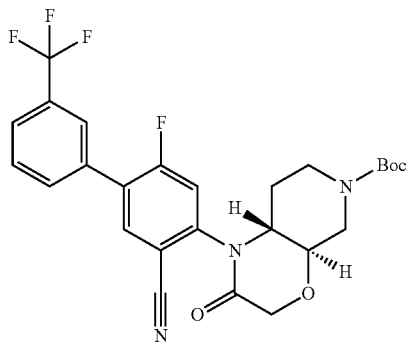 [SMILES: CC(C)(C)OC(=O)N1CC[C@@H]2[C@@H](C1)OCC(=O)N2c1cc(F)c(-c2cccc(C(F)(F)F)c2)cc1C#N]

Rac-trans-tert-butyl 1-(5-cyano-2-fluoro-3'-(trifluoromethyl)-[1,1'-biphenyl]-4-yl)-2-oxohexahydro-1H-pyrido[3,4-b][1,4]oxazine-6(7H)-carboxylate To a solution of Race-trans-tert-butyl 1-(5-chloro-2-fluoro-3'-(trifluoromethyl)-[1,1'-biphenyl]-4-yl)-2-oxohexahydro-1H-pyrido[3,4-b][1,4]oxazine-6(7H)-carboxylate (400 mg, 0.76 mmol), KOAc (223 mg, 2.27 mmol) and $K_4Fe(CN)_6$ $3H_2O$ (223 mg, 0.38 mmol) in 1,4-dioxane (4 mL) and water (4 mL) were added 2-di-tert-butylphosphino-2',4',6'-triisopropylbiphenyl (32 mg, 0.08 mmol) and [(2-di-tert-butylphosphino-2',4',6'-triisopropyl-1,1'-biphenyl)-2-(2'-amino-1,1'-biphenyl)] palladium(II) methanesulfonate (60 mg, 0.08 mmol). The reaction mixture was heated to 100° C. for 16 h under a nitrogen atmosphere. After cooling to room temperature, EtOAc (30 mL) was added, and washed with brine (10 mL). The organic layer was dried over anhydrous $Na_2SO_4$, filtered and concentrated in vacuo. The crude residue was purified by silica gel chromatography (solvent gradient: 0-25% EtOAc in petroleum ether) to give the title compound (200 mg, 51%) as a yellow solid. $^1$H NMR (400 MHz, $CDCl_3$) δ 7.86 (d, J=7.6 Hz, 1H), 7.79-7.62 (m, 4H), 7.24-7.17 (m, 1H), 4.68-4.36 (m, 3H), 4.31-4.01 (m, 1H), 3.83-3.55 (m, 2H), 2.90-2.60 (m, 2H), 1.50-1.40 (m, 11H)

Step 4:

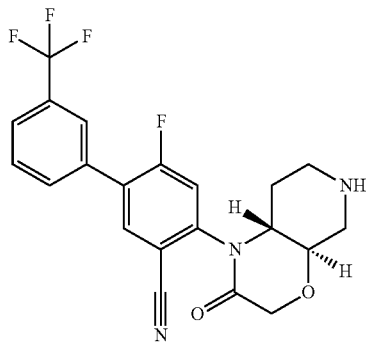 [SMILES: N#Cc1cc(-c2cccc(C(F)(F)F)c2)c(F)cc1N1C(=O)CO[C@@H]2CNCC[C@H]21]

Rac-trans-6-fluoro-4-((4aR,8aR)-2-oxooctahydro-1H-pyrido[3,4-b][1,4]oxazin-1-yl)-3'-(trifluoromethyl)-[1,1'-biphenyl]-3-carbonitrile To a solution of rac-trans-tert-butyl 1-(5-cyano-2-fluoro-3'-(trifluoromethyl)-[1,1'-biphenyl]-4-yl)-2-oxohexahydro-1H-pyrido[3,4-b][1,4]oxazine-6(7H)-carboxylate in EtOAc (4 mL) was added 4M HCl (0.48 mL, 1.92 mmol) in EtOAc. The solution was stirred at room temperature for 2 h. The reaction mixture was quenched with sat. aq. $NaHCO_3$ (30 mL) and extracted with EtOAc (30 mL). The organic layer was dried over anhydrous $Na_2SO_4$, filtered and concentrated in vacuo to give the title compound (180 mg, crude) as a yellow solid that required no further purification.

Step 5:

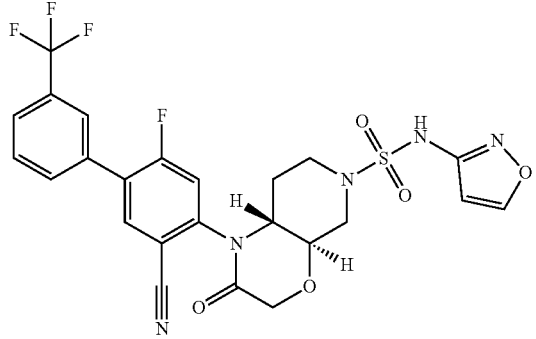 [SMILES: N#Cc1cc(-c2cccc(C(F)(F)F)c2)c(F)cc1N1C(=O)CO[C@@H]2CN(S(=O)(=O)Nc3ccon3)CC[C@H]21]

Rac-trans-1-(5-cyano-2-fluoro-3'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide Following the procedure described in Example 1, step 4 and making non-critical variations as required to replace rac-trans-1-(4-bromo-5-fluoro-2-methoxyphenyl)hexahydro-1H-pyrido[3,4-b][1,4]oxazin-2(3H)-one with rac-trans-6-fluoro-4-((4aR,8aR)-2-oxooctahydro-1H-pyrido[3,4-b][1,4]oxazin-1-yl)-3'-(trifluoromethyl)-[1,1'-biphenyl]-3-carbonitrile, rac-trans-1-(5-cyano-2-fluoro-3'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide (120 mg, 49%) was obtained as yellow oil. LCMS (ESI) m/z: 565.7 [M+H]$^+$.

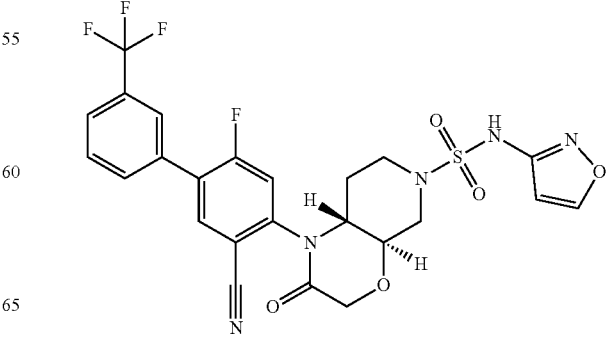

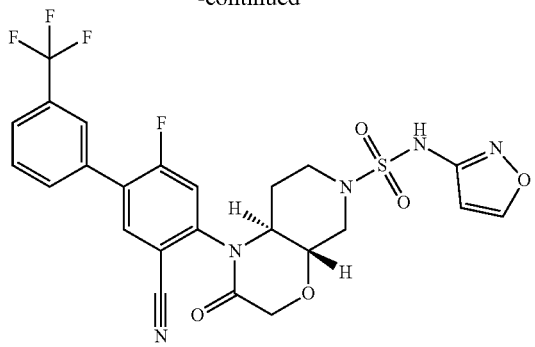
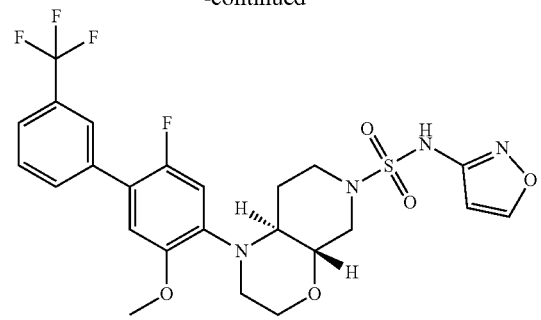

(4aR,8aR)-1-(5-cyano-2-fluoro-3'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide & (4aS,8aS)-1-(5-cyano-2-fluoro-3'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide (4aR,8aR)-1-(2-fluoro-5-methoxy-3'-(trifluoromethyl)-[1,1'-biphenyl]-4-yl)-N-(isoxazol-3-yl)hexahydro-1H-pyrido[3,4-b][1,4]oxazine-6(7H)-sulfonamide & (4aS,8aS)-1-(2-fluoro-5-methoxy-3'-(trifluoromethyl)-[1,1'-biphenyl]-4-yl-N-(isoxazol-3-yl)hexahydro-1H-pyrido[3,4-b][1,4]oxazine-6(7H)-sulfonamide Rac-trans-1-(5-cyano-2-fluoro-3'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide (120 mg) was separated by using chiral SFC (Phenomenex C2 (250 mm*30 mm, 5 um), Supercritical $CO_2$/EtOH+0.1% $NH_4OH$=60/40; 55 mL/min) to give (4aR,8aR)-1-(5-cyano-2-fluoro-3'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide (25 mg, first peak) as a white solid and (4aS,8aS)-1-(5-cyano-2-fluoro-3'-(trifluoromethyl)-[1,1'-biphenyl]-4-yl)-N-(isoxazol-3-yl)-2-oxohexahydro-1H-pyrido[3,4-b][1,4]oxazine-6(7H)-sulfonamide (23 mg, second peak) as a white solid. Absolute configuration was arbitrarily assigned to each enantiomer. Example 23: LCMS (ESI) m/z: 566.1 $[M+H]^+$. $^1$H NMR (400 MHz, DMSO-$d_6$) δ 11.23 (s, 1H), 8.75 (s, 1H), 8.42-8.30 (m, 1H), 8.01 (s, 1H), 7.96 (d, J=8.0 Hz, 1H), 7.89-7.64 (m, 3H), 6.40 (s, 1H), 4.52-4.40 (m, 2H), 4.08-3.98 (m, 1H), 3.94-3.82 (m, 1H), 3.81-3.67 (m, 1H), 3.66-3.58 (m, 1H), 2.88-2.75 (m, 2H), 1.68-1.45 (m, 1H), 1.34-1.19 (m, 1H). Example 24: LCMS (ESI) m/z: 566.1 $[M+H]^+$. $^1$H NMR (400 MHz, DMSO-$d_6$) δ 11.23 (s, 1H), 8.75 (s, 1H), 8.42-8.30 (m, 1H), 8.01 (s, 1H), 7.96 (d, J=8.0 Hz, 1H), 7.89-7.64 (m, 3H), 6.40 (d, J=1.6 Hz, 1H), 4.52-4.40 (m, 2H), 4.08-3.98 (m, 1H), 3.94-3.82 (m, 1H), 3.81-3.67 (m, 1H), 3.66-3.58 (m, 1H), 2.88-2.75 (m, 2H), 1.68-1.45 (m, 1H), 1.34-1.19 (m, 1H).

Example 25 & Example 26

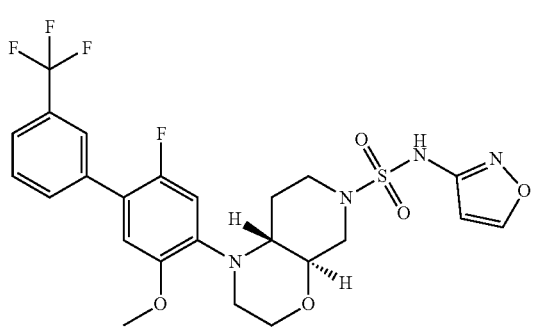

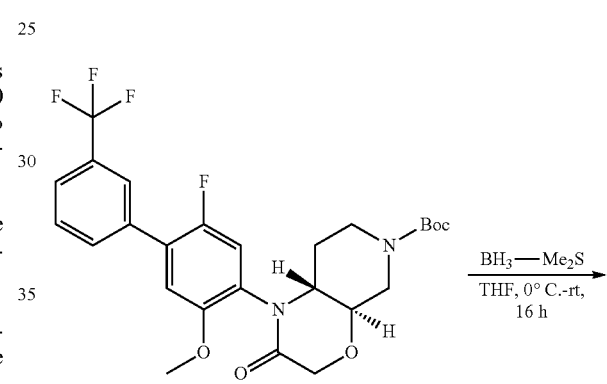

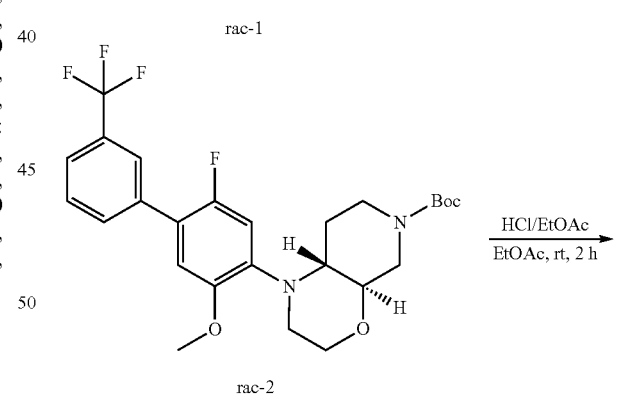

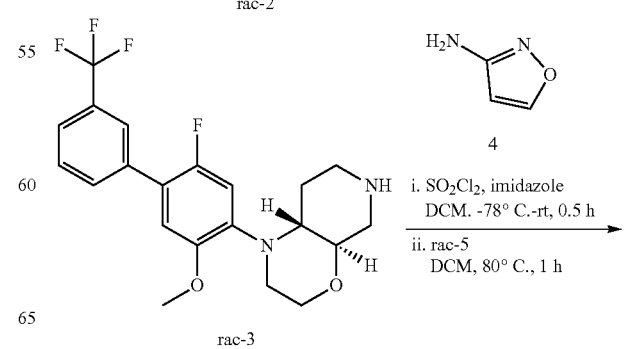

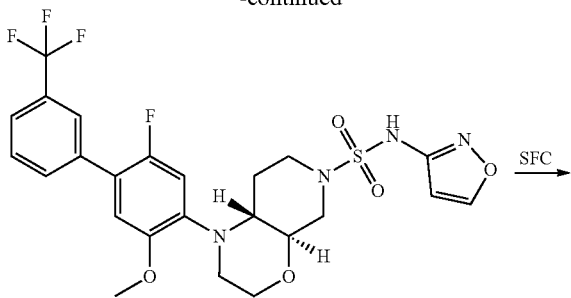

rac-5

↓ SFC

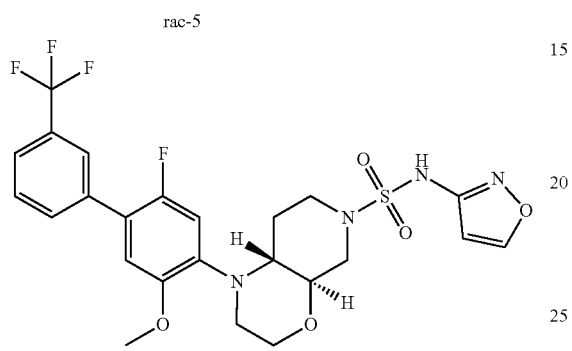

6A

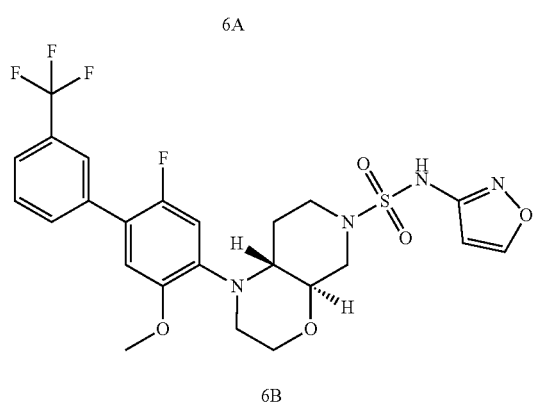

6B

Step 1:

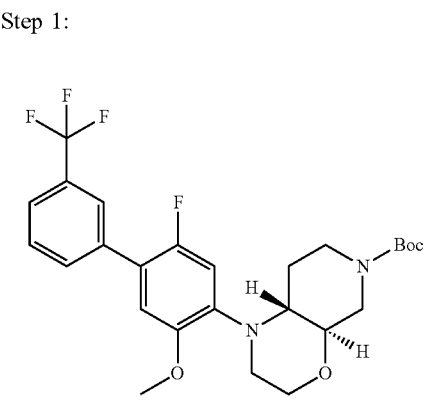

Rac-trans-tert-butyl 1-(2-fluoro-5-methoxy-3'-(trifluoromethyl)-[1,1'-biphenyl]-4-yl)hexahydro-1H-pyrido[3,4-b][1,4]oxazine-6(7H)-carboxylate To a solution of Rac-trans-tert-butyl 1-(2-fluoro-5-methoxy-3'-(trifluoromethyl)-[1,1'-biphenyl]-4-yl)-2-oxo-hexahydro-1H-pyrido[3,4-b][1,4]oxazine-6(7H)-carboxy-late (1.76 g, 3.36 mmol) in tetrahydrofuran (20 mL) was added boranedimethylsulfide complex (1.01 mL, 10.07 mmol) at 0° C. under a nitrogen atmosphere. Then the mixture was stirred at room temperature for 16 h. The mixture was quenched with MeOH (20 mL) dropwise, and then heated to 80° C. for 1 h. The reaction mixture was concentrated in vacuo and the crude residue was purified by silica gel chromatography (solvent gradient: 10-20% EtOAc in petroleum ether) to give the title compound (1.27 g, 74%) as colorless oil.

Step 2:

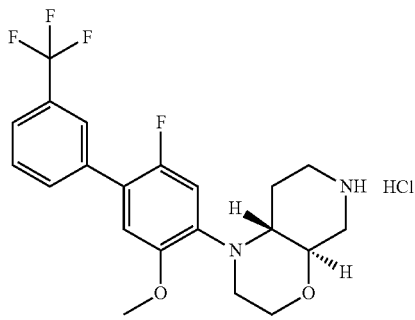 [SMILES: COc1cc(-c2cccc(C(F)(F)F)c2)c(F)cc1N1CCO[C@@H]2CNCC[C@H]21 ; Cl]

Rac-trans-1-(2-fluoro-5-methoxy-3'-(trifluoromethyl)-[1,1'-biphenyl]-4-yl)octahydro-1H-pyrido[3,4-b][1,4]oxazine hydrochloride To a solution of Rac-trans-tert-butyl 1-(2-fluoro-5-methoxy-3'-(trifluoromethyl)-[1,1'-biphenyl]-4-yl)hexahydro-1H-pyrido[3,4-b][1,4]oxazine-6(7H)-carboxylate (600 mg, 1.18 mmol) in EtOAc (5 mL) was added 4M HCl (1.47 mL, 5.88 mmol) in EtOAc. The reaction mixture was stirred at room temperature for 2 h. The reaction mixture was concentrated in vacuo to give the title compound (480 mg, crude) as colorless oil that required no further purification. LCMS (ESI) m/z: 411.2 [M+H]$^+$.

Step 3:

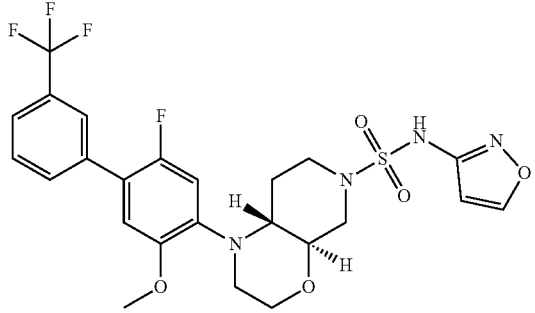 [SMILES: COc1cc(-c2cccc(C(F)(F)F)c2)c(F)cc1N1CCO[C@@H]2CN(S(=O)(=O)Nc3ccon3)CC[C@H]21]

Rac-trans-1-(2-fluoro-5-methoxy-3'-(trifluoromethyl)-[1,1'-biphenyl]-4-yl)-N-(isoxazol-3-yl)hexahydro-H-pyrido[3,4-b][1,4]oxazine-6(7H)-sulfonamide To a solution of imidazole (1.66 g, 24.37 mmol) and 3-aminoisoxazole (0.66 g, 7.8 mmol) in DCM (15 ml) was added SO$_2$Cl$_2$ (0.64 mL, 7.8 mmol) at −78° C. After stirring at room temperature for 30 min, rac-trans-1-(2-fluoro-5-methoxy-3'-(trifluoromethyl)-[1,1'-biphenyl]-4-yl)octahydro-1H-pyrido[3,4-b][1,4]oxazine hydrochloride (400 mg, 0.97 mmol) was added. The mixture was heated to 80° C. for 1 h under a nitrogen atmosphere. The reaction was diluted with water (20 mL) and extracted with dichloromethane (20 mL×3). The combined organic layers were washed with brine (20 mL×2), dried over anhydrous $Na_2SO_4$, filtered and concentrated in vacuo. The residue was purified by prep-TLC (EtOAc/petroleum ether=1/1) to give the title compound (180 mg, 29%) as light yellow oil. LCMS (ESI) m/z: 557.2 [M+H]$^+$.

Example 26: LCMS (ESI) m/z: 557.1 [M+H]$^+$. $^1$H NMR (400 MHz, DMSO-$d_6$) δ 11.13 (s, 1H), 8.76 (d, J=1.6 Hz, 1H), 7.86-7.91 (m, 2H), 7.68-7.78 (m, 2H), 7.18 (d, J=12.0 Hz, 1H), 7.13 (d, J=8.0 Hz, 1H), 6.40 (d, J=1.6 Hz, 1H), 3.84-3.85 (s, 4H), 3.71-3.80 (m, 1H), 3.64-3.70 (m, 1H), 3.58-3.55 (m, 1H), 3.27-3.31 (m, 1H), 3.07 (d, J=12.0 Hz, 1H), 2.88-2.94 (m, 2H), 2.70-2.81 (m, 2H), 1.83-1.78 (m, 1H), 1.04-1.16 (m, 1H).

Example 27 & Example 28

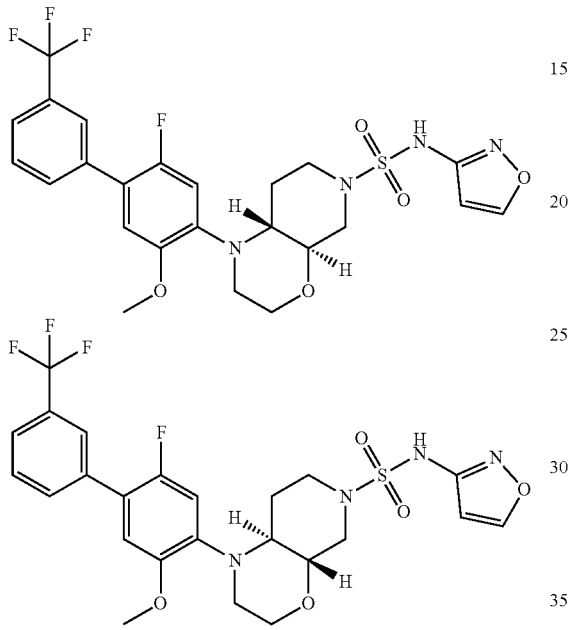

(4aR,8aR)-1-(2-fluoro-5-methoxy-3'-(trifluoromethyl)-[1,1'-biphenyl]-4-yl)-N-(isoxazol-3-yl)hexahydro-1H-pyrido[3,4-b][1,4]oxazine-6(7H)-sulfonamide & (4aS,8aS)-1-(2-fluoro-5-methoxy-3'-(trifluoromethyl)-[1,1'-biphenyl]-4-yl)-N-(isoxazol-3-yl)hexahydro-1H-pyrido[3,4-b][1,4]oxazine-6(7H)-sulfonamide Rac-trans-1-(2-fluoro-5-methoxy-3'-(trifluoromethyl)-[1,1'-biphenyl]-4-yl)-N-(isoxazol-3-yl)hexahydro-1H-pyrido[3,4-b][1,4]oxazine-6(7H)-sulfonamide (180 mg, 0.32 mmol) was separated by using chiral SFC (Chiralpak AD (250 mm*30 mm, 10 um), Supercritical $CO_2$/IPA+0.1% $NH_4OH$=70/30; 50 mL/min) to give (4aS,8aS)-1-(2-fluoro-5-methoxy-3'-(trifluoromethyl)-[1,1'-biphenyl]-4-yl)-N-(isoxazol-3-yl)hexahydro-1H-pyrido[3,4-b][1,4]oxazine-6(7H)-sulfonamide (32 mg, first peak) as a light yellow solid and (4aR,8aR)-1-(2-fluoro-5-methoxy-3'-(trifluoromethyl)-[1,1'-biphenyl]-4-yl)-N-(isoxazol-3-yl)hexahydro-1H-pyrido[3,4-b][1,4]oxazine-6(7H)-sulfonamide (45 mg, second peak) as a white solid. Absolute configuration was arbitrarily assigned to each enantiomer. Example 25: LCMS (ESI) m/z: 557.1 [M+H]$^+$. $^1$H NMR (400 MHz, DMSO-$d_6$) δ 11.13 (s, 1H), 8.75 (d, J=1.6 Hz, 1H), 7.86-7.90 (m, 2H), 7.68-7.77 (m, 2H), 7.17 (d, J=12.0 Hz, 1H), 7.12 (d, J=8.0 Hz, 1H), 6.40 (d, J=1.6 Hz, 1H), 3.84-3.85 (m, 4H), 3.71-3.78 (m, 1H), 3.64-3.70 (m, 1H), 3.58-3.55 (m, 1H), 3.26-3.31 (m, 1H), 3.07 (d, J=8.0 Hz, 1H), 2.87-2.93 (m, 2H), 2.69-2.80 (m, 2H), 1.83-1.78 (m, 1H), 1.06-1.13 (m, 1H).

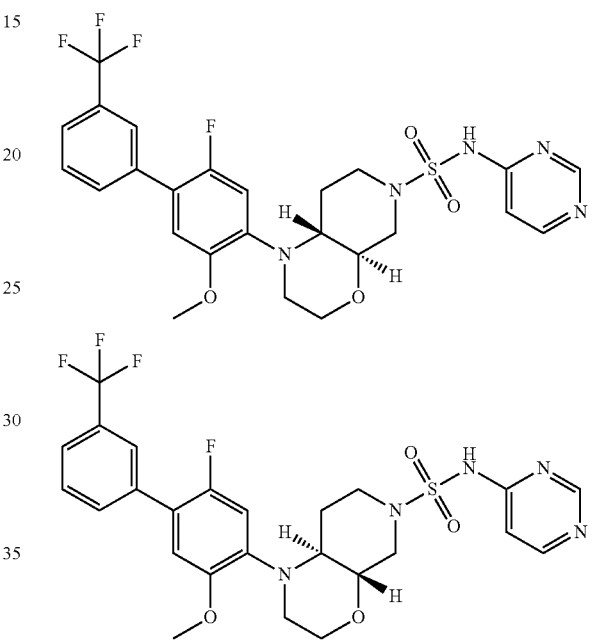

(4aR,8aR)-1-(2-fluoro-5-methoxy-3'-(trifluoromethyl)-[1,1'-biphenyl]-4-yl)-N-(pyrimidin-4-yl)hexahydro-H-pyrido[3,4-b][1,4]oxazine-6(7H)-sulfonamide & (4aS,8aS)-1-(2-fluoro-5-methoxy-3'-(trifluoromethyl)-[1,1'-biphenyl]-4-yl)-N-(pyrimidin-4-yl)hexahydro-H-pyrido[3,4-b][1,4]oxazine-6(7H)-sulfonamide

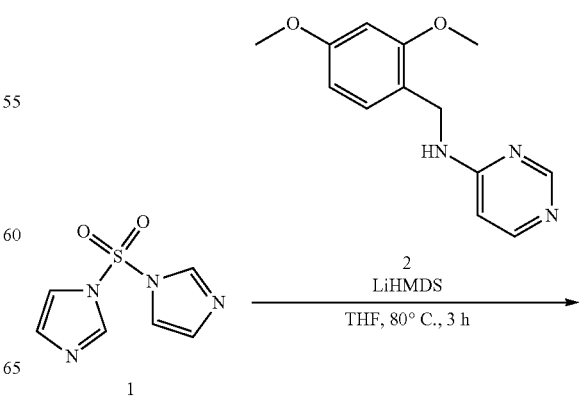

-continued

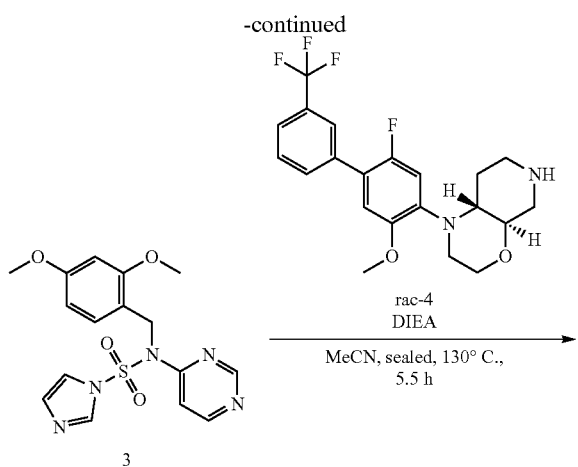

Step 1:

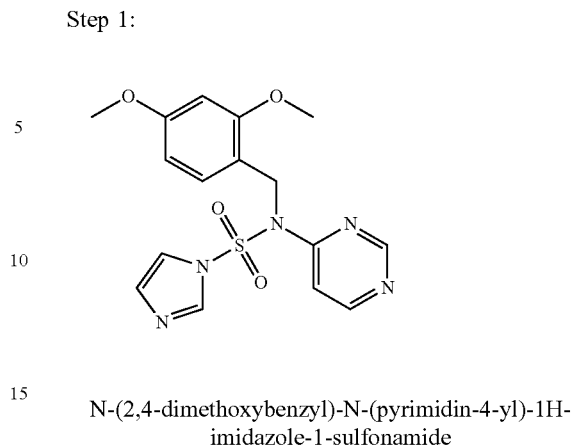

N-(2,4-dimethoxybenzyl)-N-(pyrimidin-4-yl)-1H-imidazole-1-sulfonamide

To a solution of N-[(2,4-dimethoxyphenyl)methyl]pyrimidin-4-amine (1.0 g, 4.08 mmol) and 1,1'-sulfonyldiimidazole (3.23 g, 16.31 mmol) in THF (2 mL) was added lithiumbis(trimethylsilyl)amide (1M, 12.23 mL, 12.23 mmol) dropwise. Then the mixture was heated to 80° C. for 3 h under a nitrogen atmosphere. The reaction was quenched with water (100 mL), extracted with EtOAc (50 mL×2). The combined organic layers were washed with brine (100 mL), dried over anhydrous $Na_2SO_4$, filtered and concentrated in vacuo. The residue was purified by silica gel chromatography (solvent gradient: 0-5% MeOH in DCM) to give the title compound (2.2 g, 10%) as a light yellow solid. LCMS (ESI) m/z: 376.1 $[M+H]^+$.

Step 2:

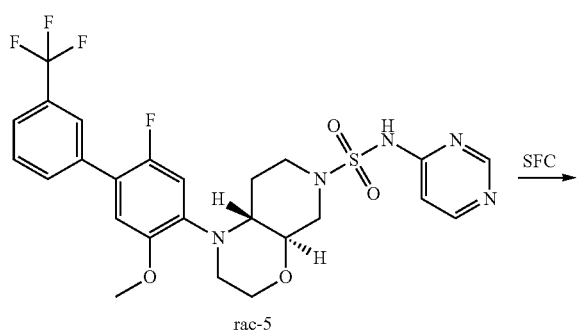

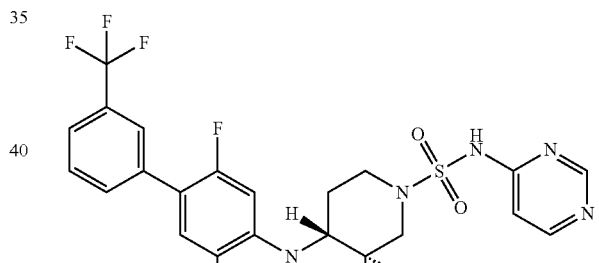

Rac-trans-1-(2-fluoro-5-methoxy-3'-(trifluoromethyl)-[1,1'-biphenyl]-4-yl)-N-(pyrimidin-4-yl)hexahydro-1H-pyrido[3,4-b][1,4]oxazine-6(7H)-sulfonamide A 20-mL vial was charged with Rac-trans-1-(2-fluoro-5-methoxy-3'-(trifluoromethyl)-[1,1'-biphenyl]-4-yl)octahydro-1H-pyrido[3,4-b][1,4]oxazine (100 mg, 0.24 mmol), N-(2,4-dimethoxybenzyl)-N-(pyrimidin-4-yl)-1H-imidazole-1-sulfonamide (1.70 g, 0.32 mmol) and N,N-diisopropylethylamine (110 mg, 0.85 mmol) in acetonitrile (10 mL). The vial was sealed with a PTFE lined cap and heat to 130° C. for 5.5 h. After cooling to room temperature, the mixture was concentrated in vacuo. The residue was diluted with EtOAc (30 mL). The organic layer was washed with sat. aq. citric acid (20 mL), brine (20 mL), dried over anhydrous $Na_2SO_4$, filtered and concentrated in vacuo. The residue was purified by reverse phase chromatography (acetonitrile

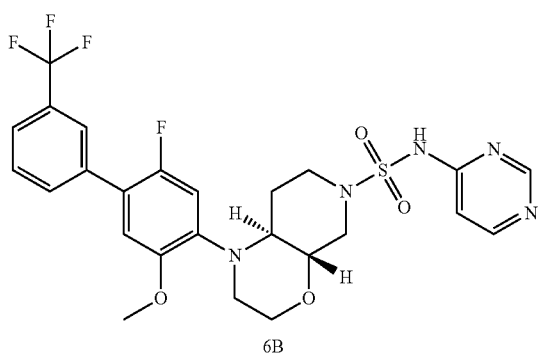 [SMILES: COc1cc(-c2cccc(C(F)(F)F)c2)c(F)cc1N1CCO[C@H]2CN(S(=O)(=O)Nc3ccncn3)CC[C@@H]21]

54-84%/0.225% formic acid in water) to give the title compound (10 mg, 7%) as a white solid. LCMS (ESI) m/z: 568.1 [M+H]⁺.

Step 3:

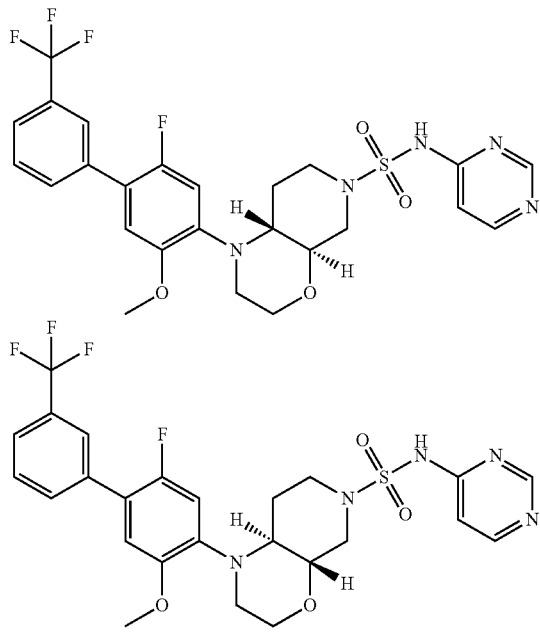

(4aR,8aR)-1-(2-fluoro-5-methoxy-3'-(trifluoromethyl)-[1,1'-biphenyl]-4-yl)-N-(pyrimidin-4-yl)hexahydro-1H-pyrido[3,4-b][1,4]oxazine-6(7H)-sulfonamide & (4aS,8aS)-1-(2-fluoro-5-methoxy-3'-(trifluoromethyl)-[1,1'-biphenyl]-4-yl)-N-(pyrimidin-4-yl)hexahydro-H-pyrido[3,4-b][1,4]oxazine-6(7H)-sulfonamide Rac-trans-1-(2-fluoro-5-methoxy-3'-(trifluoromethyl)-[1,1'-biphenyl]-4-yl)-N-(pyrimidin-4-yl)hexahydro-1H-pyrido[3,4-b][1,4]oxazine-6(7H)-sulfonamide (10 mg) was separated by using chiral SFC (Phenomenex C2 (250 mm*30 mm, 10 um), Supercritical CO₂/EtOH+0.1% NH₄OH=50/50; 60 mL/min) to give (4aR,8aR)-1-(2-fluoro-5-methoxy-3'-(trifluoromethyl)-[1,1'-biphenyl]-4-yl)-N-(pyrimidin-4-yl)hexahydro-1H-pyrido[3,4-b][1,4]oxazine-6(7H)-sulfonamide (5 mg, first peak) as a white solid and (4aS,8aS)-1-(2-fluoro-5-methoxy-3'-(trifluoromethyl)-[1,1'-biphenyl]-4-yl)-N-(pyrimidin-4-yl)hexahydro-1H-pyrido[3,4-b][1,4]oxazine-6(7H)-sulfonamide (3 mg, second peak) as a white solid. Absolute configuration was arbitrarily assigned to each enantiomer. Example 27: LCMS (ESI) m/z: 568.1 [M+H]⁺. ¹H NMR (400 MHz, DMSO-d₆) δ 8.45 (s, 1H), 8.08 (s, 1H), 7.92-7.84 (m, 2H), 7.79-7.67 (m, 2H), 7.21-7.09 (m, 2H), 6.82-6.78 (m, 1H), 3.85-3.82 (m, 4H), 3.81-3.70 (m, 1H), 3.62-3.60 (m, 1H), 3.49-3.46 (m, 2H), 3.09-3.05 (m, 1H), 2.91-2.57 (m, 4H), 1.80-1.77 (m, 1H), 1.17-1.06 (m, 1H). Example 28: LCMS (ESI) m/z: 568.1 [M+H]⁺. ¹H NMR (400 MHz, DMSO-d₆) δ 8.47 (s, 1H), 8.10 (s, 1H), 7.92-7.83 (m, 2H), 7.78-7.67 (m, 2H), 7.20-7.09 (m, 2H), 6.84-6.81 (m, 1H), 3.88-3.81 (m, 4H), 3.80-3.70 (m, 1H), 3.62-3.60 (m, 1H), 3.51-3.47 (m, 2H), 3.08-3.05 (m, 1H), 2.90-2.70 (m, 3H), 2.67-2.57 (m, 1H), 1.81-1.78 (m, 1H), 1.18-1.06 (m, 1H).

Example 29 & Example 30

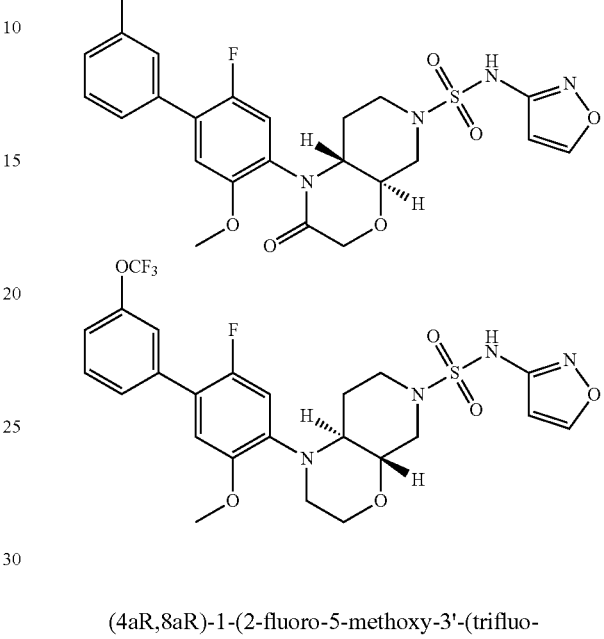

(4aR,8aR)-1-(2-fluoro-5-methoxy-3'-(trifluoromethoxy)-[1,1'-biphenyl]-4-yl)-N-(isoxazol-3-yl)-2-oxohexahydro-1H-pyrido[3,4-b][1,4]oxazine-6(7H)-sulfonamide & (4aS,8aS)-1-(2-fluoro-5-methoxy-3'-(trifluoromethoxy)-[1,1'-biphenyl]-4-yl)-N-(isoxazol-3-yl)-2-oxohexahydro-H-pyrido[3,4-b][1,4]oxazine-6(7H)-sulfonamide Following the procedure described in Example 3 and making non-critical variations as required to 3-(trifluoromethyl)phenylboronic acid with 3-(trifluoromethoxy)phenylboronic acid, (4aR,8aR)-1-(2-fluoro-5-methoxy-3'-(trifluoromethoxy)-[1,1'-biphenyl]-4-yl)-N-(isoxazol-3-yl)-2-oxohexahydro-1H-pyrido[3,4-b][1,4]oxazine-6(7H)-sulfonamide (first peak) and (4aS,8aS)-1-(2-fluoro-5-methoxy-3'-(trifluoromethyl)-[1,1'-biphenyl]-4-yl)-N-(isoxazol-3-yl)-2-oxohexahydro-H-pyrido[3,4-b][1,4]oxazine-6(7H)-sulfonamide (second peak) were obtained. Absolute configuration was arbitrarily assigned to each enantiomer. Example 29: LCMS (ESI) m/z: 587.0 [M+H]⁺. ¹H NMR (400 MHz, DMSO-d₆) δ 11.16 (s, 1H), 8.77 (dd, J=6.0, 1.8 Hz, 1H), 7.76-7.62 (m, 2H), 7.60 (s, 1H), 7.50-7.41 (m, 1H), 7.30-7.15 (m, 2H), 6.39 (t, J=2.1 Hz, 1H), 4.43-4.28 (m, 2H), 3.90-3.79 (m, 4H), 3.79-3.66 (m, 1H), 3.62 (td, J=9.7, 4.4 Hz, 1H), 2.89-2.69 (m, 2H), 1.45 (dd, J=30.8, 8.5 Hz, 2H). Example 30: LCMS (ESI) m/z: 587.0 [M+H]⁺. ¹H NMR (400 MHz, DMSO-d₆) δ 11.16 (s, 1H), 8.75 (dd, J=6.3, 1.8 Hz, 1H), 7.70-7.63 (m, 2H), 7.61 (d, J=9.9 Hz, 1H), 7.50-7.41 (m, 1H), 7.30-7.14 (m, 2H), 6.39 (t, J=2.0 Hz, 1H), 4.35 (d, J=15.4 Hz, 2H), 3.89-3.79 (m, 4H), 3.78-3.54 (m, 2H), 3.42-3.34 (m, 1H), 2.88-2.64 (m, 2H), 1.56-1.19 (m, 2H).

Example 31 & Example 32

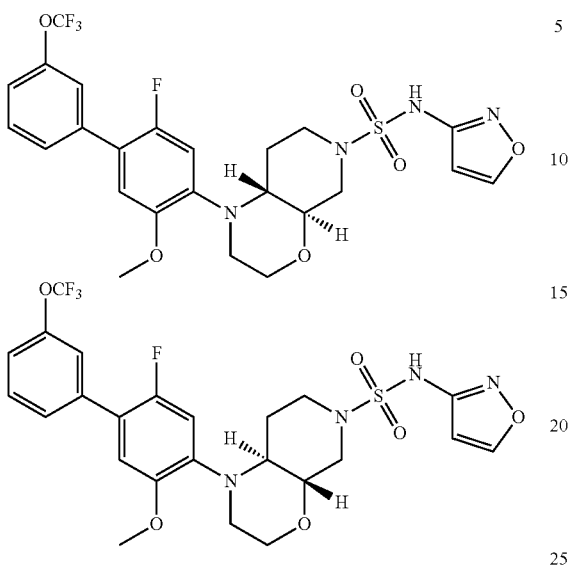

(4aR,8aR)-1-(2-fluoro-5-methoxy-3'-(trifluoromethoxy)-[1,1'-biphenyl]-4-yl)-N-(isoxazol-3-yl)hexahydro-H-pyrido[3,4-b][1,4]oxazine-6(7H)-sulfonamide & (4aS,8aS)-1-(2-fluoro-5-methoxy-3'-(trifluoromethoxy)-[1,1'-biphenyl]-4-yl)-N-(isoxazol-3-yl)hexahydro-1H-pyrido[3,4-b][1,4]oxazine-6(7H)-sulfonamide Following the procedure described in Example 25 and making non-critical variations as required to replace rac-trans-tert-butyl 1-(2-fluoro-5-methoxy-3'-(trifluoromethyl)-[1,1'-biphenyl]-4-yl)-2-oxohexahydro-1H-pyrido[3,4-b][1,4]oxazine-6(7H)-carboxylate with rac-trans-tert-butyl 1-(2-fluoro-5-methoxy-3'-(trifluoromethoxy)-[1,1'-biphenyl]-4-yl)-2-oxohexahydro-1H-pyrido[3,4-b][1,4]oxazine-6(7H)-carboxylate, (4aR,8aR)-1-(2-fluoro-5-methoxy-3'-(trifluoromethoxy)-[1,1'-biphenyl]-4-yl)-N-(isoxazol-3-yl)hexahydro-H-pyrido[3,4-b][1,4]oxazine-6(7H)-sulfonamide (first peak) and (4aS,8aS)-1-(2-fluoro-5-methoxy-3'-(trifluoromethoxy)-[1,1'-biphenyl]-4-yl)-N-(isoxazol-3-yl)hexahydro-1H-pyrido[3,4-b][1,4]oxazine-6(7H)-sulfonamide (second peak) were obtained. Example 31: LCMS (ESI) m/z: 573.1 [M+H]$^+$. $^1$H NMR (400 MHz, DMSO-$d_6$) δ 11.12 (s, 1H), 8.76 (d, J=1.8 Hz, 1H), 7.66-7.57 (m, 2H), 7.55 (dd, J=2.3, 1.3 Hz, 1H), 7.42-7.36 (m, 1H), 7.16 (d, J=12.1 Hz, 1H), 7.10 (d, J=7.5 Hz, 1H), 6.40 (d, J=1.8 Hz, 1H), 3.90-3.84 (m, 1H), 3.84 (s, 3H), 3.75 (td, J=11.4, 2.6 Hz, 1H), 3.71-3.65 (m, 1H), 3.62-3.53 (m, 1H), 3.30-3.24 (m, 1H), 3.07 (d, J=11.5 Hz, 1H), 2.96-2.86 (m, 2H), 2.83-2.69 (m, 2H), 1.81 (d, J=13.1 Hz, 1H), 1.17-1.02 (m, 1H). Example 32: LCMS (ESI) m/z: 573.1 [M+H]$^+$. $^1$H NMR (400 MHz, DMSO-$d_6$) δ 11.12 (s, 1H), 8.76 (d, J=1.8 Hz, 1H), 7.65-7.57 (m, 2H), 7.55 (dd, J=2.5, 1.4 Hz, 1H), 7.40 (ddt, J=6.5, 2.6, 1.2 Hz, 1H), 7.16 (d, J=12.1 Hz, 1H), 7.10 (d, J=7.5 Hz, 1H), 6.40 (d, J=1.8 Hz, 1H), 3.91-3.85 (m, 1H), 3.84 (s, 3H), 3.75 (td, J=11.5, 2.6 Hz, 1H), 3.71-3.64 (m, 1H), 3.62-3.53 (m, 1H), 3.07 (d, J=11.5 Hz, 1H), 2.90 (tt, J=9.3, 2.5 Hz, 2H), 2.74 (t, J=11.2 Hz, 2H), 1.81 (dd, J=13.7, 3.5 Hz, 1H), 1.09 (qd, J=11.5, 9.9, 3.0 Hz, 1H).

Example 33 & Example 34

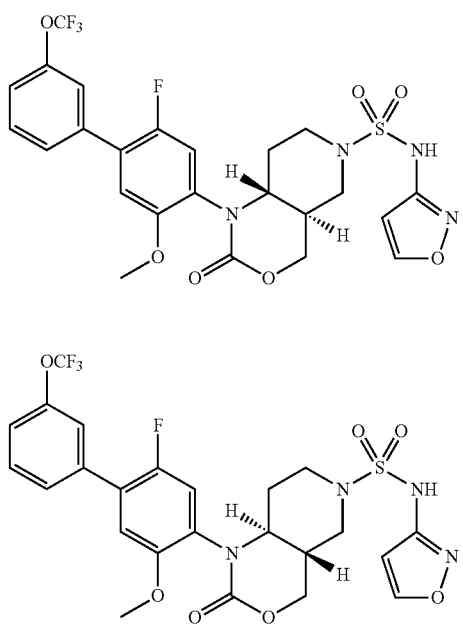

(4aR,8aR)-1-(2-fluoro-5-methoxy-3'-(trifluoromethyl)-[1,1'-biphenyl]-4-yl)-N-(isoxazol-3-yl)-2-oxohexahydro-2H-pyrido[4,3-d][1,3]oxazine-6(4H)-sulfonamide & (4aS,8aS)-1-(2-fluoro-5-methoxy-3'-(trifluoromethyl)-[1,1'-biphenyl]-4-yl)-N-(isoxazol-3-yl)-2-oxohexahydro-2H-pyrido[4,3-d][1,3]oxazine-6(4H)-sulfonamide

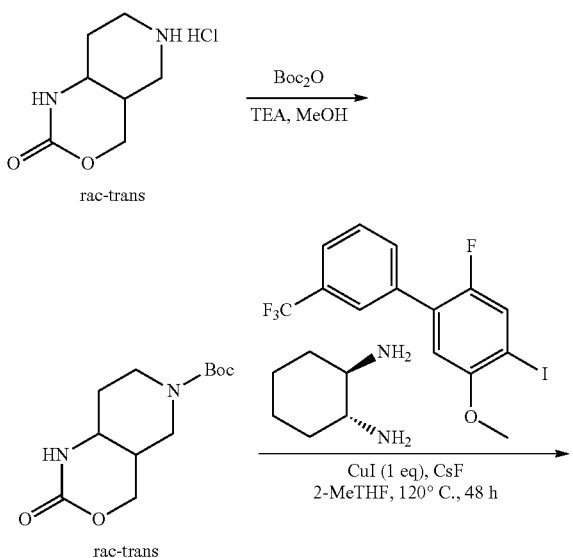

89

-continued

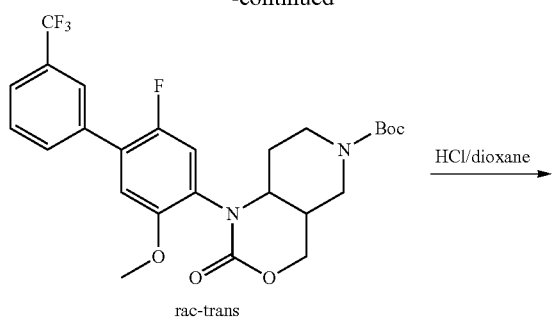

rac-trans

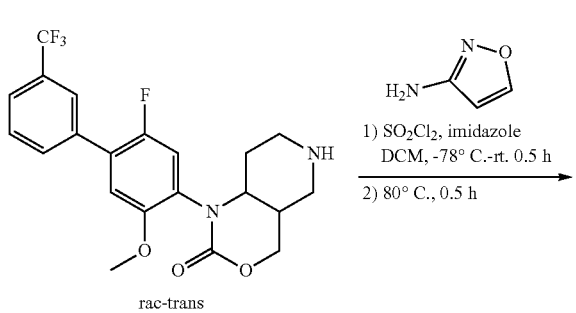

rac-trans

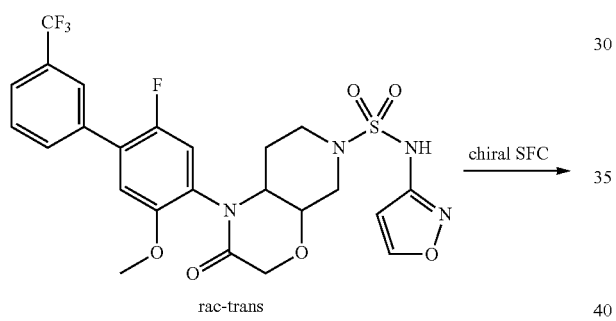

rac-trans

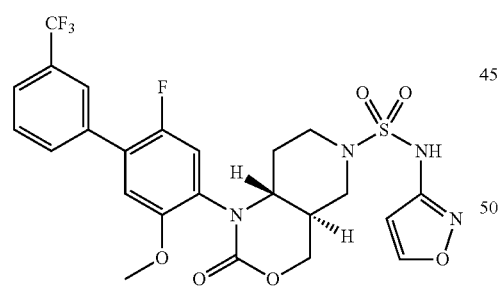

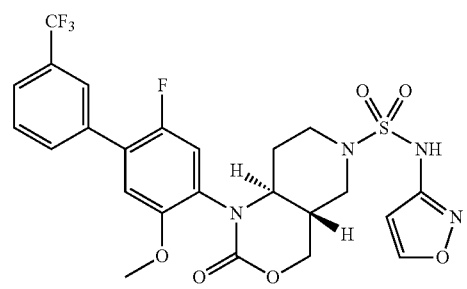

90

Step 1

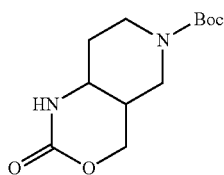 [SMILES: CC(C)(C)OC(=O)N1CCC2NC(=O)OCC2C1]

rac-trans-tert-butyl 2-oxohexahydro-2H-pyrido[4,3-d][1,3]oxazine-6(4H)-carboxylate To a suspension of rac-trans-octahydropyrido[4,3-d][1,3]oxazin-2-one hydrochloride (500 mg, 2.59 mmol) in MeOH (6 mL) was added TEA (656 mg, 6.49 mmol). Boc$_2$O (680 mg, 3.11 mmol) was added. The mixture was stirred at room temperature for 18 h. The mixture was then concentrated. The residue was partitioned between DCM and water. The aqueous layer was extracted with DCM (2×). The combined organics were dried (Na$_2$SO$_4$), filtered and concentrated. The crude product was purified by silica flash chromatography (0-10% MeOH/DCM) to give the title compound (600 mg, 90%) as a white solid. LCMS (ESI) m/z 257 [M+H]$^+$.

Step 2:

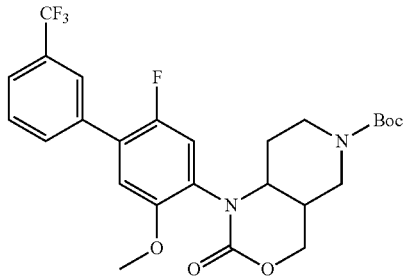

rac-trans-tert-butyl 1-[5-fluoro-2-methoxy-4-[3-(trifluoromethyl)phenyl]phenyl]-2-oxo-4,4a,5,7,8,8a-hexahydropyrido[4,3-d][1,3]oxazine-6-carboxylate The mixture of rac-trans-tert-butyl 2-oxo-4,4a,5,7,8,8a-hexahydro-1H-pyrido[4,3-d][1,3]oxazine-6-carboxylate (410 mg, 1.6 mmol), 1-fluoro-5-iodo-4-methoxy-2-[3-(trifluoromethyl)phenyl]benzene (792 mg, 2.0 mmol), CuI (335 mg, 1.76 mmol), (+/−)-TRANS-1,2-DIAMINOCYCLOHEXANE (183 mg, 1.6 mmol) and CsF (608 mg, 4.0 mmol) in 2-MeTHF (10 mL) was heated at 100° C. for 18 h then at 120° C. for 48. The mixture was filtered off celite, concentrated. The crude product was purified by silica flash chromatography (0-100% iPrOAc/heptane) to give the title compound (160 mg, 19%) as brown oil. LCMS (ESI) m/z 525 [M+H]$^+$.

Step 3:

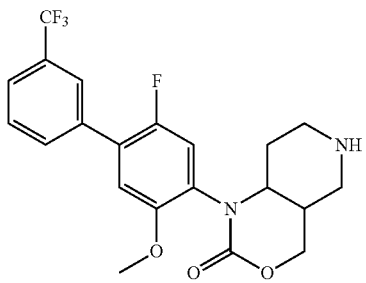

rac-trans-1-[5-fluoro-2-methoxy-4-[3-(trifluoromethyl)phenyl]phenyl]-4a,5,6,7,8,8a-hexahydro-4H-pyrido[4,3-d][1,3]oxazin-2-one To a solution of rac-trans-tert-butyl 1-[5-fluoro-2-methoxy-4-[3-(trifluoromethyl)phenyl]phenyl]-2-oxo-4,4a,5,7,8,8a-hexahydropyrido[4,3-d][1,3]oxazine-6-carboxylate (160 mg, 0.301 mmol) in 1,4-dioxane (4 mL) was added HCl (4 M in dioxane, 1.9 mL). The mixture was stirred at room temperature for 17 h. The mixture was concentrated, diluted with DCM, washed with sat. NaHCO$_3$. The aqueous layer was extracted with DCM (2×). The combined organics were dried (Na$_2$SO$_4$), filtered and concentrated to give the title compound (130 mg, 100%) as a yellow oil which was used directly in the next step. LCMS (ESI) m/z 425 [M+H]$^+$.

Step 4:

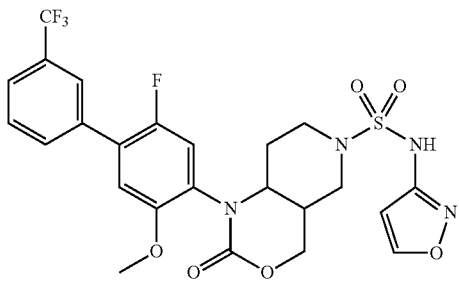

rac-trans-1-(2-fluoro-5-methoxy-3'-(trifluoromethyl)-[1,1'-biphenyl]-4-yl)-N-(isoxazol-3-yl)-2-oxohexahydro-2H-pyrido[4,3-d][1,3]oxazine-6(4H)-sulfonamide To a solution of isoxazol-3-amine (128 mg, 1.53 mmol) and imidazole (311 mg, 4.58 mmol) in DCM (4 mL) at −78° C. was added SO$_2$Cl$_2$ (206 mg, 1.53 mmol) dropwise. The mixture was warmed to room temperature and stirred for 30 min. A solution of rac-trans-1-[5-fluoro-2-methoxy-4-[3-(trifluoromethyl)phenyl]phenyl]-4a,5,6,7,8,8a-hexahydro-4H-pyrido[4,3-d][1,3]oxazin-2-one (129 mg, 0.305 mmol) in DCM (1 mL) was added. The mixture was heated at 80° C. for 30 min. The mixture was quenched with water, extracted with DCM (3×). The combined organics were dried (Na$_2$SO$_4$), filtered and concentrated. The crude product was purified by silica flash chromatography (0-10% MeOH/DCM) to give the title compound (121 mg, 69%) as yellow oil. LCMS (ESI) m/z 571 [M+H]$^+$.

Step 5:

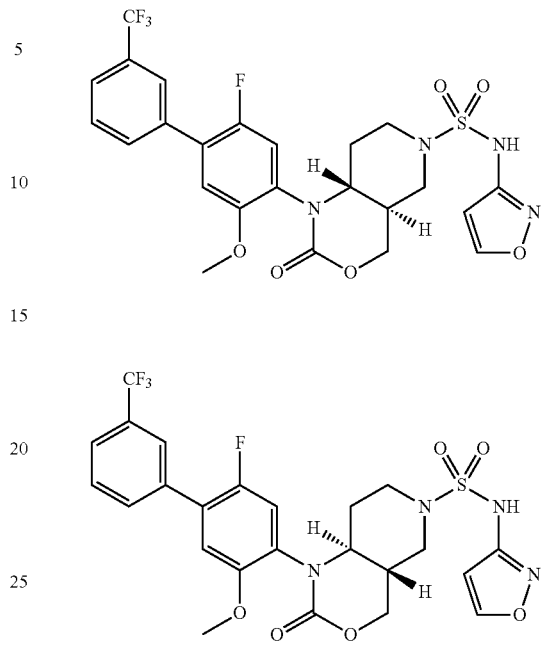

(4aR,8aR)-1-(2-fluoro-5-methoxy-3'-(trifluoromethyl)-[1,1'-biphenyl]-4-yl)-N-(isoxazol-3-yl)-2-oxohexahydro-2H-pyrido[4,3-d][1,3]oxazine-6(4H)-sulfonamide & (4aS,8aS)-1-(2-fluoro-5-methoxy-3'-(trifluoromethyl)-[1,1'-biphenyl]-4-yl)-N-(isoxazol-3-yl)-2-oxohexahydro-2H-pyrido[4,3-d][1,3]oxazine-6(4H)-sulfonamide Rac-trans-1-(2-fluoro-5-methoxy-3'-(trifluoromethyl)-[1,1'-biphenyl]-4-yl)-N-(isoxazol-3-yl)-2-oxohexahydro-2H-pyrido[4,3-d][1,3]oxazine-6(4H)-sulfonamide was separated by using chiral SFC (Whelko-01 (150 mm*21.2 mm, 5 um), Supercritical CO$_2$/MeOH+0.1% NH$_4$OH=60/40; 80 mL/min) to give (4aR,8aR)-1-(2-fluoro-5-methoxy-3'-(trifluoromethyl)-[1,1'-biphenyl]-4-yl)-N-(isoxazol-3-yl)-2-oxohexahydro-2H-pyrido[4,3-d][1,3]oxazine-6(4H)-sulfonamide (first peak) & (4aS,8aS)-1-(2-fluoro-5-methoxy-3'-(trifluoromethyl)-[1,1'-biphenyl]-4-yl)-N-(isoxazol-3-yl)-2-oxohexahydro-2H-pyrido[4,3-d][1,3]oxazine-6(4H)-sulfonamide (second peak) as an off-white solid. Absolute configuration was arbitrarily assigned to each enantiomer. Example 33: LCMS (ESI) m/z: 571.0 [M+H]$^+$. $^1$H NMR (400 MHz, DMSO-d$_6$) δ 11.08 (s, 1H), 8.75 (dd, J=5.7, 1.7 Hz, 1H), 7.92 (d, J=5.7 Hz, 2H), 7.81 (d, J=7.8 Hz, 1H), 7.75 (t, J=7.9 Hz, 1H), 7.47-7.08 (m, 2H), 6.39 (d, J=1.8 Hz, 1H), 4.40-4.29 (m, 1H), 4.11 (p, J=10.6 Hz, 1H), 3.94-3.71 (m, 4H), 3.69-3.52 (m, 2H), 2.80-2.57 (m, 2H), 2.24-1.95 (m, 1H), 1.48-1.12 (m, 2H). Example 34: LCMS (ESI) m/z: 571.0 [M+H]$^+$. $^1$H NMR (400 MHz, DMSO-d$_6$) δ 11.08 (s, 1H), 8.73 (dd, J=6.0, 1.8 Hz, 1H), 7.92 (d, J=6.1 Hz, 2H), 7.86-7.68 (m, 2H), 7.47-7.05 (m, 2H), 6.38 (d, J=1.8 Hz, 1H), 4.43-4.24 (m, 1H), 4.12 (q, J=11.0 Hz, 1H), 3.85 (d, J=26.2 Hz, 4H), 3.71-3.47 (m, 2H), 2.78-2.53 (m, 2H), 2.22-1.95 (m, 1H), 1.49-1.10 (m, 1H).

Examples 35, 36, 37 & 38

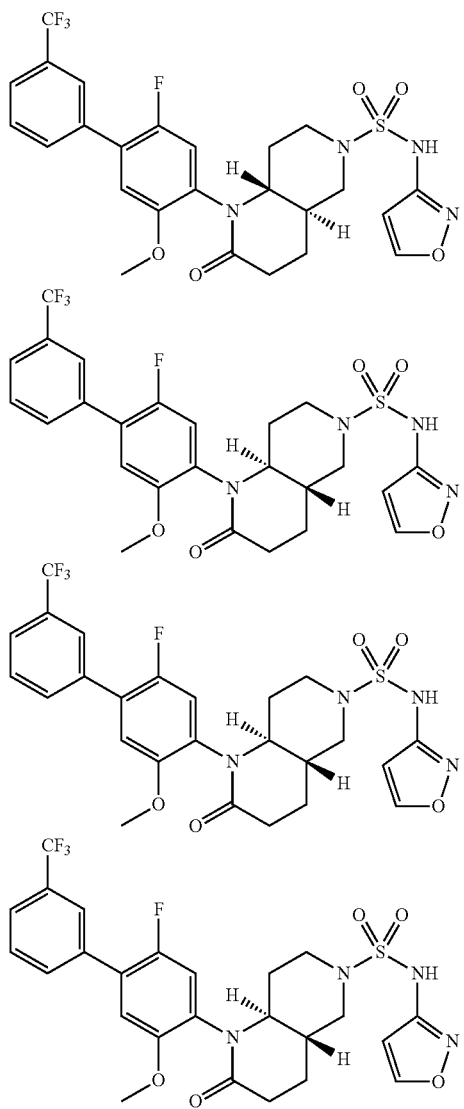

(4aR,8aR)-1-(2-fluoro-5-methoxy-3'-(trifluoromethyl)-[1,1'-biphenyl]-4-yl)-N-(isoxazol-3-yl)-2-oxooctahydro-1,6-naphthyridine-6(2H)-sulfonamide
& (4aS,8aS)-1-(2-fluoro-5-methoxy-3'-(trifluoromethyl)-[1,1'-biphenyl]-4-yl)-N-(isoxazol-3-yl)-2-oxooctahydro-1,6-naphthyridine-6(2H)-sulfonamide
& (4aS,8aR)-1-(2-fluoro-5-methoxy-3'-(trifluoromethyl)-[1,1'-biphenyl]-4-yl)-N-(isoxazol-3-yl)-2-oxooctahydro-1,6-naphthyridine-6(2H)-sulfonamide
& (4aR,8aS)-1-(2-fluoro-5-methoxy-3'-(trifluoromethyl)-[1,1'-biphenyl]-4-yl)-N-(isoxazol-3-yl)-2-oxooctahydro-1,6-naphthyridine-6(2H)-sulfonamide

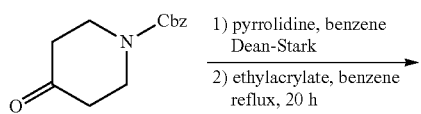

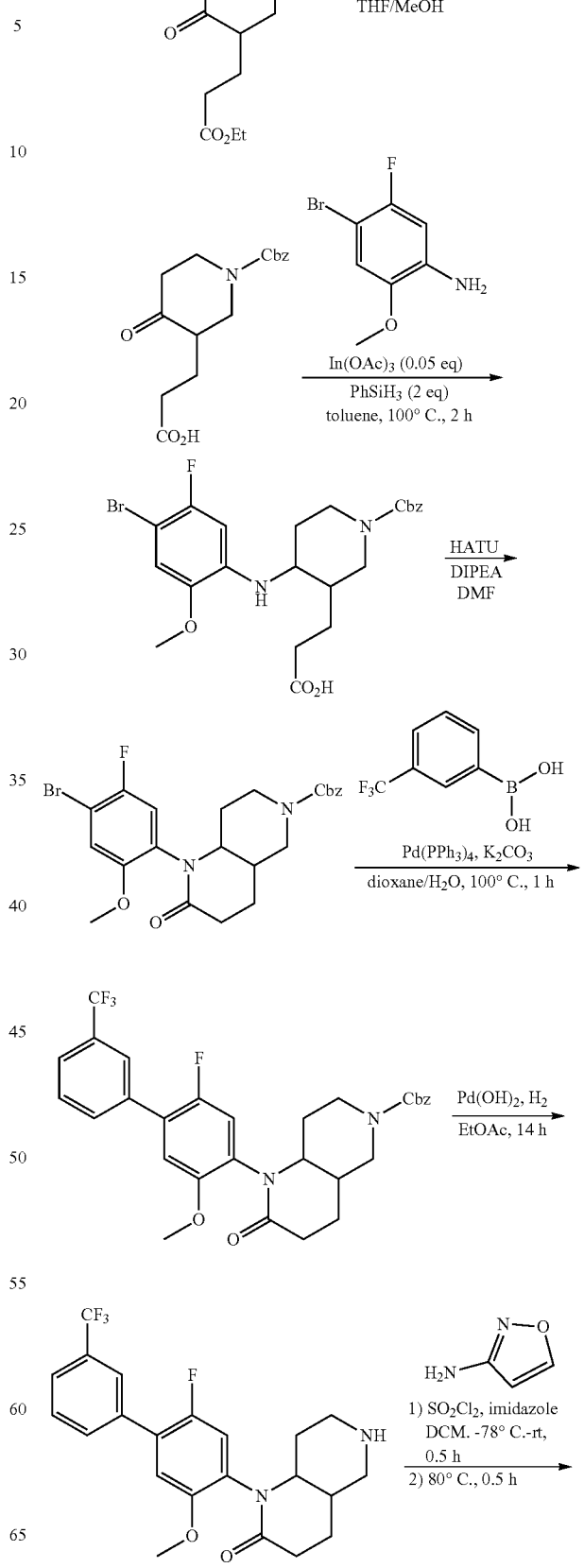

-continued

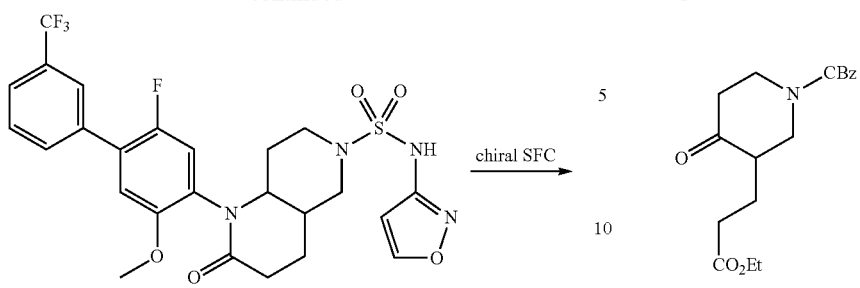

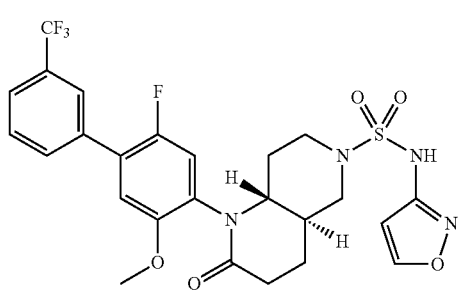

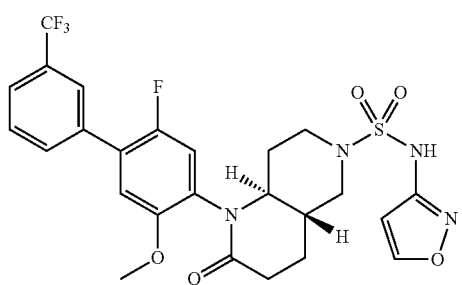

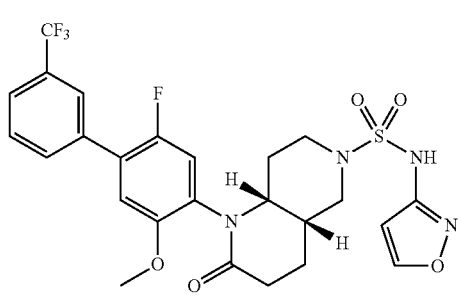

Step 1:

benzyl 3-(3-ethoxy-3-oxo-propyl)-4-oxo-piperidine-1-carboxylate

The mixture of N-benzyloxycarbonyl-4-piperidone (5 g, 21.4 mmol), pyrrolidine (2.29 g, 32.2 mmol) in benzene (60 mL) was heated at reflux for 20 h with a Dean-Stark trap. The mixture was then concentrated. The residue was again dissolved in benzene (60 mL) and ethyl acrylate (4.29 g, 42.9 mmol) was added. The mixture was heated at reflux for 24 h, then cooled to room temperature and filtered off solid. The filtrate was concentrated. The crude product was purified by silica flash chromatography with an ELSD detector (0-75% iPrOAc/heptane) to give the title compound (5.22 g, 73%) as yellow oil. $^1$H NMR (400 MHz, Chloroform-d) δ 7.43-7.30 (m, 5H), 5.23-5.11 (m, 2H), 4.31-4.05 (m, 3H), 3.47-3.35 (m, 1H), 3.07 (s, 1H), 2.59-2.28 (m, 5H), 2.14-2.02 (m, 1H), 1.66-1.58 (m, 2H), 1.32-1.17 (m, 3H).

Step 2:

3-(1-benzyloxycarbonyl-4-oxo-3-piperidyl)propanoic Acid

The mixture of benzyl 3-(3-ethoxy-3-oxo-propyl)-4-oxo-piperidine-1-carboxylate (1.0 g, 3.0 mmol) in THF (35 mL), MeOH (3 mL) and LiOH (3 M, 4 mL) was stirred at room temperature for 3 h. The volatiles were removed under reduced pressure. The aqueous residue was acidified with 2 N HCl to pH ~3, extracted with iPrOAc. The combined organics were dried (Na$_2$SO$_4$), filtered and concentrated to give the title compound (950 mg, quant. yield) as yellow oil. $^1$H NMR (400 MHz, DMSO-d$_6$) δ 12.08 (s, 1H), 7.49-7.23 (m, 5H), 5.13 (s, 2H), 4.14-3.84 (m, 2H), 3.50-3.36 (m, 1H), 3.23-2.95 (m, 1H), 2.48-2.42 (m, 2H), 2.39-2.29 (m, 1H), 2.24 (t, J=7.6 Hz, 2H), 1.85 (dq, J=14.4, 7.3 Hz, 1H), 1.56-1.29 (m, 1H).

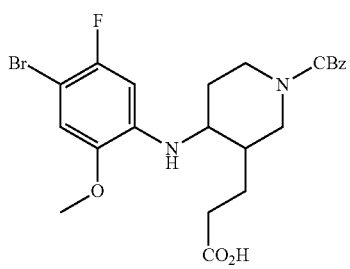

3-[1-benzyloxycarbonyl-4-(4-bromo-5-fluoro-2-methoxy-anilino)-3-piperidyl]propanoic Acid To a screw-capped vial was added 3-(1-benzyloxycarbonyl-4-oxo-3-piperidyl)propanoic acid (810 mg, 2.653 mmol), 4-bromo-5-fluoro-2-methoxy-aniline (584 mg, 2.653 mmol), toluene (5.306 mL) and phenylsilane (574 mg, 5.306 mmol). The mixture was heated at 100° C. for 3 h. The mixture was diluted with iPrOAc, washed with 2 M $Na_2CO_3$. The combined organics were dried ($Na_2SO_4$), filtered and concentrated. The crude product was purified by silica flash chromatography (0-10% MeOH/DCM) to give the title compound (1.137 g, 84%) as brown oil. LCMS (ESI) m/z 509 [M+H]$^+$.

Step 4:

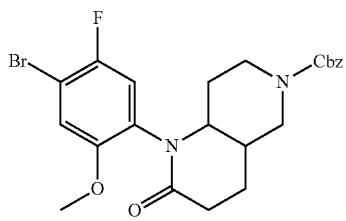 [SMILES: COc1cc(Br)c(F)cc1N1C(=O)CCC2CN(C(=O)OCc3ccccc3)CCC21]

benzyl 1-(4-bromo-5-fluoro-2-methoxy-phenyl)-2-oxo-4,4a,5,7,8,8a-hexahydro-3H-1,6-naphthyridine-6-carboxylate 3-[1-benzyloxycarbonyl-4-(4-bromo-5-fluoro-2-methoxy-anilino)-3-piperidyl]propanoic acid (1.137 g, 2.232 mmol) was dissolved in DMF (6 mL). HATU (934 mg, 2.455 mmol) was added followed by DIPEA (432.7 mg, 3.348 mmol). The mixture was stirred at room temperature for 4 h. The reaction was quenched with 2 M $Na_2CO_3$, extracted with iPrOAc (2×). The combined organics were dried ($Na_2SO_4$), filtered and concentrated. The crude product was purified by silica flash chromatography (0-100% iPrOAc/heptane) to give the title compound (920 mg, 84%) as brown foam. LCMS (ESI) m/z 491 [M+H]$^+$. $^1$H NMR (400 MHz, Chloroform-d) δ 7.44-7.29 (m, 5H), 7.10 (dd, J=8.3, 6.1 Hz, 1H), 6.89 (dd, J=29.0, 8.2 Hz, 1H), 5.24-5.05 (m, 2H), 4.26-4.06 (m, 2H), 3.87-3.72 (m, 3H), 3.69-3.54 (m, 1H), 3.20-3.04 (m, 1H), 2.76-2.45 (m, 3H), 2.40-2.20 (m, 1H), 2.12-2.02 (m, 1H), 1.90-1.65 (m, 3H).

Step 5:

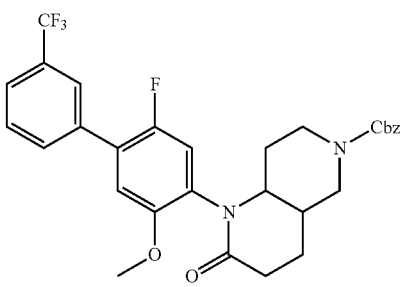

benzyl 1-[5-fluoro-2-methoxy-4-[3-(trifluoromethyl)phenyl]phenyl]-2-oxo-4,4a,5,7,8,8a-hexahydro-3H-1,6-naphthyridine-6-carboxylate The mixture of 3-(trifluoromethyl)phenylboronic acid (480 mg, 2.527 mmol), benzyl 1-(4-bromo-5-fluoro-2-methoxy-phenyl)-2-oxo-4,4a,5,7,8,8a-hexahydro-3H-1,6-naphthyridine-6-carboxylate (920 mg, 1.872 mmol), Pd(PPh$_3$)$_4$ (216 mg, 0.1872 mmol) and $K_2CO_3$ (776 mg, 5.617 mmol) in 1,4-dioxane (9 mL) and water (3 mL) was heated at 100° C. under $N_2$ for 1 h. The reaction mixture was diluted with water, extracted with iPrOAc (3×). The combined organics were dried ($Na_2SO_4$), filtered and concentrated. The crude product was purified by silica flash chromatography (0-100% iPrOAc/heptane,) to give the title compound (1.1 g, 106%) as off-white foam. LCMS (ESI) m/z 557 [M+H]$^+$.

Step 6:

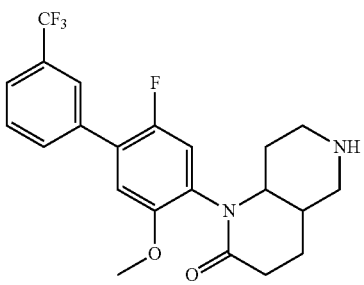 [SMILES: COc1cc(-c2cccc(C(F)(F)F)c2)c(F)cc1N1C(=O)CCC2CNCCC21]

1-[5-fluoro-2-methoxy-4-[3-(trifluoromethyl)phenyl]phenyl]-3,4,4a,5,6,7,8,8a-octahydro-1,6-naphthyridin-2-one The mixture solution of benzyl 1-[5-fluoro-2-methoxy-4-[3-(trifluoromethyl)phenyl]phenyl]-2-oxo-4,4a,5,7,8,8a-hexahydro-3H-1,6-naphthyridine-6-carboxylate (560 mg, 1.006 mmol) and Pd(OH)$_2$ on carbon (494.5 mg, 0.3521 mmol) in EtOAc (5 mL) was stirred at room temperature under $H_2$ balloon for 14 h. The mixture was filtered off solid, washed with EtOAc, concentrated. The crude product was purified by silica flash chromatography (0-10% MeOH/DCM with 1% NH$_4$OH) to give the title compound (315 mg, 74%) as brown oil. LCMS (ESI) m/z 423 [M+H]$^+$.

Step 7:

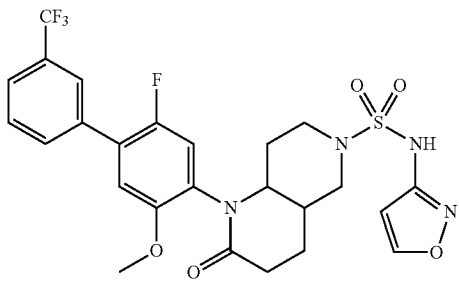 [SMILES: COc1cc(-c2cccc(C(F)(F)F)c2)c(F)cc1N1C(=O)CCC2CN(S(=O)(=O)Nc3ccon3)CCC21]

1-[5-fluoro-2-methoxy-4-[3-(trifluoromethyl)phenyl]phenyl]-N-isoxazol-3-yl-2-oxo-4,4a,5,7,8,8a-hexahydro-3H-1,6-naphthyridine-6-sulfonamide To a solution of isoxazol-3-amine (313 mg, 3.729 mmol) and imidazole (761 mg, 11.19 mmol) in DCM (9 mL) at −78° C. was added SO$_2$Cl$_2$ (503 mg, 3.729 mmol) dropwise. The mixture was warmed to room temperature and stirred for 30 min. 1-[5-fluoro-2-methoxy-4-[3-(trifluoromethyl)phenyl]phenyl]-3,4,4a,5,6,7,8,8a-octahydro-1,6-naphthyridin-2-one (315 mg, 0.7457 mmol) in DCM (1 mL) was then added. The mixture was heated at 80° C. for 30 min. The reaction was quenched with water, extracted with DCM (3×). The combined organics were dried (Na$_2$SO$_4$), filtered and concentrated. The crude product was purified by silica flash chromatography (0-10% MeOH/DCM) to give the title compound (235 mg, 55%) as yellow oil. LCMS (ESI) m/z 569 [M+H]$^+$.

Step 8:

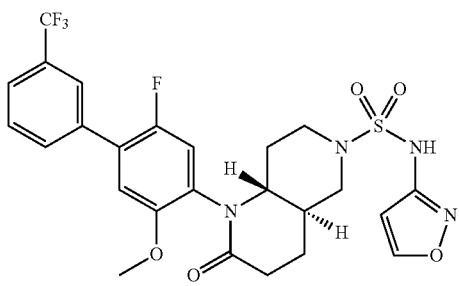

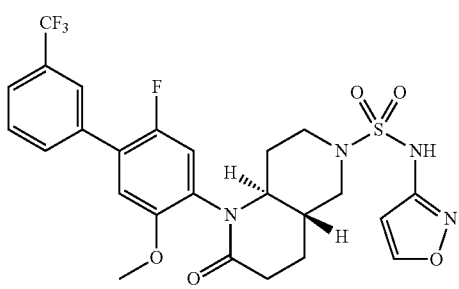

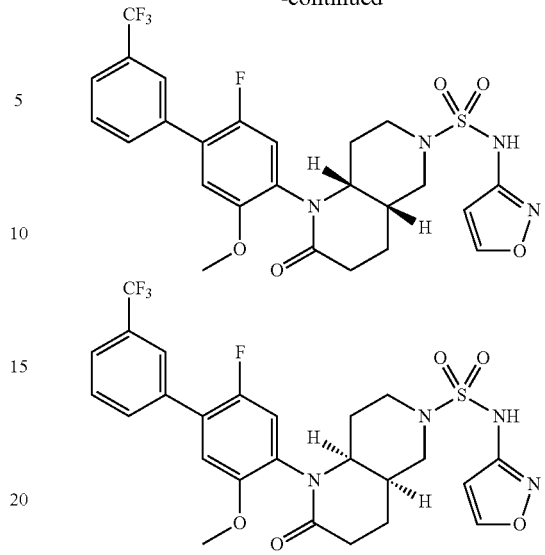

(4aR,8aR)-1-(2-fluoro-5-methoxy-3'-(trifluoromethyl)-[1,1'-biphenyl]-4-yl)-N-(isoxazol-3-yl)-2-oxooctahydro-1,6-naphthyridine-6(2H)-sulfonamide & (4aS,8aS)-1-(2-fluoro-5-methoxy-3'-(trifluoromethyl)-[1,1'-biphenyl]-4-yl)-N-(isoxazol-3-yl)-2-oxooctahydro-1,6-naphthyridine-6(2H)-sulfonamide & (4aS,8aR)-1-(2-fluoro-5-methoxy-3'-(trifluoromethyl)-[1,1'-biphenyl]-4-yl)-N-(isoxazol-3-yl)-2-oxooctahydro-1,6-naphthyridine-6(2H)-sulfonamide & (4aR,8aS)-1-(2-fluoro-5-methoxy-3'-(trifluoromethyl)-[1,1'-biphenyl]-4-yl)-N-(isoxazol-3-yl)-2-oxooctahydro-1,6-naphthyridine-6(2H)-sulfonamide 1-[5-fluoro-2-methoxy-4-[3-(trifluoromethyl)phenyl]phenyl]-N-isoxazol-3-yl-2-oxo-4,4a,5,7,8,8a-hexahydro-3H-1,6-naphthyridine-6-sulfonamide was separated by using chiral SFC (Chiralpak ID (150 mm*21.2 mm, 5 um), Supercritical CO$_2$/MeOH+0.1% NH$_4$OH=70/30, 70 mL/min) to give (4aR,8aR)-1-(2-fluoro-5-methoxy-3'-(trifluoromethyl)-[1,1'-biphenyl]-4-yl)-N-(isoxazol-3-yl)-2-oxooctahydro-1,6-naphthyridine-6(2H)-sulfonamide (first peak) & (4aS,8aS)-1-(2-fluoro-5-methoxy-3'-(trifluoromethyl)-[1,1'-biphenyl]-4-yl)-N-(isoxazol-3-yl)-2-oxooctahydro-1,6-naphthyridine-6(2H)-sulfonamide (second peak) & (4aS,8aR)-1-(2-fluoro-5-methoxy-3'-(trifluoromethyl)-[1,1'-biphenyl]-4-yl)-N-(isoxazol-3-yl)-2-oxooctahydro-1,6-naphthyridine-6(2H)-sulfonamide (third peak) & (4aR,8aS)-1-(2-fluoro-5-methoxy-3'-(trifluoromethyl)-[1,1'-biphenyl]-4-yl)-N-(isoxazol-3-yl)-2-oxooctahydro-1,6-naphthyridine-6(2H)-sulfonamide (fourth peak) as off-white solids. Absolute configuration was arbitrarily assigned to each isomer. Example 35: LCMS (ESI) m/z: 569.1 [M+H]. $^1$H NMR (400 MHz, DMSO-d$_6$) δ 11.04 (s, 1H), 8.74 (dd, J=3.4, 1.8 Hz, 1H), 7.98-7.87 (m, 2H), 7.85-7.66 (m, 2H), 7.35-7.00 (m, 2H), 6.39 (d, J=1.8 Hz, 1H), 3.81 (d, J=22.3 Hz, 3H), 3.72 (t, J=9.6 Hz, 1H), 3.61 (t, J=12.7 Hz, 1H), 3.53-3.36 (m, 1H), 3.29-3.17 (m, 1H), 2.78-2.57 (m, 2H), 2.47-2.38 (m, 1H), 1.88-1.71 (m, 2H), 1.68-1.14 (m, 3H). Example 36: LCMS (ESI) m/z: 569.1 [M+H]. $^1$H NMR (400 MHz, DMSO-d$_6$) δ 11.06 (s, 1H), 8.75 (d, J=1.8 Hz, 1H), 7.92 (d, J=6.5 Hz, 2H), 7.86-7.66 (m, 3H), 7.24 (d, J=7.1 Hz, 1H), 6.39 (d, J=1.8 Hz, 1H), 3.82 (s, 3H), 3.62-3.47 (m, 2H), 3.14-2.97 (m, 1H), 2.74-2.60 (m, 1H), 2.47-2.25 (m, 2H), 2.12-1.90 (m, 1H), 1.90-1.51 (m, 3H). Example 37: LCMS (ESI) m/z: 569.1 [M+H]$^+$. $^1$H NMR (400 MHz, DMSO-d$_6$) δ 11.05 (s, 1H), 8.66 (d, J=5.6 Hz, 1H), 7.92 (d, J=6.8 Hz, 2H), 7.86-7.66 (m, 2H), 7.35-7.00 (m, 2H), 6.37 (d, J=1.8 Hz, 1H), 3.81 (d, J=22.7 Hz, 3H), 3.76-3.52 (m, 2H), 3.51-3.39 (m, 2H), 2.72-2.53 (m, 2H), 2.46-2.36 (m, 1H), 1.87-1.69 (m, 2H), 1.69-1.12 (m, 3H). Example 38: LCMS (ESI) m/z: 569.1 [M+H]$^+$. $^1$H NMR (500 MHz, DMSO-d$_6$) δ 10.86 (s, 1H), 8.69 (d, J=1.8 Hz, 1H), 7.90 (d, J=9.0 Hz, 2H), 7.78 (d, J=7.9 Hz, 1H), 7.73 (t, J=7.6 Hz, 1H), 7.23 (d, J=7.2 Hz, 1H), 7.18 (d, J=10.5 Hz, 1H), 6.37 (d, J=1.7 Hz, 1H), 3.82 (s, 3H), 3.76-3.63 (m, 1H), 3.59-3.50 (m, 2H), 3.08 (dd, J=12.5, 3.3 Hz, 1H), 2.69 (td, J=12.1, 3.0 Hz, 1H), 2.46-2.38 (m, 2H), 2.38-2.33 (m, 1H), 2.04 (td, J=13.3, 12.1, 6.3 Hz, 1H), 1.80-1.73 (m, 1H), 1.71-1.60 (m, 2H).

Although the preparation of the free-base or a specific salt form may be illustrated in the Examples above, it is understood that the free-base and its acid or base salt forms can be interconverted using standard techniques

Example 39A. Tritiated Compound Binding to Membranes Isolated from Cells that Heterologously Express hNav1.7 and the β1 Subunit Preparation of membranes containing recombinantly expressed sodium channels: Frozen recombinant cell pellets were thawed on ice and diluted to 4 times the cell pellet weight with ice cold 50 mM Tris HCl, pH 7.4 buffer. The cell suspensions were homogenized on ice using a motorized glass dounce homogeniser. Homogenates were further diluted 8.4 times with ice cold 50 mM Tris HCl, pH 7.4 buffer and then centrifuged at 200×g at 4° C. for 15 min. The supernatants were collected and centrifuged at 10000×g at 4° C. for 50 min. The pellets were then re-suspended in 100 mM NaCl, 20 mM Tris HCl, pH 7.4 buffer containing 1% v/v protease inhibitors (Calbiochem) and re-homogenized on ice. The homogenized membranes were then processed through a syringe equipped with a 26 gauge needle. Protein concentrations were determined by Bradford Assay and the membranes were stored at −80° C.

Radioligand Binding Studies:

Saturation experiments. A competitive NaV1.7 inhibitor having a methyl group was tritiated. Three tritiums were incorporated in place of methyl hydrogens to generate [$^3$H]compound. Binding of this radioligand was performed in 5 mL borosilicate glass test tubes at room temperature. Binding was initiated by adding membranes to increasing concentrations of [$^3$H]compound in 100 mM NaCl, 20 mM Tris HCl, pH 7.4 buffer containing 0.01% w/v bovine serum albumin (BSA) for 18 h. Non-specific binding was determined in the presence of 1 μM unlabeled compound. After 18 h, the reactants were filtered through GF/C glass fiber filters presoaked in 0.5% w/v polyethylene imine. Filters were washed with 15 mL ice cold 100 mM NaCl, 20 mM Tris HCl, pH7.4 buffer containing 0.25% BSA to separate bound from free ligand. [$^3$H]compound bound to filters was quantified by liquid scintillation counting.

Competitive Binding Experiments:

Binding reactions were performed in 96-well polypropylene plates at room temperature for 18 h. In 360 μL, membranes were incubated with 100 pM [$^3$H]compound and increasing concentrations of Test Compound. Non-specific binding was defined in the presence of 1 μM unlabeled compound. Reactions were transferred and filtered through 96-well glass fiber/C filter plates presoaked with 0.5% polyethylene imine. The filtered reactions were washed 5 times with 200 μL ice cold buffer containing 0.25% BSA. Bound radioactivity was determined by liquid scintillation counting.

Data Analysis:

For saturation experiments, non-specific binding was subtracted from total binding to provide specific binding and these values were recalculated in terms of pmol ligand bound per mg protein. Saturation curves were constructed and dissociation constants were calculated using the single site ligand binding model: Beq=(Bmax*X)/(X+Kd), where Beq is the amount of ligand bound at equilibrium, Bmax is the maximum receptor density, Kd is the dissociation constant for the ligand, and X is the free ligand concentration. For competition studies percent inhibition was determined and IC$_{50}$ values were calculated using a 4 parameter logistic model (% inhibition=(A+((B−A)/(1+((x/C)^D)))) using XLfit, where A and B are the maximal and minimum inhibition respectively, C is the IC$_{50}$ concentration and D is the (Hill) slope.

Example 39B. Tritiated Compound Binding to Membranes Isolated from Cells that Heterologous Express hNav1.7 and the β1 Subunit Preparation of Membranes Containing Recombinantly Expressed Sodium Channels:

Following the procedure described in Example 39A, and making modifications as required to: centrifuge supernatants at 100000×g instead of 10000×g; re-suspend pellets in a buffer containing 0.01% BSA in addition to 100 mM NaCl, 20 mM Tris HCl, pH 7.4 buffer, and 1% v/v proteasome inhibitors; and storing membranes at −80° C. in single use aliquots instead of pooled.

Radioligand Binding Studies:

Saturation experiments: Following the procedure described in Example 243A, and making modifications as required to incubate [3H]compound for 3 hours instead of 18 hours.

Competitive Binding Experiments:

Following the procedure described in Example 243A, and making modifications as required to: perform binding experiments at room temperature for 3 hours instead of 18 hours; use 240 uL of solution and 300 pM of [3H]compound instead of 360 uL and 100 pM of [3H]compound; and wash filtered reactions 2 times instead of 5 times.

Data Analysis:

Data was analysed following the procedure described in Example 243A.

Example 39C. Electrophysiological Assay (EP) (In Vitro Assay)

Patch voltage clamp electrophysiology allows for the direct measurement and quantification of block of voltage-gated sodium channels (NaV's), and allows the determination of the time- and voltage-dependence of block which has been interpreted as differential binding to the resting, open, and inactivated states of the sodium channel (Hille, B., Journal of General Physiology (1977), 69: 497-515).

The following voltage clamp electrophysiology studies were performed on representative compounds using cells heterologously expressing Nav1.7 or Nav1.5 channels. cDNAs for Nav1.7 (NM_002977) and Nav1.5 (AC137587) were stably expressed in Chinese Hamstr Ovary (CHO) cells and CHL (Chinese Hamster Lung) cells respectively. Sodium currents were measured in the whole-cell configuration using Syncropatch 384PE (Nanlon Technologies, Germany). 1NPC®-384 chips with custom medium resistance and single hole mode are used. Internal solution consists of (in mM): 110 CsCl, 10 CsCl, 20 EGTA, and 10 Hepes (pH adjusted to 7.2); and external solution contains (in mM): 60 NMDG, 80 NaCl, 4 KCl, 1 MgCl$_2$, 2 CaCl$_2$, 2 D-Glucose monohydrate, 10 Hepes (pH adjusted to 7.4 with NaOH).

After system flushing, testing compounds are dissolved in external solution containing 0.1% Pluronic F-127. The chip is moved into the measuring head and the instrument primes the chip with external and internal solutions. 10 l cells are added to the chip from a cell hotel, and a negative pressure of −50 mBar is applied to form a seal. Following treatment with seal enhancer solution and wash-off with external solution, negative pressure of −250 mbar is applied for 1 second to achieve the whole-cell configuration, followed by three washing steps in external solution. 20 l of compounds is added to 40 l in each well (1:3 dilution of compounds), and after mixing, 20 l is removed so the volume is retained at 40 ul. After approximately 13 minutes recordings, 20 l/well of 2 uM TTX, or 333 uM Tetracaine (for Nav1.5) is added to achieve full block.

For voltage protocol, an holding potential of −50 mV is applied during the whole experiment. A depolarizing step is applied to −10 mV for 10 ms, followed by a hyperpolarization step to −150 mV for 20 ms to allow channel recovery from inactivation. A second depolarizing step is applied from −150 mV to −10 mV for 10 ms, where currents were measured to derive blocking effects of compounds. Inhibition is determined based on 7.5 min of compound incubation.

Data for representative compounds is provided in Table 1.

TABLE 1

| Example | Structure | Nav1.7 LBA EVO IC$_{50}$ (uM) | EP_SP hNav1.7 EVO IC50 (uM) |
|---|---|---|---|
| 1 | *[chemical structure]* | 0.0443 | 0.00112 |
| 2 | *[chemical structure]* | 0.0384 | 0.000915 |
| 3 | *[chemical structure]* | 0.067 | 0.00226 |

TABLE 1-continued

| Example | Structure | Nav1.7 LBA EVO IC$_{50}$ (uM) | EP_SP hNav1.7 EVO IC50 (uM) |
|---|---|---|---|
| 4 | 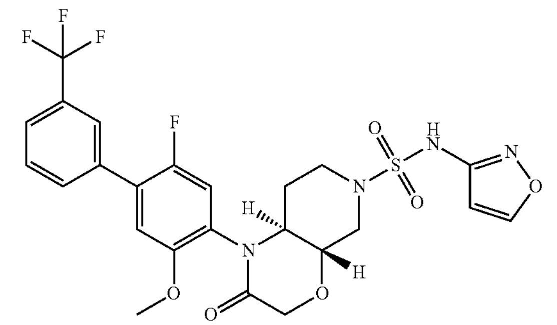 [SMILES: COc1cc(-c2cccc(C(F)(F)F)c2)c(F)cc1N1C(=O)CO[C@H]2CN(S(=O)(=O)Nc3ccon3)CC[C@@H]21] | 0.06 | 0.00352 |
| 5 | 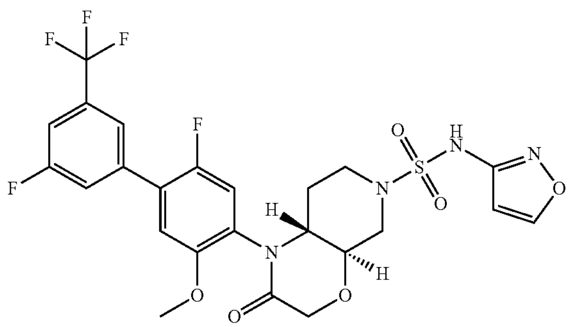 [SMILES: COc1cc(-c2cc(F)cc(C(F)(F)F)c2)c(F)cc1N1C(=O)CO[C@@H]2CN(S(=O)(=O)Nc3ccon3)CC[C@H]21] | 0.079 | 0.00279 |
| 6 | 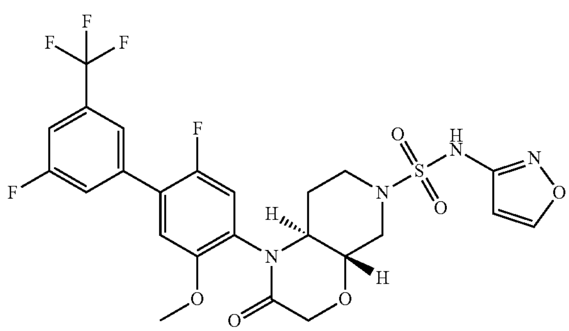 [SMILES: COc1cc(-c2cc(F)cc(C(F)(F)F)c2)c(F)cc1N1C(=O)CO[C@H]2CN(S(=O)(=O)Nc3ccon3)CC[C@@H]21] | 0.0529 | 0.00184 |
| 7 | 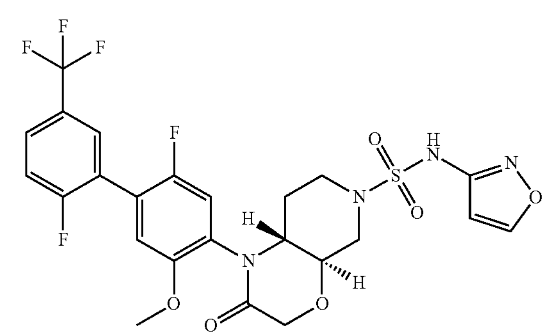 [SMILES: COc1cc(-c2cc(C(F)(F)F)ccc2F)c(F)cc1N1C(=O)CO[C@@H]2CN(S(=O)(=O)Nc3ccon3)CC[C@H]21] | 0.167 | 0.00576 |

TABLE 1-continued

| Example | Structure | Nav1.7 LBA EVO IC$_{50}$ (uM) | EP_SP hNav1.7 EVO IC50 (uM) |
|---|---|---|---|
| 8 | 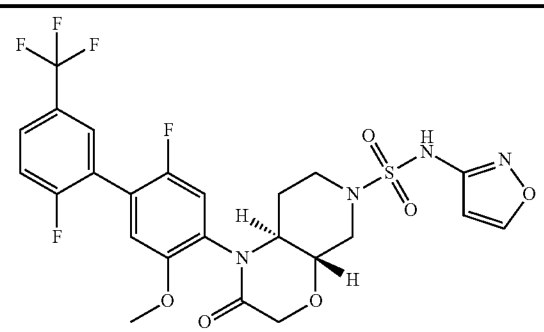 | 0.0828 | 0.00492 |
| 9 | 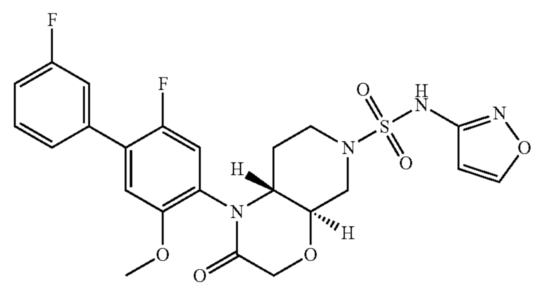 [SMILES: COc1cc(-c2cccc(F)c2)c(F)cc1N1C(=O)CO[C@@H]2CN(S(=O)(=O)Nc3ccon3)CC[C@H]21] | 2.0 | 0.0194 |
| 10 | 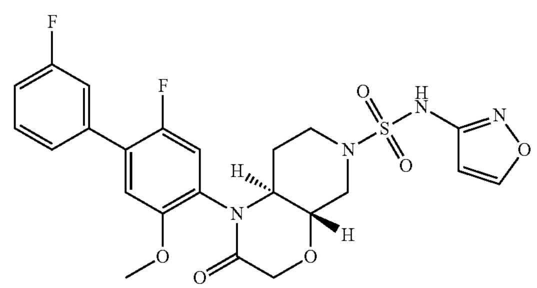 [SMILES: COc1cc(-c2cccc(F)c2)c(F)cc1N1C(=O)CO[C@H]2CN(S(=O)(=O)Nc3ccon3)CC[C@@H]21] | 0.716 | 0.0478 |
| 11 | 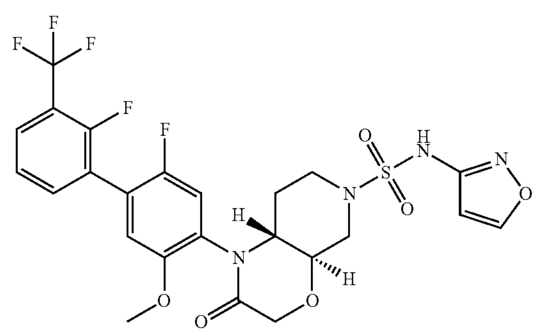 [SMILES: COc1cc(-c2cccc(C(F)(F)F)c2F)c(F)cc1N1C(=O)CO[C@@H]2CN(S(=O)(=O)Nc3ccon3)CC[C@H]21] | 0.23 | 0.0112 |
| 12 | 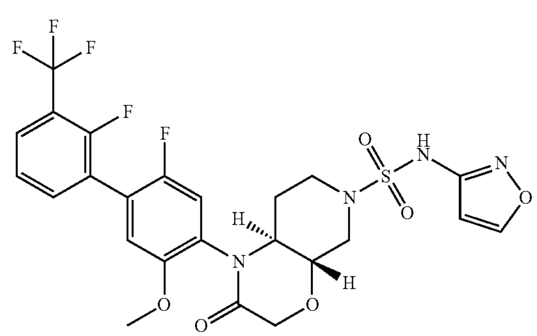 [SMILES: COc1cc(-c2cccc(C(F)(F)F)c2F)c(F)cc1N1C(=O)CO[C@H]2CN(S(=O)(=O)Nc3ccon3)CC[C@@H]21] | 0.131 | 0.00683 |

TABLE 1-continued

| Example | Structure | Nav1.7 LBA EVO IC$_{50}$ (uM) | EP_SP hNav1.7 EVO IC50 (uM) |
|---|---|---|---|
| 13 | 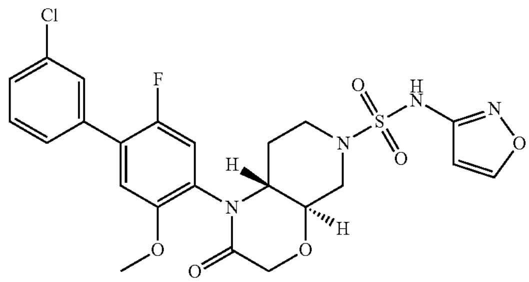 | 0.471 | 0.0117 |
| 14 | 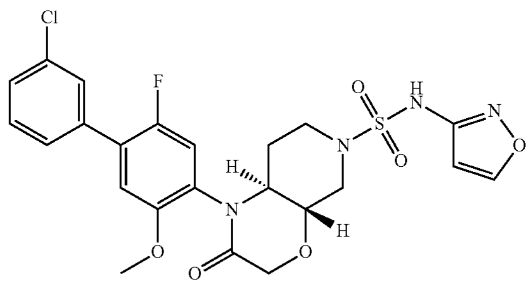 | 0.332 | 0.00721 |
| 15 | 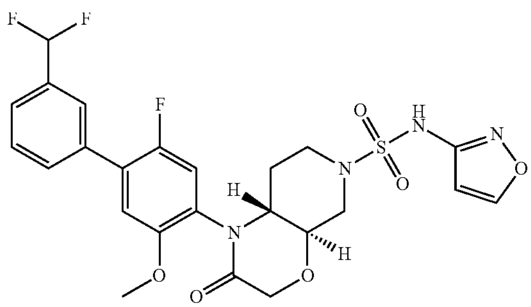 [SMILES: COc1cc(-c2cccc(C(F)F)c2)c(F)cc1N1C(=O)CO[C@@H]2CN(S(=O)(=O)Nc3ccon3)CC[C@H]21] | 2.0 | 0.0467 |
| 16 | 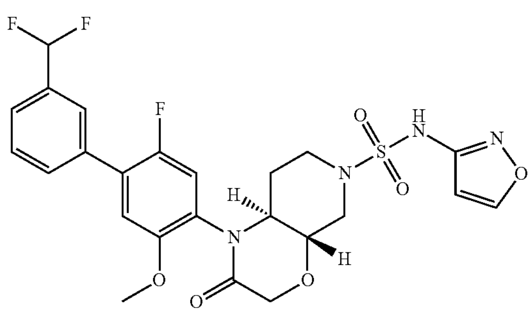 [SMILES: COc1cc(-c2cccc(C(F)F)c2)c(F)cc1N1C(=O)CO[C@H]2CN(S(=O)(=O)Nc3ccon3)CC[C@@H]21] | 1.39 | 0.0495 |
| 17 | 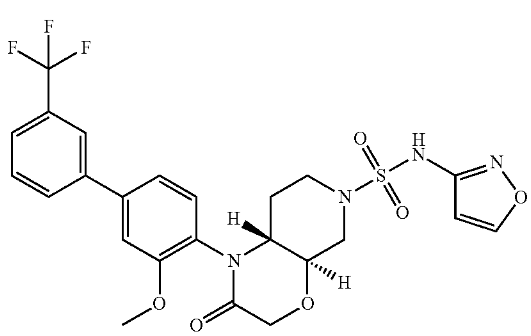 [SMILES: COc1cc(-c2cccc(C(F)(F)F)c2)ccc1N1C(=O)CO[C@@H]2CN(S(=O)(=O)Nc3ccon3)CC[C@H]21] | 0.214 | 0.00603 |

TABLE 1-continued

| Example | Structure | Nav1.7 LBA EVO IC$_{50}$ (uM) | EP_SP hNav1.7 EVO IC50 (uM) |
|---|---|---|---|
| 18 | 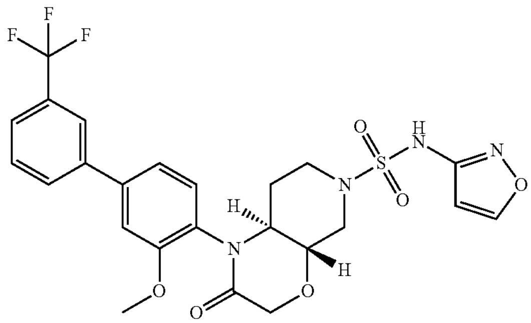 [SMILES: COc1cc(-c2cccc(C(F)(F)F)c2)ccc1N1C(=O)CO[C@H]2CN(S(=O)(=O)Nc3ccon3)CC[C@@H]21] | 0.346 | 0.00586 |
| 19 | 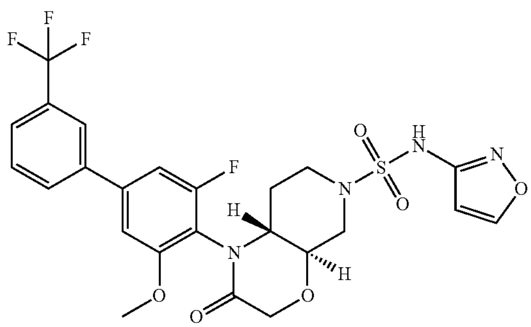 [SMILES: COc1cc(-c2cccc(C(F)(F)F)c2)cc(F)c1N1C(=O)CO[C@@H]2CN(S(=O)(=O)Nc3ccon3)CC[C@H]21] | 0.831 | 0.05 |
| 20 | 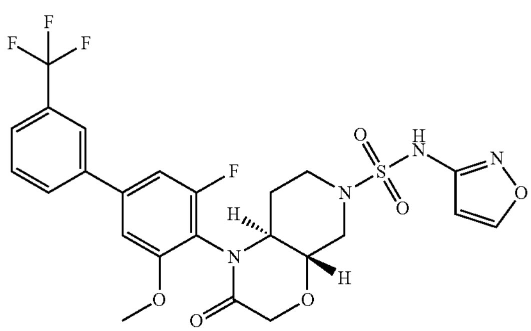 [SMILES: COc1cc(-c2cccc(C(F)(F)F)c2)cc(F)c1N1C(=O)CO[C@H]2CN(S(=O)(=O)Nc3ccon3)CC[C@@H]21] | 2.0 | 0.0398 |
| 21 | 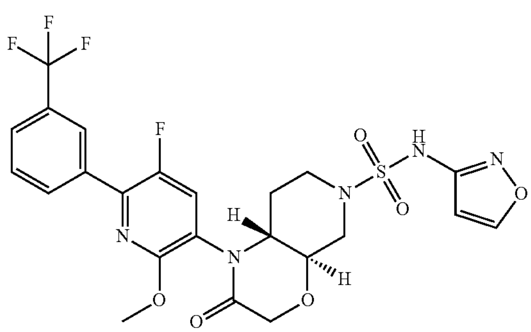 | 2.0 | 0.0475 |

TABLE 1-continued

| Example | Structure | Nav1.7 LBA EVO IC$_{50}$ (uM) | EP_SP hNav1.7 EVO IC50 (uM) |
|---|---|---|---|
| 22 | 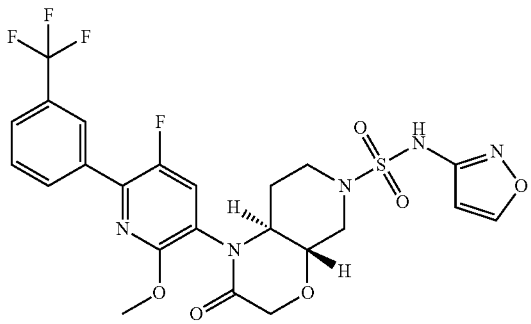 [SMILES: COc1nc(-c2cccc(C(F)(F)F)c2)c(F)cc1N1C(=O)CO[C@H]2CN(S(=O)(=O)Nc3ccon3)CC[C@@H]21] | 0.907 | 0.0668 |
| 23 | 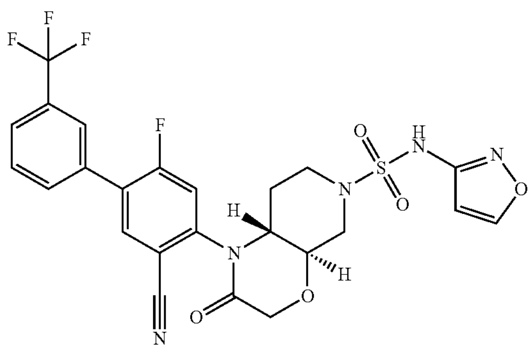 [SMILES: N#Cc1cc(-c2cccc(C(F)(F)F)c2)c(F)cc1N1C(=O)CO[C@@H]2CN(S(=O)(=O)Nc3ccon3)CC[C@H]21] | 2.0 | 0.0501 |
| 24 | 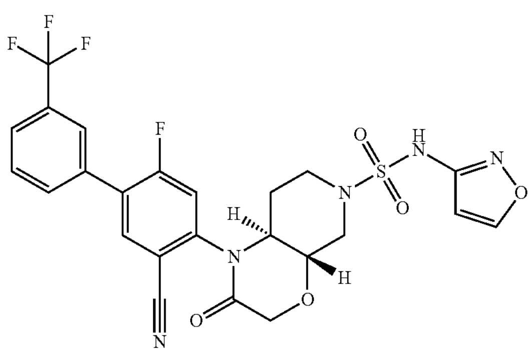 [SMILES: N#Cc1cc(-c2cccc(C(F)(F)F)c2)c(F)cc1N1C(=O)CO[C@H]2CN(S(=O)(=O)Nc3ccon3)CC[C@@H]21] | 2.0 | 0.237 |
| 25 | 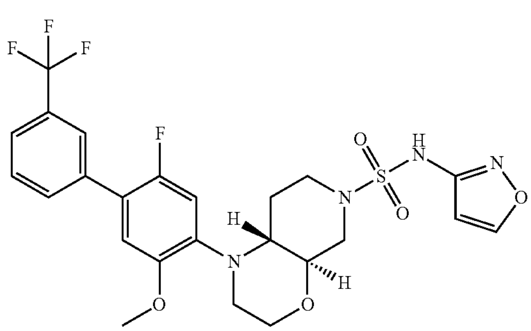 [SMILES: COc1cc(-c2cccc(C(F)(F)F)c2)c(F)cc1N1CCO[C@@H]2CN(S(=O)(=O)Nc3ccon3)CC[C@H]21] | 0.208 | 0.00236 |

TABLE 1-continued

| Example | Structure | Nav1.7 LBA EVO IC$_{50}$ (uM) | EP_SP hNav1.7 EVO IC50 (uM) |
|---|---|---|---|
| 26 | 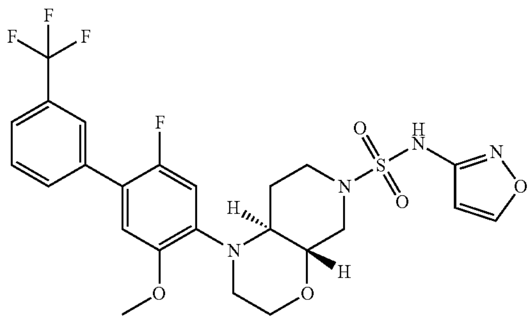 [SMILES: COc1cc(-c2cccc(C(F)(F)F)c2)c(F)cc1N1CCO[C@H]2CN(S(=O)(=O)Nc3ccon3)CC[C@@H]21] | 0.0636 | 0.0106 |
| 27 | 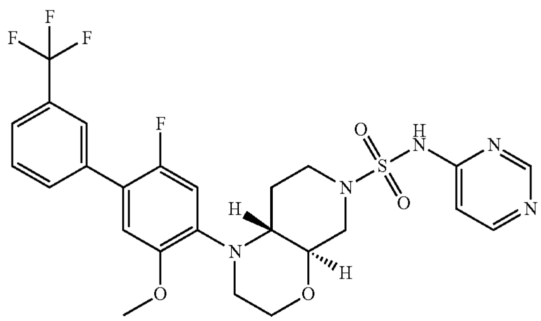 [SMILES: COc1cc(-c2cccc(C(F)(F)F)c2)c(F)cc1N1CCO[C@@H]2CN(S(=O)(=O)Nc3ccncn3)CC[C@H]21] | 0.0212 | 0.00202 |
| 28 | 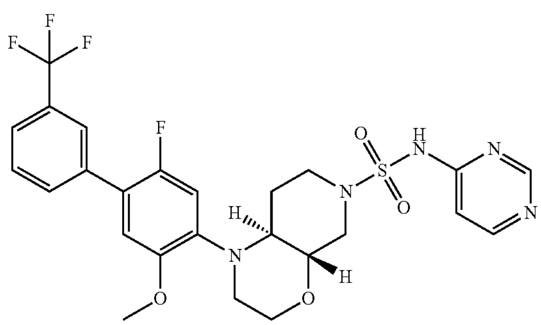 [SMILES: COc1cc(-c2cccc(C(F)(F)F)c2)c(F)cc1N1CCO[C@H]2CN(S(=O)(=O)Nc3ccncn3)CC[C@@H]21] | 0.0263 | 0.0021 |
| 29 | 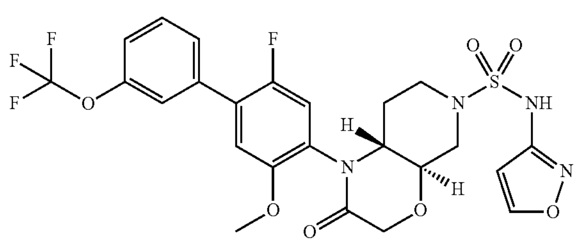 [SMILES: COc1cc(-c2cccc(OC(F)(F)F)c2)c(F)cc1N1C(=O)CO[C@@H]2CN(S(=O)(=O)Nc3ccon3)CC[C@H]21] | 0.0623 | 0.00221 |
| 30 | 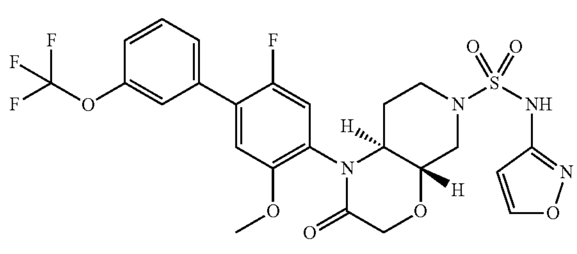 [SMILES: COc1cc(-c2cccc(OC(F)(F)F)c2)c(F)cc1N1C(=O)CO[C@H]2CN(S(=O)(=O)Nc3ccon3)CC[C@@H]21] | 0.0356 | 0.00235 |

TABLE 1-continued

| Example | Structure | Nav1.7 LBA EVO IC$_{50}$ (uM) | EP_SP hNav1.7 EVO IC50 (uM) |
|---|---|---|---|
| 31 | 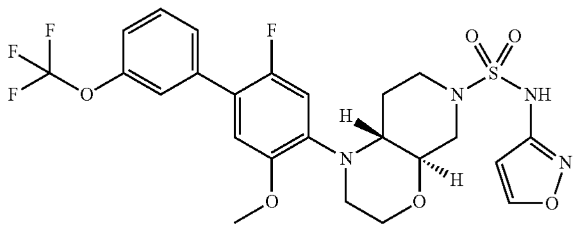 [SMILES: COc1cc(-c2cccc(OC(F)(F)F)c2)c(F)cc1N1CCO[C@@H]2CN(S(=O)(=O)Nc3ccon3)CC[C@H]21] | 0.128 | 0.00598 |
| 32 | 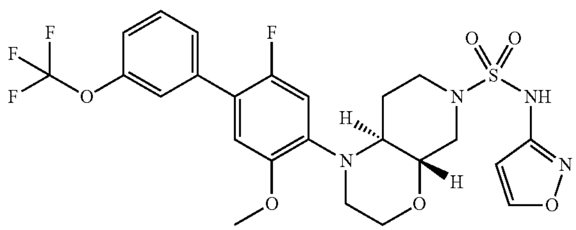 [SMILES: COc1cc(-c2cccc(OC(F)(F)F)c2)c(F)cc1N1CCO[C@H]2CN(S(=O)(=O)Nc3ccon3)CC[C@@H]21] | 0.148 | 0.0109 |
| 33 | 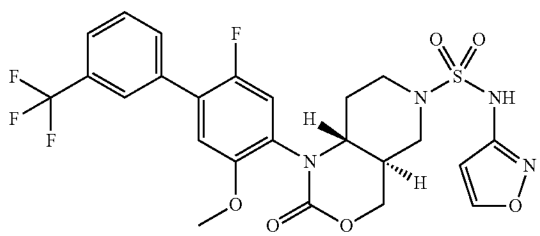 [SMILES: COc1cc(-c2cccc(C(F)(F)F)c2)c(F)cc1N1C(=O)OC[C@@H]2CN(S(=O)(=O)Nc3ccon3)CC[C@H]21] | 0.112 | 0.0104 |
| 34 | 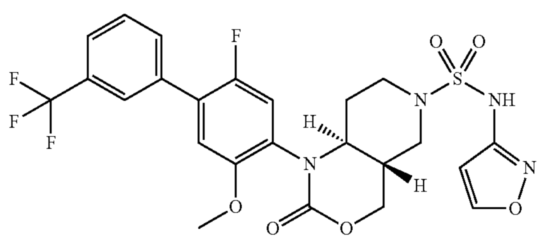 [SMILES: COc1cc(-c2cccc(C(F)(F)F)c2)c(F)cc1N1C(=O)OC[C@H]2CN(S(=O)(=O)Nc3ccon3)CC[C@@H]21] | 2.0 | 0.196 |
| 35 | 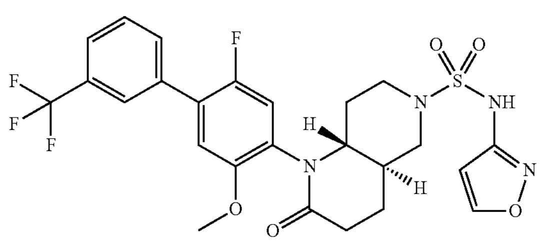 [SMILES: COc1cc(-c2cccc(C(F)(F)F)c2)c(F)cc1N1C(=O)CC[C@@H]2CN(S(=O)(=O)Nc3ccon3)CC[C@H]21] | 0.0493 | 0.00288 |
| 36 | 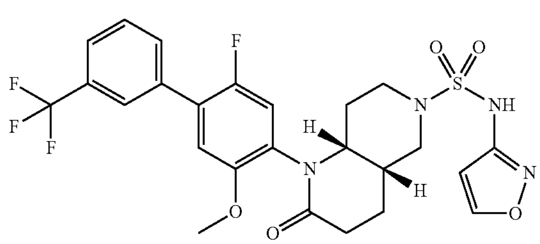 [SMILES: COc1cc(-c2cccc(C(F)(F)F)c2)c(F)cc1N1C(=O)CC[C@H]2CN(S(=O)(=O)Nc3ccon3)CC[C@H]21] | 0.0207 | 0.00219 |

TABLE 1-continued

| Example | Structure | Nav1.7 LBA EVO IC$_{50}$ (uM) | EP_SP hNav1.7 EVO IC50 (uM) |
|---|---|---|---|
| 37 | [structure] | 0.761 | 0.0129 |
| 38 | [structure] | 0.641 | 0.0107 |

Example 40

Analgesia Induced by Sodium Channel Blockers

Heat Induced Tail Flick Latency Test

In this test, the analgesia effect produced by administering a compound of the invention can be observed through heat-induced tail-flick in mice. The test includes a heat source consisting of a projector lamp with a light beam focused and directed to a point on the tail of a mouse being tested. The tail-flick latencies, which are assessed prior to drug treatment, and in response to a noxious heat stimulus, i.e., the response time from applying radiant heat on the dorsal surface of the tail to the occurrence of tail flick, are measured and recorded at 40, 80, 120, and 160 minutes.

For the first part of this study, 65 animals undergo assessment of baseline tail flick latency once a day over two consecutive days. These animals are then randomly assigned to one of the 11 different treatment groups including a vehicle control, a morphine control, and 9 compounds at 30 mg/Kg are administered intramuscularly. Following dose administration, the animals are closely monitored for signs of toxicity including tremor or seizure, hyperactivity, shallow, rapid or depressed breathing and failure to groom. The optimal incubation time for each compound is determined via regression analysis. The analgesic activity of the test compounds is expressed as a percentage of the maximum possible effect (% MPE) and is calculated using the following formula:

$$\% \; MPE \; \frac{\text{Postdrug latency} - \text{Predrug latency}}{\text{Cut-off time (10 s)} - \text{Predrug latency}} \times 100\%$$

where:
Postdrug latency=the latency time for each individual animal taken before the tail is removed (flicked) from the heat source after receiving drug.
Predrug latency=the latency time for each individual animal taken before the tail is flicked from the heat source prior to receiving drug.

Cut-off time (10 s)=is the maximum exposure to the heat source.

Acute Pain (Formalin Test)

The formalin test is used as an animal model of acute pain. In the formalin test, animals are briefly habituated to the plexiglass test chamber on the day prior to experimental day for 20 minutes. On the test day, animals are randomly injected with the test articles. At 30 minutes after drug administration, 50 μL of 10% formalin is injected subcutaneously into the plantar surface of the left hind paw of the rats. Video data acquisition begins immediately after formalin administration, for duration of 90 minutes.

The images are captured using the Actimetrix Limelight software which stores files under the *.llii extension, and then converts it into the MPEG-4 coding. The videos are then analyzed using behaviour analysis software "The Observer 5.1", (Version 5.0, Noldus Information Technology, Wageningen, The Netherlands). The video analysis is conducted by watching the animal behaviour and scoring each according to type, and defining the length of the behaviour (Dubuisson and Dennis, 1977). Scored behaviours include: (1) normal behaviour, (2) putting no weight on the paw, (3) raising the paw, (4) licking/biting or scratching the paw. Elevation, favoring, or excessive licking, biting and scratching of the injected paw indicate a pain response. Analgesic response or protection from compounds is indicated if both paws are resting on the floor with no obvious favoring, excessive licking, biting or scratching of the injected paw.

Analysis of the formalin test data is done according to two factors: (1) Percent Maximal Potential Inhibitory Effect (% MPIE) and (2) pain score. The % MPIEs is calculated by a series of steps, where the first is to sum the length of non-normal behaviours (behaviours 1,2,3) of each animal. A single value for the vehicle group is obtained by averaging all scores within the vehicle treatment group. The following calculation yields the MPIE value for each animal:

MPIE (%)=100−[(treatment sum/average vehicle value)×100%]

The pain score is calculated from a weighted scale as described above. The duration of the behaviour is multiplied by the weight (rating of the severity of the response), and divided by the total length of observation to determine a pain rating for each animal. The calculation is represented by the following formula:

$$\text{Pain rating} = [0(T0)+1(T1)+2(T2)+3(T3)]/(T0+T1+T2+T3)$$

CFA Induced Chronic Inflammatory Pain

In this test, tactile allodynia is assessed with calibrated von Frey filaments. Following a full week of acclimatization to the vivarium facility, 150 µL of the "Complete Freund's Adjuvant" (CFA) emulsion (CFA suspended in an oil/saline (1:1) emulsion at a concentration of 0.5 mg/mL) is injected subcutaneously into the plantar surface of the left hind paw of rats under light isoflurane anaesthesia. Animals are allowed to recover from the anaesthesia and the baseline thermal and mechanical nociceptive thresholds of all animals are assessed one week after the administration of CFA. All animals are habituated to the experimental equipment for 20 minutes on the day prior to the start of the experiment. The test and control articles are administrated to the animals, and the nociceptive thresholds measured at defined time points after drug administration to determine the analgesic responses to each of the six available treatments. The time points used are previously determined to show the highest analgesic effect for each test compound.

Thermal nociceptive thresholds of the animals are assessed using the Hargreaves test. Animals are placed in a Plexiglas enclosure set on top of an elevated glass platform with heating units. The glass platform is thermostatically controlled at a temperature of approximately 30° C. for all test trials. Animals are allowed to accommodate for 20 minutes following placement into the enclosure until all exploration behaviour ceases. The Model 226 Plantar/Tail Stimulator Analgesia Meter (IITC, Woodland Hills, Calif.) is used to apply a radiant heat beam from underneath the glass platform to the plantar surface of the hind paws. During all test trials, the idle intensity and active intensity of the heat source are set at 1 and 45 respectively, and a cut off time of 20 seconds is employed to prevent tissue damage.

The response thresholds of animals to tactile stimuli are measured using the Model 2290 Electrovonfrey anesthesiometer (IITC Life Science, Woodland Hills, Calif.) following the Hargreaves test. Animals are placed in an elevated Plexiglas enclosure set on a mire mesh surface. After 10 minutes of accommodation, pre-calibrated Von Frey hairs are applied perpendicularly to the plantar surface of both paws of the animals in an ascending order starting from the 0.1 g hair, with sufficient force to cause slight buckling of the hair against the paw. Testing continues until the hair with the lowest force to induce a rapid flicking of the paw is determined or when the cut off force of approximately 20 g is reached. This cut off force is used because it represent approximately 10% of the animals' body weight and it serves to prevent raising of the entire limb due to the use of stiffer hairs, which would change the nature of the stimulus.

Postoperative Models of Nociception

In this model, the hypealgesia caused by an intra-planar incision in the paw is measured by applying increased tactile stimuli to the paw until the animal withdraws its paw from the applied stimuli. While animals are anaesthetized under 3.5% isofluorane, which is delivered via a nose cone, a 1 cm longitudinal incision is made using a number 10 scalpel blade in the plantar aspect of the left hind paw through the skin and fascia, starting 0.5 cm from the proximal edge of the heel and extending towards the toes. Following the incision, the skin is apposed using 2, 3-0 sterilized silk sutures. The injured site is covered with Polysporin and Betadine. Animals are returned to their home cage for overnight recovery.

The withdrawal thresholds of animals to tactile stimuli for both operated (ipsilateral) and unoperated (contralateral) paws can be measured using the Model 2290 Electrovonfrey anesthesiometer (IITC Life Science, Woodland Hills, Calif.). Animals are placed in an elevated Plexiglas enclosure set on a mire mesh surface. After at least 10 minutes of acclimatization, pre-calibrated Von Frey hairs are applied perpendicularly to the plantar surface of both paws of the animals in an ascending order starting from the 10 g hair, with sufficient force to cause slight buckling of the hair against the paw. Testing continues until the hair with the lowest force to induce a rapid flicking of the paw is determined or when the cut off force of approximately 20 g is reached. This cut off force is used because it represent approximately 10% of the animals' body weight and it serves to prevent raising of the entire limb due to the use of stiffer hairs, which would change the nature of the stimulus.

Neuropathic Pain Model; Chronic Constriction Injury

Briefly, an approximately 3 cm incision is made through the skin and the fascia at the mid thigh level of the animals' left hind leg using a no. 10 scalpel blade. The left sciatic nerve is exposed via blunt dissection through the biceps femoris with care to minimize haemorrhagia. Four loose ligatures are tied along the sciatic nerve using 4-0 non-degradable sterilized silk sutures at intervals of 1 to 2 mm apart. The tension of the loose ligatures is tight enough to induce slight constriction of the sciatic nerve when viewed under a dissection microscope at a magnification of 4 fold. In the sham-operated animal, the left sciatic nerve is exposed without further manipulation. Antibacterial ointment is applied directly into the wound, and the muscle is closed using sterilized sutures. Betadine is applied onto the muscle and its surroundings, followed by skin closure with surgical clips.

The response thresholds of animals to tactile stimuli are measured using the Model 2290 Electrovonfrey anesthesiometer (IITC Life Science, Woodland Hills, Calif.). Animals are placed in an elevated Plexiglas enclosure set on a mire mesh surface. After 10 minutes of accommodation, pre-calibrated Von Frey hairs are applied perpendicularly to the plantar surface of both paws of the animals in an ascending order starting from the 0.1 g hair, with sufficient force to cause slight buckling of the hair against the paw. Testing continues until the hair with the lowest force to induce a rapid flicking of the paw is determined or when the cut off force of approximately 20 g is reached. This cut off force is used because it represents approximately 10% of the animals' body weight and it serves to prevent raising of the entire limb due to the use of stiffer hairs, which would change the nature of the stimulus.

Thermal nociceptive thresholds of the animals are assessed using the Hargreaves test. Following the measurement of tactile thresholds, animals are placed in a Plexiglass enclosure set on top of an elevated glass platform with heating units. The glass platform is thermostatically controlled at a temperature of approximately 24 to 26° C. for all test trials. Animals are allowed to accommodate for 10 minutes following placement into the enclosure until all exploration behaviour ceases. The Model 226 Plantar/Tail Stimulator Analgesia Meter (IITC, Woodland Hills, Calif.) is used to apply a radiant heat beam from underneath the glass platform to the plantar surface of the hind paws. During all test trials, the idle intensity and active intensity of the heat source are set at 1 and 55 respectively, and a cut off time of 20 seconds is used to prevent tissue damage.

Neuropathic Pain Model: Spinal Nerve Ligation

The spinal nerve ligation (SNL) neuropathic pain model is used as an animal (i.e. rat) model of neuropathic pain. In the SNL test, the lumbar roots of spinal nerves L5 and L6 are tightly ligated to cause nerve injury, which results in the development of mechanical hyperalgesia, mechanical allodynia and thermal hypersensitivity. The surgery is performed two weeks before the test day in order for the pain state to fully develop in the animals. Several spinal nerve ligation variations are used to characterize the analgesic properties of a compound of the invention.

Ligation of the L5 spinal nerve;
Ligation of the L5 and L6 spinal nerves;
Ligation and transection of the L5 spinal nerve;
Ligation and transection of the L5 and L6 spinal nerves; or
Mild irritation of the L4 spinal nerve in combination with any one of the above (1)-(4).

While the animals are anaesthetized under 3.5% isofluorane delivered via a nose cone, an approximately 2.5 cm longitudinal incision is made using a number 10 scalpel blade in the skin just lateral to the dorsal midline, using the level of the posterior iliac crests as the midpoint of the incision. Following the incision, the isoflourane is readjusted to maintenance levels (1.5%-2.5%). At mid-sacral region, an incision is made with the scalpel blade, sliding the blade along the side of the vertebral column (in the saggital plane) until the blade hits the sacrum. Scissors tips are introduced through the incision and the muscle and ligaments are removed from the spine to expose 2-3 cm of the vertebral column. The muscle and fascia are cleared from the spinal vertebra in order to locate the point where the nerve exits from the vertebra. A small glass hook is placed medial to the spinal nerves and the spinal nerves are gently elevated from the surrounding tissues. Once the spinal nerves have been isolated, a small length of non-degradable 6-0 sterilized silk thread is wound twice around the ball at the tip of the glass hook and passed back under the nerve. The spinal nerves are then firmly ligated by tying a knot, ensuring that the nerve bulges on both sides of the ligature. The procedure may be repeated as needed. In some animals, the L4 spinal nerve may be lightly rubbed (up to 20 times) with the small glass hook to maximize the development of neuropathic pain. Antibacterial ointment is applied directly into the incision, and the muscle is closed using sterilized sutures. Betadine is applied onto the muscle and its surroundings, followed by skin closure with surgical staples or sterile non-absorable monofilament 5-0 nylon sutures.

The analgesic effect produced by topical administration of a compound of the invention to the animals can then be observed by measuring the paw withdrawal threshold of animals to mechanical tactile stimuli. These may be measured using either the mechanical allodynia procedure or the mechanical hyperalgesia procedure as described below. After establishment of the appropriate baseline measurements by either method, topical formulation of a compound of the invention is applied on the ipsilateral ankle and foot. The animals are then placed in plastic tunnels for 15 minutes to prevent them from licking the treated area and removing the compound. Animals are placed in the acrylic enclosure for 15 minutes before testing the ipsilateral paw by either of the methods described below, and the responses are recorded at 0.5, 1.0 and 2.0 hour post treatment.

Mechanical Allodynia Method

The pain threshold of animals to mechanical alloydnia for both operated and control animals can be measured approximately 14 days post-surgery using manual calibrated von Frey filaments as follows. Animals are placed in an elevated plexiglass enclosure set on a mire mesh surface. Animals are allowed to acclimate for 20-30 minutes. Pre-calibrated Von Frey hairs are applied perpendicularly to the plantar surface of the ipsilateral paw of the animals starting from the 2.0 g hair, with sufficient force to cause slight buckling of the hair against the paw to establish the baseline measurements. Stimuli are presented in a consecutive manner, either in an ascending or descending order until the first change in response is noted, after which four additional responses are recorded for a total of six responses. The six responses measured in grams are entered into a formula as described by Chaplan, S. R. et al., J. Neurosci. Methods, 1994 July; 53(1):55-63, and a 50% withdrawal threshold is calculated. This constitutes the mechanical allodynia value.

Mechanical Hyperalgesia Method

The response thresholds of animals to tactile stimuli are measured using the Model 2290 Electrovonfrey anesthesiometer (IITC Life Science, Woodland Hills, Calif.). Animals are placed in an elevated Plexiglas enclosure set on a wire mesh surface. After 15 minutes of accommodation in this enclosure, a von Frey hair is applied perpendicularly to the plantar surface of the ipsilateral hind paws of the animals, with sufficient force, measured in grams, to elicit a crisp response of the paw. A response indicates a withdrawal from the painful stimulus and constitutes the efficacy endpoint. The data are expressed as percent change from baseline threshold measured in grams.

Example 41 In Vivo Assay for Treatment of Pruritus

The compounds of the invention can be evaluated for their activity as antipruritic agents by in vivo test using rodent models. One established model for peripherally elicited pruritus is through the injection of serotonin into the rostral back area (neck) in hairless rats. Prior to serotonin injections (e.g., 2 mg/mL, 50 µL), a dose of a compound of the present invention can be applied systemically through oral, intravenous or intraperitoneal routes or topically to a circular area fixed diameter (e.g. 18 mm). Following dosing, the serotonin injections are given in the area of the topical dosing. After serotonin injection the animal behaviour is monitored by video recording for 20 min-1.5 h, and the number of scratches in this time compared to vehicle treated animals. Thus, application of a compound of the current invention could suppress serotonin-induced scratching in rats.

All of the U.S. patents, U.S. patent application publications, U.S. patent applications, foreign patents, foreign patent applications and non patent publications referred to in this specification are incorporated herein by reference in their entireties.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

We claim:
1. A compound of formula (I)

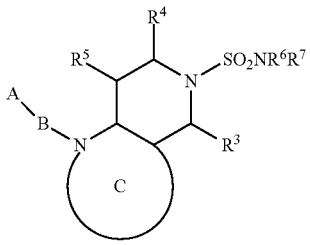

(I)

or a pharmaceutically acceptable salt thereof, wherein:
A is a 6-12 membered aryl ring that is optionally substituted with one or more groups $R^A$ independently selected from the group consisting of F, Cl, Br, I, —CN, —C(=O)O$R^{A1}$, —SO$_2$$R^{A1}$, —O$R^{A1}$, —($X^{RA}$)-(3-15 membered carbocyclyl), —($X^{RA}$)-(6 membered aryl), —($X^{RA}$)—(5-12 membered heteroaryl), and —$R^{A2}$, wherein said 3-15 membered carbocyclyl, 6-12 membered aryl, and 5-12 membered heteroaryl of $R^A$ is optionally substituted with from 1 to 5 substituents $R^a$ independently selected from the group consisting of F, Cl, Br, I, $C_{1-4}$alkyl, halo($C_{1-4}$alkyl), amino, ($C_{1-4}$alkyl)amino, di($C_{1-4}$alkyl)amino, halo($C_{1-4}$alkoxy), and —C(O)N($R^c$)$_2$; $R^{A1}$ is selected from the group consisting of hydrogen, $C_{1-8}$alkyl, $C_{2-8}$alkenyl, halo($C_{1-8}$alkyl), $C_{3-8}$cycloalkyl, phenyl and benzyl; $R^{A2}$ is selected from the group consisting of $C_{1-8}$alkyl that is optionally substituted with one or more substituents independently selected from oxo (=O), fluoro, hydroxy, amino, ($C_{1-4}$alkyl)amino and di($C_{1-4}$alkyl)amino; $X^{RA}$ is selected from the group consisting of absent, —C(=O)—, and $C_{1-4}$alkylene; wherein any $C_{1-4}$alkylene, of $X^{RA}$ is optionally substituted with 1 to 3 substituents independently selected from the group consisting of $C_{1-4}$alkyl, halo($C_{1-4}$alkyl), and phenyl that is optionally substituted with 1 to 5 substituents independently selected from, F, Cl, Br, I, —NH$_2$, —OH, —CN, —NO$_2$, $C_{1-4}$alkyl, halo($C_{1-4}$alkyl), $C_{1-4}$alkoxy, halo($C_{1-4}$alkoxy), ($C_{1-4}$alkyl)amino and di($C_{1-4}$alkyl)amino;
B is a 5-12 membered heteroaryl or a 6-12 membered aryl ring, wherein ring B is optionally substituted with one or more groups $R^B$ independently selected from the group consisting of F, Cl, Br, I, —CN, —C(=O)O$R^{B1}$, —SO$_2$$R^{B1}$, —O$R^{B1}$, —($X^{RB}$)-(3-15 membered carbocyclyl), —($X^{RB}$)-(6-12 membered aryl), —($X^{RB}$)-(5-12 membered heteroaryl), and —$R^{B2}$, wherein said 3-15 membered carbocyclyl, 6-12 membered aryl, and 5-12 membered heteroaryl of $R^B$ is optionally substituted with from 1 to 5 substituents $R^b$ independently selected from the group consisting of F, Cl, Br, I, $C_{1-4}$alkyl, halo($C_{1-4}$alkyl), amino, ($C_{1-4}$alkyl)amino, di($C_{1-4}$alkyl)amino, halo($C_{1-4}$alkoxy), and —C(O)N($R^c$)$_2$; $R^{B1}$ is selected from the group consisting of hydrogen, $C_{1-8}$alkyl, $C_{2-8}$alkenyl, halo($C_{1-8}$alkyl), $C_{3-8}$cycloalkyl, phenyl and benzyl; $R^{B2}$ is selected from the group consisting of $C_{1-8}$alkyl that is optionally substituted with one or more substituents independently selected from oxo (=O), fluoro, hydroxy, amino, ($C_{1-4}$alkyl)amino and di($C_{1-4}$alkyl)amino; $X^{RB}$ is selected from the group consisting of absent, —C(=O)—, and $C_{1-4}$alkylene; wherein any $C_{1-4}$alkylene, of $X^{RB}$ is optionally substituted with 1 to 3 substituents independently selected from the group consisting of $C_{1-4}$alkyl, halo($C_{1-4}$alkyl), and phenyl that is optionally substituted with 1 to 5 substituents independently selected from, F, Cl, Br, I, —NH$_2$, —OH, —CN, —NO$_2$, $C_{1-4}$alkyl, halo($C_{1-4}$alkyl), $C_{1-4}$alkoxy, halo($C_{1-4}$alkoxy), ($C_{1-4}$alkyl)amino and di($C_{1-4}$alkyl)amino;
ring C is a 5-, 6-, or 7-membered heterocyclyl, which 5-, 6-, or 7-membered heterocyclyl is optionally substituted with one or more groups $R^c$ independently selected from the group consisting of C1-4alkyl, halo, oxo (=O), thioxo (=S), and halo($C_{1-4}$alkyl);
$R^3$, $R^4$, and $R^5$ are each independently selected from the group consisting of H, F, Cl, Br, I, —CN, $C_{1-8}$alkyl, $C_{3-8}$cycloalkyl, halo($C_{1-4}$alkyl) and $C_{1-8}$alkoxy; and
$R^6$ is selected from the group consisting of H, $C_{1-8}$alkyl, $C_{3-8}$ cycloalkyl, aryl, and aryl($C_{1-4}$ alkyl); and $R^7$ is selected from the group consisting of $C_{1-8}$alkyl, 3-15 membered heterocyclyl, 5-12 membered heteroaryl, —C(O)N($R^d$)$_2$ and —C(=NCN)N($R^d$)$_2$; or $R^6$ and $R^7$, together with the nitrogen to which they are attached, form a 3-15 membered heterocyclyl or 5-12 membered heteroaryl; wherein any $C_{1-8}$ alkyl, $C_{3-8}$ cycloalkyl, aryl, aralkyl, 3-15 membered heterocyclyl, and 5-12 membered heteroaryl is optionally substituted with one or more groups Re that are independently selected from the group consisting of F, Cl, Br, I, —NH$_2$, —OH, —CN, —NO$_2$, $C_{1-4}$ alkyl, halo($C_{1-4}$alkyl), $C_{1-4}$alkoxy, halo($C_{1-4}$alkoxy), ($C_{1-4}$alkyl)amino and di($C_{1-4}$alkyl)amino;
each $R^d$ is independently selected from the group consisting of hydrogen, $C_{1-8}$ alkyl, $C_{3-8}$ cycloalkyl, phenyl and benzyl.

2. A compound of formula Ia:

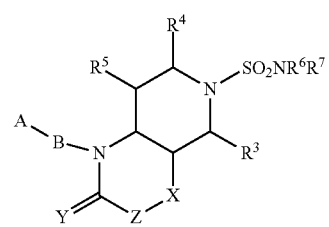

(Ia)

or a pharmaceutically acceptable salt thereof, wherein:
X is CH$_2$, O, S, SO, or SO$_2$; Y is H$_2$ or O; and Z is is CH$_2$ or O; provided that when Z is O, X is CH$_2$;
A is a 6-12 membered aryl ring that is optionally substituted with one or more groups $R^A$ independently selected from the group consisting of F, Cl, Br, I, —CN, —C(=O)O$R^{A1}$, —SO$_2$$R^{A1}$, —O$R^{A1}$, —($X^{RA}$)—(3-15 membered carbocyclyl), —($X^{RA}$)—(6-12 membered aryl), —($X^{RA}$)—(5-12) membered heteroaryl), and —$R^{A2}$, wherein said 3-15 membered carbocyclyl, 6-12 membered aryl, and 5-12 membered heteroaryl of $R^A$ is optionally substituted with from 1 to 5 substituents $R^a$ independently selected from the group consisting of F, Cl, Br, I, $C_{1-4}$ alkyl, halo($C_{1-4}$alkyl), amino, ($C_{1-4}$alkyl)amino, di($C_{1-4}$alkyl)amino, halo($C_{1-4}$alkoxy), and —C(O)N(R$^c$)$_2$; R$^{A1}$ is selected from the group consisting of hydrogen, C$_{1-8}$ alkyl, C$_{2-8}$ alkenyl, halo (C$_{1-8}$alkyl), C$_{3-8}$ cycloalkyl, phenyl and benzyl; R$^{A2}$ is selected from the group consisting of C$_{1-8}$ alkyl that is optionally substituted with one or more substituents independently selected from oxo (=O), fluoro, hydroxy, amino, (C$_{1-4}$alkyl)amino and di(C$_{1-4}$alkyl)amino; X$^{RA}$ is selected from the group consisting of absent, —C(=O)—, and C$_{1-4}$ alkylene; wherein any C$_{1-4}$alkylene, of X$^{RA}$ is optionally substituted with 1 to 3 substituents independently selected from the group consisting of C$_{1-4}$ alkyl, halo(C$_{1-4}$ alkyl), and phenyl that is optionally substituted with 1 to 5 substituents independently selected from, F, Cl, Br, I, —NH$_2$, —OH, —CN, —NO$_2$, C$_{1-4}$ alkyl, halo(C$_{1-4}$alkyl), C$_{1-4}$alkoxy, halo(C$_{1-4}$ alkoxy), (C$_{1-4}$ alkyl)amino and di(C$_{1-4}$ alkyl)amino;

B is a 5-12 membered heteroaryl or a 6-12 membered aryl ring, wherein ring B is optionally substituted with one or more groups R$^B$ independently selected from the group consisting of F, Cl, Br, I, —CN, —C(=O)OR$^{B1}$, —SO$_2$R$^{B1}$, —OR$^{B1}$, —(X$^{RB}$)-(3-15 membered carbocyclyl), —(X$^{RB}$)-(6-12 membered aryl), —(X$^{RB}$)-(5-12 membered heteroaryl), and —R$^{B2}$, wherein said 3-15 membered carbocyclyl, 6-12 membered aryl, and 5-12 membered heteroaryl of R$^B$ is optionally substituted with from 1 to 5 substituents R$^b$ independently selected from the group consisting of F, C$_1$, Br, I, C$_{1-4}$alkyl, halo(C$_{1-4}$alkyl), amino, (C$_{1-4}$alkyl)amino, di(Ci$_{1-4}$ alkyl)amino, halo(C$_{1-8}$alkoxy), and —C(O)N(R$^c$)$_2$, R$^{B1}$ is selected from the group consisting of hydrogen, C$_{1-8}$ alkyl, C$_{2-8}$ alkenyl, halo(C$_{1-8}$alkyl), C$_{3-8}$ cycloalkyl, phenyl and benzyl; R$^{B2}$ is selected from the group consisting of C$_{1-8}$ alkyl that is optionally substituted with one or more substituents independently selected from oxo (=O), fluoro, hydroxy, amino, (C$_{1-4}$ alkyl)amino and di(C$_{1-4}$ alkyl)amino; X$^{RB}$ is selected from the group consisting of absent, —C(=O)—, and C$_{1-4}$ alkylene; wherein any C$_{1-4}$ alkylene, of X$^{RB}$ is optionally substituted with 1 to 3 substituents independently selected from the group consisting of C$_{1-4}$ alkyl, halo (C$_{1-4}$alkyl), and phenyl that is optionally substituted with 1 to 5 substituents independently selected from, F, Cl, Br, I, —NH$_2$, —OH, —CN, —NO$_2$, C$_{1-4}$ alkyl, halo(C$_{1-4}$ alkyl), C$_{1-4}$ alkoxy, halo(C$_{1-4}$alkoxy), (C$_{1-4}$alkyl)amino and di(C$_{1-4}$alkyl)amino;

R$^3$, R$^4$, and R$^5$ are each independently selected from the group consisting of H, F, Cl, Br, I, —CN, C$_{1-8}$alkyl, C$_{3-8}$ cycloalkyl, halo(C$_{1-8}$alkyl) and C$_{1-8}$alkoxy; and R$^6$ is selected from the group consisting of H, C$_{1-8}$ alkyl, C$_{3-8}$ cycloalkyl, aryl, and aryl(C$_{1-4}$ alkyl); and R$^7$ is selected from the group consisting of C$_{1-8}$ alkyl, 3-15 membered heterocyclyl, 5-12 membered heteroaryl, —C(O)N(R$^d$)$_2$ and —C(=NCN)N(R$^d$)$_2$; or R$^6$ and R$^7$, together with the nitrogen to which they are attached, form a 3-15 membered heterocyclyl or 5-12 membered heteroaryl; wherein any C$_{1-8}$alkyl, C$_{3-8}$cycloalkyl, aryl, aralkyl, 3-15 membered heterocyclyl, and 5-12 membered heteroaryl is optionally substituted with one or more groups R$^e$ that are independently selected from the group consisting of F, Cl, Br, I, —NH$_2$, —OH, —CN, —NO$_2$, C$_{1-4}$ alkyl, halo(C$_{1-4}$alkyl), C$_{1-4}$alkoxy, halo(C$_{1-4}$ alkoxy), (C$_{1-4}$alkyl)amino and di(C$_{1-4}$ alkyl)amino;

each R$^d$ is independently selected from the group consisting of hydrogen, C$_{1-8}$alkyl, C$_{3-8}$cycloalkyl, phenyl and benzyl.

3. The compound of claim 2, which is a compound of formula Ib:

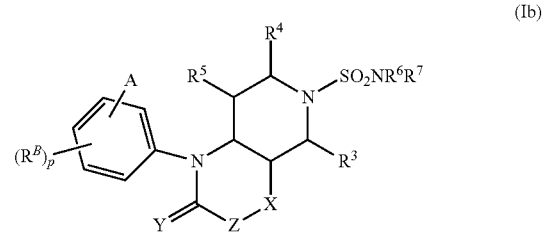

(Ib)

wherein X is CH$_2$, O, S, SO, or SO$_2$; Y is H$_2$, or O; Z is CH$_2$ or O; provided that when Z is O, X is CH$_2$; and p is 1, 2, 3, or 4; or a pharmaceutically acceptable salt thereof.

4. The compound of claim 2, which is a compound of formula Ic:

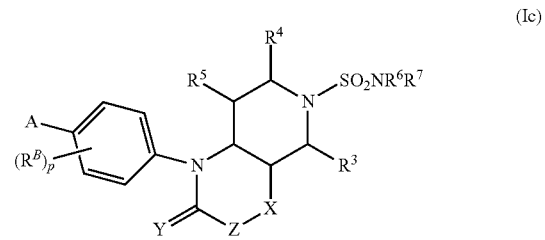

(Ic)

wherein, X is CH$_2$, O, S, SO, or SO$_2$; Y is H$_2$, or O; Z is CH$_2$ or O; provided that when Z is O, X is CH$_2$; and p is 1, 2, 3, or 4; or a pharmaceutically acceptable salt thereof.

5. The compound of claim 2, which is a compound of formula Id:

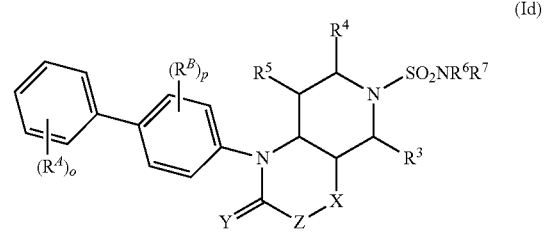

(Id)

wherein, X is CH$_2$, O, S, SO, or SO$_2$; Y is H$_2$, or O; Z is CH$_2$ or O; provided that when Z is O, X is CH$_2$; p is 1, 2, 3, or 4; and o is 1, 2, 3, 4, or 5; or a pharmaceutically acceptable salt thereof.

6. The compound of claim 2, which is a compound of formula Ie:

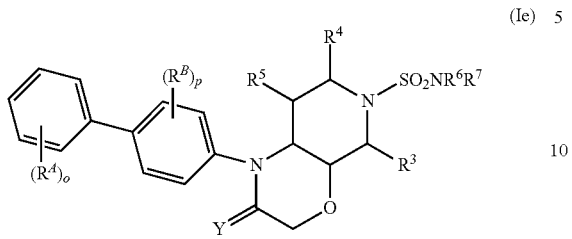

(Ie)

wherein Y is $H_2$ or O; p is 1, 2, 3, or 4; and o is 1, 2, 3, 4, or 5; or a pharmaceutically acceptable salt thereof.

7. The compound of claim 2, which is a compound of formula If:

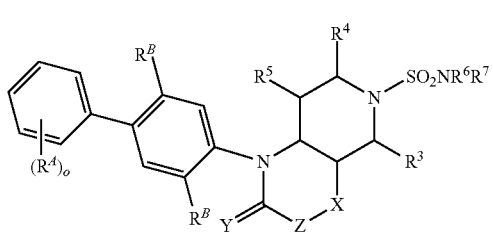

(If)

wherein, X is $CH_2$, O, S, SO, or $SO_2$; Y is $H_2$, or O; Z is $CH_2$ or O; provided that when Z is O, X is $CH_2$; and o is 1, 2, 3, 4, or 5; or a pharmaceutically acceptable salt thereof.

8. The compound of claim 2, which is a compound of formula Ig:

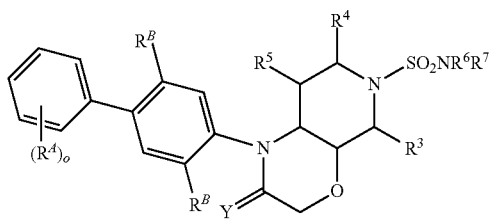

(Ig)

wherein Y is $H_2$ or O; and o is 1, 2, 3, 4, or 5; or a pharmaceutically acceptable salt thereof.

9. The compound of claim 7, or a pharmaceutically acceptable salt thereof, wherein X is O, S, SO, or $SO_2$; Y is $H_2$; and Z is $CH_2$.

10. The compound of claim 7, or a pharmaceutically acceptable salt thereof, wherein X is O, S, SO, or $SO_2$; Y is O; and Z is $CH_2$.

11. The compound of claim 8, or a pharmaceutically acceptable salt thereof, wherein Y is O.

12. The compound of claim 1, or a pharmaceutically acceptable salt thereof, wherein $R^3$, $R^4$, and $R^5$ are each independently selected from the group consisting of H, F, and $C_{1-4}$alkyl.

13. The compound of claim 1, or a pharmaceutically acceptable salt thereof, wherein —$NR^6R^7$ is:

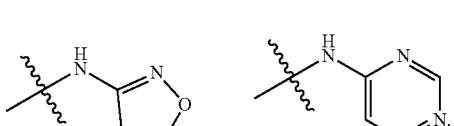

or

14. The compound of claim 1, or a pharmaceutically acceptable salt thereof, wherein —$NR^6R^7$ is:

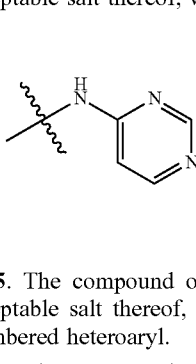

15. The compound of claim 1, or a pharmaceutically acceptable salt thereof, wherein $R^6$ is H and $R^7$ is a 5-6 membered heteroaryl.

16. The compound of claim 1, or a pharmaceutically acceptable salt thereof, wherein each $R^A$ is independently selected from the group consisting of F, Cl, trifluoromethoxy, $CF_2$, and $CF_3$.

17. The compound of claim 1, or a pharmaceutically acceptable salt thereof, wherein each $R^B$ is independently selected from the group consisting of F, —CN, and methoxy.

18. A compound selected from the group consisting of:

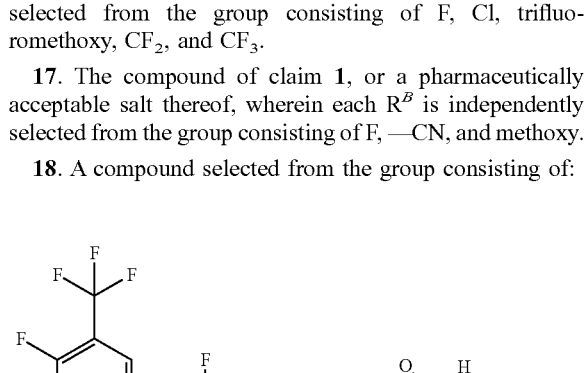

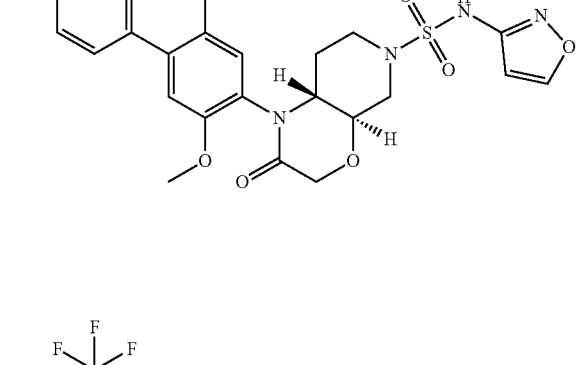

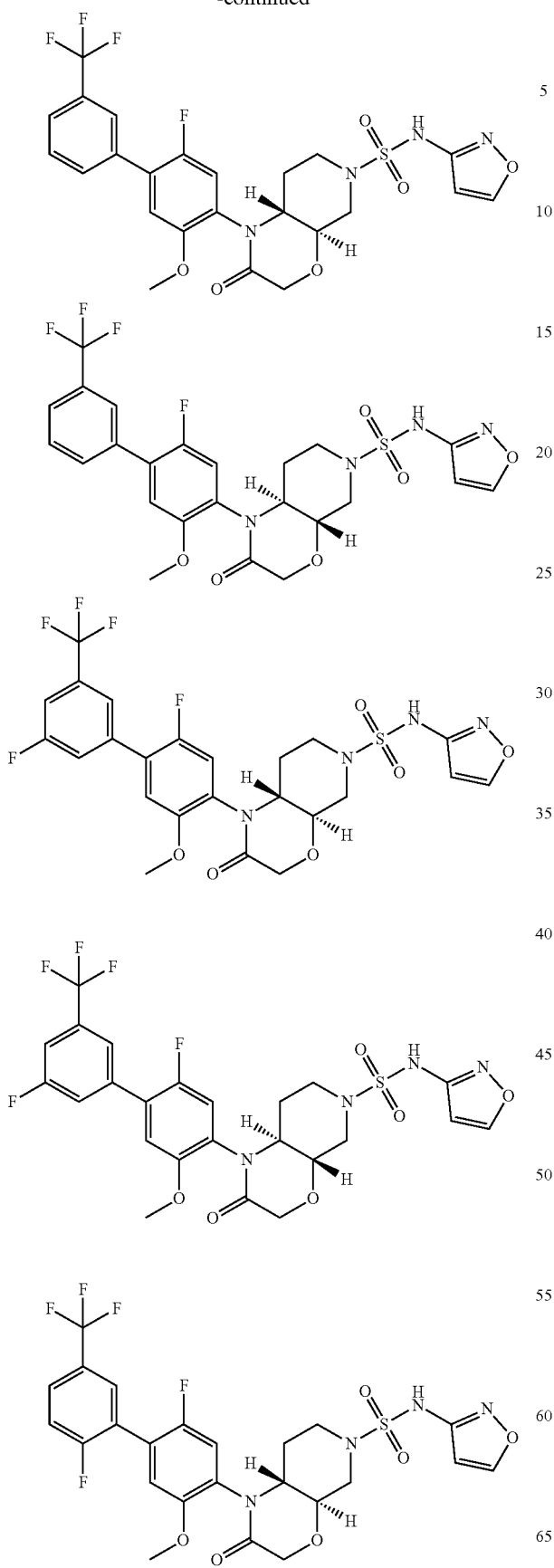
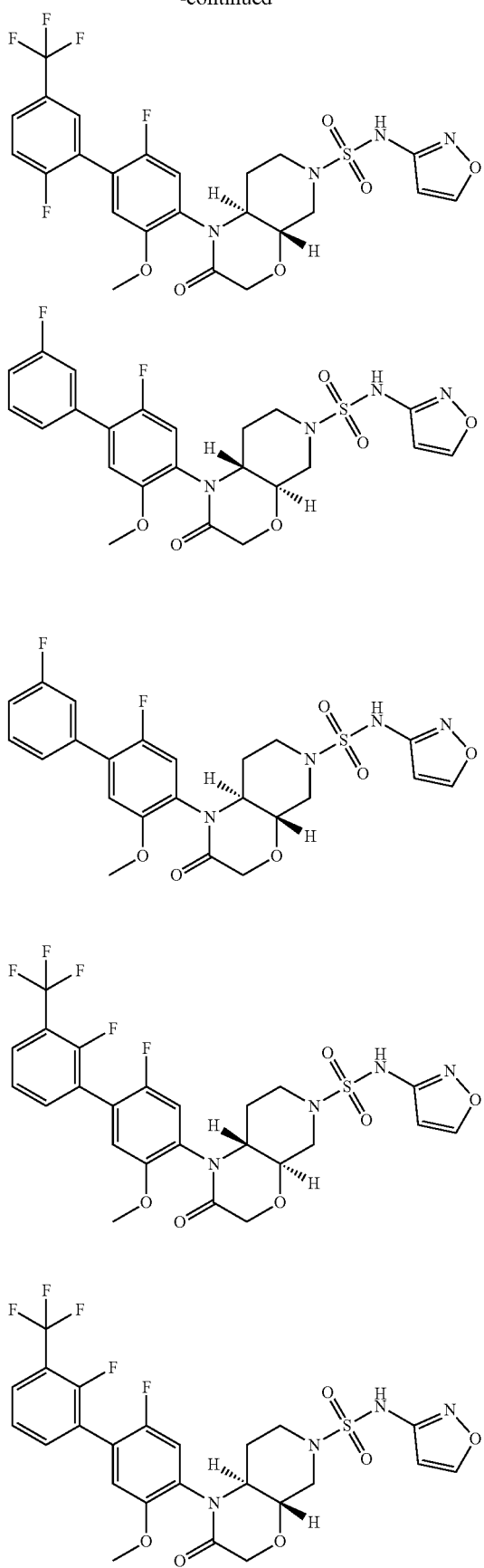

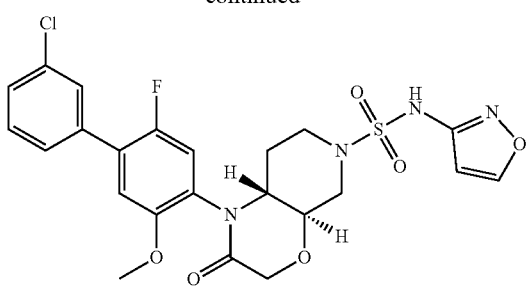
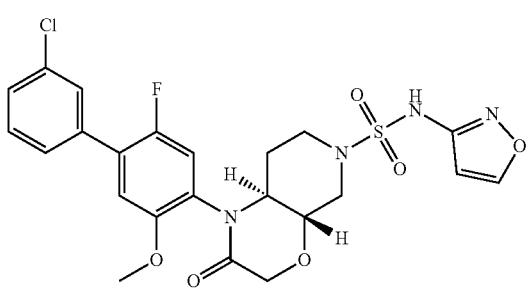
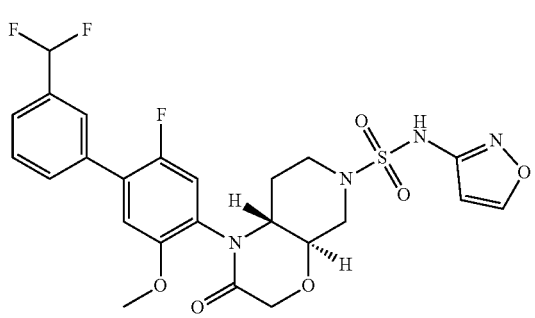
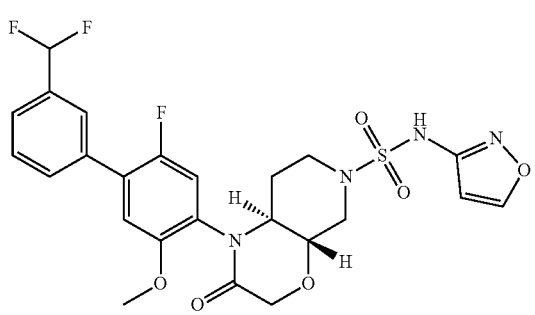
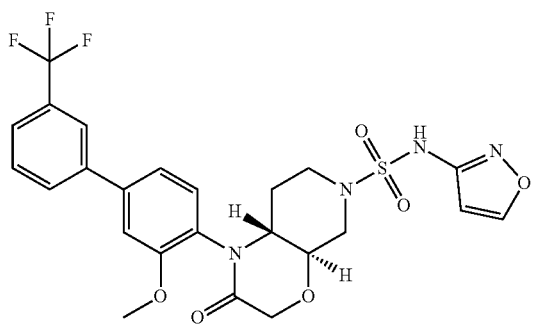
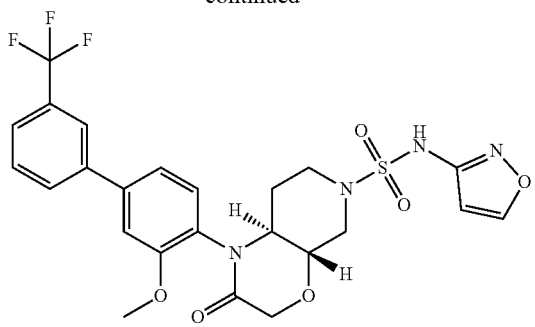
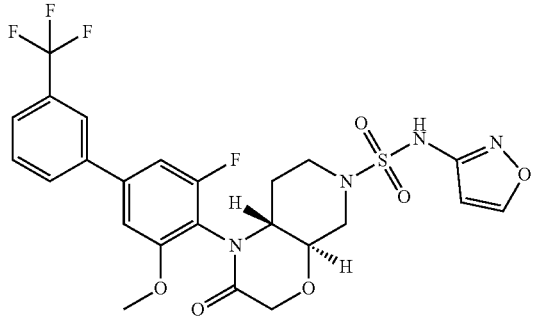
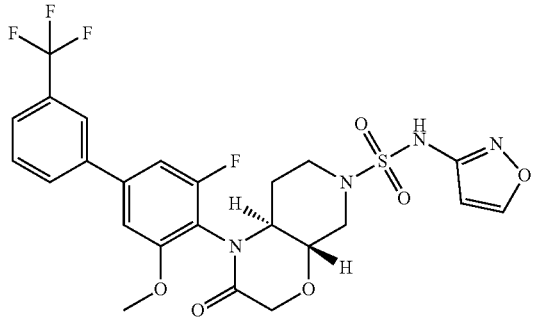
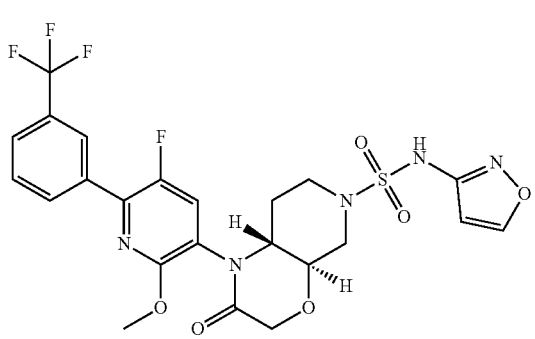
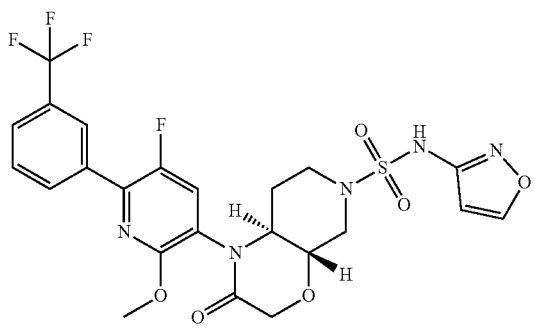

135
-continued
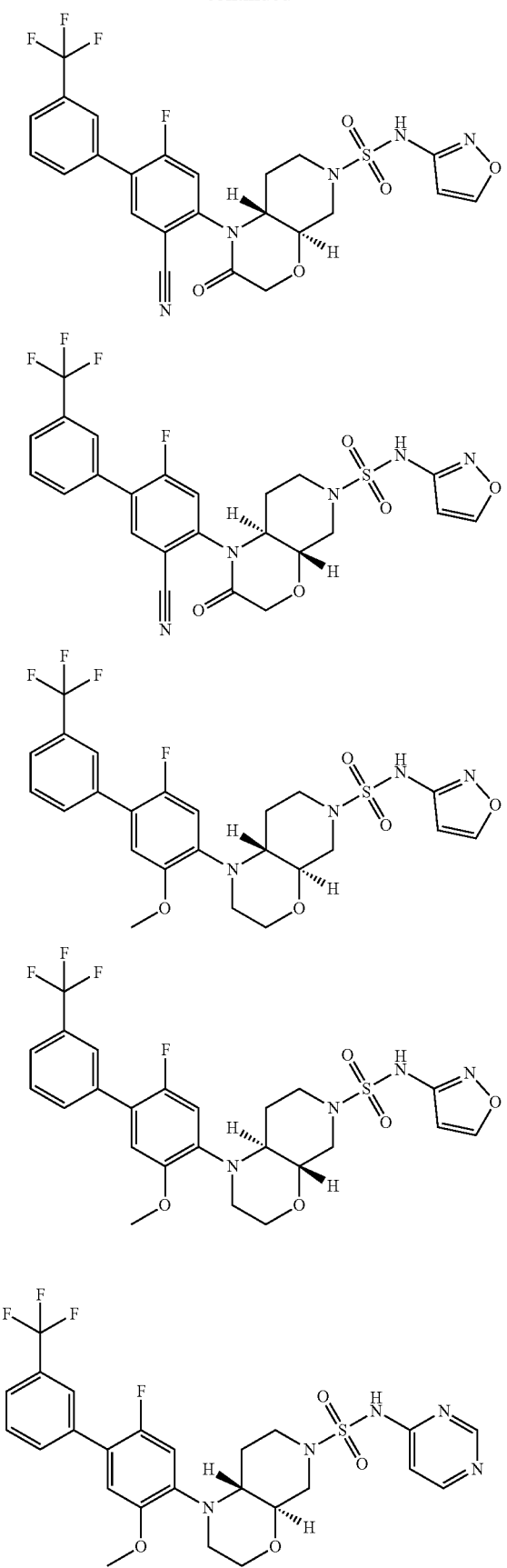
136
-continued
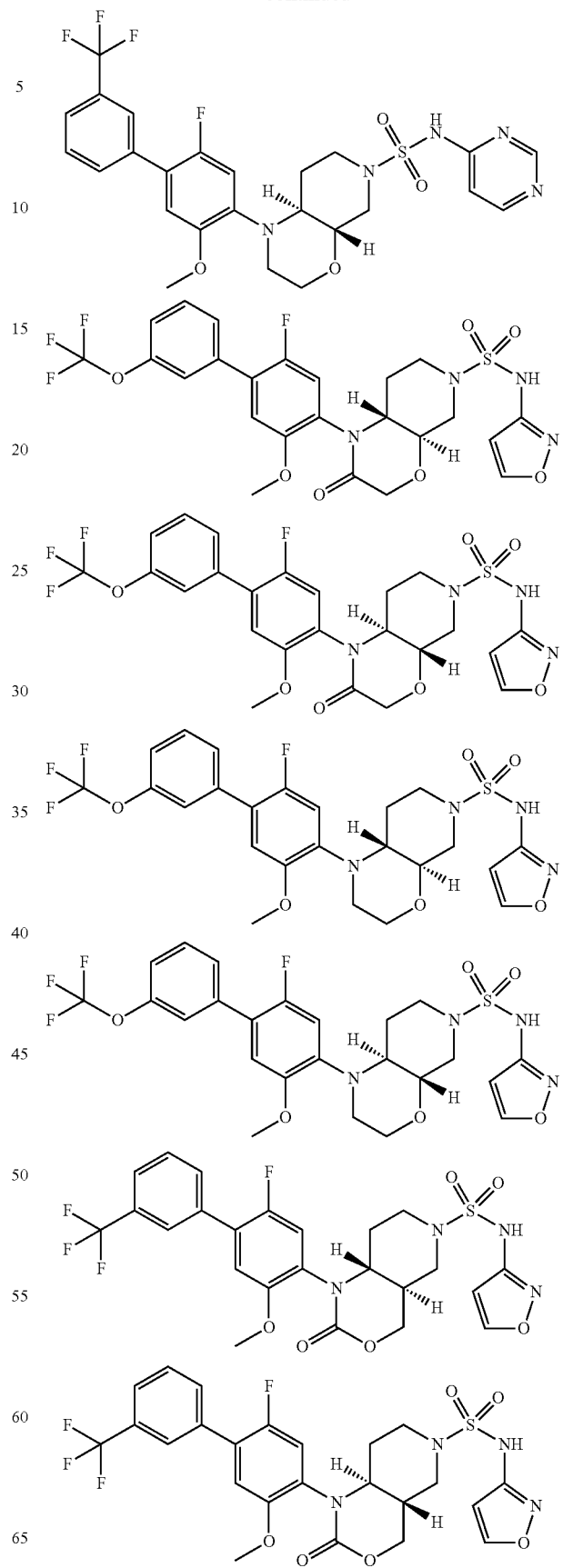

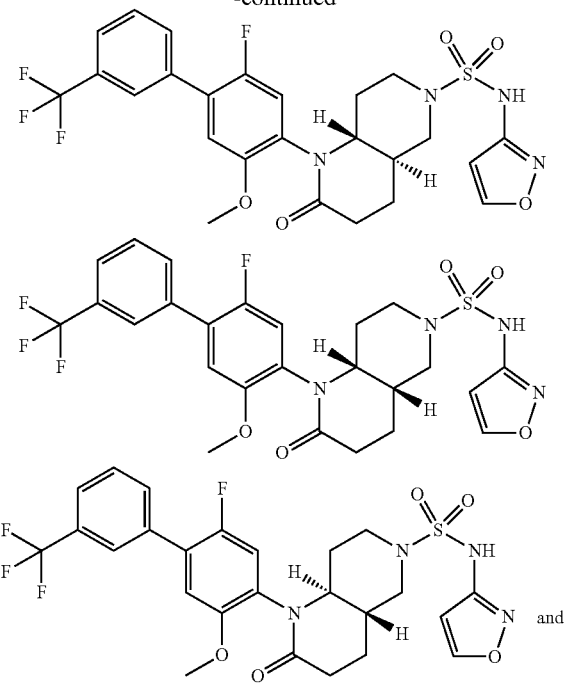
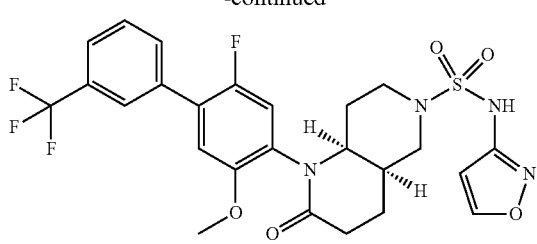

or a pharmaceutically acceptable salt thereof.

19. A pharmaceutical composition comprising a compound of claim 1 or a pharmaceutically acceptable salt thereof, and a pharmaceutically acceptable excipient.

20. The compound of claim 1, wherein ring C is a 5-, 6-, or 7-membered saturated heterocyclyl, which 5-, 6-, or 7-membered saturated heterocyclyl is optionally substituted with one or more groups $R^c$ independently selected from the group consisting of $C_{1-4}$alkyl, halo, oxo (=O), thioxo (=S), and halo($C_{1-4}$alkyl).

* * * * *

UNITED STATES PATENT AND TRADEMARK OFFICE
CERTIFICATE OF CORRECTION

PATENT NO. : 10,947,251 B2
APPLICATION NO. : 16/370756
DATED : March 16, 2021
INVENTOR(S) : Steven McKerrall et al.

It is certified that error appears in the above-identified patent and that said Letters Patent is hereby corrected as shown below:

In the Claims

Claim 1, Column 126, Line 9, "-NH2," should read -- -NH$_2$,--,

Claim 1, Column 126, Line 30, "groups Re that" should read --groups R$^e$ that--, Claim 2, Column 127, Line 34, "halo(C$_{1-8}$alkoxy)," should read --halo(C$_{1-4}$alkoxy)--, Claim 2, Column 127, Line 2, "C$_{1-8}$ alkyl, C$_{2-8}$ alkenyl," should read --C$_{1-8}$alkyl, C$_{2-8}$alkenyl,--, Claim 2, Column 127, Line 3, "C$_{3-8}$ cycloalkyl," should read --C$_{3-8}$cycloalkyl,--, Claim 2, Column 127, Line 4, "C$_{1-8}$ alkyl," should read --C$_{1-8}$alkyl,--, Claim 2, Column 127, Line 10, "C$_{1-4}$ alkylene," should read --C$_{1-4}$alkylene,--, Claim 2, Column 127, Line 14, "C$_{1-4}$ alkyl, halo(C$_{1-4}$ alkyl)" should read --C$_{1-4}$alkyl, halo(C$_{1-4}$alkyl)--, Claim 2, Column 127, Line 17, "C$_{1-4}$ alkyl," should read --C$_{1-4}$alkyl,--, Claim 2, Column 127, Line 18, "halo(C$_{1-4}$ alkoxy), (C$_{1-4}$ alkyl)amino" should read --halo(C$_{1-4}$alkoxy), (C$_{1-4}$alkyl)amino--, Claim 2, Column 127, Line 19, "di(C$_{1-4}$ alkyl)amino;" should read --di(C$_{1-4}$alkyl)amino;--, Claim 2, Column 127, Line 36, "C$_{1-8}$ alkyl, C$_{2-8}$ alkenyl, halo(C$_{1-8}$alkyl), C$_{3-8}$ cycloalkyl" should read --C$_{1-8}$alkyl, C$_{2-8}$alkenyl, halo(C$_{1-8}$alkyl), C$_{3-8}$cycloalkyl--, Claim 2, Column 127, Line 38, "of C$_{1-8}$ alkyl that" should read --of C$_{1-8}$alkyl that--, Signed and Sealed this
Seventeenth Day of August, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,947,251 B2

Claim 2, Column 127, Line 41, "($C_{1-4}$ alkyl)amino" should read --($C_{1-4}$alkyl)amino--, Claim 2, Column 127, Line 42, "di($C_{1-4}$ alkyl)amino;" should read --di($C_{1-4}$alkyl)amino;--, Claim 2, Column 127, Line 44, "any $C_{1-4}$ alkylene, of" should read --any $C_{1-4}$alkylene, of--, Claim 2, Column 127, Line 46, "of $C_{1-4}$ alkyl," should read --of $C_{1-4}$alkyl,--, Claim 2, Column 127, Line 49, "$C_{1-4}$ alkyl," should read --$C_{1-4}$alkyl,--, Claim 2, Column 127, Line 50, "halo($C_{1-4}$ alkyl), $C_{1-4}$ alkoxy," should read --halo($C_{1-4}$alkyl), $C_{1-4}$alkoxy,--, Claim 2, Column 127, Line 54, "$C_{1-8}$ cycloalkyl," should read --$C_{1-8}$cycloalkyl,--, Claim 2, Column 127, Line 55, "of H, $C_{1-8}$ alkyl," should read --of H, $C_{1-8}$alkyl,--, Claim 2, Column 127, Line 56, "$C_{3-8}$ cycloalkyl, aryl, and aryl($C_{1-4}$ alkyl);" should read --$C_{3-8}$ cycloalkyl, aryl, and aryl($C_{1-4}$alkyl);--, Claim 2, Column 127, Line 57, "of $C_{1-8}$ alkyl," should read --of $C_{1-8}$alkyl,--, Claim 2, Column 128, Line 1, "$NO_2$, $C_{1-4}$ alkyl," should read --$NO_2$, $C_{1-4}$alkyl,--, Claim 2, Column 128, Line 2, "halo($C_{1-4}$ alkoxy)," should read --halo($C_{1-4}$alkoxy),--.